US009745581B2

(12) United States Patent
Karni et al.

(10) Patent No.: US 9,745,581 B2
(45) Date of Patent: Aug. 29, 2017

(54) METHODS OF TREATING AND DIAGNOSING DISEASES USING AGENTS THAT REGULATE THE ALTERNATIVE SPLICING PATHWAY

(71) Applicant: Yissum Research Development Company of the Hebrew University of Jerusalem Ltd., Jerusalem (IL)

(72) Inventors: Rotem Karni, Mevasseret Zion (IL); Vered Ben Hur, Jerusalem (IL); Avraham Maimon, Petach-Tikva (IL)

(73) Assignee: Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 0 days.

(21) Appl. No.: 14/401,571

(22) PCT Filed: May 16, 2013

(86) PCT No.: PCT/IL2013/050424
§ 371 (c)(1),
(2) Date: Nov. 17, 2014

(87) PCT Pub. No.: WO2013/171753
PCT Pub. Date: Nov. 21, 2013

(65) Prior Publication Data

US 2015/0141489 A1 May 21, 2015

Related U.S. Application Data

(60) Provisional application No. 61/704,909, filed on Sep. 24, 2012, provisional application No. 61/665,554, filed on Jun. 28, 2012, provisional application No. 61/647,594, filed on May 16, 2012, provisional application No. 61/647,587, filed on May 16, 2012.

(51) Int. Cl.

| | |
|---|---|
| ***A61K 48/00*** | (2006.01) |
| ***C12N 15/113*** | (2010.01) |
| ***C12Q 1/68*** | (2006.01) |
| ***A61K 31/437*** | (2006.01) |
| ***A61K 31/44*** | (2006.01) |
| ***A61K 31/506*** | (2006.01) |
| ***A61K 31/519*** | (2006.01) |
| ***G01N 33/573*** | (2006.01) |

(52) U.S. Cl.
CPC ........ *C12N 15/1137* (2013.01); *A61K 31/437* (2013.01); *A61K 31/44* (2013.01); *A61K 31/506* (2013.01); *A61K 31/519* (2013.01); *C12Q 1/6886* (2013.01); *G01N 33/573* (2013.01); *C12N 2310/14* (2013.01); *C12N 2310/315* (2013.01); *C12N 2310/322* (2013.01); *C12N 2310/3231* (2013.01); *C12N 2320/30* (2013.01); *C12Q 2600/106* (2013.01); *C12Q 2600/158* (2013.01); *G01N 2333/91205* (2013.01); *G01N 2800/52* (2013.01)

(58) Field of Classification Search
CPC ..................................................... A61K 48/00
See application file for complete search history.

(56) References Cited

FOREIGN PATENT DOCUMENTS

| | | |
|---|---|---|
| WO | WO 2009/021675 | 2/2009 |
| WO | WO 2011/158243 | 12/2011 |
| WO | WO 2013/171753 | 11/2013 |

OTHER PUBLICATIONS

Dolniak et al. (JBC 2008, vol. 283:12034-12042).*
Shveygert et al. (Mol and Cell Bio 2010: 5160-5167).*
Hou et al. (Oncotarget 2013: vol. 3:118-131).*
Communication Relating to the Results of the Partial International Search Dated Aug. 6, 2013 From the International Searching Authority Re. Application No. PCT/IL2013/050424.
International Preliminary Report on Patentability Dated Nov. 27, 2014 From the International Bureau of WIPO Re. Application No. PCT/IL2013/050424.
International Search Report and the Written Opinion Dated Oct. 10, 2013 From the International Searching Authority Re. Application No. PCT/IL2013/050424.
Adesso et al. "Gemeitabine Triggers A Pro-Survival Response in Pancreatic Cancer Cells Through Activation of the MNK2/eIF4E Pathway", Oncogene, Advance Online Publication, p. 1-10, Jul. 16, 2012.
Ben-Hur et al. "S6K1 Alternative Splicing Modulates Its Oncogenic Activity and Regulates mTORC1", Cell Reports, 3: 1-13, Jan. 31, 2013.
Cohen-Eliav et al. "The Splicing Factor SRSF6 Is Amplified and Is an Oncoprotein in Lung and Colon Cancers", Journal of Pathology, XP055072597, 229(4): 630-639, Mar. 15, 2013.
Ghigna et al. "Altered Expression of Heterogeneous Nuclear Ribonucleoproteins and SR Factors in Human Colon Adenocarcinomas", Cancer Research, XP001182387, 58(24): 5818-5824, Dec. 15, 1998. p. 5819, 1-h Col., Para 2—p. 520, 1-h Col., Fig.4.
Karni et al. "The Gene Encoding the Splicing Factor SF2/ASF Is a Proto-Oncogene", Nature Structural & Molecular Biology, XP055072595, 14(3): 185193, Mar. 2007. Figs.1, 3, 5.
Martinez et al. "Transcriptional and Proteomic Profiling of the Intestinal Mucosa of Diarrhea—IBS Patients Reveals Enhanced Active Cellular Pathways Compared to Healthy Subjects", Geastroenterology, AGA Abstracts, XP026111245, 136(5): A-155, # 1000, May 1, 2009.
Piekielko-Witkowska et al. "Disturbed Expression of Splicing Factors in Renal Cancer Affects Alternative Splicing of Apoptosis Regulators, Oncogenes, and Tumor Suppressors", PLoS One, XP055072990, 5(10): e13690-1-e13690-12, Oct. 27, 2010. Figs.1, 2.

(Continued)

*Primary Examiner* — Kimberly Chong

(57) ABSTRACT

A method of determining a treatment for an inflammatory disorder in a subject, is disclosed. The method comprises determining an amount of SRSF6 in a sample from the subject, wherein an amount of the SRSF6 is indicative of the treatment. Methods of diagnosing inflammatory disorders and treating same are also disclosed.

7 Claims, 73 Drawing Sheets

(56) References Cited

OTHER PUBLICATIONS

Stickeler et al. “Stage-Specific Changes in SR Splicing Factors and Alternative Splicing in Mammary Tumorigenesis”, Oncogene, XP05507288, 18(24): 3574-3582, Jun. 1, 1999. Fig.2.
Younis et al. “Rapid-Response Splicing Reporter Screens Identify Differential Regulators of Constitutive and Alternative Splicing”, Molecular and Cellular Biology, XP055073212, 30(7): 1718-1728, Apr. 1, 2010. p. 1726, r-h Col., Fig.6.

* cited by examiner

Mnk2a/Mnk2b
0
10
20
30
40
50
60
*
(N)
(T)

MCF-10A
HMLE
HMT-3522-S1
HMEC
MCF-7
MDA-MB-231
MDA-MB-468
SUM-149
SUM-159
Mnk2a
Mnk2b
GAPDH

HMLE
MCF-10A
BT-1
BT-10
BT-28
BT-37
BT-201
BT-209
BT-212 pBABE
Mnk2a
Mnk2b
Mnk2aKD
T7-Mnk2a
T7-Mnk2b
β- catenin pBABE
Mnk2a
Mnk2b
Mnk2aKD
MCF-10A
T7-Mnk2a
T7-Mnk2b
Ras
β- catenin
MCF-10A + Ras Colonies / well
pBABE
Mnk2a
Mnk2b
Mnk2aKD Colonies / well
pBABE
Mnk2a
Mnk2b
Mnk2aKD Colonies / well
Mnk1/2 WT
Mnk1-/-
Mnk2-/- pBABE 6/6
Mnk2a 0/8
Mnk2b 6/6
Tumor volume (mm3)
Days after injection

MLP 8/8
Sh2a-2 8/8
Tumor volume (mm3)
Days after injection

% Cell death
pBABE
Mnk2a
Mnk2b
Mnk2aKD

MLP
sh2a-1
sh2a-2

Colonies/well
pBABE
Mnk2a
Mnk2b
Mnk2aKD

β-catenin
Caspase-3
p-p-38α
p-38α
p-eIF4E
eIF4E
pBABE
Mnk2a
Mnk2b
Mnk2aKD

MLP
sh2a-1
sh2a-2 pBABE
MnK2a
MnK2b
Mnk2akD

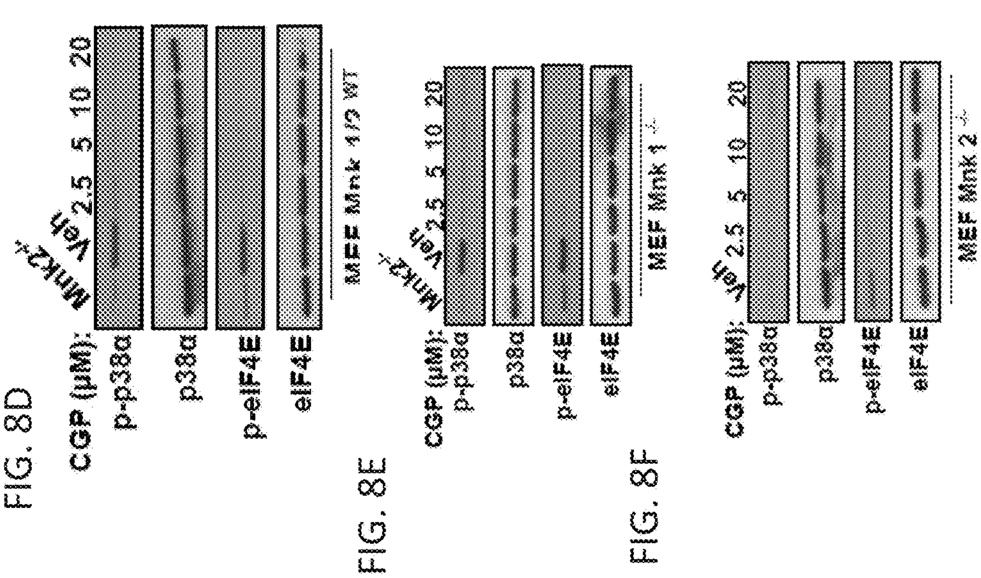
FIG. 8D
FIG. 8E
FIG. 8F
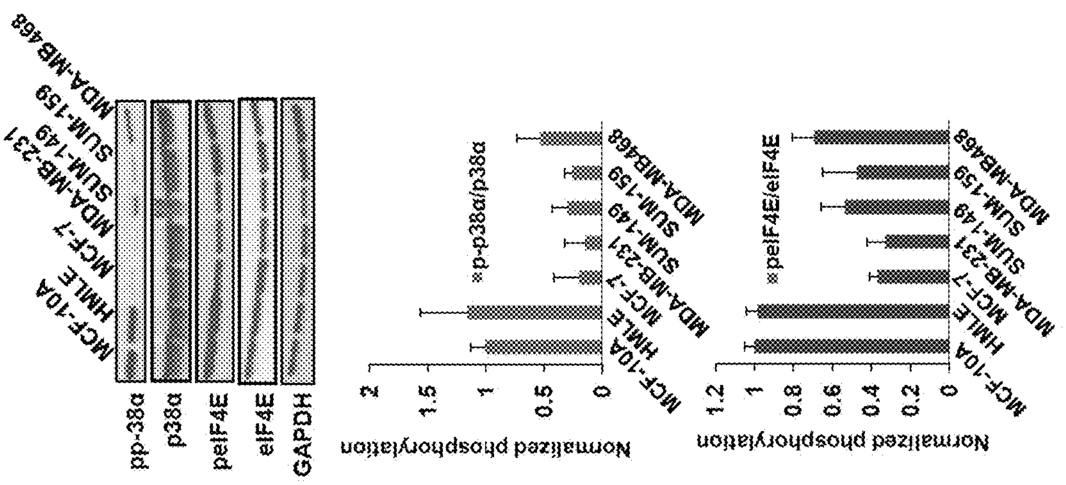
FIG. 8A
FIG. 8B
FIG. 8C

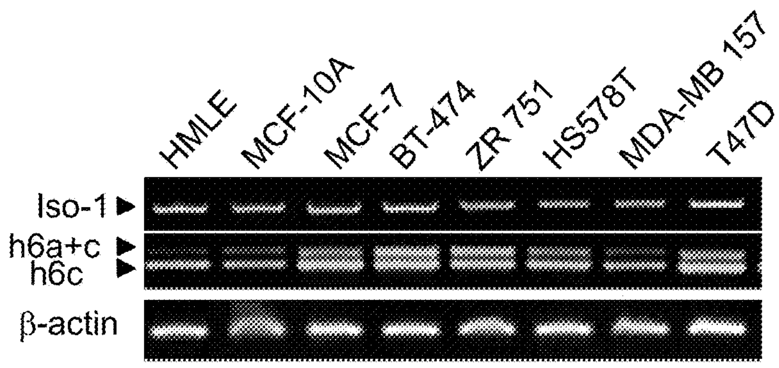

FIG. 18A

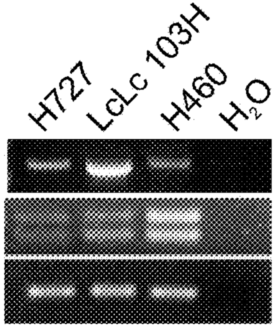

FIG. 18B

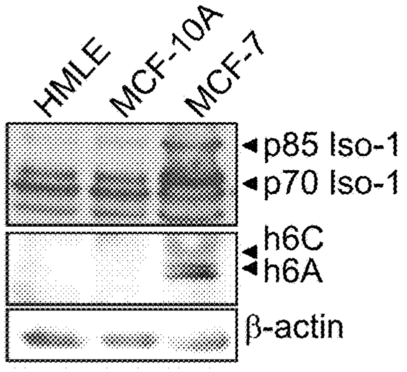

FIG. 18C

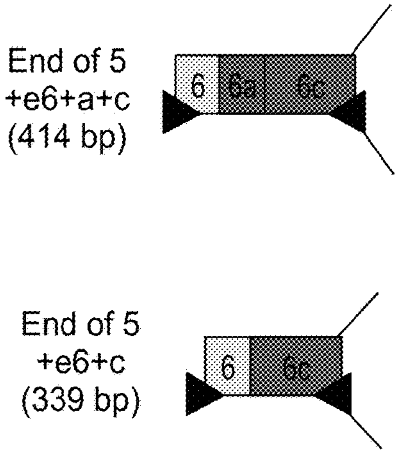

CTCTACCTCATCCTTGAGTATCTCAGTGGAGGAGAACTATTTATGCAGTTAGAAAGAGAGGGAATA
TTTATGGAAGACACTGCCTGGCTTGAGTGGAACGCTCTTCACACCAGTTGTTCCTAACAGAACCAT
TCTCATTGCGGCTTTCTTTCCTTGAATTGGCCTTTTCTAACAAAGAAGCTGCATTTAAGAGCCTTA
GGGATGAAGTGCCCTTTTTTGGAGGAGGCTCACTGAGCCGTGTTGGAGGCTGTGTTTGTGGTCGTG
CTGGCTGTGAAACTGCCTCAGTCCTCTAGGACACACCCTCTCCATCCTGGAGTAATCTGCAGGATT
GCAACATTGTTATGCAGCCAGTATTGCAGTGCCTTGTGCTTTTCGAATCCAGACAGGGTTGATTCA
GCCCTTTATTCTTTTGAG

CTCTACCTCATCCTTGAGTATCTCAGTGGAGGAGAACTATTTATGCAGTTAGAAAGAGAGGGAATA
TTTATGGAAGACACTGCCTGGCCTTTTCTAACAAAGAAGCTGCATTTAAGAGCCTTAGGGATGAAG
TGCCCTTTTTTGGAGGAGGCTCACTGAGCCGTGTTGGAGGCTGTGTTTGTGGTCGTGCTGGCTGTG
AAACTGCCTCAGTCCTCTAGGACACACCCTCTCCATCCTGGAGTAATCTGCAGGATTGCAACATTG
TTATGCAGCCAGTATTGCAGTGCCTTGTGCTTTTCGAATCCAGACAGGGTTGATTCAGCCCTTTAT
TCTTTTGAG

FIG. 18D

FIG. 18E gtaagtgaacttttgtggttgcatagattcaggtaattacaagcaaagccccattcccactatgggcagccacatgattcagtaaattg
agctggagccagtcactcactcaggacctcaagggggagaagcagttttgggactgggcagctatggaggtcacatcattcctttgccct
taggcttgagtggaacgctcttcacaccagttgttcc[redacted]cagaaccattctcattgcggctttctttccttgaattggtaagctgcctg
ccttggctgtgggtgagtgtggtttcccagtgaacctttatgtgtggaacaatggaaattatcagaaatcatcccttttttttaggctt
tctatttctcaaggtacagtcttagggaggtgataaacctgggcatatcatctgtagattgattatgtagtcagggtgggatttaccctc
ctatttctaaacatgtcatctgcttcaaattaaaaatatgcacatcctttgtgaagcaacaatattgggtcac[redacted]tcagtttatc
ctacacattaatttaatagaaaacaacacttaaatgtttttttctaccttgattaccaaaactgcattccattgtttaatttcaggcctc
ttctaacaaagaagctgcatttaagagccttagggatgaagtgcccttttttggaggaggctcac[redacted]gccgtgttggaggctgtgtttg
tggtcgtgctggctgtgaaactgcctcagtcctctaggacacaccctctccatcctggagtaatctgcaggattgcaacattgttatgca
gccagtattgcagtgccttgtgctttcgaatccagacagggttgattcagcccttattctttgaggtagataaatttgggtgtcaca
cagtttatagttgtgggctggctggcaggtggagggcagatactgtgggcctcagctgtctataaatatgtagctgtattaagtaaggg
atgagtgggcttctaagggtcaggttataagatacctttgaaatcaagatgtgatctctgag[redacted]caaagttcctatttcctatggg
attttaaagttgggtgtggatgggagaaatttgcttgaaatgaatggctattagcttaattcctacacagacagaacaaaacatgaccaa
tggcagtttagcatattctggacatctttgcaattttagcaatatattctaatggcaa[redacted]gcactttatagtttcactaaaatgag
tgaaacataaatgtccccatgccttttggcagcatcctatgccatctcttttccaatacatcccctaccccactaatttggtctttgg
tgcatgtctgtttctttcaaggaattttgctccatacgtaaactgctttggatagattacactctttttaattttattaaatcactttg
tttccag p-mTOR
mTOR
S6K1
non specific
S6K2
p-4E-BP1
4E-BP1
β-catenin
β-actin
WT
DKO Colonies/well
1500
1000
500
0
WT
DKO normalized luciferase activity
6
5
4
3
2
1
0
WT
DKO
Cap
IRES Mcl-1
β-catenin
WT
DKO normalized luciferase activity
1.2
1
0.8
0.6
0.4
0.2
0
DKO pB(-)
DKO Iso-1
Cap
IRES
*

DKO pB(-)
DKO Iso-1

MLP(-)
SRSF6-Sh1
SRSF6-Sh2
SRSF6
β catenin
NCI-H460 cells

Colonies /well
3500
3000
2500
2000
1500
1000
500
0
MLP(-)
SRSF6 Sh1
SRSF6 Sh2

MLP(-)
SRSF6 Sh1
SRSF6 Sh2

MLP(-)
Sh1
Sh2
Tumor volume (mm3)
500
450
400
350
300
250
200
150
100
50
0
11
12
16
22
24
Days after injection

SEQUENCE LISTING

```
<160> NUMBER OF SEQ ID NOS: 171

<210> SEQ ID NO 1
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 1

caggagtacg ccgtcgcgat cattgagaag cag                                33


<210> SEQ ID NO 2
<211> LENGTH: 33
<212> TYPE: DNA
<213> ORGANISM: Artificial sequence
<220> FEATURE:
<223> OTHER INFORMATION: Single strand DNA oligonucleotide

<400> SEQUENCE: 2

ctgcttctca atgatcgcga cggcgtactc ctg                                33


<210> SEQ ID NO 3
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 3

tgcgacctgt ggagcagtgg cgtcatcagt tatatcctac tcagcg                  46


<210> SEQ ID NO 4
<211> LENGTH: 46
<212> TYPE: DNA
<213> ORGANISM: Artificial sequence
<220> FEATURE:
<223> OTHER INFORMATION: Single strand DNA oligonucleotide

<400> SEQUENCE: 4

cgctgagtag gatataactg atgacgccac tgctccacag gtcgca                  46


<210> SEQ ID NO 5
<211> LENGTH: 56
<212> TYPE: DNA
<213> ORGANISM: Artificial sequence
<220> FEATURE:
<223> OTHER INFORMATION: Single strand DNA oligonucleotide
```

<400> SEQUENCE: 5
gacgccaaga agaggggcaa gaaggcggcg gccggccggg ccaccgacag cttctc 56

<210> SEQ ID NO 6
<211> LENGTH: 56
<212> TYPE: DNA
<213> ORGANISM: Artificial sequence
<220> FEATURE:
<223> OTHER INFORMATION: Single strand DNA oligonucleotide

<400> SEQUENCE: 6
gagaagctgt cggtggcccg gccggccgcc gccttcttgc ccctcttctt ggcgtc 56

<210> SEQ ID NO 7
<211> LENGTH: 21
<212> TYPE: DNA
<213> ORGANISM: Artificial sequence
<220> FEATURE:
<223> OTHER INFORMATION: Mnk2a shRNA target sequence

<400> SEQUENCE: 7
cagtgattcc atgtttcgta a 21

<210> SEQ ID NO 8
<211> LENGTH: 21
<212> TYPE: DNA
<213> ORGANISM: Artificial sequence
<220> FEATURE:
<223> OTHER INFORMATION: Mnk2a shRNA target sequence

<400> SEQUENCE: 8
caggtttgaa gacgtctacc a 21

<210> SEQ ID NO 9
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 9
ccaagtcctg cagcacccct g 21

<210> SEQ ID NO 10
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 10
gatgggaggg tcaggcgtgg tc 22

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
gaggaggaag tgactgtccc ac 22

<210> SEQ ID NO 12
<211> LENGTH: 21

-continued

<212> TYPE: DNA
<213> ORGANISM: Artificial sequence
<220> FEATURE:
<223> OTHER INFORMATION: Single strand DNA oligonucleotide

<400> SEQUENCE: 12
atcaagaagg tggtgaagca g 21

<210> SEQ ID NO 13
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 13
cttactcctt ggaggccatg t 21

<210> SEQ ID NO 14
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 14
tacaagcagt ggcaaaggc 19

<210> SEQ ID NO 15
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 15
cagtattgag gagaacagat ggg 23

<210> SEQ ID NO 16
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 16
ggctttccca aacttcgacc 20

<210> SEQ ID NO 17
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 17
ggcggctaca caaagccaaa c 21

<210> SEQ ID NO 18
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 18

-continued aatcaacggc acagttcaag gc 22

<210> SEQ ID NO 19
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 19
ggatgcaggg atgatgttct gg 22

<210> SEQ ID NO 20
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 20
tcattcacca ggcaaattgc 20

<210> SEQ ID NO 21
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 21
tcttcaaatg attcataggg 20

<210> SEQ ID NO 22
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 22
gctcgcctgt caacgcgcag 20

<210> SEQ ID NO 23
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 23
tgaggggctc tggtctgcga 20

<210> SEQ ID NO 24
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 24
aggaggattg aggaggatca g 21

<210> SEQ ID NO 25
<211> LENGTH: 20
<212> TYPE: DNA
<213> ORGANISM: Artificial sequence -continued
<220> FEATURE:
<223> OTHER INFORMATION: Single strand DNA oligonucleotide

<400> SEQUENCE: 25
cgctccatga atcctggtaa 20

<210> SEQ ID NO 26
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 26
ccgaggtgta tgtatgagtg t 21

<210> SEQ ID NO 27
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 27
ctgtgtttgg agtgggtttc 20

<210> SEQ ID NO 28
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 28
gaacagttat ctccagaa 18

<210> SEQ ID NO 29
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 29
ttctcatctt ctagttgg 18

<210> SEQ ID NO 30
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 30
gagttcgagg acccgcgaga cg 22

<210> SEQ ID NO 31
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 31
gagctccgcc acctccac 18

<210> SEQ ID NO 32
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 32
tccgtgacgc caagcag 17

<210> SEQ ID NO 33
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 33
ggtctttggc acagctg 17

<210> SEQ ID NO 34
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 34
gaggaagtga ctgtcccac 19

<210> SEQ ID NO 35
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 35
cccagcacaa tgaagatcaa 20

<210> SEQ ID NO 36
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 36
tagaagcatt tgcggtggac 20

<210> SEQ ID NO 37
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 37
tatatcttcc cagact 16

<210> SEQ ID NO 38
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 38
ctcagaggga tgccagtaat cta 23

<210> SEQ ID NO 39
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 39
tgacactggc aaaacaatgc a 21

<210> SEQ ID NO 40
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 40
ggtccttttc accagcaagc t 21

<210> SEQ ID NO 41
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 41
gaccattgag gacctgagga 20

<210> SEQ ID NO 42
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 42
catacttggt gcggaagtca 20

<210> SEQ ID NO 43
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 43
tcaccaccat ggagaaggc 19

<210> SEQ ID NO 44
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 44
gctaagcagt tggtggtgca 20

<210> SEQ ID NO 45

<211> LENGTH: 9
<212> TYPE: PRT
<213> ORGANISM: Artificial sequence
<220> FEATURE:
<223> OTHER INFORMATION: Mnk2a putative nuclear localization signal

<400> SEQUENCE: 45

Lys Lys Arg Gly Lys Lys Lys Lys Arg
1               5

<210> SEQ ID NO 46
<211> LENGTH: 9
<212> TYPE: PRT
<213> ORGANISM: Artificial sequence
<220> FEATURE:
<223> OTHER INFORMATION: Mnk2a putative nuclear localization signal
      mutated (KKR to AAA)

<400> SEQUENCE: 46

Lys Lys Arg Gly Lys Lys Ala Ala Ala
1               5

<210> SEQ ID NO 47
<211> LENGTH: 67
<212> TYPE: DNA
<213> ORGANISM: Artificial sequence
<220> FEATURE:
<223> OTHER INFORMATION: Single strand DNA oligonucleotide

<400> SEQUENCE: 47
ggggaaggat ccatggcatc gatgacaggt ggccaacaga tgggtatgag gcgacgaagg     60
aggcggg                                                               67

<210> SEQ ID NO 48
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 48
ggggaactta agcaattcaa ggaaagaaag ccgc                                 34

<210> SEQ ID NO 49
<211> LENGTH: 36
<212> TYPE: DNA
<213> ORGANISM: Artificial sequence
<220> FEATURE:
<223> OTHER INFORMATION: Single strand DNA oligonucleotide

<400> SEQUENCE: 49
ggggaactta agctcaaaag aataaagggc tgaatc                               36

<210> SEQ ID NO 50
<211> LENGTH: 34
<212> TYPE: DNA
<213> ORGANISM: Artificial sequence
<220> FEATURE:
<223> OTHER INFORMATION: Single strand DNA oligonucleotide

<400> SEQUENCE: 50
ggggaactta agtcatagat tcatacgcag gtgc                                 34

<210> SEQ ID NO 51
<211> LENGTH: 28
<212> TYPE: DNA

<213> ORGANISM: Artificial sequence
<220> FEATURE:
<223> OTHER INFORMATION: Single strand DNA oligonucleotide

<400> SEQUENCE: 51
ctctacctca tccttgagta tctcagtg 28

<210> SEQ ID NO 52
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 52
ctcaaaagaa taaagggctg aatc 24

<210> SEQ ID NO 53
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 53
catagattca tacgcaggtg c 21

<210> SEQ ID NO 54
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 54
atcaagaagg tggtgaagca g 21

<210> SEQ ID NO 55
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 55
cttactcctt ggaggccatg t 21

<210> SEQ ID NO 56
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 56
cgtggacatc cgcaaag 17

<210> SEQ ID NO 57
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 57
ggaaggtgga cagcgag 17

<210> SEQ ID NO 58
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 58
atatttgcca tggcggtgct taaaaaggca 30

<210> SEQ ID NO 59
<211> LENGTH: 30
<212> TYPE: DNA
<213> ORGANISM: Artificial sequence
<220> FEATURE:
<223> OTHER INFORMATION: Single strand DNA oligonucleotide

<400> SEQUENCE: 59
tgccttttta agcaccgcca tggcaaatat 30

<210> SEQ ID NO 60
<211> LENGTH: 97
<212> TYPE: DNA
<213> ORGANISM: Artificial sequence
<220> FEATURE:
<223> OTHER INFORMATION: S6K1 Iso-1 sh1 forward ShRNA oligonucleotide

<400> SEQUENCE: 60
tgctgttgac agtgagcgcg gcatggaaca ttgtgagaaa tagtgaagcc acagatgtat 60
ttctcacaat gttccatgcc atgcctactg cctcgga 97

<210> SEQ ID NO 61
<211> LENGTH: 97
<212> TYPE: DNA
<213> ORGANISM: Artificial sequence
<220> FEATURE:
<223> OTHER INFORMATION: S6K1 Iso-1 sh2 forward ShRNA oligonucleotide

<400> SEQUENCE: 61
tgctgttgac agtgagcgct ggaacattgt gagaaatttg tagtgaagcc acagatgtac 60
aaatttctca caatgttcca ttgcctactg cctcgga 97

<210> SEQ ID NO 62
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 62
gggcatttac atcaaaaggg 20

<210> SEQ ID NO 63
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 63
ccaaagtctg ttagtttcac atgac 25

<210> SEQ ID NO 64

<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 64
cctttcagac tggtggaaaa ctctacc 27

<210> SEQ ID NO 65
<211> LENGTH: 27
<212> TYPE: DNA
<213> ORGANISM: Artificial sequence
<220> FEATURE:
<223> OTHER INFORMATION: Single strand DNA oligonucleotide

<400> SEQUENCE: 65
gcttctttgt tagaaaaggc caggcag 27

<210> SEQ ID NO 66
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 66
gaatatttat ggaagacact gcctg 25

<210> SEQ ID NO 67
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 67
gttagaaaag gccaattcaa ggaaag 26

<210> SEQ ID NO 68
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 68
ggcacccagc acaatgaaga 20

<210> SEQ ID NO 69
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 69
aggatggagc cgccgatc 18

<210> SEQ ID NO 70
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 70
cctccagatg gctcccctgc 20

<210> SEQ ID NO 71
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 71
cccgggggca ggtccaagcg 20

<210> SEQ ID NO 72
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 72
aagcccagaa ggtgttcgag 20

<210> SEQ ID NO 73
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 73
tggctgagat ggggactt 18

<210> SEQ ID NO 74
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 74
agatcctgaa ggagctggag gag 23

<210> SEQ ID NO 75
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 75
ggtcgaggaa gtgttgggga a 21

<210> SEQ ID NO 76
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 76
gaggagacgt tggggaaatc tg 22

<210> SEQ ID NO 77
<211> LENGTH: 21
<212> TYPE: DNA

<213> ORGANISM: Artificial sequence
<220> FEATURE:
<223> OTHER INFORMATION: Single strand DNA oligonucleotide

<400> SEQUENCE: 77
ccaagtcctg cagcacccct g 21

<210> SEQ ID NO 78
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 78
gatgggaggg tcaggcgtgg tc 22

<210> SEQ ID NO 79
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 79
gaggaggaag tgactgtccc ac 22

<210> SEQ ID NO 80
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 80
gtacggcttc gtggagttcg agg 23

<210> SEQ ID NO 81
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 81
ggcaaaaggc tgctgtcgtc atgg 24

<210> SEQ ID NO 82
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 82
ctggatctgc ttccagagta agat 24

<210> SEQ ID NO 83
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 83
cgatccccta aagaaaatgg aa 22

<210> SEQ ID NO 84
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 84
ggcctttgag ggtggaaca 19

<210> SEQ ID NO 85
<211> LENGTH: 26
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 3' TAMRA conjugated

<400> SEQUENCE: 85
atcaaggagc cagtcccgtt ccaatt 26

<210> SEQ ID NO 86
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 86
atgaacatgc cgtagtgcct tt 22

<210> SEQ ID NO 87
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 87
ggtgaacaat cgggaggaa 19

<210> SEQ ID NO 88
<211> LENGTH: 28
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 3' TAMRA conjugated

<400> SEQUENCE: 88
tggccagttt gagtcctgcc tactttga 28

<210> SEQ ID NO 89
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 89
gcaaagacct gtacgccaac a 21

<210> SEQ ID NO 90
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 90
tgcatcctgt cggcaatg 18

<210> SEQ ID NO 91
<211> LENGTH: 20
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<223> OTHER INFORMATION: 3' TAMRA conjugated

<400> SEQUENCE: 91
tggcggcacc accatgtacc 20

<210> SEQ ID NO 92
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 92
ccaactctct aaccttggaa ctgtg 25

<210> SEQ ID NO 93
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 93
cttccagccc atctgttatg ttg 23

<210> SEQ ID NO 94
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 94
gaaatctgtc tacattgaac tag 23

<210> SEQ ID NO 95
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 95
cctttcagtt gcatgattct c 21

<210> SEQ ID NO 96
<211> LENGTH: 17
<212> TYPE: DNA

<213> ORGANISM: Artificial sequence
<220> FEATURE:
<223> OTHER INFORMATION: Single strand DNA oligonucleotide

<400> SEQUENCE: 96
ggacggacgc cgatgcc 17

<210> SEQ ID NO 97
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 97
ggtccatggt gctgctcagc 20

<210> SEQ ID NO 98
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 98
aggggacgca gcgaaaccgg g 21

<210> SEQ ID NO 99
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 99
ggaaccagac agcacctact tc 22

<210> SEQ ID NO 100
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 100
cgtccaggtg gctgacttgg c 21

<210> SEQ ID NO 101
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 101
gcatccaggc gaggaggcaa cg 22

<210> SEQ ID NO 102
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 102
gcactgctga gcaaattgaa ctggg 25

<210> SEQ ID NO 103
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 103
aggtacagtc ctctgctcag g 21

<210> SEQ ID NO 104
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 104
gactacttca gccttatgga ctg 23

<210> SEQ ID NO 105
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 105
atgtgtgaat gacaactact gg 22

<210> SEQ ID NO 106
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 106
tgatgtattc atctcttaat gcc 23

<210> SEQ ID NO 107
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 107
ctttacctct ccacaggcac c 21

<210> SEQ ID NO 108
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 108
aagagccacc tggcagcaaa gg 22

<210> SEQ ID NO 109
<211> LENGTH: 22
<212> TYPE: DNA
<213> ORGANISM: Artificial sequence
<220> FEATURE:

<223> OTHER INFORMATION: Single strand DNA oligonucleotide

<400> SEQUENCE: 109
catggcagca ttatgttcct cc 22

<210> SEQ ID NO 110
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 110
ggcctcaaca atcgcatccg 20

<210> SEQ ID NO 111
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 111
ccaacatcca tccactgcag g 21

<210> SEQ ID NO 112
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 112
gagtcctccc tcctgaacct g 21

<210> SEQ ID NO 113
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 113
gcaggcaggg tgtacagctt gg 22

<210> SEQ ID NO 114
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 114
ccacacatgc agctaccccg 20

<210> SEQ ID NO 115
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 115
cacagtctgg tctctatgaa atgg 24

-continued

<210> SEQ ID NO 116
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 116
ggaagtcttc tgaccaactg gc 22

<210> SEQ ID NO 117
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 117
gcagcatgtt tctggtgcag ggg 23

<210> SEQ ID NO 118
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 118
cgccaggagc cggacccgcg c 21

<210> SEQ ID NO 119
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 119
gccagggggg cacaggcag 19

<210> SEQ ID NO 120
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 120
caatttggac atctccaaca ag 22

<210> SEQ ID NO 121
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 121
ctggatgtcg atggccttgg tg 22

<210> SEQ ID NO 122
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 122
cacgggacac ctccattact c 21

<210> SEQ ID NO 123
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 123
cttgtcctgg atattgggat ttg 23

<210> SEQ ID NO 124
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 124
tctggagaga tggccctcca cg 22

<210> SEQ ID NO 125
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 125
ggcagaggct gtcaggaggg g 21

<210> SEQ ID NO 126
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 126
aacttcgacg gcgagccgca g 21

<210> SEQ ID NO 127
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 127
ctgtgtcagc cgctccaggt c 21

<210> SEQ ID NO 128
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 128
ccctaatgtg tccagcagcc a 21

<210> SEQ ID NO 129
<211> LENGTH: 22

```
<212> TYPE: DNA
<213> ORGANISM: Artificial sequence
<220> FEATURE:
<223> OTHER INFORMATION: Single strand DNA oligonucleotide

<400> SEQUENCE: 129

cctctccagg cggggtggcc tc                                              22


<210> SEQ ID NO 130
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 130

atgagcccat ccagccaatt g                                               21


<210> SEQ ID NO 131
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 131

agctctcaca gccaccactg ag                                              22


<210> SEQ ID NO 132
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 132

ccagtggcgc cggggaggca g                                               21


<210> SEQ ID NO 133
<211> LENGTH: 23
<212> TYPE: DNA
<213> ORGANISM: Artificial sequence
<220> FEATURE:
<223> OTHER INFORMATION: Single strand DNA oligonucleotide

<400> SEQUENCE: 133

gaagaagttt gggaggccag gcc                                             23


<210> SEQ ID NO 134
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 134

tctgtgccca aatcaacaag                                                 20


<210> SEQ ID NO 135
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 135
```

gccaccagct aaaaacattc c 21

<210> SEQ ID NO 136
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 136
agaccagtgg acattggttc 20

<210> SEQ ID NO 137
<211> LENGTH: 19
<212> TYPE: DNA
<213> ORGANISM: Artificial sequence
<220> FEATURE:
<223> OTHER INFORMATION: Single strand DNA oligonucleotide

<400> SEQUENCE: 137
ggtccctcca ggaaacaaa 19

<210> SEQ ID NO 138
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 138
atcaagaagg tggtgaagca g 21

<210> SEQ ID NO 139
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 139
cttactcctt ggaggccatg t 21

<210> SEQ ID NO 140
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 140
cgtggacatc cgcaaag 17

<210> SEQ ID NO 141
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 141
ggaaggtgga cagcgag 17

<210> SEQ ID NO 142
<211> LENGTH: 29
<212> TYPE: DNA
<213> ORGANISM: Artificial sequence
<220> FEATURE:
<223> OTHER INFORMATION: SRSF6 shRNA target sequence

<400> SEQUENCE: 142
ttataaagct tgagttatgt aagatttaa 29

<210> SEQ ID NO 143
<211> LENGTH: 100
<212> TYPE: DNA
<213> ORGANISM: Artificial sequence
<220> FEATURE:
<223> OTHER INFORMATION: Single strand DNA oligonucleotide

<400> SEQUENCE: 143
gaattcaaaa attaaatctt acataactca agctttataa ccaattataa agcttgagtt 60
atgtaagatt taagtcgacg gtgtttcgtc ctttccacaa 100

<210> SEQ ID NO 144
<211> LENGTH: 29
<212> TYPE: DNA
<213> ORGANISM: Artificial sequence
<220> FEATURE:
<223> OTHER INFORMATION: SRSF6 shRNA target sequence

<400> SEQUENCE: 144
tgttaatagg acatcatatg gtaatagac 29

<210> SEQ ID NO 145
<211> LENGTH: 100
<212> TYPE: DNA
<213> ORGANISM: Artificial sequence
<220> FEATURE:
<223> OTHER INFORMATION: Single strand DNA oligonucleotide

<400> SEQUENCE: 145
gaattcaaaa agtctattac catatgatgt cctattaaca ccaatgttaa taggacatca 60
tatggtaata gacgtcgacg gtgtttcgtc ctttccacaa 100

<210> SEQ ID NO 146
<211> LENGTH: 465
<212> TYPE: PRT
<213> ORGANISM: Homo sapiens

<400> SEQUENCE: 146

Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
            20                  25                  30

His Gly Asp Ser Asp Phe Gly Leu Gln Cys Ser Ala Arg Pro Asp Met
        35                  40                  45

Pro Ala Ser Gln Pro Ile Asp Ile Pro Asp Ala Lys Lys Arg Gly Lys
    50                  55                  60

Lys Lys Lys Arg Gly Arg Ala Thr Asp Ser Phe Ser Gly Arg Phe Glu
65                  70                  75                  80

Asp Val Tyr Gln Leu Gln Glu Asp Val Leu Gly Glu Gly Ala His Ala
                85                  90                  95

Arg Val Gln Thr Cys Ile Asn Leu Ile Thr Ser Gln Glu Tyr Ala Val
            100                 105                 110

Lys Ile Ile Glu Lys Gln Pro Gly His Ile Arg Ser Arg Val Phe Arg
        115                 120                 125

-continued

```
Glu Val Glu Met Leu Tyr Gln Cys Gln Gly His Arg Asn Val Leu Glu
    130                 135                 140

Leu Ile Glu Phe Phe Glu Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Glu Ala Ser Ile Tyr
            260                 265                 270

Asp Lys Arg Cys Asp Leu Trp Ser Leu Gly Val Ile Leu Tyr Ile Leu
        275                 280                 285

Leu Ser Gly Tyr Pro Pro Phe Val Gly Arg Cys Gly Ser Asp Cys Gly
    290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Phe Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

Gln Gly Cys Ala Pro Glu Asn Thr Leu Pro Thr Pro Met Val Leu Gln
    370                 375                 380

Arg Asn Ser Cys Ala Lys Asp Leu Thr Ser Phe Ala Ala Glu Ala Ile
385                 390                 395                 400

Ala Met Asn Arg Gln Leu Ala Gln His Asp Glu Asp Leu Ala Glu Glu
                405                 410                 415

Glu Ala Ala Gly Gln Gly Gln Pro Val Leu Val Arg Ala Thr Ser Arg
            420                 425                 430

Cys Leu Gln Leu Ser Pro Pro Ser Gln Ser Lys Leu Ala Gln Arg Arg
        435                 440                 445

Gln Arg Ala Ser Leu Ser Ser Ala Pro Val Val Leu Val Gly Asp His
    450                 455                 460

Ala
465


<210> SEQ ID NO 147
<211> LENGTH: 414
<212> TYPE: PRT
<213> ORGANISM: Homo sapiens

<400> SEQUENCE: 147

Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
            20                  25                  30
```

```
His Gly Asp Ser Asp Phe Gly Leu Gln Cys Ser Ala Arg Pro Asp Met
        35                  40                  45

Pro Ala Ser Gln Pro Ile Asp Ile Pro Asp Ala Lys Lys Arg Gly Lys
    50                  55                  60

Lys Lys Lys Arg Gly Arg Ala Thr Asp Ser Phe Ser Gly Arg Phe Glu
65                  70                  75                  80

Asp Val Tyr Gln Leu Gln Glu Asp Val Leu Gly Glu Gly Ala His Ala
                85                  90                  95

Arg Val Gln Thr Cys Ile Asn Leu Ile Thr Ser Gln Glu Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
    130                 135                 140

Leu Ile Glu Phe Phe Glu Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Glu Ala Ser Ile Tyr
            260                 265                 270

Asp Lys Arg Cys Asp Leu Trp Ser Leu Gly Val Ile Leu Tyr Ile Leu
        275                 280                 285

Leu Ser Gly Tyr Pro Pro Phe Val Gly Arg Cys Gly Ser Asp Cys Gly
    290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Phe Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

Gln Gly Cys Ala Pro Glu Asn Thr Leu Pro Thr Pro Met Val Leu Gln
    370                 375                 380

Arg Trp Asp Ser His Phe Leu Leu Pro Pro His Pro Cys Arg Ile His
385                 390                 395                 400

Val Arg Pro Gly Gly Leu Val Arg Thr Val Thr Val Asn Glu
                405                 410
```

<210> SEQ ID NO 148
<211> LENGTH: 3576
<212> TYPE: DNA
<213> ORGANISM: Homo sapiens

<400> SEQUENCE: 148

```
cggtcccctc cccgctggc ggggcccgga cagaagatgg tgcagaagaa accagccgaa      60
cttcagggtt tccaccgttc gttcaagggg cagaacccct tcgagctggc cttctcccta     120
gaccagcccg accacggaga ctctgacttt ggcctgcagt gctcagcccg ccctgacatg     180
cccgccagcc agcccattga catcccggac gccaagaaga ggggcaagaa gaagaagcgc     240
ggccgggcca ccgacagctt ctcgggcagg tttgaagacg tctaccagct gcaggaagat     300
gtgctggggg agggcgctca tgcccgagtg cagacctgca tcaacctgat caccagccag     360
gagtacgccg tcaagatcat tgagaagcag ccaggccaca ttcggagcag ggttttcagg     420
gaggtggaga tgctgtacca gtgccaggga cacaggaacg tcctagagct gattgagttc     480
ttcgaggagg aggaccgctt ctacctggtg tttgagaaga tgcggggagg ctccatcctg     540
agccacatcc acaagcgccg gcacttcaac gagctggagg ccagcgtggt ggtgcaggac     600
gtggccagcg ccttggactt tctgcataac aaaggcatcg cccacaggga cctaaagccg     660
gaaaacatcc tctgtgagca ccccaaccag gtctcccccg tgaagatctg tgacttcgac     720
ctgggcagcg gcatcaaact caacggggac tgctccccta tctccacccc ggagctgctc     780
actccgtgcg gctcggcgga gtacatggcc ccggaggtag tggaggcctt cagcgaggag     840
gctagcatct acgacaagcg ctgcgacctg tggagcctgg gcgtcatctt gtatatccta     900
ctcagcggct acccgccctt cgtgggccgc tgtggcagcg actgcggctg ggaccgcggc     960
gaggcctgcc ctgcctgcca gaacatgctg tttgagagca tccaggaggg caagtacgag    1020
ttccccgaca aggactgggc ccacatctcc tgcgctgcca aagacctcat ctccaagctg    1080
ctggtccgtg acgccaagca gaggctgagt gccgcccaag tcctgcagca cccctgggtt    1140
caggggtgcg ccccggagaa caccttgccc actcccatgg tcctgcagag gaacagctgt    1200
gccaaagacc tcacgtcctt cgcggctgag gccattgcca tgaaccggca gctggcccag    1260
cacgacgagg acctggctga ggaggaggcc gcggggcagg gccagcccgt cctggtccga    1320
gctacctcac gctgcctgca gctgtctcca ccctcccagt ccaagctggc gcagcggcgg    1380
caaagggcca gtctgtcctc ggccccagtg gtcctggtgg gagaccacgc ctgaccctcc    1440
catctcccct ctgtacatag gtcacccgtc cccaatcaa atctaaaggt tttttaagct    1500
atcgccagcc ggtgtccagc gggctgcccc tcctctgcct ggattcccag gcactaagct    1560
cagctgaggg gggtgtttta tagaaggttt ttgcttttgg gttttttttt tcctgtttcc    1620
acccctcccc gttatttttt cctttggatg gttaaaagca ttgcaggcac ccgggaaggt    1680
gagcagaggg taggtgggtg ggcttgtccc ctccccggtc ccccgccctg ctcacctcta    1740
ctatgaaggt gcccccaggt cacctgtgct gcccgccatc tgcccacgtg gcttgcagtg    1800
actcaggaga gcaggcccac agcgtttgcc atcttgcaga gctggggagg ggcacaggac    1860
cctgccctcg tgttccctcc cagcccgcag tatttcaggg acaggctctt cccctctatc    1920
cctcaccctg agagcacccc tggtggcttg gttggggaag ggaggggctg cctgtctctg    1980
gaggtgtcag gcaggcaggt ggcaggcagc tcacccaccc accccatggg atcccccagc    2040
ccttcacccg cgcctgcctt gtccccatga tagttgacaa tcggggcttc ctgcaaggcc    2100
cgtctgtctg tccaggactc ctggtggcca gattcggcct ccgaccttga ccttaaactg    2160
cagctgaccc caggggctcg ccgctgcccc tcccctccac accaaggcct gagacagcag    2220
gagccccgcc tggcccgaag ccgtttccac cgcagcaggc agaggggctg gacaggcact    2280
gtcagccaat gtggggggtc ctgaagacac ccccttgggg cacccgagtg ccccttctca    2340
```

-continued

```
gggctcagtc tgaccgtagc cacgtcctgc ctcgcgccgc ccctcgggcc tgacctggaa   2400

gctccgtcag ctccgtcctt gtccttagag ctgagcccag accccggggt ctggccgaat   2460

cctcaccccc agggcagtgt ttttggtctg ccaccttcag gaaaacggct gcggcctcgg   2520

cctcccttcg ggcacccagg aatgcggggg tctgctcagt ccccccaccc tccatgctcc   2580

aacccccggg ggctgcggag cctgctgccc cctccccgcg ggtggggacg ttctatgcaa   2640

tacagggttc cactttagaa gtgcgcgcgg ctagggtcac cgcccgccct tcccggcgca   2700

gcccccgagc tccacagctg gggcagcccc tctggcttct aaatccgcgg tcgggattct   2760

tcctcctgtt tagtttttta gtttttcctt aaaaaaaaac aacacatcga tggactttgc   2820

ttccctgttc ttgaagaata cttgaatgtc ggggggcctg gggggtgggg cctcggagac   2880

cgtctgcctg gccctgctgc ccctcctgaa tctcgtatga tggtcacagt ccggtggccg   2940

tgggggtgct ctgccttccc tggtccccac tgcccatatc tgtggactgc cccttccaaa   3000

gacccctggg gggggtgggg cattccgccc accccttcc cccatcactt ctcgcctgtc   3060

agtgattcca tgtttcgtaa cggggggattc tctgcctttt tgtatcaaag aacaagcaaa   3120

tggacccccg cccgctgcag gcgcccatag ccatcgggtc tctaaagctg agtggctagc   3180

agcgtttgtt tgtttgtttt tttttttttt tctgaaggtg ggacagtcac ttcctcctcc   3240

ctccccaccc ctgtcgcatc cacgtgcgac ctggaggact ggtcagaacc gttactgtga   3300

atgagtgaag atcctggagg accctgggcc ccaggccagc tcccatcgct gggggacggt   3360

gaacggccat gtgttaatgt tacgatgttt ttaaaagaca aaaaaaaaaa aaaaacctca   3420

aaagtttttt taaagtgggg gaaaaacatc caagcacttt aattccaatg taccaggtga   3480

actgacggag ctcagaagtt ttcctttaca ccaactgtca atgccggaat tttgtattct   3540

gttttgtaaa gatttaataa aagtcaaaaa acttgc                             3576
```

```
<210> SEQ ID NO 149
<211> LENGTH: 1398
<212> TYPE: DNA
<213> ORGANISM: Homo sapiens

<400> SEQUENCE: 149

atggtgcaga agaaaccagc cgaacttcag ggtttccacc gttcgttcaa ggggcagaac     60

cccttcgagc tggccttctc cctagaccag cccgaccacg gagactctga ctttggcctg    120

cagtgctcag cccgccctga catgcccgcc agccagccca ttgacatccc ggacgccaag    180

aagaggggca agaagaagaa gcgcggccgg gccaccgaca gcttctcggg caggtttgaa    240

gacgtctacc agctgcagga agatgtgctg gggagggcg ctcatgcccg agtgcagacc     300

tgcatcaacc tgatcaccag ccaggagtac gccgtcaaga tcattgagaa gcagccaggc    360

cacattcgga gcagggtttt cagggaggtg gagatgctgt accagtgcca gggacacagg    420

aacgtcctag agctgattga gttcttcgag gaggaggacc gcttctacct ggtgtttgag    480

aagatgcggg gaggctccat cctgagccac atccacaagc gccggcactt caacgagctg    540

gaggccagcg tggtggtgca ggacgtggcc agcgccttgg actttctgca taacaaaggc    600

atcgcccaca gggacctaaa gccggaaaac atcctctgtg agcaccccaa ccaggtctcc    660

cccgtgaaga tctgtgactt cgacctgggc agcggcatca aactcaacgg ggactgctcc    720

cctatctcca ccccggagct gctcactccg tgcggctcgg cggagtacat ggccccggag    780

gtagtggagg ccttcagcga ggaggctagc atctacgaca agcgctgcga cctgtggagc    840
```

ctgggcgtca tcttgtatat cctactcagc ggctacccgc ccttcgtggg ccgctgtggc 900
agcgactgcg gctgggaccg cggcgaggcc tgccctgcct gccagaacat gctgtttgag 960
agcatccagg agggcaagta cgagttcccc gacaaggact gggcccacat ctcctgcgct 1020
gccaaagacc tcatctccaa gctgctggtc cgtgacgcca agcagaggct gagtgccgcc 1080
caagtcctgc agcacccctg ggttcagggg tgcgccccgg agaacacctt gcccactccc 1140
atggtcctgc agaggaacag ctgtgccaaa gacctcacgt ccttcgcggc tgaggccatt 1200
gccatgaacc ggcagctggc ccagcacgac gaggacctgg ctgaggagga ggccgcgggg 1260
cagggccagc ccgtcctggt ccgagctacc tcacgctgcc tgcagctgtc tccaccctcc 1320
cagtccaagc tggcgcagcg gcggcaaagg gccagtctgt cctcggcccc agtggtcctg 1380
gtgggagacc acgcctga 1398

<210> SEQ ID NO 150
<211> LENGTH: 1738
<212> TYPE: DNA
<213> ORGANISM: Homo sapiens

<400> SEQUENCE: 150
ggcccaggta gaggggtccg cgctggcggc ggcggcggcg ctgttccccg cgcggtccgc 60
ggagcggggt ccgggctgcg cgacgtgggg cggcggcggc actgcggccc cggcccaagc 120
ccgaccccgg gtcccctcct cggccgcccc ccgcccggcc gcccgccctc gggcctcccc 180
ccgggccctc ggtcccctcc cccgctggcg gggcccggac agaagatggt gcagaagaaa 240
ccagccgaac ttcagggttt ccaccgttcg ttcaaggggc agaacccctt cgagctggcc 300
ttctccctag accagcccga ccacggagac tctgactttg gcctgcagtg ctcagcccgc 360
cctgacatgc ccgccagcca gcccattgac atcccggacg ccaagaagag gggcaagaag 420
aagaagcgcg gccgggccac cgacagcttc tcgggcaggt ttgaagacgt ctaccagctg 480
caggaagatg tgctggggga gggcgctcat gcccgagtgc agacctgcat caacctgatc 540
accagccagg agtacgccgt caagatcatt gagaagcagc caggccacat tcggagcagg 600
gttttcaggg aggtggagat gctgtaccag tgccagggac acaggaacgt cctagagctg 660
attgagttct tcgaggagga ggaccgcttc tacctggtgt ttgagaagat gcggggaggc 720
tccatcctga gccacatcca caagcgccgg cacttcaacg agctggaggc cagcgtggtg 780
gtgcaggacg tggccagcgc cttggacttt ctgcataaca aaggcatcgc ccacagggac 840
ctaaagccgg aaaacatcct ctgtgagcac cccaaccagg tctcccccgt gaagatctgt 900
gacttcgacc tgggcagcgg catcaaactc aacggggact gctcccctat ctccaccccg 960
gagctgctca ctccgtgcgg ctcggcggag tacatggccc cggaggtagt ggaggccttc 1020
agcgaggagg ctagcatcta cgacaagcgc tgcgacctgt ggagcctggg cgtcatcttg 1080
tatatcctac tcagcggcta cccgcccttc gtgggccgct gtggcagcga ctgcggctgg 1140
gaccgcggcg aggcctgccc tgcctgccag aacatgctgt ttgagagcat ccaggagggc 1200
aagtacgagt tccccgacaa ggactgggcc cacatctcct gcgctgccaa agacctcatc 1260
tccaagctgc tggtccgtga cgccaagcag aggctgagtg ccgcccaagt cctgcagcac 1320
ccctgggttc aggggtgcgc cccggagaac accttgccca ctcccatggt cctgcagagg 1380
tgggacagtc acttcctcct ccctccccac ccctgtcgca tccacgtgcg acctggagga 1440
ctggtcagaa ccgttactgt gaatgagtga agatcctgga ggaccctggg ccccaggcca 1500
gctcccatcg ctgggggacg gtgaacggcc atgtgttaat gttacgatgt ttttaaaaga 1560

```
caaaaaaaaa aaaaaaacct caaaagtttt tttaaagtgg gggaaaaaca tccaagcact   1620

ttaattccaa tgtaccaggt gaactgacgg agctcagaag ttttccttta caccaactgt   1680

caatgccgga attttgtatt ctgttttgta aagatttaat aaaagtcaaa aaacttgc     1738
```

<210> SEQ ID NO 151
<211> LENGTH: 1245
<212> TYPE: DNA
<213> ORGANISM: Homo sapiens

<400> SEQUENCE: 151

```
atggtgcaga agaaaccagc cgaacttcag ggtttccacc gttcgttcaa ggggcagaac     60

cccttcgagc tggccttctc cctagaccag cccgaccacg gagactctga ctttggcctg    120

cagtgctcag cccgccctga catgcccgcc agccagccca ttgacatccc ggacgccaag    180

aagaggggca agaagaagaa gcgcggccgg gccaccgaca gcttctcggg caggtttgaa    240

gacgtctacc agctgcagga agatgtgctg ggggagggcg ctcatgcccg agtgcagacc    300

tgcatcaacc tgatcaccag ccaggagtac gccgtcaaga tcattgagaa gcagccaggc    360

cacattcgga gcagggtttt cagggaggtg gagatgctgt accagtgcca gggacacagg    420

aacgtcctag agctgattga gttcttcgag gaggaggacc gcttctacct ggtgtttgag    480

aagatgcggg gaggctccat cctgagccac atccacaagc gccggcactt caacgagctg    540

gaggccagcg tggtggtgca ggacgtggcc agcgccttgg actttctgca taacaaaggc    600

atcgcccaca gggacctaaa gccggaaaac atcctctgtg agcaccccaa ccaggtctcc    660

cccgtgaaga tctgtgactt cgacctgggc agcggcatca aactcaacgg ggactgctcc    720

cctatctcca ccccggagct gctcactccg tgcggctcgg cggagtacat ggccccggag    780

gtagtggagg ccttcagcga ggaggctagc atctacgaca agcgctgcga cctgtggagc    840

ctgggcgtca tcttgtatat cctactcagc ggctacccgc ccttcgtggg ccgctgtggc    900

agcgactgcg gctgggaccg cggcgaggcc tgccctgcct gccagaacat gctgtttgag    960

agcatccagg agggcaagta cgagttcccc gacaaggact gggcccacat ctcctgcgct   1020

gccaaagacc tcatctccaa gctgctggtc cgtgacgcca agcagaggct gagtgccgcc   1080

caagtcctgc agcacccctg ggttcagggg tgcgccccgg agaacacctt gcccactccc   1140

atggtcctgc agaggtggga cagtcacttc ctcctccctc cccacccctg tcgcatccac   1200

gtgcgacctg gaggactggt cagaaccgtt actgtgaatg agtga                   1245
```

<210> SEQ ID NO 152
<211> LENGTH: 525
<212> TYPE: PRT
<213> ORGANISM: Homo sapiens

<400> SEQUENCE: 152

```
Met Arg Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80
```

```
Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
        195                 200                 205

Leu His Gln Lys Gly Ile Ile Tyr Arg Asp Leu Lys Pro Glu Asn Ile
    210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270

Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
    290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
            340                 345                 350

Arg His Ile Asn Trp Glu Glu Leu Leu Ala Arg Lys Val Glu Pro Pro
        355                 360                 365

Phe Lys Pro Leu Leu Gln Ser Glu Glu Asp Val Ser Gln Phe Asp Ser
    370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
                405                 410                 415

Ser Val Leu Glu Ser Val Lys Glu Lys Phe Ser Phe Glu Pro Lys Ile
            420                 425                 430

Arg Ser Pro Arg Arg Phe Ile Gly Ser Pro Arg Thr Pro Val Ser Pro
        435                 440                 445

Val Lys Phe Ser Pro Gly Asp Phe Trp Gly Arg Gly Ala Ser Ala Ser
    450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495
```

```
Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
        515                 520                 525


<210> SEQ ID NO 153
<211> LENGTH: 662
<212> TYPE: DNA
<213> ORGANISM: Homo sapiens

<400> SEQUENCE: 153

atgaggcgac gaaggaggcg ggacggcttt tacccagccc cggacttccg agacagggaa      60

gctgaggaca tggcaggagt gtttgacata gacctggacc agccagagga cgcgggctct     120

gaggatgagc tggaggaggg gggtcagtta aatgaaagca tggaccatgg gggagttgga     180

ccatatgaac ttggcatgga acattgtgag aaatttgaaa tctcagaaac tagtgtgaac     240

agagggccag aaaaaatcag accagaatgt tttgagctac ttcgggtact tggtaaaggg     300

ggctatggaa aggtttttca agtacgaaaa gtaacaggag caaatactgg gaaaatattt     360

gccatgaagg tgcttaaaaa ggcaatgata gtaagaaatg ctaaagatac agctcataca     420

aaagcagaac ggaatattct ggaggaagta aagcatccct tcatcgtgga tttaatttat     480

gcctttcaga ctggtggaaa actctacctc atccttgagt atctcagtgg aggagaacta     540

tttatgcagt tagaaagaga gggaatattt atggaagaca ctgcctggct tgagtggaac     600

gctcttcaca ccagttgttc ctaacagaac cattctcatt gcggctttct ttccttgaat     660

tg                                                                    662


<210> SEQ ID NO 154
<211> LENGTH: 207
<212> TYPE: PRT
<213> ORGANISM: Homo sapiens

<400> SEQUENCE: 154

Met Arg Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175
```

-continued

```
Gly Gly Glu Leu Phe Met Gln Leu Glu Arg Glu Gly Ile Phe Met Glu
            180                 185                 190

Asp Thr Ala Trp Leu Glu Trp Asn Ala Leu His Thr Ser Cys Ser
        195                 200                 205
```

<210> SEQ ID NO 155
<211> LENGTH: 840
<212> TYPE: DNA
<213> ORGANISM: Homo sapiens

<400> SEQUENCE: 155

```
atgaggcgac gaaggaggcg ggacggcttt tacccagccc cggacttccg agacagggaa     60

gctgaggaca tggcaggagt gtttgacata gacctggacc agccagagga cgcgggctct    120

gaggatgagc tggaggaggg gggtcagtta aatgaaagca tggaccatgg gggagttgga    180

ccatatgaac ttggcatgga acattgtgag aaatttgaaa tctcagaaac tagtgtgaac    240

agagggccag aaaaaatcag accagaatgt tttgagctac ttcgggtact tggtaaaggg    300

ggctatggaa aggtttttca agtacgaaaa gtaacaggag caaatactgg gaaaatattt    360

gccatgaagg tgcttaaaaa ggcaatgata gtaagaaatg ctaaagatac agctcataca    420

aaagcagaac ggaatattct ggaggaagta aagcatccct tcatcgtgga tttaatttat    480

gcctttcaga ctggtggaaa actctacctc atccttgagt atctcagtgg aggagaacta    540

tttatgcagt tagaaagaga gggaatattt atggaagaca ctgcctggcc ttttctaaca    600

aagaagctgc atttaagagc cttagggatg aagtgccctt ttttggagga ggctcactga    660

gccgtgttgg aggctgtgtt tgtggtcgtg ctggctgtga aactgcctca gtcctctagg    720

acacaccctc tccatcctgg agtaatctgc aggattgcaa cattgttatg cagccagtat    780

tgcagtgcct tgtgcttttc gaatccagac agggttgatt cagcccttta ttcttttgag    840
```

<210> SEQ ID NO 156
<211> LENGTH: 219
<212> TYPE: PRT
<213> ORGANISM: Homo sapiens

<400> SEQUENCE: 156

```
Met Arg Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
            20                  25                  30

Asp Gln Pro Glu Asp Ala Gly Ser Glu Asp Glu Leu Glu Glu Gly Gly
        35                  40                  45

Gln Leu Asn Glu Ser Met Asp His Gly Gly Val Gly Pro Tyr Glu Leu
    50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
        115                 120                 125

Met Ile Val Arg Asn Ala Lys Asp Thr Ala His Thr Lys Ala Glu Arg
    130                 135                 140

Asn Ile Leu Glu Glu Val Lys His Pro Phe Ile Val Asp Leu Ile Tyr
145                 150                 155                 160
```

```
Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Trp Pro Phe Leu Thr Lys Lys Leu His Leu Arg Ala Leu
        195                 200                 205

Gly Met Lys Cys Pro Phe Leu Glu Glu Ala His
    210                 215


<210> SEQ ID NO 157
<211> LENGTH: 18
<212> TYPE: DNA
<213> ORGANISM: Artificial sequence
<220> FEATURE:
<223> OTHER INFORMATION: PNA modified antisense oligonucleotide
<220> FEATURE:
<221> NAME/KEY: misc_feature
<223> OTHER INFORMATION: Polyarginine tail conjugated oligonucleotide

<400> SEQUENCE: 157

agacttccac cctgtcag                                                   18


<210> SEQ ID NO 158
<211> LENGTH: 46
<212> TYPE: DNA
<213> ORGANISM: Artificial sequence
<220> FEATURE:
<223> OTHER INFORMATION: An example of an RPS6KB1 antisense
      oligonucleotide specific for the short variant 6C

<400> SEQUENCE: 158

actgcattcc attgtttaat ttcaggcctt ttctaacaaa gaagct                    46


<210> SEQ ID NO 159
<211> LENGTH: 44
<212> TYPE: DNA
<213> ORGANISM: Artificial sequence
<220> FEATURE:
<223> OTHER INFORMATION: An example of an RPS6KB1 antisense
      oligonucleotide specific for the short variant 6A

<400> SEQUENCE: 159

cacatcattc ctttgccctt aggcttgagt ggaacgctct tcac                      44


<210> SEQ ID NO 160
<211> LENGTH: 22
<212> TYPE: DNA
<213> ORGANISM: Artificial sequence
<220> FEATURE:
<223> OTHER INFORMATION: An exemplary SRSF6 siRNA target sequence

<400> SEQUENCE: 160

tgttaatagg acatcatatg gt                                              22


<210> SEQ ID NO 161
<211> LENGTH: 22
<212> TYPE: DNA
<213> ORGANISM: Artificial sequence
<220> FEATURE:
<223> OTHER INFORMATION: An exemplary SRSF6 siRNA target sequence

<400> SEQUENCE: 161

ttataaagct tgagttatgt aa                                              22
```

<210> SEQ ID NO 162
<211> LENGTH: 26
<212> TYPE: DNA
<213> ORGANISM: Artificial sequence
<220> FEATURE:
<223> OTHER INFORMATION: An example for an antisense oligonucleotides suitable for targeting the SRSF6 mRNA

<400> SEQUENCE: 162
cccgccacgg acatgccgcg cgtcta 26

<210> SEQ ID NO 163
<211> LENGTH: 2040
<212> TYPE: DNA
<213> ORGANISM: Artificial sequence
<220> FEATURE:
<223> OTHER INFORMATION: Exon 14a of mnk2a

<400> SEQUENCE: 163
gaacagctgt gccaaagacc tcacgtcctt cgcggctgag gccattgcca tgaaccggca 60
gctggcccag cacgacgagg acctggctga ggaggaggcc gcggggcagg gccagcccgt 120
cctggtccga gctacctcac gctgcctgca gctgtctcca ccctcccagt ccaagctggc 180
gcagcggcgg caaagggcca gtctgtcctc ggccccagtg gtcctggtgg gagaccacgc 240
ctgaccctcc catctcccct ctgtacatag gtcacccgtc cccaatcaa atctaaaggt 300 tttttaagct atcgccagcc ggtgtccagc gggctgcccc tcctctgcct ggattcccag 360
gcactaagct cagctgaggg gggtgtttta tagaaggttt ttgcttttgg gttttttttt 420
tcctgtttcc acccctcccc gttatttttt cctttggatg gttaaaagca ttgcaggcac 480
ccgggaaggt gagcagaggg taggtgggtg ggcttgtccc ctccccggtc ccccgccctg 540
ctcacctcta ctatgaaggt gcccccaggt cacctgtgct gcccgccatc tgcccacgtg 600
gcttgcagtg actcaggaga gcaggcccac agcgtttgcc atcttgcaga gctggggagg 660
ggcacaggac cctgccctcg tgttccctcc cagcccgcag tatttcaggg acaggctctt 720
cccctctatc cctcaccctg agagcacccc tggtggcttg gttggggaag ggaggggctg 780
cctgtctctg gaggtgtcag gcaggcaggt ggcaggcagc tcacccaccc accccatggg 840
atcccccagc ccttcacccg cgcctgcctt gtccccatga tagttgacaa tcggggcttc 900
ctgcaaggcc cgtctgtctg tccaggactc ctggtggcca gattcggcct ccgaccttga 960
ccttaaactg cagctgaccc caggggctcg ccgctgcccc tcccctccac accaaggcct 1020
gagacagcag gagccccgcc tggcccgaag ccgtttccac cgcagcaggc agaggggctg 1080
gacaggcact gtcagccaat gtggggggtc ctgaagacac cccctggggg cacccgagtg 1140
ccccttctca gggctcagtc tgaccgtagc cacgtcctgc ctcgcgccgc ccctcgggcc 1200
tgacctggaa gctccgtcag ctccgtcctt gtccttagag ctgagcccag accccggggt 1260
ctggccgaat cctcaccccc agggcagtgt ttttggtctg ccaccttcag gaaaacggct 1320
gcggcctcgg cctcccttcg ggcacccagg aatgcggggg tctgctcagt ccccccaccc 1380
tccatgctcc aacccccggg ggctgcggag cctgctgccc cctccccgcg ggtggggacg 1440
ttctatgcaa tacagggttc cactttagaa gtgcgcgcgg ctagggtcac cgcccgccct 1500
tcccggcgca gcccccgagc tccacagctg gggcagcccc tctggcttct aaatccgcgg 1560
tcgggattct tcctcctgtt tagtttttta gtttttcctt aaaaaaaaac aacacatcga 1620
tggactttgc ttccctgttc ttgaagaata cttgaatgtc ggggggcctg ggggtggggg 1680
cctcggagac cgtctgcctg gccctgctgc ccctcctgaa tctcgtatga tggtcacagt 1740
ccggtggccg tgggggtgct ctgccttccc tggtccccac tgcccatatc tgtggactgc 1800
cccttccaaa gacccctggg gggggtgggg cattccgccc accccttttcc cccatcactt 1860 ctcgcctgtc agtgattcca tgtttcgtaa cgggggattc tctgcctttt tgtatcaaag 1920
aacaagcaaa tggacccccg cccgctgcag gcgcccatag ccatcgggtc tctaaagctg 1980
agtggctagc agcgtttgtt tgtttgtttt tttttttttt tctgaaggtg ggacagtcac 2040

<210> SEQ ID NO 164
<211> LENGTH: 40
<212> TYPE: DNA
<213> ORGANISM: Artificial sequence
<220> FEATURE:
<223> OTHER INFORMATION: mnk2b splice variant specific sequence spanning the bridging region between exon 13 and exon 14b

<400> SEQUENCE: 164
actcccatgg tcctgcagag gtgggacagt cacttcctcc 40

<210> SEQ ID NO 165
<211> LENGTH: 74
<212> TYPE: DNA
<213> ORGANISM: Artificial sequence
<220> FEATURE:
<223> OTHER INFORMATION: S6K1 h6A splice variant Exon 6A

<400> SEQUENCE: 165
gcttgagtgg aacgctcttc acaccagttg ttcctaacag aaccattctc attgcggctt 60
tctttccttg aatt 74

<210> SEQ ID NO 166
<211> LENGTH: 253
<212> TYPE: DNA
<213> ORGANISM: Artificial sequence
<220> FEATURE:
<223> OTHER INFORMATION: S6K1 h6C splice variant exon 6C

<400> SEQUENCE: 166
gccttttcta acaaagaagc tgcatttaag agccttaggg atgaagtgcc ctttttttgga 60 ggaggctcac tgagccgtgt tggaggctgt gtttgtggtc gtgctggctg tgaaactgcc 120
tcagtcctct aggacacacc ctctccatcc tggagtaatc tgcaggattg caacattgtt 180
atgcagccag tattgcagtg ccttgtgctt ttcgaatcca gacagggttg attcagccct 240
ttattctttt gag 253

<210> SEQ ID NO 167
<211> LENGTH: 1035
<212> TYPE: DNA
<213> ORGANISM: Artificial sequence
<220> FEATURE:
<223> OTHER INFORMATION: SRSF6 specific sequence

<400> SEQUENCE: 167
atgccgcgcg tctacatagg acgcctgagc tacaacgtcc gggagaagga catccagcgc 60
tttttcagtg gctatggccg cctcctcgaa gtagacctca aaaatgggta cggcttcgtg 120
gagttcgagg actcccgcga cgccgacgac gccgtttacg agctgaacgg caaggagctc 180
tgcggcgagc gcgtgatcgt agagcacgcc cggggcccgc gtcgcgatcg cgacggctac 240
agctacggaa gccgcagtgg tggaggtgga tacagcagtc ggagaacatc tggcagagac 300
aaatacggac cacctgttcg tacagaatac aggcttattg tagaaaatct ttctagtcgg 360
tgcagttggc aagatttaaa ggattttatg cgacaagcag gtgaagtaac ctatgcggat 420
gcccacaagg aacgaacaaa tgagggtgta attgagtttc gctcctactc tgacatgaag 480
cgtgctttgg acaaactgga tggcacagaa ataaatggca gaaatattag gcttattgaa 540
gataagccac gcacaagcca taggcgatct tactctggaa gcagatccag gtctcgatct 600
agaagacggt cacgaagtag gagtcgcagg agcagccgca gtagatctcg aagtatctca 660
aaaagtcgct cccgttccag gtcgcggagc aaaggtcgat cacgttctcg atcaaaaggc 720
aggaaatcta gatcaaagag caaatctaag cccaagtctg atcggggctc ccattcacat 780
tctcgaagca gatctaagga tgagtatgag aaatctcgaa gcaggtctcg gtcccgatcc 840
cctaaagaaa atggaaaggg tgatataaag tcaaaatcca gatcaaggag ccagtcccgt 900
tccaattcgc cgctacctgt tccaccctca aaggcccgtt ctgtgtcccc tccaccaaaa 960
agagctactt caagatcccg ttctagatct cgctcaaagt caagatcaag gtccaggtcg 1020
agttccagag attaa 1035

<210> SEQ ID NO 168
<211> LENGTH: 414
<212> TYPE: DNA
<213> ORGANISM: Artificial sequence
<220> FEATURE:
<223> OTHER INFORMATION: Sequenced PCR fragment that represent S6K1 alternative exon inclusion of both a and c

<400> SEQUENCE: 168
ctctacctca tccttgagta tctcagtgga ggagaactat ttatgcagtt agaaagagag 60
ggaatattta tggaagacac tgcctggctt gagtggaacg ctcttcacac cagttgttcc 120
taacagaacc attctcattg cggctttctt tccttgaatt ggccttttct aacaaagaag 180
ctgcatttaa gagccttagg gatgaagtgc cctttttgg aggaggctca ctgagccgtg 240
ttggaggctg tgtttgtggt cgtgctggct gtgaaactgc ctcagtcctc taggacacac 300
cctctccatc ctggagtaat ctgcaggatt gcaacattgt tatgcagcca gtattgcagt 360
gccttgtgct tttcgaatcc agacagggtt gattcagccc tttattcttt tgag 414

<210> SEQ ID NO 169
<211> LENGTH: 339
<212> TYPE: DNA
<213> ORGANISM: Artificial sequence
<220> FEATURE:
<223> OTHER INFORMATION: Sequenced PCR fragment that represent S6K1 alternative exon inclusion h6C alone

<400> SEQUENCE: 169
ctctacctca tccttgagta tctcagtgga ggagaactat ttatgcagtt agaaagagag 60
ggaatattta tggaagacac tgcctggcct tttctaacaa agaagctgca tttaagagcc 120
ttagggatga agtgcccttt tttggaggag gctcactgag ccgtgttgga ggctgtgttt 180
gtggtcgtgc tggctgtgaa actgcctcag tcctctagga cacaccctct ccatcctgga 240
gtaatctgca ggattgcaac attgttatgc agccagtatt gcagtgcctt gtgcttttcg 300
aatccagaca gggttgattc agccctttat tcttttgag 339

<210> SEQ ID NO 170
<211> LENGTH: 1447
<212> TYPE: DNA
<213> ORGANISM: Homo sapiens -continued

```
<400> SEQUENCE: 170

gtaagtgaac tttttgtggt tgcatagatt caggtaatta caagcaaagc cccattccca     60

ctatgggcag ccacatgatt cagtaaattg agctggagcc agtcactcac tcaggacctc    120

aagggggaga agcagttttg ggactgggca gctatggagg tcacatcatt cctttgccct    180

taggcttgag tggaacgctc ttcacaccag ttgttcctaa cagaaccatt ctcattgcgg    240

ctttctttcc ttgaattggt aagctgcctg ccttggctgt gggtgagtgt ggtttcccag    300

tgaaccttta tgtgtggaac aatggaaatt atcagaaatc atcccttttt ttttaggctt    360

tctatttctc aaggtacagt cttagggagg tgataaacct gggcatatca tctgtagatt    420

gattatgtag tcagggtggg atttaccctc ctatttctaa acatgtcatc tgcttcaaat    480

taaaaatatg cacatccttt tgtgaagcaa caatattggg tcacaataaa tcagtttatc    540

ctacacatta atttaataga aaacaacact taaatgtttt tttctacctt gattaccaaa    600

actgcattcc attgtttaat ttcaggcctt ttctaacaaa gaagctgcat ttaagagcct    660

tagggatgaa gtgccctttt ttggaggagg ctcactgagc cgtgttggag gctgtgtttg    720

tggtcgtgct ggctgtgaaa ctgcctcagt cctctaggac acaccctctc catcctggag    780

taatctgcag gattgcaaca ttgttatgca gccagtattg cagtgccttg tgcttttcga    840

atccagacag ggttgattca gccctttatt cttttgaggt agataaattt gggtgtcaca    900

cagtttatag ttgtgggctg gctggcaggt gggagggcag atactgtggg cctcagctgt    960

ctataaatat gtagctgtat taagtaaggg atgagtgggc ttctaagggt caggttataa   1020

gataccttttt gaaatcaaga tgtgatctct gagaataaca aagttcctat ttcctatggg   1080

attttaaagt tgggtgtgga tgggagaaat ttgcttgaaa tgaatggcta ttagcttaat   1140

tcctacacag acagaacaaa acatgaccaa tggcagttta gcatattctg gacatctttg   1200

caattttagc aatatattct aatggcaaaa taaagcactt tatagtttca ctaaaatgag   1260

tgaaacataa atgtccccat gccttttggc agcatcctat gccatctctt tttccaatac   1320

atccccctac cccactaatt tggtctttgg tgcatgtctg tttctttcaa ggaattttgc   1380

tccatacgta aactgctttg gatagattac actcttttta attttattaa atcacttttg   1440

tttccag                                                              1447


<210> SEQ ID NO 171
<211> LENGTH: 10
<212> TYPE: DNA
<213> ORGANISM: Artificial sequence
<220> FEATURE:
<223> OTHER INFORMATION: Bridging region between blue-intron, black-exon
      14b of Mnk2b

<400> SEQUENCE: 171

tgaaggtggg                                                             10
```

METHODS OF TREATING AND DIAGNOSING DISEASES USING AGENTS THAT REGULATE THE ALTERNATIVE SPLICING PATHWAY

RELATED APPLICATIONS

This application is a National Phase of PCT Patent Application No. PCT/IL2013/050424 having International filing date of May 16, 2013, which claims the benefit of priority under 35 USC§119(e) of U.S. Provisional Patent Application Nos. 61/647,587 filed on May 16, 2012, 61/647,594 filed on May 16, 2012, 61/665,554 filed on Jun. 28, 2012 and 61/704,909 filed on Sep. 24, 2012. The contents of the above applications are all incorporated by reference as if fully set forth herein in their entirety.

SEQUENCE LISTING STATEMENT

The ASCII file, entitled 60746SequenceListing.txt, created on Oct. 26, 2014, comprising 70,539 bytes, submitted concurrently with the filing of this application is incorporated herein by reference.

FIELD AND BACKGROUND OF THE INVENTION

The present invention, in some embodiments thereof, relates to the use of agents which regulate alternative splicing pathways for the treatment and diagnosis of cancer and related diseases.

The process of alternative splicing is widely misregulated in cancer and many tumors express new splicing isoforms, which are absent in the corresponding normal tissue. Many oncogenes and tumor suppressors are differentially spliced in cancer cells and it has been shown that many of these cancer-specific isoforms contribute to the transformed phenotype of cancer.

Splicing factor SRSF1 (SF2/ASF) is a potent proto-oncogene. It is upregulated by several mechanisms such as gene amplification (Karni et al. 2007) or transcriptional activation (Das et al. 2012). SRSF1 modulates the splicing of numerous genes including Mnk2, RPS6KB1 which encodes S6K1 in both mouse and human.

The serine/threonine kinases Mnk1 and Mnk2 were discovered by their direct interaction with and activation by the MAP kinases ERK and p38 Mnk1 and Mnk2 phosphorylate the translation initiation factor eIF4E on serine 209. The eIF4E protein binds to the 5' cap structure of mRNAs and is essential for cap-dependent translational initiation. In mice lacking both kinases (MNK-DKO mice) eIF4E is completely unphosphorylated on serine 209. Intriguingly, these mice develop and live normally displaying no adverse phenotype. Mnk1 and Mnk2 are 72% identical in their amino acid sequence. Biochemically, it has been shown that while Mnk1 is activated only after stimulation of the upstream MAPK signaling, Mnk2 possesses intrinsic basal activity when introduced into cells. There is no direct evidence connecting Mnk1/2 to human cancer. It would seem that the notion that Mnk1 and Mnk2 are positive drivers in human cancer stems from the important role eIF4E, their known substrate, plays in cancer.

In humans, each of the MKNK1 and MKNK2 genes gives rise to at least two distinct proteins, with different C termini, as a consequence of 3' prime alternative splicing. The longer forms of human Mnk1 and Mnk2, referred to as Mnk1a and Mnk2a respectively, possess a MAPK-binding motif that is absent from the shorter isoforms Mnk1b and Mnk2b.

Adesso et al. 2012, [Oncogene, doi: 10.1038/onc.2012.306.] teach that resistance of pancreatic cancer cells to Gemcitabine is mediated by SRSF1 up-regulation and a switch in Mnk2 alternative splicing, which enhances eIF4E phosphorylation implicating this alternative splicing event with chemotherapy resistance.

The PI3K/Akt/mTOR pathway is one of the major signaling pathways hyper activated in many cancers, and leads to uncontrolled proliferation, increased survival, motility and invasiveness of cancer cells. mTOR resides in two distinct complexes: mTOR complex-1 (mTORC1) and complex-2 (mTORC2). mTORC1 core contains mTOR, Raptor, G-β-L and is considered to be sensitive to rapamycin. mTORC2 contains Rictor, as the mTOR partner instead of Raptor, and depending on the cell type, is less sensitive to rapamycin. The best-characterized substrates of mTORC1 are S6 Kinase 1 (S6K1) and eukaryotic initiation factor 4E (eIF4E)-binding protein 1 (4E-BP1), while Akt is a substrate of mTORC2. Several components of the mTOR signaling cascade have been identified as oncogenes or tumor suppressors that activate or repress this pathway respectively. Among the two well characterized mTORC1 substrates, S6K1 and 4E-BP1, the latter has been shown to be important for efficient protein translation, proliferation, and for oncogenic transformation. S6K1 has been implicated in the regulation of cell size. A link between S6K1 function and cancer was suggested by the finding that RPS6KB1, the gene encoding for S6K1, resides in the chromosomal region 17q22-17q23, which is often amplified in breast and lung cancers (Bepler and Koehler, 1995; Monni et al., 2001). However, direct evidence that S6K1 expression or activity is sufficient to lead to cellular transformation is lacking.

Karni et al. 2007, [Nature structural & molecular biology 14: 185-193] teach that SRSF1 increases the expression of the shorter S6K1 isoform (referred to herein as h6A and h6C in human) as opposed to the long active kinase p85/p70 S6K1 (referred to herein as Iso-1).

SUMMARY OF THE INVENTION

According to an aspect of some embodiments of the present invention there is provided a method of determining a treatment for an inflammatory disorder in a subject, the method comprising determining an amount of SRSF6 in a sample from the subject, wherein an amount of the SRSF6 is indicative of the treatment.

According to an aspect of some embodiments of the present invention there is provided a method of treating a disease associated with an increased activity of p38-MAPK in a subject in need thereof, the method comprising administering to the subject a therapeutically effective amount of an agent which directly increases the ratio of to Mnk2a: Mnk2b, thereby treating the disease.

According to an aspect of some embodiments of the present invention there is provided a method of diagnosing a disease associated with an increased activity of p38-MAPK in a subject, the method comprising determining an amount of Mnk2a and/or Mnk2b in a sample from the subject, wherein an amount of the Mnk2a below a predetermined level and/or an amount of the Mnk2b above a predetermined is indicative of the disease.

According to an aspect of some embodiments of the present invention there is provided a composition of matter comprising a human sample and an agent which can specifically measure a level of Mnk2a and/or an agent which can specifically measure a level of Mnk2b.

According to an aspect of some embodiments of the present invention there is provided a method of determining whether a cancer is susceptible to an agent that inhibits the Ras-Raf MAPK pathway comprising determining an amount of Mnk2a and/or Mnk2b in a sample from the subject, wherein an amount of Mnk2b above a predetermined level and/or an amount of Mnk2a below a predetermined level is indicative of a cancer that is susceptible to the agent.

According to an aspect of some embodiments of the present invention there is provided a method of monitoring an anti cancer treatment in a subject, the method comprising:

(a) administering at least one agent that inhibits the Ras-Raf MAPK pathway to the subject;

(b) detecting a level of Mnk2a and/or Mnk2b in a sample of the subject, wherein an increase in the level of Mnk2a following the administering compared with a level of the Mnk2a prior to the administering and/or a decrease in the level of Mnk2b following the administering compared with a level of the Mnk2b prior to the administering is indicative of a positive response to the anti cancer treatment.

According to an aspect of some embodiments of the present invention there is provided a method of screening for an agent which can treat treating a disease associated with an increased activity of p38-MAPK comprising:

(a) contacting a cell which expresses the Mnk2 gene with the agent;

(b) measuring a level of Mnk2a and/or Mnk2b, wherein an increase in the level of the Mnk2a and/or a decrease in the level of Mnk2b following the contacting as compared to before the contacting is indicative of an agent which can treat the disease.

According to an aspect of some embodiments of the present invention there is provided a method of treating cancer in a subject in need thereof, the method comprising administering to the subject a therapeutically effective amount of an agent which directly increases the ratio of long:short isoforms of S6K1, thereby treating the disease.

According to an aspect of some embodiments of the present invention there is provided a method of diagnosing cancer in a subject, the method comprising determining an amount of a short isoform of S6K1 and/or an amount of the long isoform of the S6K1 in a sample from the subject, wherein an amount of the short isoform above a predetermined level and/or an amount of the long isoform below a predetermined level is indicative of the cancer.

According to an aspect of some embodiments of the present invention there is provided a composition of matter comprising a human sample and an agent which can specifically detect the level of an S6K1 short isoform and/or an agent which can specifically detect the level of the S6K1 long isoform.

According to an aspect of some embodiments of the present invention there is provided a method of screening for an agent which can treat treating cancer comprising:

(a) contacting a cell which expresses the RPS6KB1 gene with the agent;

(b) measuring a level of S6K1 short isoform and/or S6K1 long isoform, wherein an increase in the level of the long isoform and/or a decrease in the level of the short isoform following the contacting as compared to before the contacting is indicative of an agent which can treat the cancer.

According to an aspect of some embodiments of the present invention there is provided a method of determining whether a cancer is susceptible to an agent that inhibits the pTEN pI3K-mTOR pathway comprising determining an amount of a short isoform of S6K1 and/or the long isoform of the S6K1 in a tumor sample from the subject, wherein an amount of the short isoform above a predetermined level is indicative of a cancer that is susceptible to the agent and/or an amount of the long isoform below a predetermined level is indicative of a cancer that is susceptible to the agent.

According to an aspect of some embodiments of the present invention there is provided a method of monitoring an anti cancer treatment in a subject, the method comprising:

(a) administering at least one agent that inhibits the pTEN pI3K-mTOR pathway to the subject;

(b) detecting a level of a short isoform of S6K1 and/or a long isoform of S6K1 in a sample of the subject, wherein a decrease in the level of the short isoform of S6K1 following the administering compared with a level of the short isoform of S6K1 prior to the administering is indicative of a positive response to the anti cancer treatment and/or an increase in the level of the long isoform of S6K1 following the administering compared with a level of the long isoform of S6K1 prior to the administering is indicative of a positive response to the anti cancer treatment.

According to an aspect of some embodiments of the present invention there is provided a method of diagnosing an inflammatory disorder in a subject, the method comprising determining an amount SRSF6 in a sample from the subject, wherein an amount of SRSF6 in the sample above a predetermined level is indicative of the inflammatory disorder.

According to an aspect of some embodiments of the present invention there is provided a composition of matter comprising a human sample and an agent which can determine an amount of SRSF6 in the sample.

According to an aspect of some embodiments of the present invention there is provided a method of treating an inflammatory disorder in a subject in need thereof, comprising administering to the subject a therapeutically effective amount of an agent which directly down-regulates an amount and/or activity of SRSF6, thereby treating the inflammatory disorder.

According to an aspect of some embodiments of the present invention there is provided a pharmaceutical composition comprising an agent which directly down-regulates an amount and/or activity of SRSF6 and a pharmaceutically acceptable carrier.

According to an aspect of some embodiments of the present invention there is provided an agent which directly down-regulates an amount and/or activity of SRSF6 for treating an inflammatory disorder.

According to an aspect of some embodiments of the present invention there is provided an isolated polynucleotide which increases the ratio of Mnk2a:Mnk2b and hybridizes to a polynucleotide comprising a nucleic acid sequence as set forth in SEQ ID NO: 171, being between 10 and 30 bases long.

According to an aspect of some embodiments of the present invention there is provided an isolated polynucleotide which increases the ratio of long:short isoforms of S6K1 and hybridizes to a polynucleotide comprising a nucleic acid sequence as set forth in SEQ ID NO: 158 or 159 and is between 10-30 bases.

According to an aspect of some embodiments of the present invention there is provided a pharmaceutical composition comprising an agent which directly increases the ratio of Mnk2a:Mnk2b and a pharmaceutically acceptable carrier.

According to an aspect of some embodiments of the present invention there is provided a pharmaceutical composition comprising an agent which directly increases the ratio of long:short isoforms of S6K1, and a pharmaceutically acceptable carrier.

According to an aspect of some embodiments of the present invention there is provided an agent which directly increases the ratio of Mnk2a:Mnk2b for treating a disease associated with an increased activity of p38-MAPK.

According to an aspect of some embodiments of the present invention there is provided an agent which directly increases the ratio of long:short isoforms of S6K1 for treating cancer.

According to some embodiments of the invention, the inflammatory disorder is cancer.

According to some embodiments of the invention, the inflammatory disorder is inflammatory bowel disorder.

According to some embodiments of the invention, the cancer is colon cancer.

According to some embodiments of the invention, the subject has undergone surgery to remove the cancer prior to the determining.

According to some embodiments of the invention, the amount of SRSF6 is above a predetermined level, the treatment is chemotherapy.

According to some embodiments of the invention, when the amount of SRSF6 is above a predetermined level, the treatment is colon surgery.

According to some embodiments of the invention, the sample comprises a tissue sample.

According to some embodiments of the invention, the cancer is breast cancer.

According to some embodiments of the invention, the method further comprises treating the subject following the determining.

According to some embodiments of the invention, the agent is a polynucleotide agent.

According to some embodiments of the invention, the polynucleotide agent hybridizes to a Mnk2b specific splice site.

According to some embodiments of the invention, the polynucleotide agent comprises peptide nucleic acids or locked nucleic acids.

According to some embodiments of the invention, the sample is a human sample.

According to some embodiments of the invention, the sample comprises a tumor sample.

According to some embodiments of the invention, the sample comprises a tissue sample.

According to some embodiments of the invention, the sample comprises a bodily fluid.

According to some embodiments of the invention, the bodily fluid comprises blood.

According to some embodiments of the invention, the disease is selected from the group consisting of cancer, a neurodegenerative disease, an inflammatory disease and an autoimmune disease.

According to some embodiments of the invention, the method further comprises treating the cancer following the determining.

According to some embodiments of the invention, the agent is selected from the group consisting of a Ras inhibitor, a Raf kinase inhibitor and a MEK inhibitor.

According to some embodiments of the invention, the MEK inhibitor is selected from the group consisting of GSK2118436, GSK1120212, Sorafenib and vemurafenib.

According to some embodiments of the invention, the method further comprises synthesizing a pharmaceutical composition comprising the agent which is indicative for treating the disease.

According to some embodiments of the invention, the agent is a polynucleotide agent.

According to some embodiments of the invention, the polynucleotide agent hybridizes to a S6K1 short isoform specific splice site.

According to some embodiments of the invention, the polynucleotide agent comprises peptide nucleic acids or locked nucleic acids.

According to some embodiments of the invention, the sample is a human sample.

According to some embodiments of the invention, the sample is a tumor sample.

According to some embodiments of the invention, the sample is a bodily fluid.

According to some embodiments of the invention, the bodily fluid comprises blood.

According to some embodiments of the invention, the method further comprises synthesizing a pharmaceutical composition comprising the agent which is indicative for treating the cancer.

According to some embodiments of the invention, the agent is selected from the group consisting of an mTOR inhibitor, a PI3K inhibitor and an Akt inhibitor.

According to some embodiments of the invention, the method further comprises determining an amount of the long isoform of S6K1 in a tumor sample from the subject, wherein an amount of the long isoform below a predetermined level is further indicative of a cancer that is susceptible to the agent.

According to some embodiments of the invention, the method further comprises treating the cancer following the determining.

According to some embodiments of the invention, the inflammatory disorder is cancer or inflammatory bowel disorder.

According to some embodiments of the invention, the cancer is selected from the group consisting of lung cancer, colon cancer and breast cancer.

According to some embodiments of the invention, the agent is a polynucleotide agent.

According to some embodiments of the invention, the agent is a polypeptide agent.

According to some embodiments of the invention, the inflammatory disorder is cancer or inflammatory bowel disorder.

According to some embodiments of the invention, the cancer is lung or colon cancer.

According to some embodiments of the invention, the isolated polynucleotide comprises PNA or LNA.

According to some embodiments of the invention, the isolated polynucleotide is attached to a nuclear penetrating agent.

According to some embodiments of the invention, the nuclear penetrating agent comprises arginine.

According to some embodiments of the invention, the isolated polynucleotide comprises a nucleic acid sequence as set forth in SEQ ID NO: 157.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figures 1A, 1B, 1C:
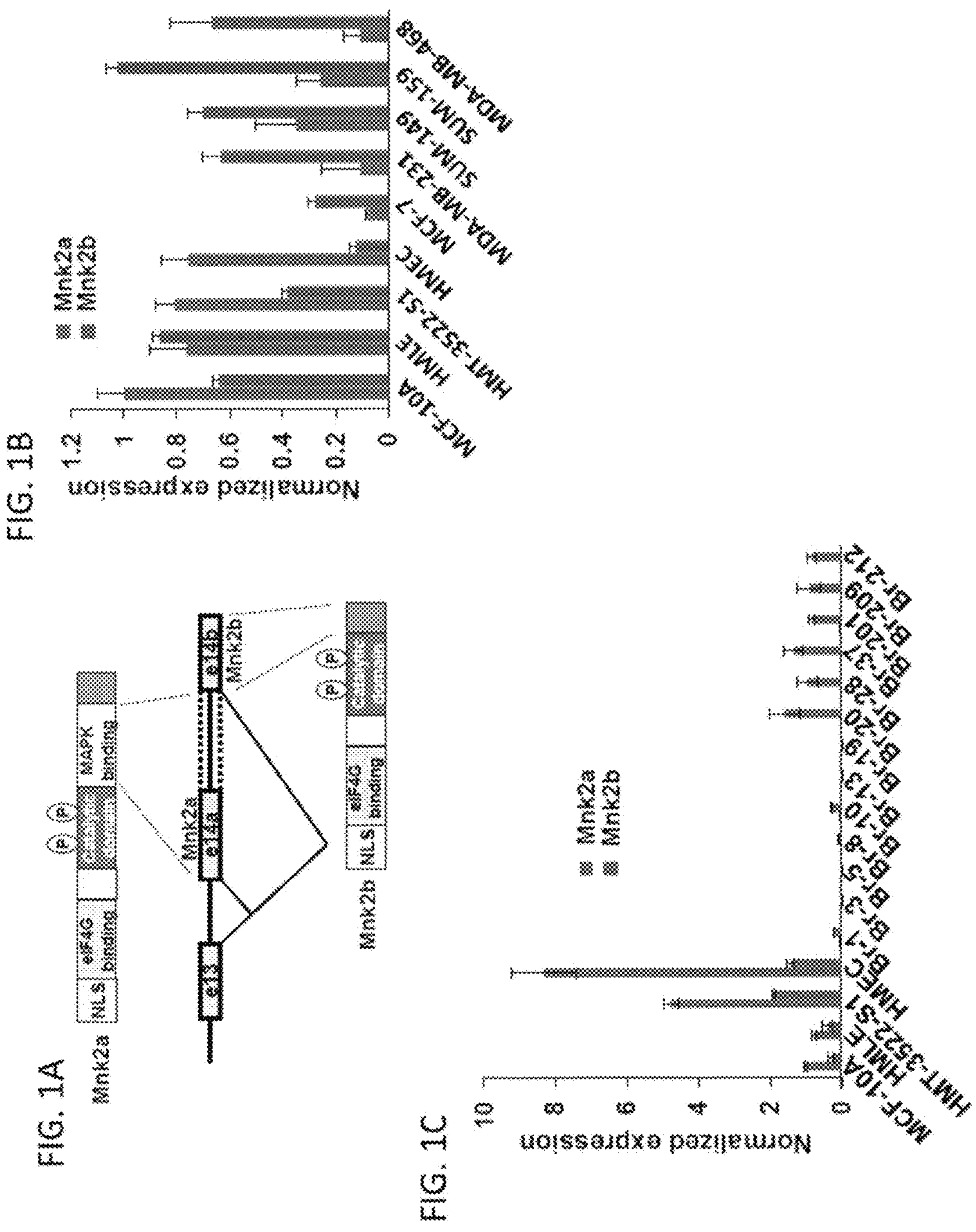

FIGS. 1A-F: A switch in MKNK2 alternative splicing in primary tumors and cancer cell lines. (A). The human splicing isoforms of MKNK2 contain a basic region important for eIF4G binding in their N-terminus as well as a putative NLS. The catalytic domain contains two conserved threonine residues (T197, T202) in the activation loop that need to be phosphorylated (P) by MAP kinases for kinase activation. Mnk2a contains a binding site for MAP kinases located in the C-terminus. Mnk2b is generated by an alternative 3' splice site in intron 14 that generates a shorter last exon (14b), lacking the MAPK binding site. (B, C). RNA from the indicated primary or immortal breast cell lines, breast cancer cell lines (B) or primary breast tumors (C) was extracted and the levels of Mnk2a and Mnk2b RNA were detected by Q-RT-PCR. (D). Human breast immortal and tumor cell lines were subjected to Western blot analysis and the protein levels of Mnk2a and Mnk2b were measured. β-catenin was used as a loading control. (E). RNA from immortal breast cell lines and human breast tumors was extracted and Q-RT-PCR was performed to detect SRSF1 mRNA levels. (F). Immortal breast cell lines and human breast cancer cell lines were lysed and proteins separated by SDS-PAGE. After Western blotting membranes were probed with the indicated antibody to detect the levels of SRSF1. Antibodies against GAPDH served as control.

FIGS. 1G-K: MKNK2 alternative splicing is switched in human cancers.

(G) The average mRNA ratios of Mnk2a to Mnk2b in breast tumors (T) and normal (N) breast tissue samples. T-test two tail analysis of average tumors from human breast, representative of 4 normal (N) and 13 tumor (T) samples, *P<0.03. (H,I) RNA from immortal, primary and cancer breast cell lines and human breast tumors was extracted and RT-PCR was performed to detect the levels of Mnk2a and Mnk2b transcripts. PCR products were run in a 2% agarose gel. GAPDH mRNA was used as a control. (J) Mnk2a and 2b transcript levels were measured by Q-RT-PCR in five normal and 50 lung carcinoma samples. The average of the five normal lung samples was arbitrarily set at 1. (K) RNA from primary normal human colon tissue and colon tumors was extracted and RT-PCR was performed to detect Mnk2a and Mnk2b transcript levels as described in (H,I).

FIGS. 2A-K: Mnk2a inhibits Ras-induced transformation and tumorigenesis.

(A). MCF-10A cells were transduced with the indicated retroviruses encoding for Mnk2 isoforms and a kinase-dead version of Mnk2a (Mnk2aKD). After selection cells were lysed and Western blotting membranes were probed with the indicated antibodies. (B) Cells described in (A) were transduced with H-RAS$^{V12}$ and after selection with hygromycin cells were lysed and analyzed by Western blot with the indicated antibodies. (C) Cells described in (A) were seeded into soft agar (see Materials and Methods) in duplicates and colonies were allowed to grow for 14 days. Colonies in ten fields of each well were counted and the mean and standard deviation of colonies per well of 3 wells is shown (n=3). (D). Cells described in (B) were seeded into soft agar and counted as in (C) (n=3). (E) Immortal MEFs from WT, MKNK1$^{-/-}$ or MKNK2$^{-/-}$ mice were seeded into soft agar and counted as in (C) (n=3). (F). Pools of MCF-10A cells transformed with the indicated retroviruses encoding Mnk2 isoforms followed by H-RAS$^{V12}$ transduction or (G) cells transduced with shRNA against Mnk2a (Sh2a-2) followed by transformation by H-RAS$^{V12}$ were injected ($2\times10^6$ cells/injection, in matrigel) subcutaneously into NOD-SCID mice. Tumor growth curves were calculated as described in Experimental procedures. The number of tumors formed per injection is shown near the legend bars. (*p≤0.01). (H-K). Formalin fixed, paraffin-embedded tissue sections from tumors derived from the indicated cell pools described in (F, G) were stained with anti-phospho-H3 to detect mitotic cells (H, J). Graphs shows the average and SD of p-H3 positive cells from 10 counted fields of 3 different tumors (I, K) (*p≤0.01).

FIGS. 2L-V: Both Mnk2 isoforms phosphorylate eIF4E, yet Mnk2a suppresses whereas Mnk2b promotes tumorigenesis in vitro.

(L) NIH 3T3 cells were transduced with the indicated retroviruses encoding for Mnk2 isoforms and a kinase-dead version of Mnk2a (Mnk2aKD) and after selection for puromycin resistance were lysed and subjected to Western blot analysis with the indicated antibodies. (M) Cells described in (L) were seeded into soft agar in duplicate and colonies were allowed to grow for 14 days. Colonies in ten fields of each well were counted and the mean±standard deviation of colonies per well in a representative experiment is shown. (N) Photographs of representative fields of colonies in soft agar described above. (O) U2OS osteosarcoma cells were transduced with the indicated retroviruses encoding for Mnk2 isoforms and a kinase-dead version of Mnk2a (Mnk2aKD) and after selection were lysed and subjected to Western blot analysis with the indicated antibodies. (P) Cells described in (O) were analyzed for colony formation as described in (M). (Q). Photographs of representative fields of colonies in soft agar described above. (R). NCI-H460 lung carcinoma cells were transduced with the indicated retroviruses encoding for isoform-specific shRNAs against Mnk2a. Cells were seeded and analyzed for colony formation as described in (M). (S). Photographs of representative fields of colonies in soft agar described above. (T-U) Representative photographs of colonies in soft agar formed by MCF-10A (T) and MCF-10A-Ras cells (U) transduced with retroviruses encoding for the indicated Mnk2 isoforms. (V) Representative photographs of colonies in soft agar formed by WT, Mnk1$^{-/-}$ or Mnk2$^{-/-}$ MEFs as indicated.

FIGS. 3A-F: Mnk2a sensitizes MCF-10A cells to stress-induced apoptosis.

(A, C). MCF-10A cells transduced by the indicated retroviruses encoding for Mnk2 isoforms and a kinase-dead version of Mnk2a (Mnk2aKD) (A) or MLP vectors encoding for shRNAs against Mnk2a isoform (C) were seeded in 6-well plates. After 24 hours cells were starved in growth factor free media for an additional 24 h. Following starvation cells were treated with 0.5 μM anisomycin for 24 h (A) or 48 h (C) and subjected to trypan-blue exclusion assay. (*P≤0.05). (B, D). Cells described in (A, C) were centrifuged and lysed with Laemmli buffer and proteins were separated by SDS-PAGE. Cleaved caspase-3 served as a marker for apoptosis and was analyzed by Western blot. Levels of p-p38, p38, p-eIF4E and eIF4E were detected with the indicated antibodies. β-catenin served as loading control. (E). Pools of MCF-10A cells transduced with the indicated retroviruses encoding Mnk2 isoforms were transformed by H-RAS$^{V12}$. Cells were plated at low density (400 cells/well) 10 days after retroviral gene transduction and selection and assessed for colony formation with methylene blue staining 20 days later. Average and standard deviation of the number of colonies per well is shown. n=3. (*, **P≤0.05). (F). Representative wells with colonies described in (E).

FIGS. 3G-J: Mnk2a knockdown reduces p38-MAPK phosphorylation and induces colony formation in soft agar:

(G) Pools of MCF-10A cells were transduced with retroviruses encoding empty vector (MLP) or the indicated shRNAs against Mnk2a. After selection with puromycin, RNA was extracted and the levels of Mnk2a and Mnk2b mRNAs were measured by Q-RT-PCR. (H) Cells described in (G) were seeded into 6-well plates. 24 h later cells were lysed and proteins were subjected to Western blot analysis with the indicated antibodies. (I) Cells described in (G) were seeded into soft agar and 14 days later colonies were counted n=3. (J) Representative pictures of cells described in (I).

FIGS. 4A-G: Mnk2a but not Mnk2b enhances p38α-mediated cell death and inhibits Ras transformation in a p38-dependent manner.

(A) MCF-10A cells were transduced with the indicated Mnk2 isoforms and a kinase-dead version of Mnk2a (Mnk2aKD). Stable pools of cells were transduced with a constitutively active form of p38α or an empty vector (pWZL), and selected with hygromycin in the presence or absence of 20 μM SB203580 for 48 hours. Following selection, the morphology of cells was analyzed using a light microscope. (B) Methylene blue used for staining cells treated as in (A) was extracted and O.D. was measured as described in Experimental procedures. % cell death in each column was normalized to that of the empty vector. n=4 (*p≤0.05). (C-D). MCF-10A cells transduced with the indicated viruses expressing isoform-specific shRNAs against Mnk2a were transduced with a constitutively active form of p38α or an empty vector and analyzed as described in (A) and (B), respectively. Cell death in (B, D) was calculated by normalizing the absorbance values for cells co-transduced pWZL-active p38 mutant and Mnk2 isoforms to that of cells co-transduced pWZL (−) and Mnk2 isoforms. n=4, (**p≤0.05). (E) MCF-10A cells transduced with retroviruses containing the indicated Mnk2 isoforms or a kinase dead version of Mnk2a (Mnk2aKD) or with isoform specific shRNAs against Mnk2a were treated with 1 μM anisomycin, in the presence or absence of 10 μM SB203580. Cells were lysed and proteins were subjected to Western blot analysis with the indicated antibodies. (F) MCF-10A cells were transduced with the indicated retroviruses followed by transduction with H-RAS$^{V12}$. After selection transductants cells were seeded into soft agar in the presence or absence of the indicated concentrations of SB203580 and colonies were counted 14 days later. (*, , *p≤0.01n=3). (G) Photographs of representative fields of colonies in soft agar obtained as described in (E).

FIGS. 4H-M: Analyses of proliferation and cell cycle of MCF-10A cells transduced with Mnk2 isoforms.

MCF-10A transduced with retroviruses encoding for Mnk2 isoforms (H) or viruses expressing isoform-specific shRNAs (I) were seeded in sixplicates in 96 well plates and growth curves were measured, as described in Experimental procedures (n=6). (J-M) cells described in (H) were stained with PI and subjected to flow cytometry analysis for DNA content assessment. Percent of cells gated in each phase is indicated.

FIGS. 5A-H: Mnk2a interacts with p38-MAPK and leads to its activation and translocation into the nucleus.

(A) MCF-10A cells were transduced with the indicated retroviruses encoding for Mnk2 isoforms or Mnk2aKD. Total protein from stable pools was extracted and separated on SDS-PAGE and was subjected to Western blot analysis with the indicated antibodies. Numbers represent ratio of p-p38/total p38 normalized to that of pBABE (arbitrarily set at 1)±SD (n=2). (B) MCF-10A cells described in (A) were transduced by H-RAS$^{V12}$ and after selection cells were lysed and subjected to Western blot analysis with the indicated antibodies. Numbers representing ratio of p-p38/total p38 were calculated as described in (A) (n=2). (C) Immortal MEFs from Mnk2$^{-/-}$ mouse were transduced with retrovirus encoding either no mammalian protein (pBABE) or various Mnk2 variants. These cells, as well as immortal MEFs from WT mouse were harvested and proteins were subjected to Western blot analysis with the indicated antibodies. (D) Immortal MEFs from WT, Mnk1$^{-/-}$ or Mnk2$^{-/-}$ mice were lysed and analyzed as in (A). (E) Immortal MEFs described in (D) were seeded in 6-well plates. 24 h later cells were treated either with the vehicle (DMSO) or the Mnk1/2 kinase inhibitor, CGP 57380 (2.5 μM) for 4 h, and subjected to Western blot analysis with the indicated antibodies. (F) HEK293 cells were cotransfected with the indicated Mnk2 isoforms together with HA-p38α-MAPK. HA-p38α or T7-Mnk2 isoforms were co-immunoprecipitated from lysates with either anti-HA or anti-T7 antibody. Precipitated and input proteins were subjected to Western blot analysis with the indicated antibodies. * represents a non specific band. (G) Distribution between cytoplasmic (C) and nuclear (N) fractions of p38α in immortal Mnk2$^{-/-}$ MEFs, transduced with retrovirus encoding empty vector (pBABE) or Mnk2a. c-myc (nuclear) and caspase-2 (cytoplasmic) served as controls for fractionation. (H). MCF-10A cells transduced with Mnk2 isoforms or a kinase-dead version of Mnk2a (Mnk2aKD) were subjected to fractionation and analysis as described in (G).

FIGS. 5I-M illustrate that Mnk2a sensitizes cells to stress-induced apoptosis.

(I) MCF-10A cells transduced with the indicated retroviruses encoding for Mnk2 isoforms and a kinase-dead version of Mnk2a (Mnk2aKD) were transduced with H-RAS$^{V12}$. After selection with hygromycin transductants were maintained in growth factor-free medium in suspension for 48 h. Cell death was measured using the trypan blue exclusion assay. (J) Human pancreatic cancer cells Panc-1 were seeded on 96-well plates (6000 cells/well). Following starvation cells were treated with 0.5 μM anisomycin in the presence or absence of 20 μM SB203580. (*, **p≤0.01). (K) MCF-10A cells were transduced as in (I). After selection cells were seeded in 6-well plates. 24 h later cells were serum starved in a growth factor-free medium for 24 h. Following starvation cells were treated with 0.5 M Sorbitol (to induce osmotic shock) and 24 h later were stained with trypan blue (n=2). (L) MCF-10A transduced with the indicated retroviruses encoding for shRNAs against Mnk2a were seeded as in (K). (*, p≤0.01, ** p≤0.05). Following starvation cells were treated with 0.25 M Sorbitol and 24 h later were fixed and stained with trypan blue (n=2). (M) Pools MCF-10A cells co-transduced with the indicated retroviruses and oncogenic Ras were plated at a low density (400 cells/well). 10 days post selection with hygromycin cells were assessed for colony formation with methylene blue staining. n=3. (*p≤0.01).

Figure 6B:
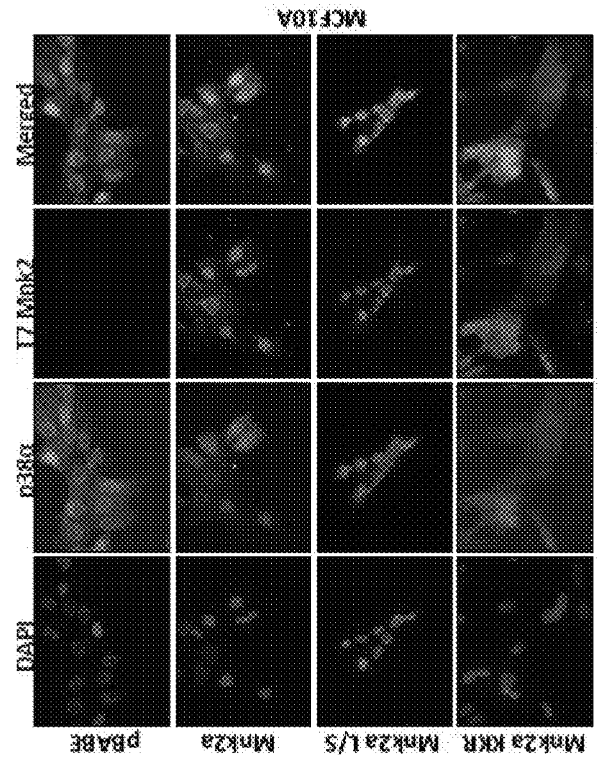
Figure 6A:
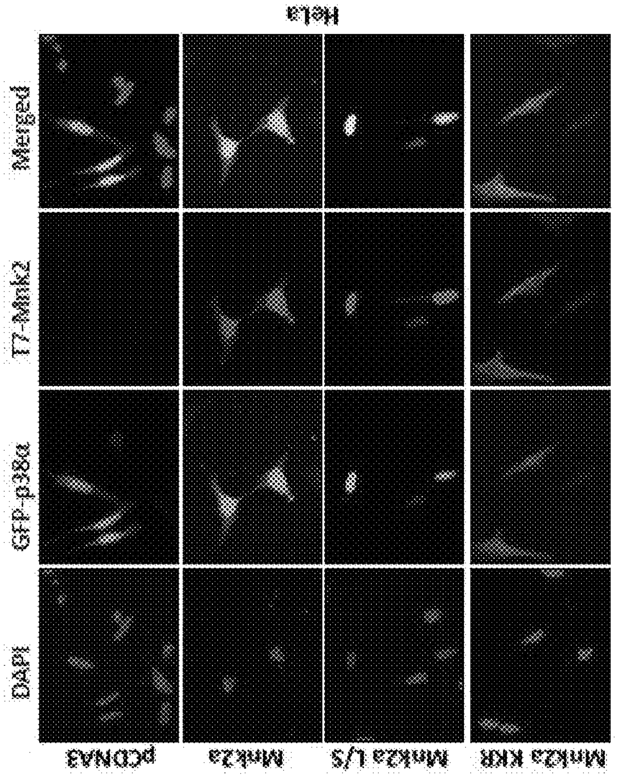
Figure 6C:
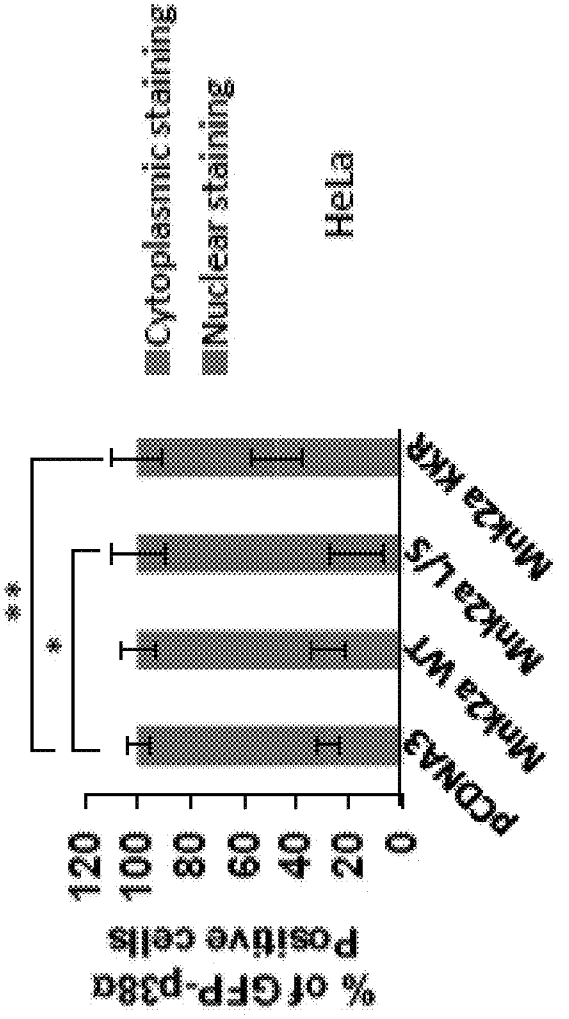

FIGS. 6A-C illustrates that Mnk2a colocalizes with p38-MAPK and affects its cellular localization.

(A) HeLa cells were seeded on coverslips in 12-well plates and 24 h later cells were co-transfected with either empty pcDNA3 vector or pcDNA3-based expression vectors for T7-tagged Mnk2a, Mnk2aL/S or Mnk2aKKR, together with pCDNA3-GFP-p38α (WT). 24 h later cells were fixed with 4% paraformaldehyde, stained with the indicated antibodies and subjected to immunofluorescence assay, as described in Experimental Procedures. (T7-tag was stained red and GFP-p38α is green). (B) MCF-10A cells transduced with the indicated retroviruses, were seeded fixed and subjected to immunofluorescence assay, as described in (A) to detect endogenous p38α. (T7-tag was stained red and p38α was stained green). (C) Quantification of cytoplasmic/nuclear distribution of GFP-p38α in cells similar to those described in (A). n=40 for each mutant. (*, **p≤0.01).

FIGS. 7A-F illustrate that Mnk2a localization and kinase activity are required for induction of p38α targets genes and apoptosis.

(A, B) RNA from MCF-10A cells transduced with the indicated Mnk2 isoforms and a kinase-dead version of Mnk2a (Mnk2aKD) or with MLP vectors encoding for shRNAs against Mnk2a isoform was extracted and the levels of FOS and COX-2 were measured by Q-RT-PCR. (C). RNA from WT MEFs, Mnk2$^{-/-}$ MEFS and Mnk2$^{-/-}$ MEFS transduced with Mnk2a was extracted and the levels of FOS and COX-2 were analyzed by Q-RT-PCR. (D). RNA from MCF-10A cells transduced with the indicated Mnk2 isoforms and the indicated Mnk2a mutants was extracted and the levels of FOS and COX-2 were measured as described above. (E). MCF-10A cells were seeded in 10 cm plates. 24 h later, cells were serum starved for an additional 24 h, then treated with Mnk1/2 inhibitor CGP 57380 at the indicated concentrations for 8-10 h. RNA from cells was extracted and the levels of p38α-targets genes; FOS and COX-2 were measured by Q-RT-PCR as described above. (F). MCF-10A cells described in (D) were serum starved for 24 h and then treated with 0.5 μM anisomycin for 24 h and were subjected to trypan-blue exclusion assay (Graph). Bottom panel: cells described in (F) were centrifuged and lysed with Laemmli buffer and proteins were subjected to Western blot analysis. Cleaved caspase-3 served as a marker for apoptosis and β-catenin as a loading control.

FIGS. 8A-H: Phosphorylation of p38-MAPK and eIF4E is regulated by Mnk2 kinase activity and modulates p38α localization.

(A) Cell lines from breast immortal or cancer (MCF-7, MDA-MB-231, SUM-149, SUM-159, MDA-MB-468) cell lines were seeded in 6-well plates and 24 h later were lysed and subjected to Western blot analysis with the indicated antibodies. (B-C) Quantitation of p38 and eIF4E phosphorylation levels. The level of phosphorylated p38 and eIF4E was normalized to that of their total level. Results are presented as an average±SD (n=2). (D-F) Immortal MEFs from WT (Mnk 1/2 WT), Mnk1$^{-/-}$ or Mnk2$^{-/-}$ mice were seeded in 6-well plates. 24 h later cells were either treated with the vehicle (DMSO) or treated with the Mnk1/2 kinase inhibitor, CGP 57380 (CGP) at the indicated concentrations for 4 h, and subjected to Western blot analysis with the indicated antibodies. (G) MCF-10A cells were seeded in 6-well plates, treated and analyzed as in (D). (H) Distribution between cytoplasmic (C) and nuclear (N) fractions of p38α, p-p38α and T7-Mnk2 isoforms in MCF-10A cells transduced with Mnk2 isoforms or a kinase-dead version of Mnk2a (Mnk2aKD). C-myc (nuclear) and caspase-2 (cytoplasmic) served as fractionation controls.

Figure 9:
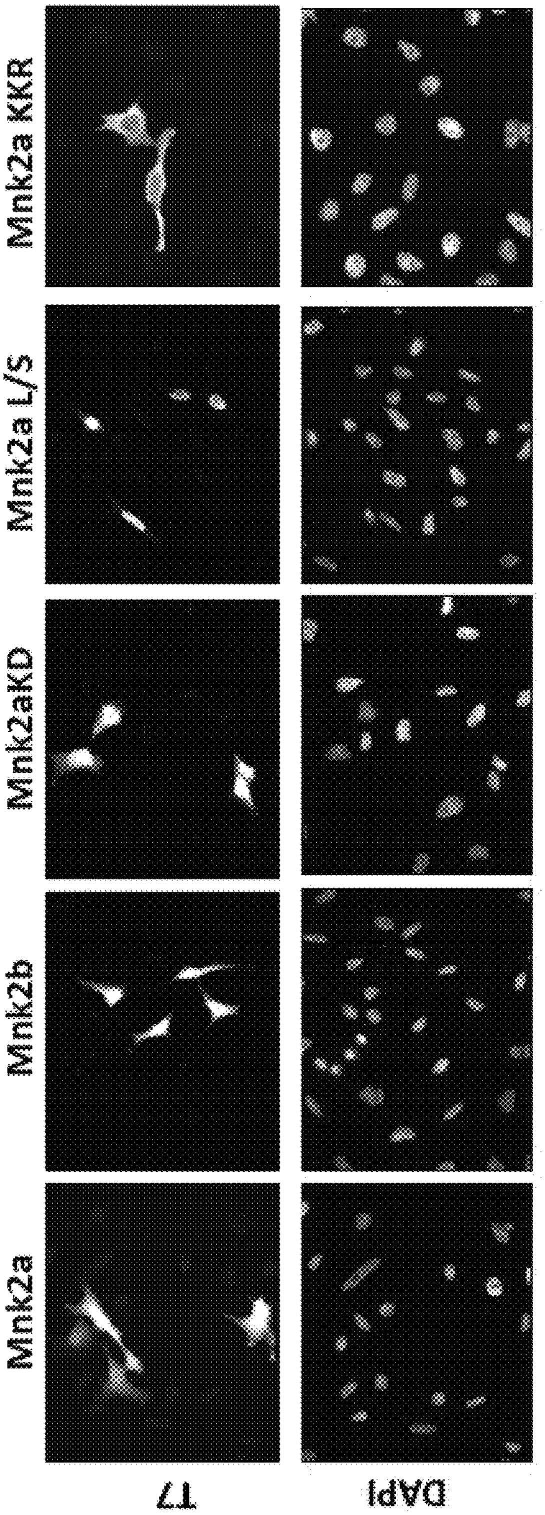

FIG. 9: Cellular localization of Mnk2 isoforms, Mnk2aKKR and Mnk2aL/S mutants. HeLa cells were seeded on a coverslip in 12-well plates and 24 h later were transfected with pCDNA3 vectors encoding for T7-Mnk2 isoforms, Mnk2aKD, Mnk2aL/S and Mnk2aKKR. 24 h posttransfection cells were fixed with 4% paraformaldehyde and subjected to immunofluorescence assay using an antibody against the T7 tag, as described in Experimental procedures.

FIGS. 10A-D: Mnk2a mutants colocalized, interact with and can induce phosphorylation of p38α.

(A) HeLa cells were seeded on a coverslip in 12-well plates and 24 h later were co-transfected with empty vector pCDNA3 or with pCDNA3 encoding for T7-Mnk2a, Mnk2aL/S and Mnk2aKKR and HA-tagged p38α. 24 h posttransfection cells were fixed with 4% paraformaldehyde and subjected to immunofluorescence assay, as described in Experimental procedures (Mnk2 was stained green and HA-tag was stained red). (B) Quantification of cytoplasmic/nuclear distribution of HA-p38α in cells similar to those described in (A). n=35 cells for each mutant. (*, **p≤0.01).

(C) HeLa cells were seeded and 24 h later were co-transfected with pCDNA3 vectors encoding for T7-Mnk2a, Mnk2aL/S and Mnk2aKKR and HA-tagged p38α. Cells were lysed 48 h posttransfection and the Mnk2a mutants and p38α were co-immunoprecipitated as described in the Experimental procedures Immunoprecipitated and input proteins were subjected to Western blot analysis with the indicated antibodies. (D) Correlation between T7-Mnk2a localization (Cy3) and GFP-p38α localization (FITC) in 40 HeLa cells co-transfected with T7-Mnk2a and GFP-p38α as described in FIG. 6A (pearson correlation=0.358).

FIGS. 11A-F. Expression of housekeeping genes in MCF-10A cells expressing Mnk2a isoforms and mutants and in WT and Mnk2$^{-/-}$ MEFs.

(A,D) Expression of FOS, COX-2, GAPDH, HPRT and krt14 mRNAs as measured by Q-RT-PCR (normalized to beta actin) in MCF-10A cells expressing Mnk2 isoforms and mutants. (B, E) Expression of FOS, COX-2, GAPDH, HPRT and krt14 mRNAs was measured as in (A) in MCF-10A cells expressing Mnk2a shRNAs. (C, F) Expression of FOS, COX-2 and Ndufb9 mRNAs was measured as in (A) and normalized to GAPDH. The levels of each mRNA are presented relative to the empty vectors pBABE or MLP or WT MEFs that were arbitrarily set as one.

Figure 12B:
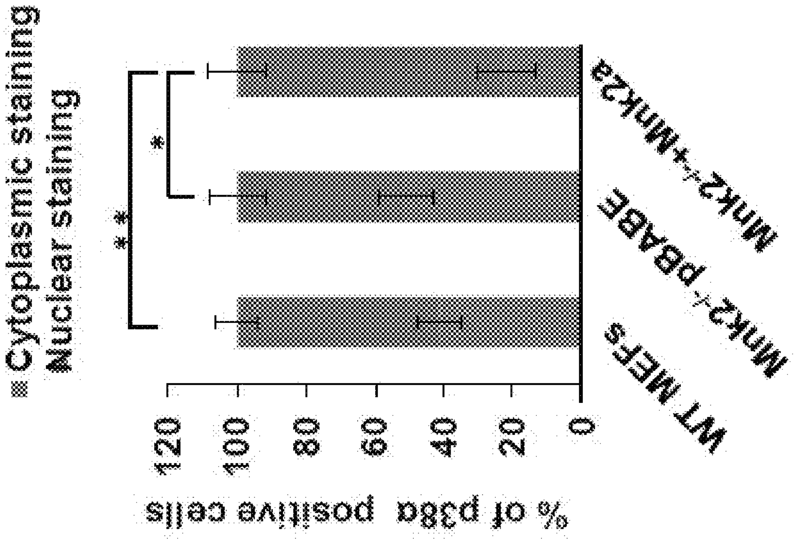
Figure 12A:
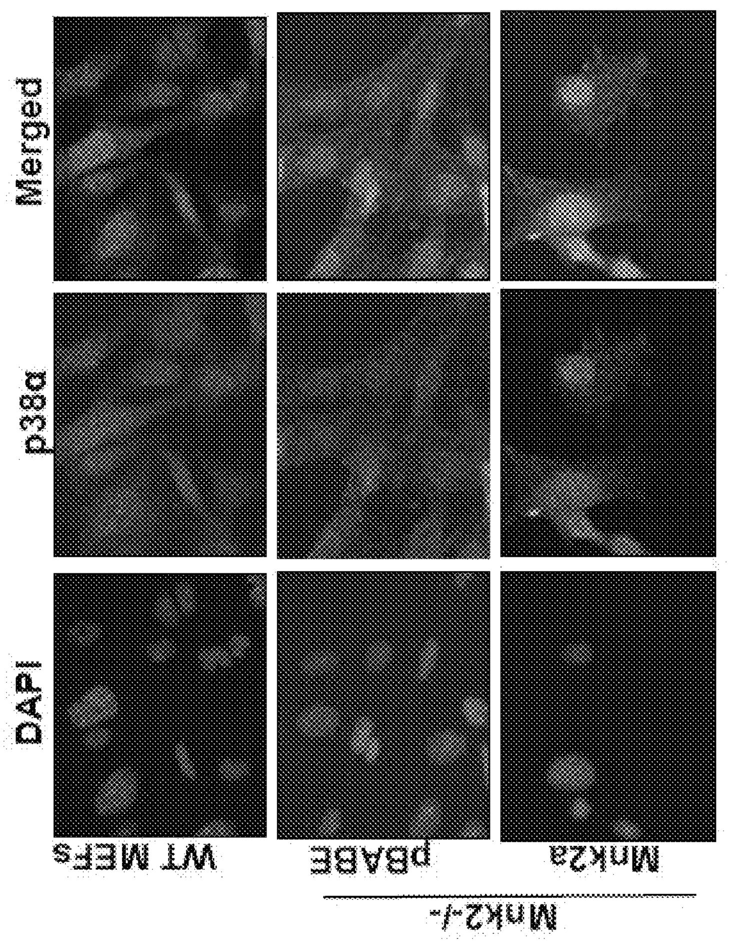

FIGS. 12A-B: Mnk2a induces translocation of endogenous p38α-MAPK into the nucleus. (A) Pools of Mnk2$^{-/-}$ MEFs were transduced with empty vector (pBABE) or a retrovirus encoding Mnk2a, selected with puromycin and seeded on a coverslips in 12-well plates alongside with WT MEFs. 24 h later cells were fixed with 4% paraformaldehyde and subjected to immunofluorescence assay as described in Experimental procedures. Endogenous p38α is shown in green. (B) Quantification of cytoplasmic/nuclear distribution of endogenous p38α in WT MEFs or Mnk2$^{-/-}$ MEFs transduced with pBABE or retrovirus expressing Mnk2a (n=12 cells for each cell line). (*, **p≤0.01).

Figure 13A:
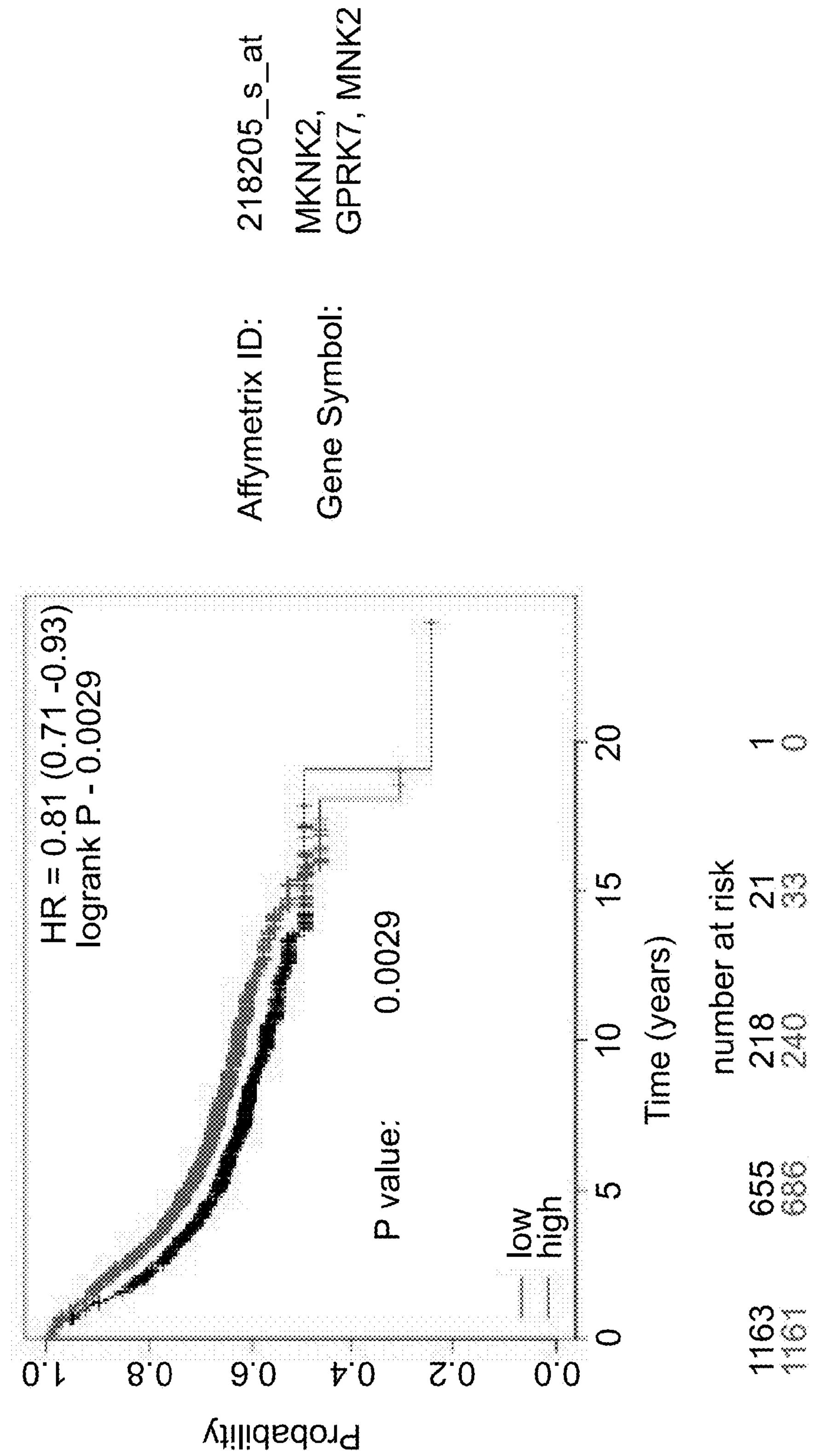
Figure 13B:
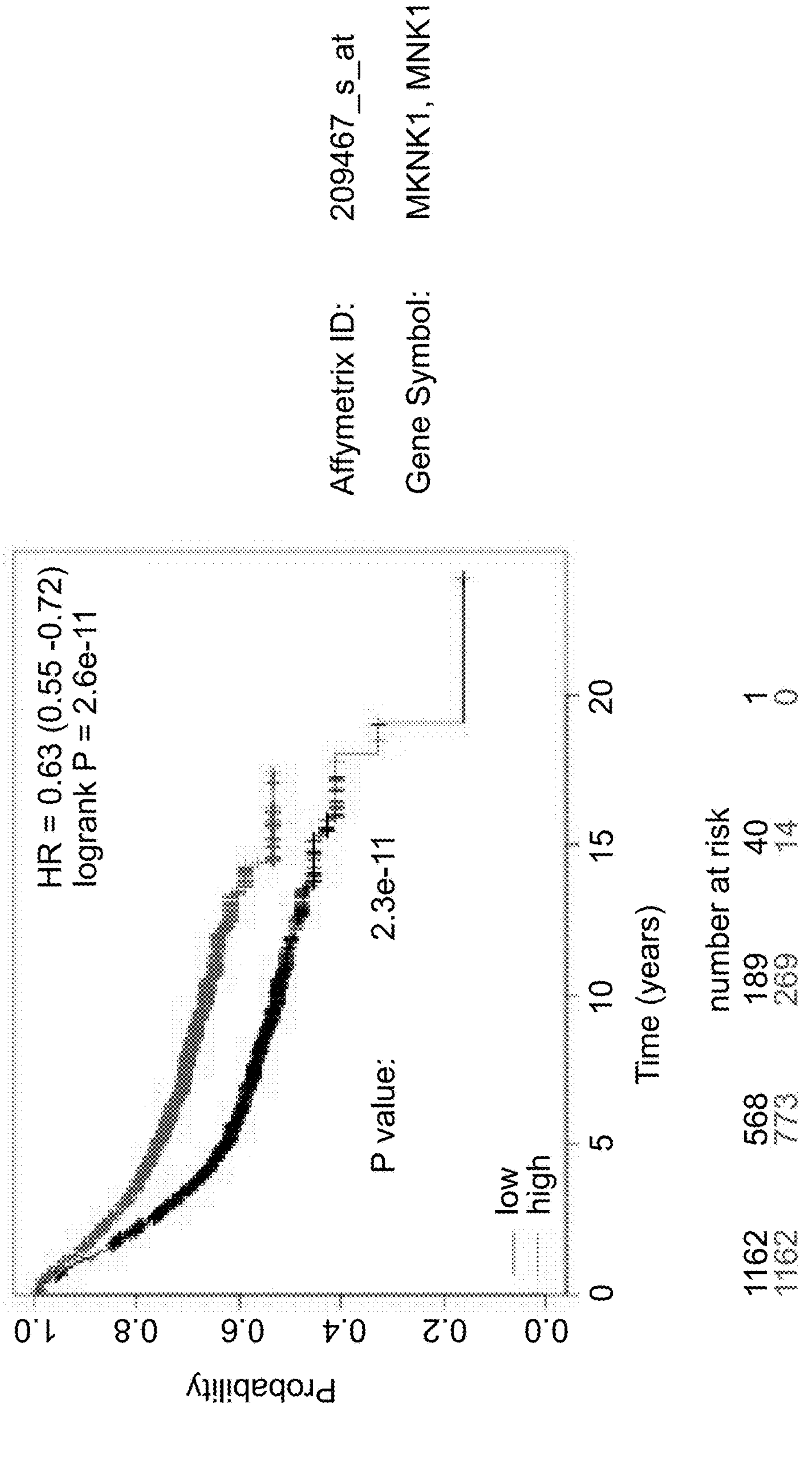

FIGS. 13A-B. MKNK1 and MKNK2 expression correlates with good survival of breast cancer patients. Kaplan-Meier plots of 2324 breast cancer patients with high (Over 2 fold, red), or intermediate (black) expression. A. MKNK2. B. MKNK1. Analysis was performed using kmplot.

Figure 14B:
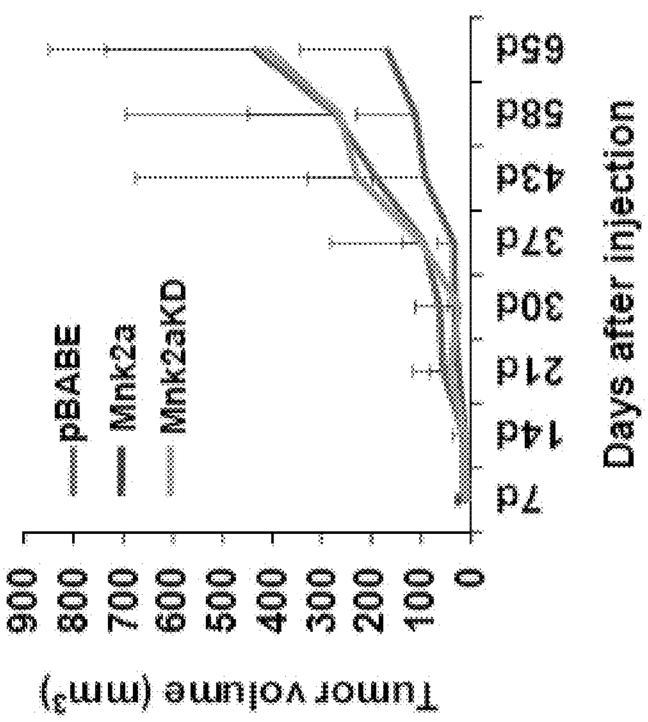
Figure 14A:
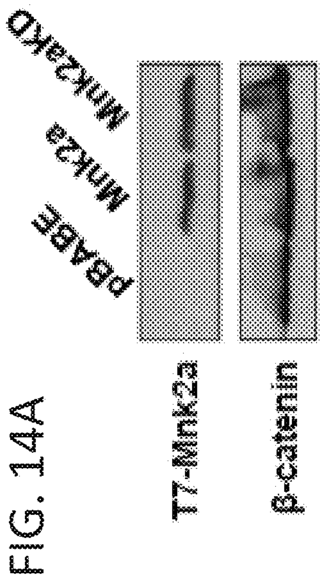

FIGS. 14A-B: Mnk2a delays tumor growth of Panc-1 cancer cells in vivo. A. Pools of the pancreatic cancer cell line Panc-1 were transduced with the indicated retroviruses encoding either Mnk2a or its kinase-dead version (Mnk2aKD) and after selection were lysed and subjected to Western blot analysis. Membranes were probed with the indicated antibodies. B. Cells described in (A) were injected ($2\times10^6$ cells/injection) subcutaneously into both rear flanks of nude mice. Tumor volume was calculated as described in Experimental procedures.

Figures 15A, 15B, 15C:
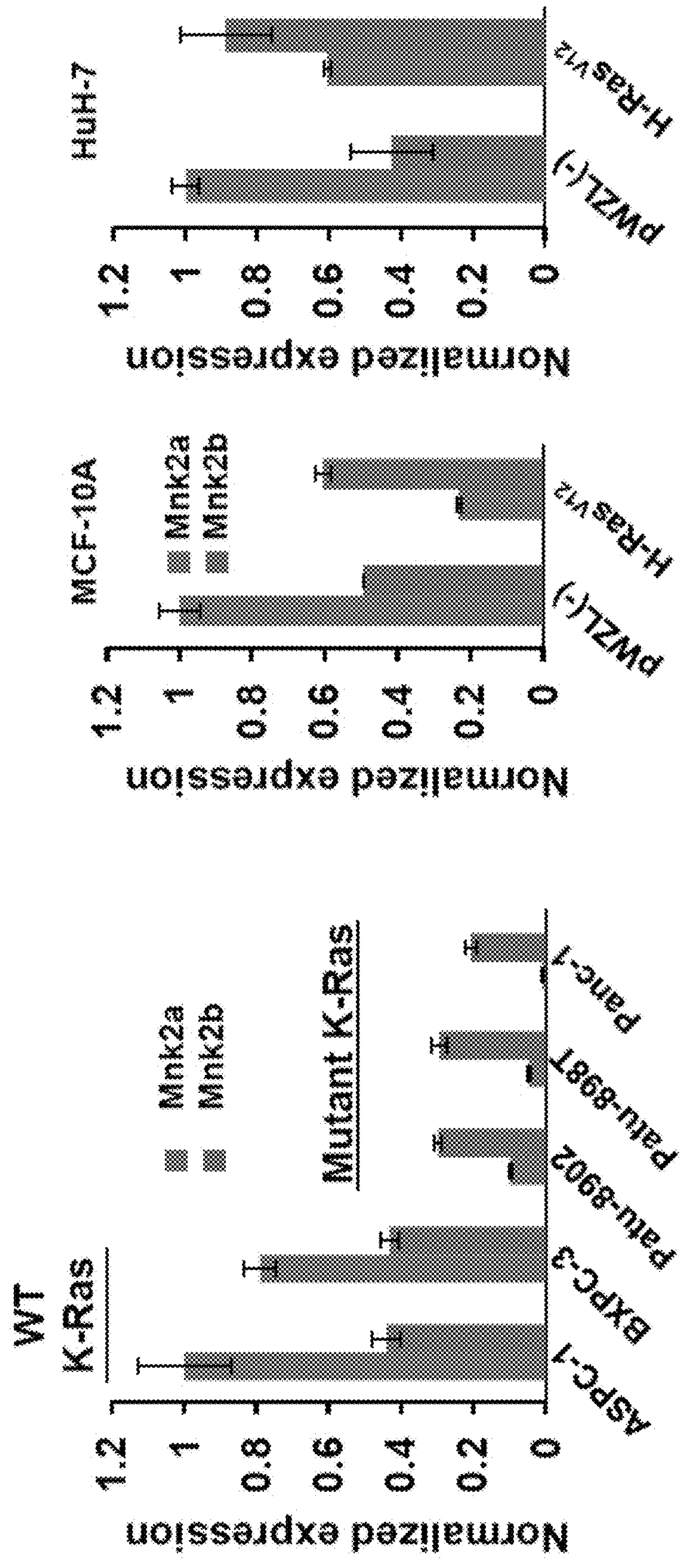
Figure 16B:
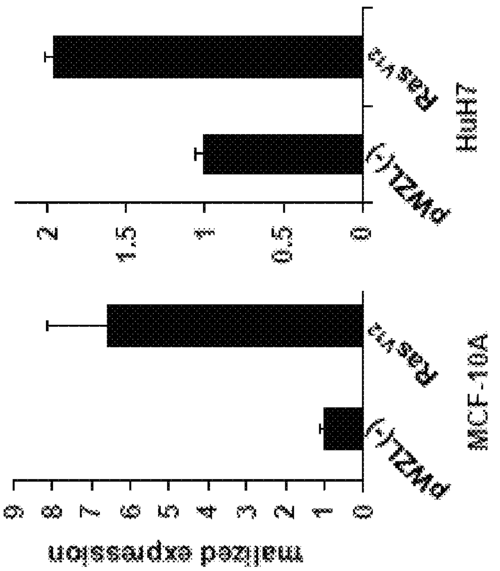
Figure 16A:
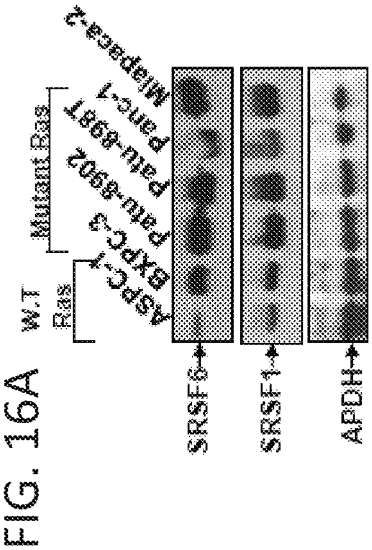
Figure 16D:
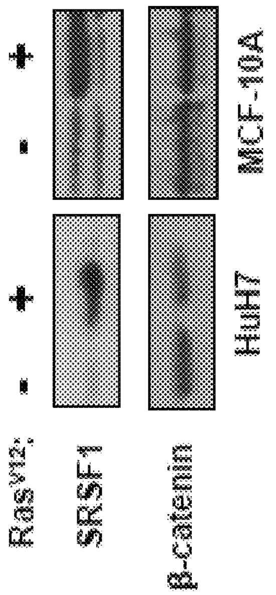
Figure 16C:
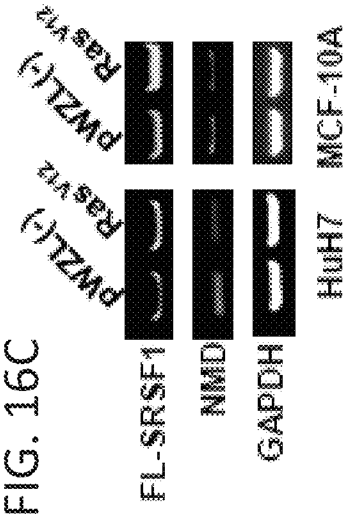

FIGS. 15A-C: A switch in MKNK2 alternative splicing in primary tumors and tumor cell lines. (A) RNA from the indicated pancreatic cancer cell lines was extracted and levels of Mnk2a and Mnk2b were detected by Q-RT-PCR. RNA from MCF-10A (B) and HuH-7 (C) transformed with pWZL empty or pWZL-H-Ras$^{V12}$ was extracted and the levels of Mnk2a and Mnk2b were detected by Q-RT-PCR.

FIGS. 16A-D. Increased RNA and protein levels of SRSF1 are found in Breast and Pancreatic cancer cell lines, and are modulated by the Ras oncogene.

(A) Cells from pancreatic cancer cell lines harboring WT or oncogenic K-ras mutations were lysed and proteins separated by SDS-PAGE. After Western blotting membranes were probed with the indicated antibodies to detect the levels of SRSF1 and SRSF6. GAPDH levels served as control. (B) RNA from MCF-10A and HuH7 cell lines transduced with empty vector or with pWZL H-RAS$^{V12}$ retroviruses cells was extracted and the levels of SRSF1 was detected by Q-RT-PCR. (C) RNA from cells described in (B) was subjected to RT-PCR with primers that detect the NMD-prone or normal (FL) SRSF1 transcript. (D) Cells described in (C) were lysed and subjected to Western blot analysis. The levels of SRSF1 were detected by specific antibodies. β-catenin level served as loading control.

FIGS. 17A-D: Increased expression of human S6K1 short variants 6A and 6C in breast cancer cell lines and tumors. A. Schematic representation of RPS6KB1 pre-mRNA and its splicing isoforms. Isoform-1 (encoding for p70/p85 S6K1 protein) is composed of 15 exons (blue boxes). S6K1 mouse spliced variant-2 (Iso-2) contains three alternative exons between exon 6 and 7; a,b,c (red boxes) a different poly adenylation site and 3' UTR region (yellow area) and a stop codon in exon 6C. Human short S6K1 isoforms, h6C and h6A, lack the alternative 6b exon and contain a combination of two alternative exons: exon a followed by 3' UTR or followed by exon c. In both cases, a stop codon in exon a terminates translation at the same amino acid and both transcripts give rise to one protein, h6A. The other isoform includes only exon 6C followed by a poly A tail and encodes a protein with a different C-terminus. All S6K1 short variants are identical up to the $6^{th}$ exon, and differ from Iso-1, and from each other in their C-terminus. B. RNA from the indicated immortalized breast cell lines (HMLE, MCF-10A) or breast cancer cell lines (MCF-7, BT474, T47D, ZR-75-1, MDA-MB-231, MDA-MB-468, SUM149, SUM159) was extracted and the levels of S6K1 h6A and h6C short isoforms and Iso-1 were detected by RT-PCR with primers specific for each isoform. The splice variants are indicated by boxes at the right side of each transcription variant. C-D. qRT-PCR quantitation of S6K1 isoforms: Iso-1, h6A and h6C. Quantitation was done on total RNA extracted from breast cell lines (C) or tumors (D). All samples were normalized to β-actin mRNA levels and to the average expression of the immortal breast cell lines (HMLE and MCF-10A)(Error bars represent standard deviation (SD) of 3 repeats).

FIGS. 18A-G: Increased Expression of Human S6K1 Short Variants 6A and 6C in Lung and Breast Cancer Cell Lines and Tumors, Related to FIG. 17. (A and B) RNA from the indicated immortalized breast cell line (HMLE, MCF-10A) or breast cancer (MCF-7, BT474, ZR751, HS578T, MDA-MB 157, T47D) (A) and lung cancer (H727, LcLc103H, H460) cell lines (B) was extracted and the levels of S6K1 h6A and h6C short isoforms and p70/p85 Iso-1 were detected by RT-PCR with primers specific for each isoform. The splice variants are indicated by boxes at the right side of each transcription variant. (C) Immunoprecipitation (IP) and western blot for detection of S6K1 endogenous isoforms using a monoclonal antibody against the N0 terminus of S6K1 and a secondary True Blot antibody that detects only the membrane probed antibody without residual signal from the heavy or light chain present in the lysate from the IP. b-actin was analyzed as a total protein control. (D) Sequenced PCR fragments isolated from MCF-7 and BT-474 cDNA represent alternative exon inclusion of both a and c (upper sequence-414 bp-SEQ ID NO: 168) or h6C alone (lower sequence-339 bp-SEQ ID NO: 169). Green sequence represents end of exon 5 forward primer, red sequence represents end of exon c reverse primer. (E) Full intronic sequence (SEQ ID NO: 170) residing between exon 6-7 taken from the Ensemble browser. Sequence marked in yellow or light blue represents alternative exons a and c respectively. Sequence marked in red represents translational stop codon, magenta sequence represents polyadenylation signal and light green represents weak polyadenylation signal. (F and G) Q-RT-PCR calculated ratio of S6K1 short isoforms (h6A and h6C) expression normalized to the long isoform Iso-1. Quantitation was done on total RNA extracted from breast cell lines (F) or tumors (G). All samples were normalized to the average expression of the two immortal breast cell lines (HMLE and MCF-10A).

FIGS. 19A-E: S6K1 short isoforms enhance transformation of breast epithelial cells. A. The predicted protein structure of mouse and human RPS6KB1 splicing isoforms. All isoforms contain Raptor binding motif mTOR-signaling (TOS) at the N terminus (white boxes), and a lysine residue (K123) at the ATP binding site in the catalytic domain that is essential for its protein kinase activity. S6K1 isoform-1 kinase dead version (Iso-1 K123>A) contains a lysine to alanine (K123A) substitution. S6K1 short isoforms lack 6 out of the 12 conserved kinase helical domains as well as the C-terminal autoinhibitory domain which harbors the mTOR activatory phosphorylation site at threonine 389. B. MCF-10A cells were transduced with retroviruses encoding for the indicated S6K1 isoforms and protein extracts subjected to Western blotting. Membranes were probed with a monoclonal antibody against the N' terminus of S6K1 to detect the endogenous and exogenous isoforms. β-actin was analyzed as a loading control. C. Pools of MCF-10A cells transduced with the indicated retroviruses as in (B) were seeded into soft agar in duplicates and colonies were allowed to grow for 14 days. Data represent the average number±SD of colonies per well. n=2. $*p=0.0049**p\leq0.005$ relative to empty vector. The results shown are a representative experiment out of three individual experiments. An unpaired, two-tailed t test was used to determine p values for FIG. 19C. D. MCF-10A pools of cells transduced with the indicated retroviruses as in (B) were stimulated to migrate by physical wounding of cells seeded in monolayer. n=3. E. Representative images of the wound area of cells described in (D).

FIGS. 20A-G: S6K1 Short Isoforms Transform NIH 3T3 Cells and Are Catalytically Inactive, Related to FIG. 19A-E. (A) MCF-10A cells were transduced with retroviruses encoding for the indicated T7-tagged S6K1 isoforms. Total protein from stable pools was extracted separated by SDS-PAGE and subjected to western blot analysis with monoclonal antibody against the T7-tag to detect the exogenous isoforms. b-actin was analyzed as a loading control. (B) NIH 3T3 cells transduced with the indicated retroviruses. Total protein from stable pools was extracted and separated by SDSPAGE. After western blotting the membranes were probed with a monoclonal antibody against the N0 terminus of S6K1 to detect the endogenous and exogenous isoforms. (C) NIH 3T3 cells described in (B) were seeded into soft agar in duplicates and colonies were allowed to grow for 21 days. Colonies in ten fields of each well were counted and representative fields of colonies were photographed in phase image (×100 magnification). Data represent the average number±SD of colonies per well. n=2. The results shown are a representative experiment of at least three individual experiments. (D) MCF-10A cells transduced with the indicated retroviruses as in (A) were seeded (2000 cells/well) into 96 wells. Growth curves were measured as described in Materials and methods. Results represent means±SD (n=6). Results in (D) were obtained in three independent experiments. (E) S6K1 and S6K2 double-knockout (DKO) mouse embryonic fibroblasts (MEFs) cells transduced with retroviruses encoding for empty vector (pBABE), S6K1 Isoform-1 (Iso-1), mouse S6K1 Isoform-2 (Iso-2), and its Kinase Dead (KD) version. Total protein from wild-type (WT), non-transduced and stable pools was extracted and separated by SDS-PAGE. After Western blotting the membranes were probed with a monoclonal antibody against the N0 terminus of S6K1 to detect the endogenous and exogenous isoforms, phospho-S6 (S240-244), S6 and b-catenin as a loading control. (F and G) HEK293 cells were transfected with empty vector (PCDNA3[_]) or the indicated T7-tagged S6K1 isoforms. Whole cell lysates were examined to assess expression levels of the constructs (F) and for immunoprecipitation (IP) of T7-tagged S6K1 isoforms (G). The activity of immunoprecipitated T7-tagged S6K1 was assayed using recombinant GST-S6 as a substrate. Each in vitro kinase assay was subjected to Western blot analysis using the indicated antibodies; phospho-S6 (S240-244), GST and monoclonal antibody against the T7-tag to detect the transfected isoforms. Secondary antimouse True Blot antibody was used to detect only the membrane probed antibody without the heavy or the light chain that remains in the lysate from the IP.

FIGS. 21A-G: S6K1 inactive isoforms enable growth factor-independent three dimensional growth of MCF-10A cells and enhance 4E-BP1 phosphorylation. A-C. Phase images of MCF-10A cells transduced with the indicated retroviruses seeded in matrigel as described in Materials and methods, in the absence of EGF (A), Insulin (B) or in the presence of both (C). Cells were allowed to grow for two weeks to form acini structures. These results were obtained in at least 3 individual experiments. (D-G) Total protein was isolated from cells and subjected to Western blotting using the indicated antibodies. D-E. MCF-10A transduced cells described above were seeded in 6 well plates ($3\times10^5$ cells/well). Cells were starved for 24 h and then induced with EGF (D) or IGF-1 (E) for 4 h. Fold increase of 4E-BP1 was normalized (Phosphorylated/total protein levels) to that of untreated (starved) pB(−) (empty vector) which was arbitrarily set at 1 (Quantitation values are shown under each panel). F. MCF-10A cells were transduced with the indicated retroviruses expressing empty vector (mlp(−)) or the indicated S6K1 Iso-1-specific shRNAs (Karni et al., 2007). G. MCF-10A cells transduced with the indicated retroviruses as described in (F) were grown for 24 h in the presence of 0.5% or 5% serum. Arrows show the phosphorylation states of 4E-BP1, where gamma is the fully phosphorylated form. β-actin was analyzed as a loading control.

FIGS. 22A-E: S6K1 Kinase Inactive Isoforms Enhance 4E-BP1 Phosphorylation with Only Slight Effect on Akt and ERK Phosphorylation, Related to FIG. 21. (A) Phase images of MCF-10A cells transduced with the indicated retroviruses seeded in matrigel as described in Materials and Methods, in the absence of EGF and allowed to grow for 2 weeks to form acini structures. In the lower panel acini were stained with the DNA dye Sytox-green to visualize acini structure and lumen filling by confocal microscopy. (B-D) MCF-10A transduced cells expressing the indicated S6K1 isoforms were seeded in 6 well plates (3×105 cells/well). Cells were starved for 24 h and then induced with the indicated growth factor (EGF, 4 h) (B), (IGF-1, 4 h) (C), or IGF for 24 h (D). Fold increase of Akt or ERK phosphorylation (phospho-ERK or Akt/total ERK or Akt) was normalized to that of untreated pB (empty vector) which was arbitrarily set at 1. Western blots were carried out using the indicated primary antibodies. (E) Western blot analysis showing the phosphorylation status of 4E-BP1 in immortal (HMLE, MCF-10A) and breast cancer cell lines (MCF-7, MDA-MB 231, MDAMB 486, Sum 159).

FIGS. 23A-E. S6K1 Iso-1 knockdown increases transformation and its over expression blocks RAS-induced transformation in vitro and in vivo. A. MCF-10A pools of cells were transduced as in (FIG. 21F), seeded into soft agar in duplicates and colonies were allowed to grow for 14 days. Data represents the average number±SD of colonies per well. n=2. B. MCF-10A cells were transduced with retroviruses encoding pB(−) empty vector or S6K1 Iso-1 followed by transduction with an active Ras mutant (H-Ras$^{v12}$). Cells were seeded into soft agar in duplicates and colonies were allowed to grow for 14 days. C. MCF-10A pools of cells transduced with the indicated retroviruses as in (B) were photographed 24 h after seeding (×100 magnification). D. RAS-transformed MCF-10A cells expressing empty vector (pB(−)) or S6K1 Iso-1 were injected into NOD-SCID mice ($2\times10^6$ cells/injection). Tumor volume was measured weekly and tumor growth curve was calculated as described in Materials and methods; error bars indicate SD of 8 tumors. n/n=number of tumors per number of injections. E. Ras transformed MCF-10A cells expressing the indicated retroviruses as described in (B). Total protein from stable pools was extracted and subjected to Western blotting. The membranes were probed with the indicated antibodies. β-actin was analyzed as a loading control.

FIGS. 24A-G Knockdown of S6K1 Iso-1 Enhances Colony Formation in Soft Agar, Motility, and Acini Formation, Related to FIG. 23. (A) NCI-H460 Lung cancer cells were transduced with the indicated retroviruses expressing empty vector (MLP[_]) or the indicated S6K1 Iso-1-specific shRNAs. Total protein from stable pools was extracted and separated by SDS-PAGE. After western blotting the membranes were probed with a monoclonal antibody against the N0 terminus of S6K1 to detect the endogenous isoforms. b-actin was analyzed as a loading control. (B) NCI-H460 pools of cells transduced with the indicated retroviruses as in (B) were seeded into soft agar in duplicates and colonies were allowed to grow for 14 days. Colonies in ten fields of each well were counted and representative fields of colonies were photographed in phase image (×10 magnification). Data represent the average number±SD of colonies per well. n=2. (C) MCF-10A cells transduced with the indicated retroviruses expressing empty vector (MLP[_]) or the indicated S6K1 Iso-1-specific shRNAs were seeded in matrigel as described in Materials and Methods, in the presence of insulin and in the absence of EGF. Acini were photographed after 13 days. (D) MCF-10A pools of cells transduced with the indicated retroviruses as in (C) were stimulated to migrate by physical wounding of cells seeded in monolayer. Data represent the average number of quantified wound area from three individual experiments. (E) RAS-transformed MCF-10A cells expressing S6K1 Iso-1 or empty vector (pB) were lysed and total protein was extracted and separated by SDS-PAGE. After Western blotting the membranes were probed with the indicated antibodies. (F) photos of representative mice bearing tumors mentioned in FIG. 4E. (G) Ras transformed MCF-10A cells expressing S6K1 Iso-1 or empty vector (pB) were transfected with dual reporter vector (Cap-Renilla-IRES-Luciferase) and starved 24 h post transfection. Cap-dependent translation (Renilla luciferase activity) and IRES-mediated translation (Firefly luciferase activity) were measured (n=3 experiments, *p=0.003; n.s., no statistical significance).

FIGS. 25A-F. S6K1 kinase short isoforms interact with mTOR, enhance cap-dependent translation and increase Mcl-1 expression. A-B. HEK293 cells were co-transfected with myc-tagged mTOR and the indicated T7-tagged S6K1 isoforms. Whole cell lysates were examined for construct expression (A) and for immunoprecipitation of T7-tagged S6K1 isoforms (B). Myc-tagged bound mTOR and T7-tagged S6K1 isoforms were detected by immunoblotting using anti-myc or monoclonal antibody against the N' terminus of S6K1, respectively. First two left lanes represent anti T7 antibody alone, and pull down from untransfected HEK293 cells, respectively. An unpaired, two-tailed t test was used to determine p values for FIG. 25B. C. Schematic representation of pLPL Cap-Renilla-IRES-Luciferase bicistronic dual reporter vector (Gerlitz et al., 2002). D. MCF-10A cells were co-transfected with dual reporter vector (C) and with the indicated S6K1 isoforms and starved for serum and growth factors for 24 h post transfection. Cap-dependent translation (Renilla luciferase activity) and IRES-mediated translation (Firefly luciferase activity) were measured (n=4 experiments, *p 0.019, p=0.008, *p=0.033). E. MCF-10A cells were transduced with retroviruses encoding for the indicated S6K1 isoforms. $3\times10^5$ transductants were seeded in 6 well plates and starved for 24 h for serum and growth factors. After Western blotting the membranes were probed with the indicated antibodies. β-catenin was analyzed as a loading control. F. MCF-10A cells described in (FIG. 3F) were seeded ($3\times10^5$ cells/well) in 6-well plate. 24 h later cells were lysed, total protein was extracted and separated by SDS-PAGE. The membranes were probed with the indicated antibodies. β-actin was analyzed as a loading control.

Figure 25B:
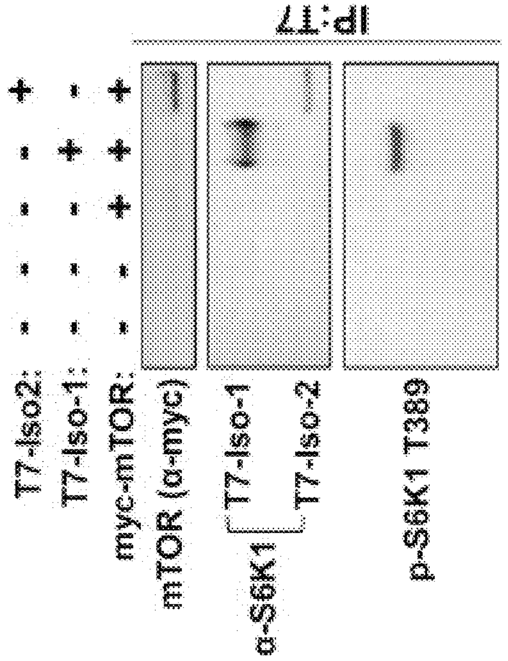
Figure 25A:
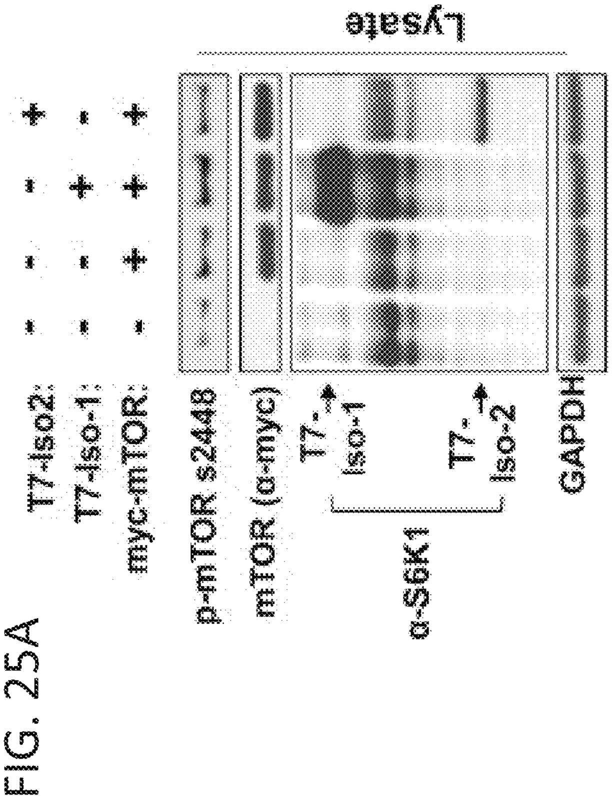
Figures 25C, 25D, 25E, 25F:
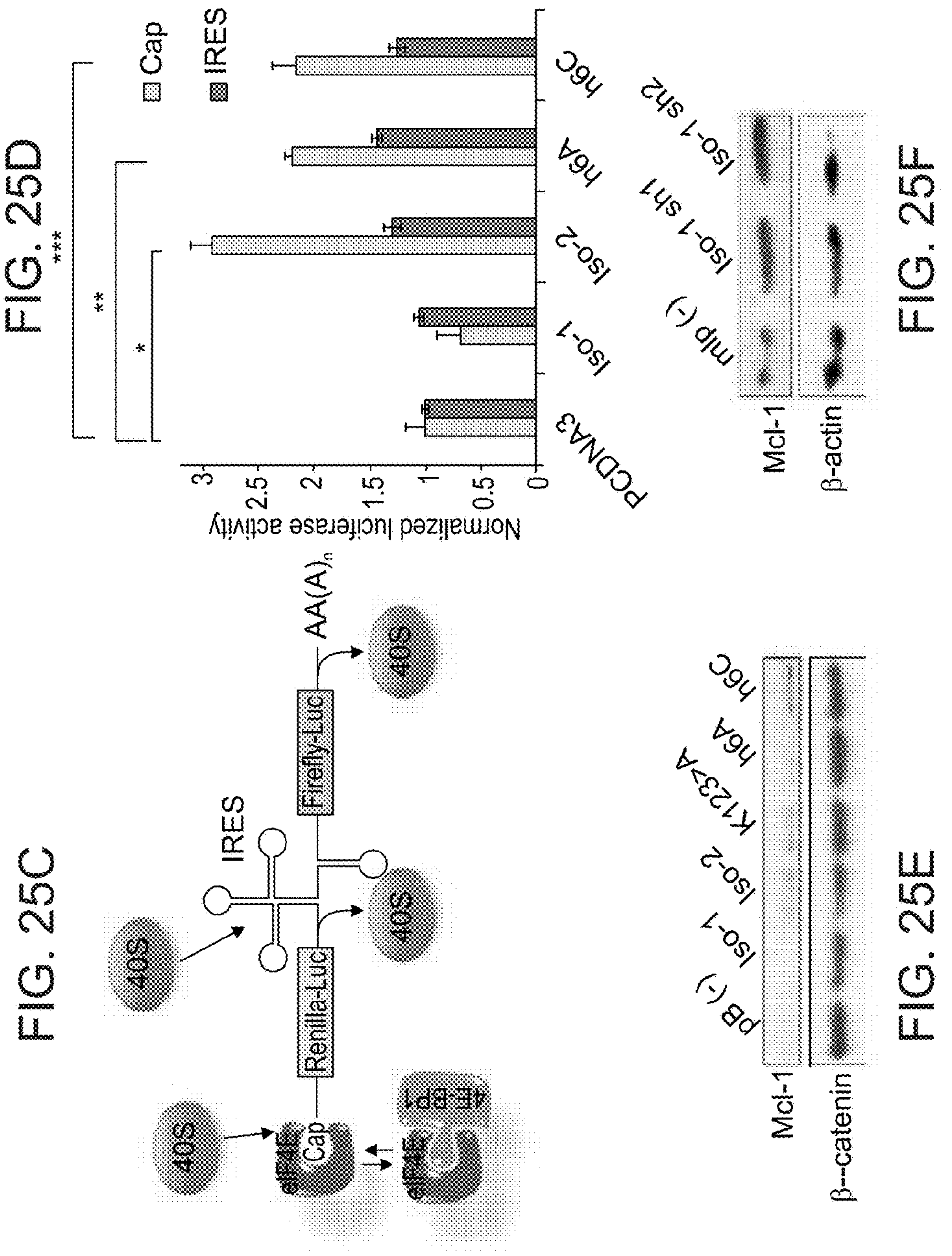
Figure 26B:
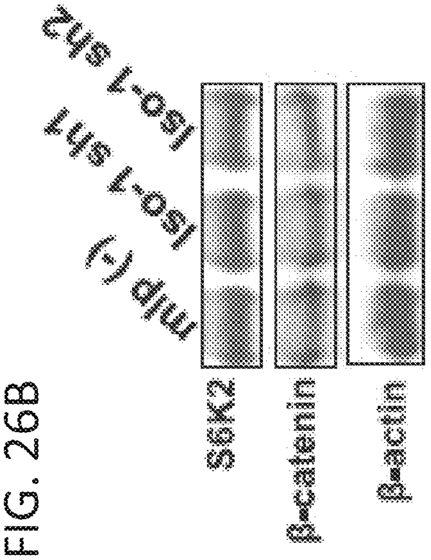
Figure 26A:
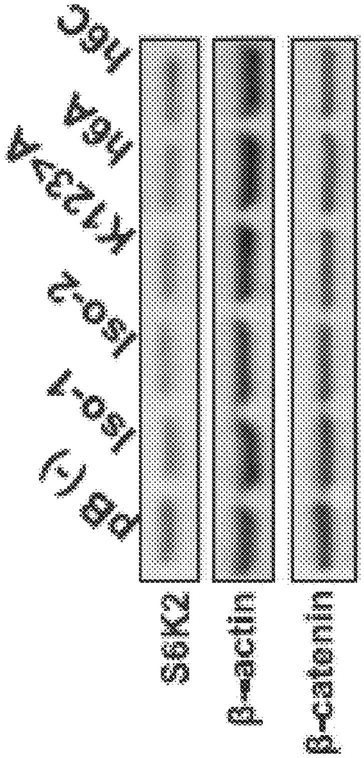

FIGS. 26A-B. S6K1 Iso-1 Overexpression or Silencing Does Not Effect S6K2 Expression, Related to FIG. 25. (A) MCF-10A cells were transduced with retroviruses encoding for the indicated T7-tagged S6K1 isoforms. Total protein from stable pools was extracted and separated by SDS-PAGE. After western blotting the membranes were probed with the indicated antibodies. b-catenin and b-actin were analyzed as a loading control. (B) MCF-10A cells were transduced with the indicated retroviruses expressing empty vector (mlp[_]) or the indicated S6K1 Iso-1-specific shRNAs were seeded in 6 well plates and lysed the day after. Total protein from stable pools was extracted and separated by SDS-PAGE. After western blotting the membranes were probed with the indicated antibodies. b-catenin and b-actin were analyzed as a loading control.

FIGS. 27A-G. Loss of S6K1/2 enhances cap-dependent translation, Mcl-1 expression and transformation. A. Wild type (WT) or S6K1 and S6K2 double-knockout (DKO) mouse embryonic fibroblasts (MEFs) were seeded at 80% confluency and serum starved for 5 hours. Total protein was extracted and subjected to Western blotting. The membranes were probed with the indicated antibodies. B. WT and DKO MEFs were seeded into soft agar in triplicates and colonies were allowed to grow for 14 days. Data represents the average number±SD of colonies per well. n=3. The results shown are a representative experiment out of three individual experiments. C. WT and DKO MEFs were transfected with dual reporter vector (Cap-Renilla-IRES-Luciferase described in FIG. 25C). 24 h post transfection cells were serum starved for another 24 h. Cap-dependent translation (Renilla luciferase activity) and IRES-mediated translation (Firefly luciferase activity) were measured (Data represents the average number±SD of n=6 experiments). D. Total protein from WT and DKO MEFs described in (A) was separated by SDS-PAGE. After Western blotting the membranes were probed with the indicated antibodies. E. S6K1 and S6K2 DKO MEFs cells transduced with retroviruses encoding for empty vector (pB(−)) or S6K1 Isoform-1 (Iso-1) were transfected with dual reporter vector (Cap-Renilla-IRES-Luciferase) 24 h post transfection cells were serum starved for another 24 h. Cap-dependent translation (Renilla luciferase activity) and IRES-mediated translation (Firefly luciferase activity) were measured (n=3 experiments, *p<0.004). F. MEF cells described in (E) were seeded (200 cells/well) in 6 well plates and grown for 14 days. Colonies were fixed and stained with methylene blue. G. MEF cells described in (E) were seeded into soft agar in triplicates and colonies were allowed to grow for 14 days. Data represent the average number±SD of colonies per well. n=3. The results shown are a representative experiment out of three individual experiments.

Figure 28B:
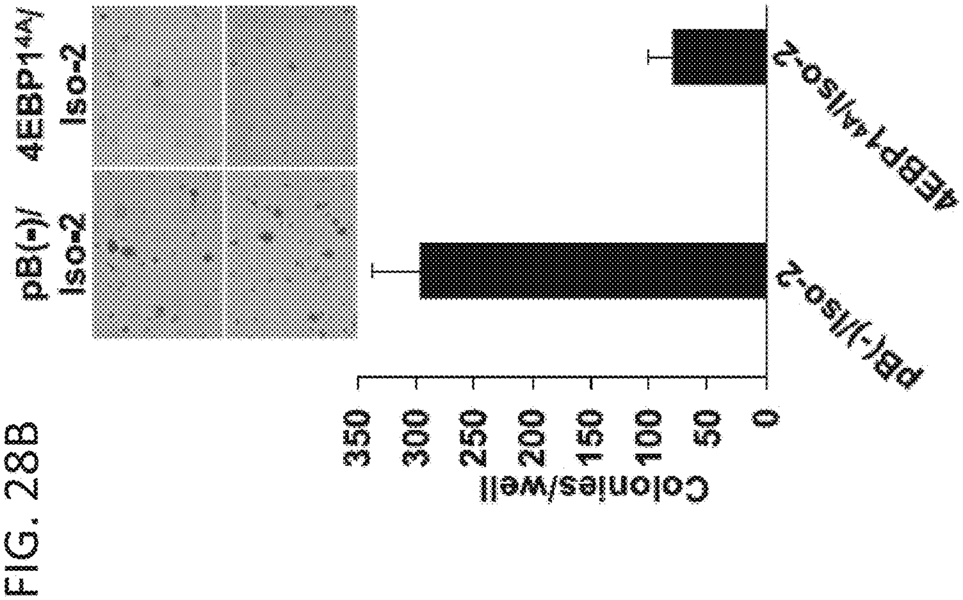
Figure 28A:
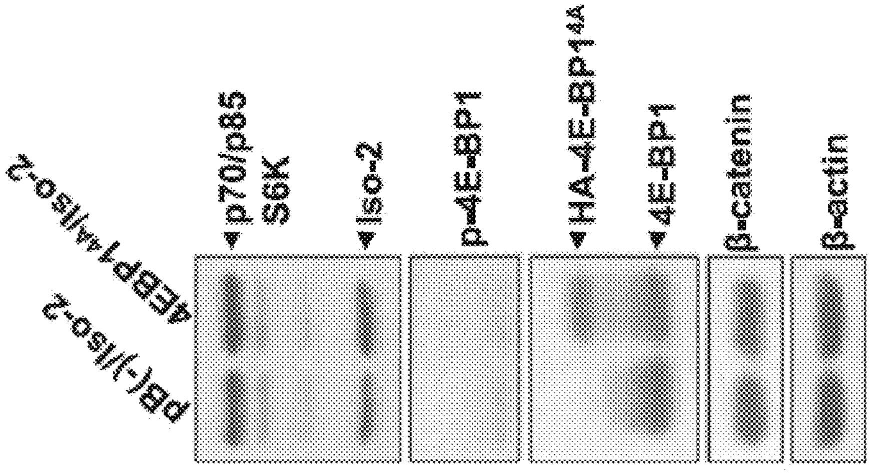

FIGS. 28A-B. S6K1 Iso-2 Transformation Is Mediated by 4E-BP1 Inactivation, Related to FIG. 29. (A and B) MCF-10A cells were transduced with retroviruses encoding for empty vector pBABE (pB) or pB-4E-BP1 phosphorylation defective mutant in which four of the five phosphorylation sites were mutated to alanine (4EBP14A). After puromycin selection the resistant pools of cells were transduced with pWZl-Hygro-Iso2 and selected again for hygromycin. Total protein from stable pools was extracted and separated by SDS-PAGE. After western blotting the membranes were probed with monoclonal antibodies against 4E-BP1 or S6K1 to detect the endogenous and exogenous isoforms. b-actin and b-catenin were analyzed as loading controls, anti-phospho T70 4E-BP1 antibody was used to verify lack of phosphorylation. (B) MCF-10A pools of cells transduced with the indicated retroviruses as in (A) were seeded into soft agar in duplicates and colonies were allowed to grow for 14 days. Colonies in ten fields of each well were counted and representative fields of colonies were photographed in phase image (×10 magnification). Data represent the average number ±SD of colonies per well. n=2. The results shown are a representative experiment out of three individual experiments.

FIGS. 29A-F. 4E-BP1 inactivation and mTORC1 activity is required for the oncogenic activities of S6K1 short isoforms. A. MCF-10A cells were co-transduced with retroviruses encoding for empty vector pWZl-Hygro (pW) or pW-4E-BP1 phosphorylation defective mutant in which all five phosphorylation sites were mutated to alanine (4E-$BP1^{5A}$) and empty vector pBABE (pB(−)) or pB-Iso-2. Total protein from stable pools was extracted and separated by SDS-PAGE. Membranes were probed with monoclonal antibodies against 4E-BP1 or S6K1 to detect the endogenous and exogenous isoforms. β-actin was analyzed as a loading control. B. MCF-10A pools of cells transduced with the indicated retroviruses as in (A) were seeded into soft agar in duplicates, with or without 100 nM Rapamycin and colonies were allowed to grow for 14 days. Colonies from ten fields of each well were counted and representative fields of colonies were photographed in phase image (×100 magnification). Data represents the average number±SD of colonies per well. n=2. C. MCF-10A pools of cells transduced with the indicated retroviruses as in (A) were stimulated to migrate by physical wounding of cells seeded in monolayer. Data represents the average number of quantified wound area and SD from three individual experiments. D. Representative images of the wound area of cells described in C. E. Phase images of MCF-10A cells transduced with the indicated retroviruses seeded in matrigel. Cells were allowed to grow for two weeks to form acini structures. F. A proposed model of mTORC1 regulation by S6K1 isoforms. In non-transformed cells upon mitogen stimulation, S6K1 Iso-1 is activated by mTORC1 and generates a feedback signal loop resulting in phosphorylation of mTOR at S2448 in the repressor domain. This might attenuate mTOR's ability to phosphorylate and repress 4E-BP1 leading to decreased cap-dependent translation. Other cellular substrates might contribute to the tumor suppressive activity of Iso-1 independently of cap-dependent translation (left panel). In transformed cells S6K1 short isoforms are upregulated, bind mTORC1 and increase its activity. mTORC1 activation leads to enhanced 4E-BP1 phosphorylation, cap-dependent translation elevation of the anti-apoptotic protein Mcl-1 and other proliferating or anti apoptotic proteins and increased cell survival and transformation (right panel).

Figure 30A:
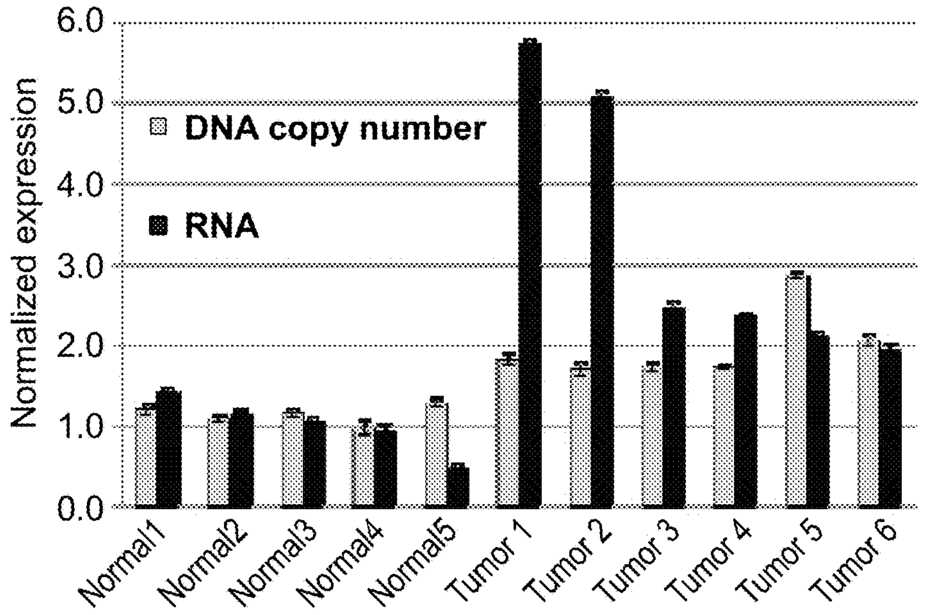
Figure 30B:
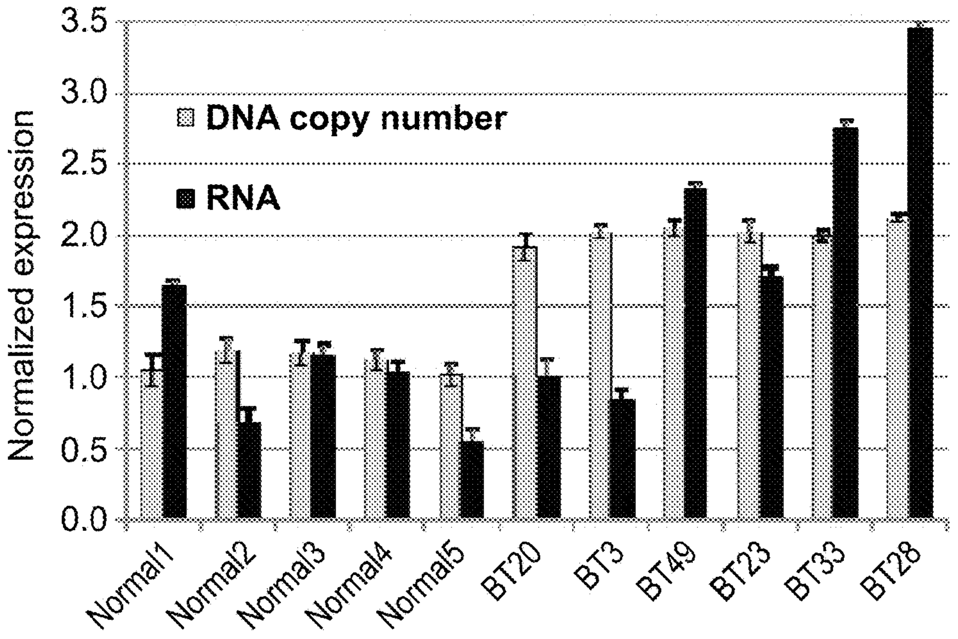

FIGS. 30A-B. Elevated gene copy number and expression of SRSF6 in lung and breast tumors. A-B. Q-PCR and Q-RT-PCR analyses of SRSF6 DNA copy numbers and mRNA expression respectively from five normal lung or six lung tumor tissues (A) or breast normal or tumor tissues (B).

FIGS. 31A-G. SRSF6 enhances proliferation of mouse and human lung epithelial cells and protects them from cell death. A. Pools of mouse lung epithelial cells (MLE) (A-B), or BEAS-2B human lung bronchial cells (C-D) where transduced with the indicated retroviruses encoding SRSF6 or an empty vector. After puromycin selection cells were lysed and after Western blotting membranes were probed with the indicated antibodies against SRSF6, T7. β-catenin served as loading control (A, C). To measure proliferation (B, D) cells mentioned in (A) and (C) were seeded on 96-well plated and proliferation was measured as described in Materials and methods. *p≤0.001**p≤0.001. E. MLE cells were transduced with the indicated retroviruses encoding shRNAs against SRSF6 or an empty vector. After selection levels of SRSF6 knockdown were measured by Western blot analysis as in (A). F. Cells mentioned in (E) were seeded on 96-well plates and proliferation was measured as described in Materials and methods. G. MLE cells described in (A) were seeded on 96-well plates and 24 hours later were treated with cis-platinum (CDDP) and cell survival was measured as described in Materials and methods *p≤1.80018E-06; p≤2.78911E-05; *p≤3.12537E-11.

FIGS. 32A-F. SRSF6 expression induced transformation of mouse and human lung epithelial cells and cooperates with c-myc. Pools of MLE cells were co-transduced with the indicated retroviruses encoding SRSF6 or empty vector, and c-myc. Pools of BEAS-2B cells were transduced with the indicated retroviruses encoding SRSF6 or an empty vector. After puromycin selection cells were seeds into soft agar as indicated in Materials and methods. A. Graph represents the average and standard deviation of number of colonies per plate of MLE cells. n=2*p=1.6787E-09. B. Representative fields of colonies were photographed 14 days after cells were seeded. C. Graph represents the average and standard deviation of number of colonies per plate of BEAS-2B cells n=2. **p=2.9926E-14. D. Representative fields of colonies were photographed 14 days after cells were seeded. E. MLE cells described in (A) were injected ($2\times10^6$ cells/site) into the rear flanks of NOD-SCID mice (n=8) and tumor volume was measured and calculated as described in Materials and methods. F. BEAS-2B cells described in (C) were injected and measured as in (E) (n=8).

FIGS. 33A-H. SRSF6 knockdown inhibits transformation and tumorigenesis of lung and colon cancer cells. A. Pools of NCI-H460 lung cancer cells were transduced with the indicated retroviruses encoding shRNAs or the empty vector and after selection cells were lysed, and after Western blotting membranes were probed with the indicated antibodies against SRSF6 or β-catenin as loading control. B. Cells described in (A) were seeded into soft agar as indicated in Materials and methods. Graph represents the average and standard deviation of number of colonies per plate of MLE cells. n=2. *p=3.9721E-19, **p=6.3129E-21. C. Representative fields of colonies were photographed 14 days after cells were seeded. D. Cells described in (A) were injected ($2\times10^6$ cells/site, n=8) into the rear flanks of Nude mice and tumor volume was measured and calculated as described in Materials and methods. E. Pools of RKO colon carcinoma cells were transduced with the indicated retroviruses encoding an shRNA against SRSF6 or the empty vector and after selection cells were lysed and following Western blotting membranes were probed with the indicated antibodies against SRSF6 or β-actin as loading control. F. Cells described in (E) were seeded into soft agar as indicated in Materials and methods. Graph represents the average and standard deviation of number of colonies per plate of RKO cells. n=2. *p=1.5293E-14. G. Representative fields of colonies were photographed 14 days after cells were seeded. H. Cells described in (E) were injected ($2\times10^6$ cells/site, n=8) into the rear flanks of Nude mice and tumor volume was measured and calculated as described in Materials and methods.

Figures 34A, 34B:
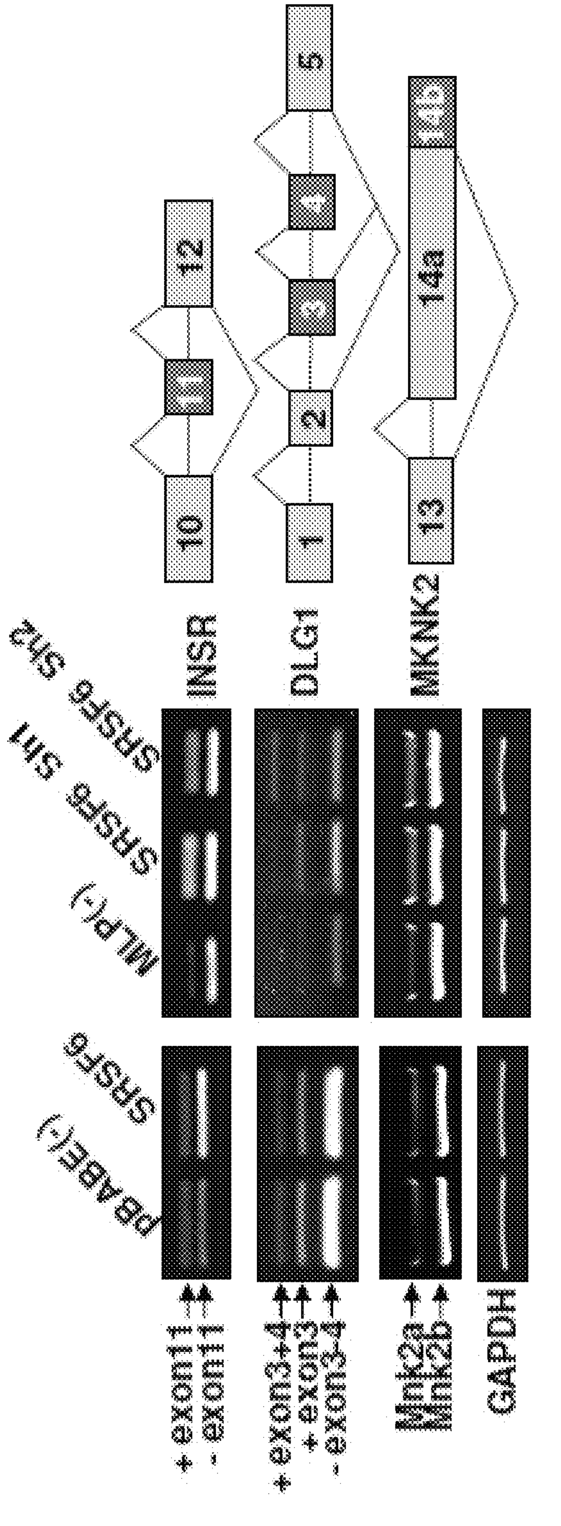

FIGS. 34A-B. SRSF6 regulates the splicing of tumor suppressors and oncogenes A. Pools of BEAS-2B cells were transduced with the indicated retroviruses encoding SRSF6 or an empty vector. After puromycin selection cells were lysed and total RNA was extracted. After reverse transcription, cDNA was subjected to PCR using primers that detect the indicated alternative splicing events. B. Pools of NCI-H460 lung cancer cells were transduced with the indicated retroviruses encoding shRNAs or the empty vector and after selection cells were lysed and total RNA was extracted. After reverse transcription, cDNA was subjected to PCR using primers that detect the indicated alternative splicing events.

Figure 35A:
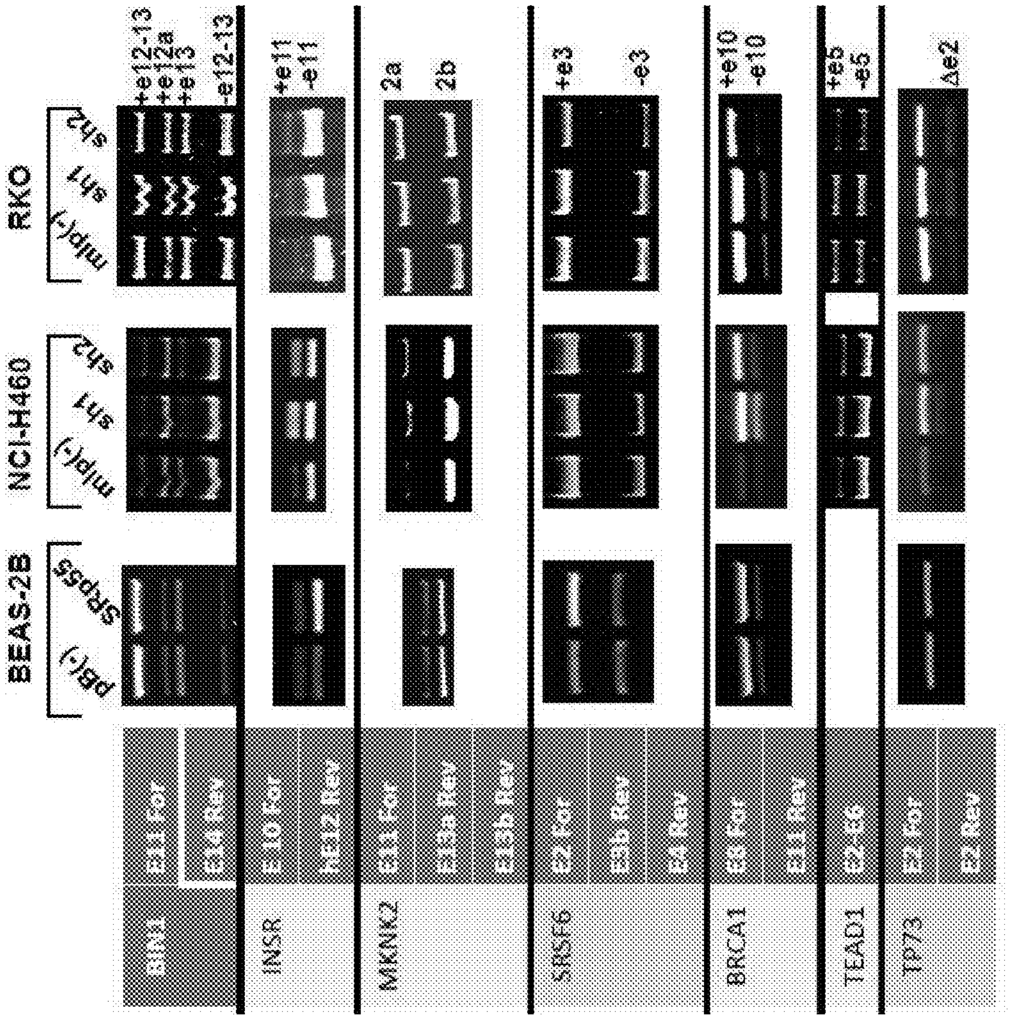
Figure 35B:
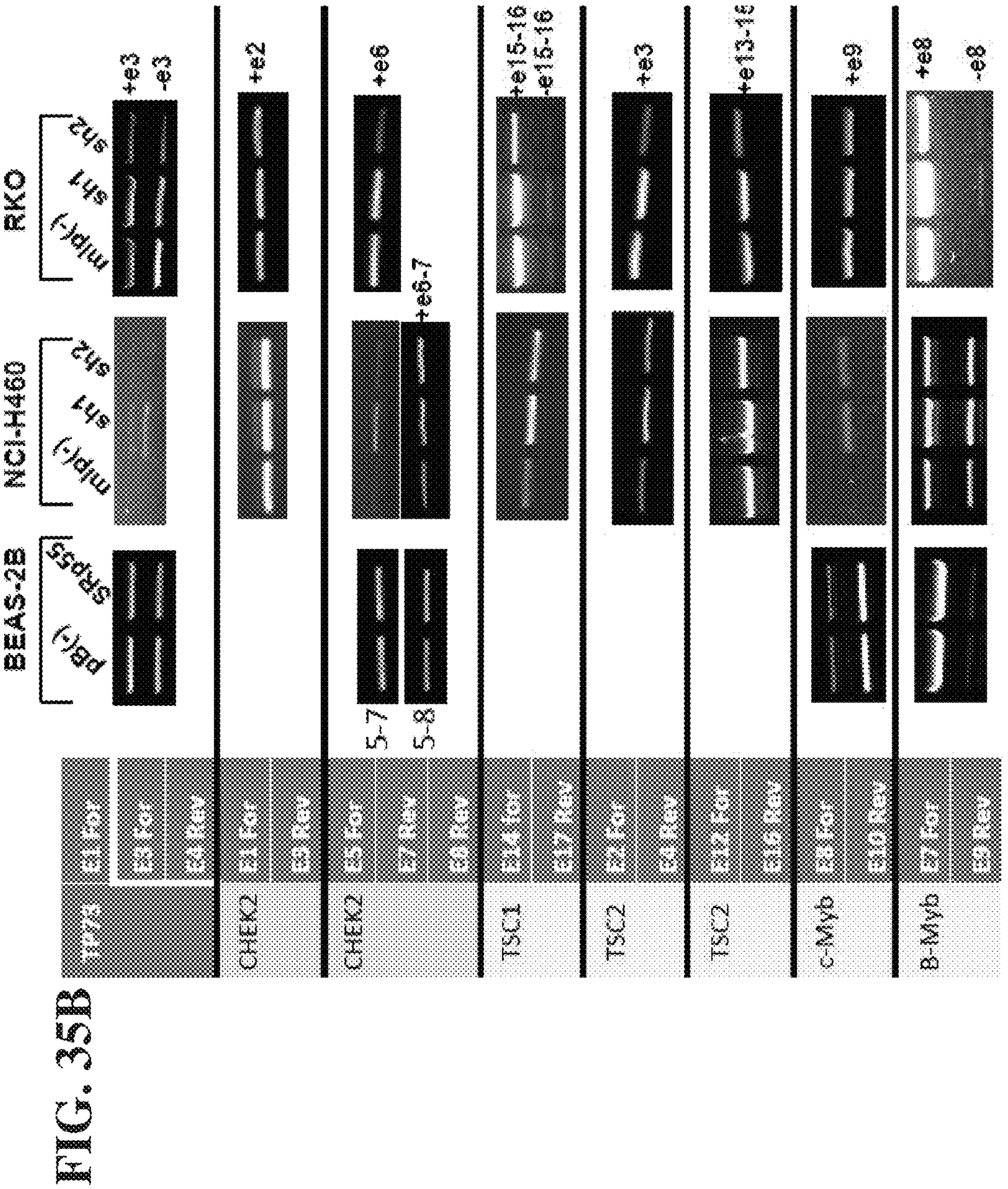
Figure 35C:
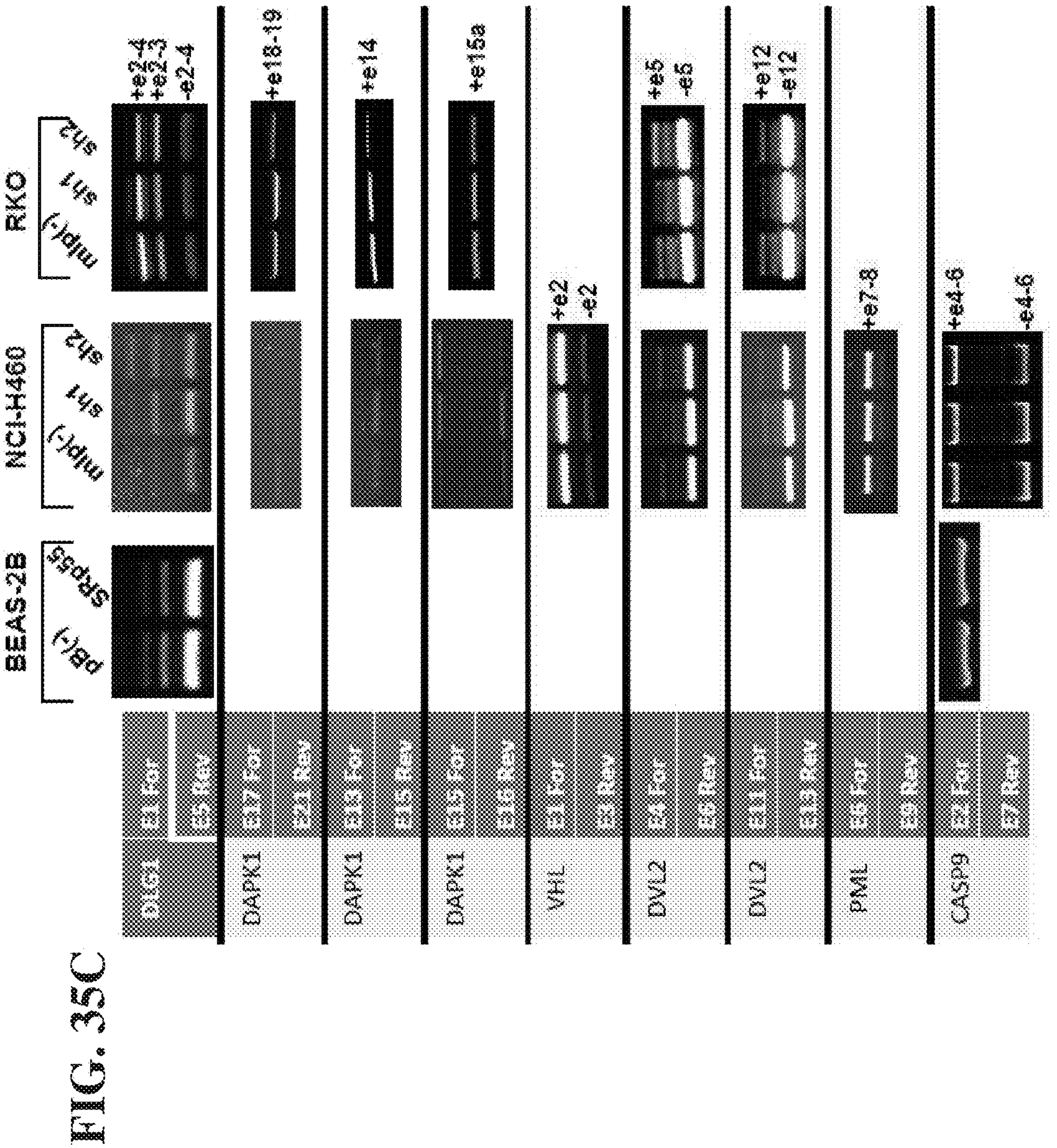

FIGS. 35A-C. Alternative Splicing changes affected by SRSF6 overexpression or knockdown. Total RNA from BEAS-2B transduced with empty vector (pBABE) or SRSF6, and from NCI-H460 and RKO cells transduced with the indicated shRNA against SRSF6 was extracted and subjected to reverse transcription. cDNA was subjected to PCR with the indicated primers and products were separated and visualized by agarose gels. Alternative splicing products are indicated on the right.

Figure 36C:
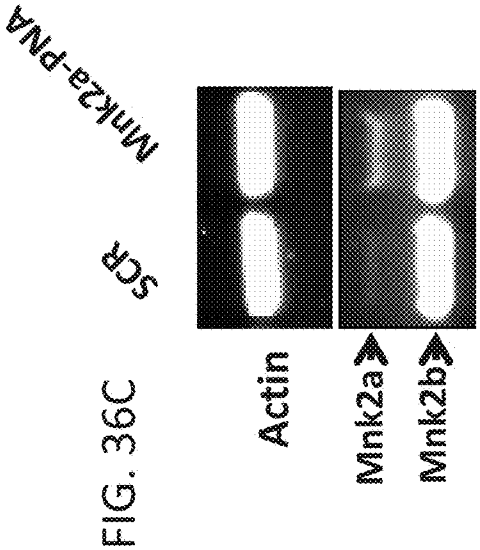
Figure 36A:
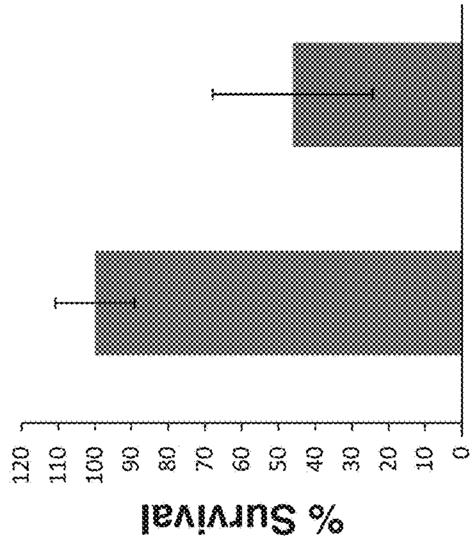
Figure 36B:
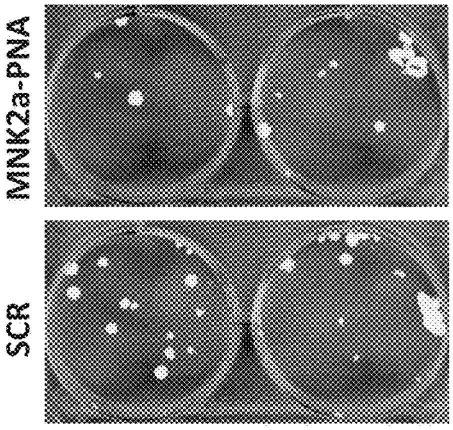

FIGS. 36A-C. PNA-induced alternative splicing switch up-regulates Mnk2a and reduces survival of Ras-transformed MCF-10A breast cells. Ras-transformed MCF-10A cells were incubated for 5 hours with 0.05 μM scrambled (non-specific) PNA or MNK2a specific PNA (see the position of the PNA marked in red in the scheme). 24 h later cells were counted and seeded in low density (20 cells/well) in 6-well plates. 14 days later, surviving colonies were counted and photographed. FIG. 36C is an RT-PCR that shows that the PNA can modulate Mnk2 splicing to elevate Mnk2a.

DESCRIPTION OF SPECIFIC EMBODIMENTS OF THE INVENTION

The present invention, in some embodiments thereof, relates to the use of agents which regulate alternative splicing pathways for the treatment and diagnosis of cancer and related diseases.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. The process of alternative splicing is widely misregulated in cancer and many tumors express new splicing isoforms, which are absent in the corresponding normal tissue. Many oncogenes and tumor suppressors are differentially spliced in cancer cells and it has been shown that many of these cancer-specific isoforms contribute to the transformed phenotype of cancer.

The present inventors have now shown that particular splice variants of genes which are substrates of the splice factor SRSF1 act as cancer inducers whereas other variants of the same genes act as tumor suppressors. These genes include Mnk2 and RPS6KB1 which encodes S6K1 in both mouse and human.

The present inventors have demonstrated that MKNK2 alternative splicing is modulated in cancer cells to down-regulate the expression of the tumor suppressive isoform Mnk2a and enhance the expression of the pro-oncogenic isoform Mnk2b. Both splicing isoforms phosphorylate the translation initiation factor eIF4E. However, only Mnk2a binds to and activates p38-MAPK leading to enhanced activation of the p38 stress pathway, induction of its target genes and enhanced cell death and suppression of Ras-induced transformation in vitro and in vivo. Alternatively, Mnk2b which is upregulated in many tumors, is pro-oncogenic and does not activate p38-MAPK while enhancing eIF4E phosphorylation. Oncogenic Ras by elevating the production of the splicing factor SRSF1, modulates Mnk2 alternative splicing to downregulate the tumor suppressive isoform Mnk2a and upregulate Mnk2b. Thus, the present inventors propose that Mnk2a downregulation by alternative splicing is a new tumor suppressor mechanism which is lost in breast, colon and lung cancers and is regulated by Ras.

Whilst reducing the present invention to practice the present inventors synthesized a PNA based molecule which hybridizes to the bridging region between exon 14b and the intron immediately preceding it, preventing the generation of Mnk2b. As illustrated in FIGS. 36A-B, the PNA molecule decreased the survival of Ras-transformed MCF-10A breast cells.

Based on these results, the present inventors propose the use of agents that upregulate the amount of Mnk2a (and/or downregulate the amount of Mnk2b) as therapeutics for the treatment of cancers and other conditions which are associated with an increased activity of p38-MAPK such as inflammatory, autoimmune and neurodegenerative diseases.

In addition, the present inventors propose a new method of diagnosing cancer and related diseases which is based on detecting the level of the Mnk2 isoforms.

Further the present inventors propose that the level of Mnk2 isoforms may be used to determine the susceptibility of a tumor to therapeutic agents that inhibit the Ras-Raf MAPK pathway, wherein an amount of Mnk2b above a predetermined level is indicative of a tumor that is sensitive to these agents.

Whilst further reducing the present invention to practice, the present inventors have found that short isoforms of S6K1 are over-produced in breast cancer cell lines and tumors. Overexpression of S6K1 short isoforms induces transformation of human breast epithelial cells. The long S6K1 variant (Iso-1) induced opposite effects: It inhibits Ras-induced transformation and tumor formation, while its knockdown or knockout induced transformation, suggesting that Iso-1 has a tumor suppressor activity. It was further found that S6K1 short isoforms bind and activate mTORC1, elevating 4E-BP1 phosphorylation, cap-dependent translation and Mcl-1 protein levels. Both a phosphorylation-defective 4E-BP1 mutant and the mTORC1 inhibitor rapamycin partially blocked the oncogenic effects of S6K1 short isoforms, suggesting that these are mediated by mTORC1 and 4E-BP1. Thus, alternative splicing of S6K1 acts as a molecular switch in breast cancer cells elevating oncogenic isoforms that activate mTORC1.

Based on these results, the present inventors propose a new method of diagnosing cancer which is based on detecting the level of the S6K1 isoforms.

Further the present inventors propose that the level of S6K1 isoforms may be used to determine the susceptibility of a tumor to therapeutic agents that inhibit the pTEN pI3K-mTOR pathway, wherein an amount of the short S6K1 isoforms above a predetermined level is indicative of a tumor that is sensitive to these agents.

In addition, the present inventors propose the use of agents that upregulate the amount of the long S6K1 isoform (and/or downregulate the amount of the short S6K1 isoform) as therapeutics for the treatment of cancers.

The present inventors also found that the splice factor SRSF6 is amplified and upregulated in lung and colon cancers and acts as a potent oncoprotein able to transform immortal lung epithelial cells. SRSF6 is also important for tumor maintenance as its knockdown inhibits transformation and tumorigenesis of lung and colon cancer cells. Finally, SRSF6 regulates alternative splicing to down-regulate tumor suppressors and activate oncogenic isoforms that contribute to the cancerous phenotype.

Based on these results, the present inventors propose a new method of diagnosing cancer which is based on detecting the level of the SRSF6 splice factor.

In addition, the present inventors propose the use of agents that downregulate the amount and/or activity SRSF6 as therapeutics for the treatment of cancers.

1. Therapeutics:

a. Mnk2 Gene

According to one aspect of the present invention there is provided a method of treating a disease associated with an increased activity of p38-MAPK in a subject in need thereof, the method comprising administering to the subject a therapeutically effective amount of an agent which directly increases the ratio of Mnk2a:Mnk2b, thereby treating the disease.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

Subjects which may be treated according to aspects of the present invention include mammalian subjects (e.g. mammalian subjects).

The MAP Kinase Interacting Serine/Threonine Kinase (Mnk2 gene, also referred to as MKNK2) gene gives rise to at least two distinct proteins, with different C termini, as a consequence of 3' prime alternative splicing. The longer form of human Mnk2, referred to as Mnk2a (amino acid sequence as set forth in SEQ ID NO: 146, cDNA sequence as set forth in SEQ ID NO: 149), possesses a MAPK-binding motif that is absent from the shorter isoform Mnk2b (amino acid sequence as set forth in SEQ ID NO: 147, cDNA sequence as set forth in SEQ ID NO: 151).

It will be appreciated that to increase the ratio of Mnk2a:Mnk2b, agents can be provided which increase the amount of Mnk2a and/or decrease the amount of Mnk2b. According to one embodiment, an agent may increase the amount of Mnk2a and concomitantly decrease the amount of Mnk2b by preventing the splicing of the Mnk2 gene at exon 14b.

The phrase "agent which directly decreases Mnk2b" refers to an agent which interacts directly with Mnk2b and or the DNA or RNA sequence encoding same, and not on an upstream or downstream effector thereof.

Agents which directly decrease Mnk2b include agents which act directly on the protein itself (e.g. antibody) or agents which act directly on the DNA or RNA sequence encoding same (e.g. polynucleotide sequences which hybridize to same).

Agents which directly increase Mnk2a include Mnk2a itself or the polynucleotide sequence encoding same.

Thus, according to one embodiment, the agent is an antibody which is capable of specifically downregulating Mnk2b protein. Preferably, the antibody is capable of binding to Mnk2b with at least 2 fold higher affinity, more preferably at least 5 fold higher affinity and even more preferably at least 10 fold higher affinity than to Mnk2a.

The term "antibody" as used in this invention includes intact molecules as well as functional fragments thereof, such as Fab, F(ab')2, and Fv that are capable of binding to macrophages. These functional antibody fragments are defined as follows: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule that can be obtained by treating whole antibody with pepsin, followed by reduction, to yield an intact light chain and a portion of the heavy chain; two Fab' fragments are obtained per antibody molecule; (3) (Fab')2, the fragment of the antibody that can be obtained by treating whole antibody with the enzyme pepsin without subsequent reduction; F(ab')2 is a dimer of two Fab' fragments held together by two disulfide bonds; (4) Fv, defined as a genetically engineered fragment containing the variable region of the light chain and the variable region of the heavy chain expressed as two chains; and (5) Single chain antibody ("SCA"), a genetically engineered molecule containing the variable region of the light chain and the variable region of the heavy chain, linked by a suitable polypeptide linker as a genetically fused single chain molecule.

Methods of producing polyclonal and monoclonal antibodies as well as fragments thereof are well known in the art (See for example, Harlow and Lane, Antibodies: A Laboratory Manual, Cold Spring Harbor Laboratory, New York, 1988, incorporated herein by reference).

Antibody fragments according to some embodiments of the invention can be prepared by proteolytic hydrolysis of the antibody or by expression in *E. coli* or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)]. Methods for humanizing non-human antibodies are well known in the art.

Another agent which directly decreases the amount of Mnk2b in the cell is an oligonucleotide agent which hybridizes to the pre-mRNA transcribed from the Mnk2 gene at a position that downregulates or prevents splicing between exon 13, to the last exon, exon 14b. Such an agent may hybridize to the splice site itself (e.g. or may hybridize to a part of the exon 14b gene sequence which is involved in enhancement of splicing (exonic splicing enhancer, ESE). By masking the splice site, or splicing enhancer, generation of Mnk2b is decreased, whilst generation of Mnk2a is increased. Preferably, an oligonucleotide agent is selected that does not cause degradation of the pre-mRNA itself, such as siRNA, DNAzymes or RNAzymes. According to one embodiment, the oligonucleotide hybridizes to a sequence as set forth in SEQ ID NO: 171.

As used herein, the term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly to respective naturally-occurring portions.

Oligonucleotides designed according to the teachings of some embodiments of the invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988) and "Oligonucleotide Synthesis" Gait, M. J., ed. (1984) utilizing solid phase chemistry, e.g. cyanoethyl phosphoramidite followed by deprotection, desalting and purification by for example, an automated trityl-on method or HPLC.

The oligonucleotide of some embodiments of the invention is of at least 10, at least 11, at least 12, at least 13, at least 14, at least 15, at least 16, at least 17, at least 18, at least 19, at least 20, at least 22, at least 25, at least 30 or at least 40, bases specifically hybridizable with the splicing sequences described hereinabove.

The oligonucleotides of some embodiments of the invention may comprise heterocylic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder.

Specific examples of preferred oligonucleotides useful according to some embodiments of the invention include oligonucleotides containing modified backbones or non-natural internucleoside linkages. Oligonucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466, 677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to some embodiments of the invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in some embodiments of the invention are disclosed in U.S. Pat. No. 6,303,374.

Additionally, or alternatively the oligonucleotides of the present invention may be phosphorothioated, 2-o-methyl protected and/or LNA modified.

Oligonucleotides of some embodiments of the invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

According to one embodiment, the oligonucleotide is a PNA modified oligonucleotide comprising a sequence as set forth in SEQ ID NO: 157. (agacttcCACCCTGTCAG).

Since the oligonucleotides described herein hybridize with the pre-mRNA transcript, it is preferable that they are attached to a cell penetrating peptide. As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptides of some embodiments of the invention preferably include, but are not limited to, penetratin, transportan, pIsl, TAT(48-60), pVEC, MTS, MAP and polyarginine.

According to a specific embodiment, the oligonucleotide agent is set forth in SEQ ID NO: 157 and at its 3' end is attached to a polyarginine tail.

As mentioned, another way of increasing the ratio of mnk2a:mnk2b is by administering mnk2a. It will be appreciated that the mnk2a splice variant can also be expressed from a nucleic acid construct administered to the individual employing any suitable mode of administration (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Diseases associated with an increased activity of p38-MAPK which can be treated by agents which increase the mnk2a:mnk2b ratio include cancer, a neurodegenerative disease, an inflammatory disease and an autoimmune disease, which are summarized herein below.

Cancer

Examples of cancers that may be treated using the agents described herein include, but are not limited to adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; triple negative breast cancer, Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, malignant melanoma, meningioma; multiple endocrine neoplasia; multiple myeloma, myeloid malignancy, predisposition to; myxosarcoma, neuroblastoma; osteosarcoma; osteocarcinoma, ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, basal cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Neurodegenerative diseases—The term "neurodegenerative disease" is used herein to describe a disease which is caused by damage to the central nervous system. Exemplary neurodegenerative diseases which may be treated using the cells and methods according to the present invention include for example, Parkinson's disease, Huntington's disease, amyotrophic lateral sclerosis (ALS), Alzheimer's disease, Rett Syndrome, lysosomal storage diseases ("white matter disease" or glial/demyelination disease, as described, for example by Folkerth, J. Neuropath. Exp. Neuro., September 1999, 58:9), including Sanfilippo, Gaucher disease, Tay Sachs disease (beta hexosaminidase deficiency), other genetic diseases, multiple sclerosis, brain injury or trauma caused by ischemia, accidents, environmental insult, etc., spinal cord damage, ataxia and alcoholism. In addition, the present invention may be used to reduce and/or eliminate the effects on the central nervous system of a stroke or a heart attack in a patient, which is otherwise caused by lack of blood flow or ischemia to a site in the brain of the patient or which has occurred from physical injury to the brain and/or spinal cord. Neurodegenerative diseases also include neurodevelopmental disorders including for example, autism and related neurological diseases such as schizophrenia, among numerous others.

Inflammatory diseases—Include, but are not limited to, chronic inflammatory diseases and acute inflammatory diseases.

Inflammatory Diseases Associated with Hypersensitivity

Examples of hypersensitivity include, but are not limited to, Type I to hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 December 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 January 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. May; 7 (3): 191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 August 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 June 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 January 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 January 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood.

1991 March 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 March 27; 98 (7):3988), cardiovascular diseases, cardiac autoimmunity in Chagas' disease (Cunha-Neto E. et al., J Clin Invest 1996 October 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 December 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 August 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 June 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 October 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 January 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. Diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 December 15; 165 (12):7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 March 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 January 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 January 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 March 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 December 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a particular embodiment, the agents (and combinations thererof) are used to treat pre-malignant lesions.

b. RPS6KB1 Gene

According to another aspect of the present invention there is provided a method of treating cancer in a subject in need thereof, the method comprising administering to the subject a therapeutically effective amount of an agent which directly increases the ratio of long:short isoforms of S6K1, thereby treating the disease.

The gene RPS6KB1 encoding for p85/p70 S6K1 can be alternatively spliced to form a number of truncated isoforms. In humans, at least three variants are known—the long variant, referred to herein as Iso-1 (amino acid sequence SEQ ID NO: 152) and the h6A and h6C variants which include combinations of exons 6 (a-c), referred to herein S6K1 short isoforms (amino acid sequence SEQ ID NO: 154 and 156 respectively, DNA sequence 153 and 155 respectively). Inclusion of the alternative exons mentioned above results in exposure of alternative poly adenylation sites and alterations in the reading frame that in turn generate a stop codon in exons 6a or 6c in humans. The presence of these stop codons creates transcripts containing approximately half of the original S6K1 coding sequence (Iso-1), and lacking more than half of the conserved kinase domain.

It will be appreciated that to increase the ratio of long: short isoforms of S6K1, agents can be provided which increase the amount of long isoform and/or decrease the amount of short isoforms. According to one embodiment, an agent may increase the amount of the long isoform and concomitantly decrease the amount of the short isoforms by preventing the splicing of the RPS6KB1 gene at the relevant splice sites.

The phrase "agent which directly decreases the short isoforms of S6K1" refers to an agent which interacts directly with the short isoforms of S6K1 and or the DNA or RNA sequence encoding same, and not on an upstream or downstream effector thereof.

Agents which directly decrease the short isoforms of S6K1 include agents which act directly on the protein itself (e.g. antibody, as described herein above) or agents which act directly on the DNA or RNA sequence encoding same (e.g. polynucleotide sequences which hybridize to same, as described herein above).

Agents which directly increase the long isoform of S6K1 include S6K1 itself or the polynucleotide sequence encoding same.

Thus, according to one embodiment, the agent is an antibody which is capable of specifically downregulating at least one of the short variants of S6K1. Preferably, the antibody is capable of binding to one of the short variants with at least 2 fold higher affinity, more preferably at least 5 fold higher affinity and even more preferably at least 10 fold higher affinity than to the long variant.

Another agent which directly decreases the amount of one of the short S6K1 variants in the cell is an oligonucleotide agent which hybridizes to the pre-mRNA transcribed from the RPS6KB1 gene at a position that downregulates or prevents splicing between exon 6 to exon 6A or 6C. Such an agent may hybridize to the splice site itself or may hybridize to a part of the exons 6A or 6C gene sequence which is involved in enhancement of splicing. By masking the splice site, or splice site enhancer, generation of the short variants is decreased, whilst generation of the long variant is increased. Preferably, an oligonucleotide agent is selected that does not cause degradation of the pre-mRNA itself, such as siRNA, DNAzymes or RNAzymes.

Thus for example, to down-regulate generation of short variant 6C, an oligonucleotide agent may be used that hybridizes to the splice site between intron 6 and exon 6C. Thus, the oligonucletide may be designed to hybridize with at least part of the sequence as set forth in SEQ ID NO: 158 (actgcattccattgtttaatttcagGC-CTTTTCTAACAAAGAAGCT).

To down-regulate generation of short variant 6A, an oligonucleotide agent may be used that hybridizes to the splice site between intron 6 and exon 6A. Thus, the oligonucletide may be designed to hybridize with at least part of the sequence as set forth in SEQ ID NO: 159 (cacatcattc-ctttgcccttagGCTTGAGTGGAACGCTCTTCAC).

It will be appreciated that the present invention contemplates oligonucleotides which have modifications as further described herein above with respect to Mnk2 directed oligonucleotides.

As mentioned, another way of increasing the ratio of S6K1 long:short variants is by administering the long variant of S6K1. It will be appreciated that the long S6K1 splice variant can also be expressed from a nucleic acid construct administered to the individual employing any suitable mode of administration (i.e., in-vivo gene therapy). Alternatively, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

Diseases which can be treated by increasing the long splice variant: short splice variant of S6K1 include cancerous diseases which are listed herein above with respect to Mnk2.

c. SRSF6

According to another aspect of the present invention there is provide a method of treating an inflammatory disorder in a subject in need thereof, comprising administering to the subject a therapeutically effective amount of an agent which directly down-regulates an amount and/or activity of SRSF6, thereby treating the inflammatory disorder.

The term “SRSF6” refers to any of the 3 splice variants of Serine/Arginine-Rich Splicing Factor 6, having a Swiss Prot Number Q13247 (Q13247-1, Q13247-2 or Q13247-3).

Downregulation of SRSF6 can be effected on the genomic and/or the transcript level using a variety of molecules which interfere with transcription and/or translation [e.g., RNA silencing agents (e.g., antisense, siRNA, shRNA, micro-RNA), Ribozyme and DNAzyme], or on the protein level using e.g., antibodies, antagonists, enzymes that cleave the polypeptide and the like.

Following is a list of agents capable of downregulating expression level and/or activity of SRSF6.

One example, of an agent capable of downregulating SRSF6 is an antibody or antibody fragment capable of specifically binding SRSF6. Preferably, the antibody specifically binds at least one epitope of SRSF6. As used herein, the term “epitope” refers to any antigenic determinant on an antigen to which the paratope of an antibody binds.

Epitopic determinants usually consist of chemically active surface groupings of molecules such as amino acids or carbohydrate side chains and usually have specific three dimensional structural characteristics, as well as specific charge characteristics.

Antibodies and types thereof have been described herein above.

Downregulation of SRSF6 can be also achieved by RNA silencing. As used herein, the phrase “RNA silencing” refers to a group of regulatory mechanisms [e.g. RNA interference (RNAi), transcriptional gene silencing (TGS), post-transcriptional gene silencing (PTGS), quelling, co-suppression, and translational repression] mediated by RNA molecules which result in the inhibition or “silencing” of the expression of a corresponding protein-coding gene. RNA silencing has been observed in many types of organisms, including plants, animals, and fungi.

As used herein, the term “RNA silencing agent” refers to an RNA which is capable of specifically inhibiting or “silencing” the expression of a target gene. In certain embodiments, the RNA silencing agent is capable of preventing complete processing (e.g, the full translation and/or expression) of an mRNA molecule through a post-transcriptional silencing mechanism. RNA silencing agents include noncoding RNA molecules, for example RNA duplexes comprising paired strands, as well as precursor RNAs from which such small non-coding RNAs can be generated. Exemplary RNA silencing agents include dsRNAs such as siRNAs, miRNAs and shRNAs. In one embodiment, the RNA silencing agent is capable of inducing RNA interference. In another embodiment, the RNA silencing agent is capable of mediating translational repression.

According to an embodiment of the invention, the RNA silencing agent is specific to the target RNA (e.g., SRSF6 encoding RNA) and does not cross inhibit or silence a gene or a splice variant which exhibits 99% or less global homology to the target gene, e.g., less than 98%, 97%, 96%, 95%, 94%, 93%, 92%, 91%, 90%, 89%, 88%, 87%, 86%, 85%, 84%, 83%, 82%, 81% global homology to the target gene.

RNA interference refers to the process of sequence-specific post-transcriptional gene silencing in animals mediated by short interfering RNAs (siRNAs). The corresponding process in plants is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla. Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA.

The presence of long dsRNAs in cells stimulates the activity of a ribonuclease III enzyme referred to as dicer. Dicer is involved in the processing of the dsRNA into short pieces of dsRNA known as short interfering RNAs (siRNAs). Short interfering RNAs derived from dicer activity are typically about 21 to about 23 nucleotides in length and comprise about 19 base pair duplexes. The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex.

Accordingly, some embodiments of the invention contemplate use of dsRNA to downregulate protein expression from mRNA.

According to one embodiment, the dsRNA is greater than 30 bp. The use of long dsRNAs (i.e. dsRNA greater than 30 bp) has been very limited owing to the belief that these longer regions of double stranded RNA will result in the induction of the interferon and PKR response. However, the use of long dsRNAs can provide numerous advantages in that the cell can select the optimal silencing sequence alleviating the need to test numerous siRNAs; long dsRNAs will allow for silencing libraries to have less complexity than would be necessary for siRNAs; and, perhaps most importantly, long dsRNA could prevent viral escape mutations when used as therapeutics.

Various studies demonstrate that long dsRNAs can be used to silence gene expression without inducing the stress response or causing significant off-target effects—see for example [Strat et al., Nucleic Acids Research, 2006, Vol. 34, No. 13 3803-3810; Bhargava A et al. Brain Res. Protoc. 2004; 13:115-125; Diallo M., et al., Oligonucleotides. 2003; 13:381-392; Paddison P. J., et al., Proc. Natl. Acad. Sci. USA. 2002; 99:1443-1448; Tran N., et al., FEBS Lett. 2004; 573:127-134].

In particular, the invention according to some embodiments thereof contemplates introduction of long dsRNA (over 30 base transcripts) for gene silencing in cells where the interferon pathway is not activated (e.g. embryonic cells and oocytes) see for example Billy et al., PNAS 2001, Vol 98, pages 14428-14433. and Diallo et al, Oligonucleotides, Oct. 1, 2003, 13(5): 381-392. doi:10.1089/154545703322617069.

The invention according to some embodiments thereof also contemplates introduction of long dsRNA specifically designed not to induce the interferon and PKR pathways for down-regulating gene expression. For example, Shinagwa and Ishii [*Genes & Dev.* 17 (11): 1340-1345, 2003] have developed a vector, named pDECAP, to express long double-strand RNA from an RNA polymerase II (Pol II) promoter. Because the transcripts from pDECAP lack both the 5'-cap structure and the 3'-poly(A) tail that facilitate ds-RNA export to the cytoplasm, long ds-RNA from pDECAP does not induce the interferon response.

Another method of evading the interferon and PKR pathways in mammalian systems is by introduction of small inhibitory RNAs (siRNAs) either via transfection or endogenous expression.

The term "siRNA" refers to small inhibitory RNA duplexes (generally between 18-30 basepairs) that induce the RNA interference (RNAi) pathway. Typically, siRNAs are chemically synthesized as 21 mers with a central 19 bp duplex region and symmetric 2-base 3'-overhangs on the termini, although it has been recently described that chemically synthesized RNA duplexes of 25-30 base length can have as much as a 100-fold increase in potency compared with 21 mers at the same location. The observed increased potency obtained using longer RNAs in triggering RNAi is theorized to result from providing Dicer with a substrate (27 mer) instead of a product (21 mer) and that this improves the rate or efficiency of entry of the siRNA duplex into RISC.

It has been found that position of the 3'-overhang influences potency of an siRNA and asymmetric duplexes having a 3'-overhang on the antisense strand are generally more potent than those with the 3'-overhang on the sense strand (Rose et al., 2005). This can be attributed to asymmetrical strand loading into RISC, as the opposite efficacy patterns are observed when targeting the antisense transcript.

The strands of a double-stranded interfering RNA (e.g., an siRNA) may be connected to form a hairpin or stem-loop structure (e.g., an shRNA). Thus, as mentioned the RNA silencing agent of some embodiments of the invention may also be a short hairpin RNA (shRNA).

The term "shRNA", as used herein, refers to an RNA agent having a stem-loop structure, comprising a first and second region of complementary sequence, the degree of complementarity and orientation of the regions being sufficient such that base pairing occurs between the regions, the first and second regions being joined by a loop region, the loop resulting from a lack of base pairing between nucleotides (or nucleotide analogs) within the loop region. The number of nucleotides in the loop is a number between and including 3 to 23, or 5 to 15, or 7 to 13, or 4 to 9, or 9 to 11. Some of the nucleotides in the loop can be involved in base-pair interactions with other nucleotides in the loop. Examples of oligonucleotide sequences that can be used to form the loop include 5'-UUCAAGAGA-3' (Brummelkamp, T. R. et al. (2002) Science 296: 550) and 5'-UUUGUGUAG-3' (Castanotto, D. et al. (2002) RNA 8:1454). It will be recognized by one of skill in the art that the resulting single chain oligonucleotide forms a stem-loop or hairpin structure comprising a double-stranded region capable of interacting with the RNAi machinery.

Synthesis of RNA silencing agents suitable for use with some embodiments of the invention can be effected as follows. First, the SRSF6 mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level www(dot)ambion(dot)com/techlib/tn/91/912(dot)html).

Second, potential target sites are compared to an appropriate genomic database (e.g., human, mouse, rat etc.) using any sequence alignment software, such as the BLAST software available from the NCBI server (www(dot)ncbi(dot)nlm(dot)nih(dot)gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

An exemplary siRNA which can downregulate SRSF6 is set forth in SEQ ID NO: 160 (TGTTAATAGGACATCATATGGT) or SEQ ID NO: 161 (TTATAAAGCTTGAGTTATGTAA).

It will be appreciated that the RNA silencing agent of some embodiments of the invention need not be limited to those molecules containing only RNA, but further encompasses chemically-modified nucleotides and non-nucleotides, as further described herein above.

In some embodiments, the RNA silencing agent provided herein can be functionally associated with a cell-penetrating peptide, as further described herein above.

According to another embodiment the RNA silencing agent may be a miRNA.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O,4'-C-ethylene-bridged nucleic acids (ENA)). For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA.

Another agent capable of downregulating SRSF6 is a DNAzyme molecule capable of specifically cleaving an mRNA transcript or DNA sequence of the SRSF6. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262) A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad Sci. USA 199; for rev of DNAzymes see Khachigian, L M [Curr Opin Mol Ther 4:119-21 (2002)].

Downregulation of a SRSF6 can also be effected by using an antisense polynucleotide capable of specifically hybridizing with an mRNA transcript encoding the SRSF6.

Design of antisense molecules which can be used to efficiently downregulate a SRSF6 must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

For example, a suitable antisense oligonucleotides targeted against the SRSF6 mRNA (which is coding for the SRSF6 protein) would be as set forth in SEQ ID NO:162 (CCCGCCACGGACATGCCGCGCGTCTA).

Another agent capable of downregulating SRSF6 is a ribozyme molecule capable of specifically cleaving an mRNA transcript encoding SRSF6. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials.

An additional method of regulating the expression of an SRSF6 gene in cells is via triplex forming oligonucleotides (TFOs). Recent studies have shown that TFOs can be designed which can recognize and bind to polypurine/polypirimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988; 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence:

```
oligo
3'--A G G T

duplex
5'--A G C T

duplex
3'--T C G A
```

However, it has been shown that the A-AT and G-GC triplets have the greatest triple helical stability (Reither and Jeltsch, BMC Biochem, 2002, September 12, Epub). The same authors have demonstrated that TFOs designed according to the A-AT and G-GC rule do not form non-specific triplexes, indicating that the triplex formation is indeed sequence specific.

Thus for any given sequence in the SRSF6 regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression.

Another agent capable of downregulating SRSF6 would be any molecule which binds to and/or cleaves SRSF6. Such molecules can be SRSF6 antagonists, or SRSF6 inhibitory peptide.

It will be appreciated that a non-functional analogue of at least a catalytic or binding portion of SRSF6 can be also used as an agent which downregulates SRSF6.

Another agent which can be used along with some embodiments of the invention to downregulate SRSF6 is a molecule which prevents SRSF6 activation or substrate binding.

The present inventors have shown that down-regulators of SRSF6 may be used to treat inflammatory disorders. Such inflammatory disorders have been described herein above with respect to mnk2 variant regulators.

According to a particular embodiment, the inflammatory disorder is inflammatory bowel disorder (IBD).

According to another embodiment, the inflammatory disorder is cancer (e.g. is lung or colon cancer).

Any of the agents described herein can be administered to the subject per se or as part of a pharmaceutical composition which also includes a physiologically acceptable carrier. The purpose of a pharmaceutical composition is to facilitate administration of the active ingredient to an organism.

Herein the term "active ingredient" refers to the nuclear targeting peptides of the present invention either alone or linked to a heterologous agent, or polynucleotides encoding same, which are accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases. One of the ingredients included in the pharmaceutically acceptable carrier can be for example polyethylene glycol (PEG), a biocompatible polymer with a wide range of solubility in both organic and aqueous media (Mutter et al. (1979).

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the preparation in a local rather than systemic manner, for example, via injection of the preparation directly into a specific region of a patient's body.

A recombinant vector can be administered in several ways. If vectors are used which comprise cell specific promoters, for example, the procedure can take advantage of their target specificity and consequently, do not have to be administered locally at the diseased site.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the invention may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The preparations described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The preparation of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients effective to prevent, alleviate or ameliorate symptoms of disease or prolong the survival of the subject being treated.

Determination of a therapeutically effective amount is well within the capability of those skilled in the art.

For any preparation used in the methods of the invention, the therapeutically effective amount or dose can be estimated initially from in vitro assays. For example, a dose can be formulated in animal models and such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. [See e.g., Fingl, et al., (1975) "The Pharmacological Basis of Therapeutics", Ch. 1 p. 1].

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

It will be appreciated that the polypeptides and polynucleotides of the present invention can be provided to the individual with additional active agents to achieve an improved therapeutic effect as compared to treatment with each agent by itself. In such therapy, measures (e.g., dosing and selection of the complementary agent) are taken to adverse side effects which may be associated with combination therapies.

Compositions including the preparation of the present invention formulated in a compatible pharmaceutical carrier may also be prepared, placed in an appropriate container, and labeled for treatment of an indicated condition.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

2. Diagnostics:

According to another aspect of the present invention there is provided a method of diagnosing a disease associated with an increased activity of p38-MAPK in a subject, the method comprising determining an amount of Mnk2a and/or Mnk2b in a sample from the subject, wherein an amount of the Mnk2a below a predetermined level and/or an amount of the Mnk2b above a predetermined is indicative of the disease.

According to still another aspect of the present invention there is provided a method of diagnosing cancer in a subject, the method comprising determining an amount of a short isoform of S6K1 and/or an amount of the long isoform of the S6K1 in a sample from the subject, wherein an amount of the short isoform above a predetermined level and/or an amount of the long isoform below a predetermined level is indicative of the cancer.

According to yet another aspect of the present invention there is provided a method of diagnosing an inflammatory disorder in a subject, the method comprising determining an amount SRSF6 in a tumor sample from the subject, wherein an amount of SRSF6 above a predetermined level is indicative of the inflammatory disorder.

The term "diagnosing" as used herein refers to determining the presence of a disease, classifying a disease, staging a disease, determining a severity of a disease, monitoring disease progression, forecasting an outcome of the disease, predicting survival and/or prospects of recovery (i.e. prognosis).

The subject may be a healthy animal or human subject undergoing a routine well-being check up. Alternatively, the subject may be at risk of having the disease (e.g., a genetically predisposed subject, a subject with medical and/or family history of cancer, a subject who has been exposed to carcinogens, occupational hazard, environmental hazard]

and/or a subject who exhibits suspicious clinical signs of the disease [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness). Still alternatively, the subject may be diagnosed as having the disease, but the stage is being evaluated.

According to a particular embodiment, the amount of the particular splice variant or splice factor may be used for predicting a level of metastasis.

The term "predicting metastasis" as used herein refers to determining the presence of metastasis either prior to the event of metastasis or following the event of metastasis i.e. diagnosing.

Determining an expression of the particular splice variant and/or splice factor may be effected on the RNA or protein level as detailed below.

According to one embodiment, the determining is effected ex vivo.

According to another embodiment, the determining is effected in vivo.

Methods of Detecting Expression of the Splice Variants and/or Splice Factor on the RNA Level In order to detect expression of the particular splice variants and/or splice factor on the RNA level, typically polynucleotide probes (e.g. oligonucleotides or primers) are used that are capable of specifically hybridizing to their RNA or cDNA generated therefrom.

Preferably, the oligonucleotide probes and primers utilized by the various hybridization techniques described hereinabove are capable of hybridizing to their targets under stringent hybridization conditions.

By way of example, hybridization of short nucleic acids (below 200 bp in length, e.g. 17-40 bp in length) can be effected by the following hybridization protocols depending on the desired stringency; (i) hybridization solution of 6×SSC and 1% SDS or 3 M TMACl, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 1-1.5° C. below the Tm, final wash solution of 3 M TMACl, 0.01 M sodium phosphate (pH 6.8), 1 mM EDTA (pH 7.6), 0.5% SDS at 1-1.5° C. below the Tm (stringent hybridization conditions) (ii) hybridization solution of 6×SSC and 0.1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature of 2-2.5° C. below the Tm, final wash solution of 3 M TMACl, 0.01 M sodium phosphate (pH 6.8), 1 mM EDTA (pH 7.6), 0.5% SDS at 1-1.5° C. below the Tm, final wash solution of 6×SSC, and final wash at 22° C. (stringent to moderate hybridization conditions); and (iii) hybridization solution of 6×SSC and 1% SDS or 3 M TMACI, 0.01 M sodium phosphate (pH 6.8), 1 mM EDTA (pH 7.6), 0.5% SDS, 100 μg/ml denatured salmon sperm DNA and 0.1% nonfat dried milk, hybridization temperature at 2.5-3° C. below the Tm and final wash solution of 6×SSC at 22° C. (moderate hybridization solution).

It will be appreciated that in order to detect a particular isoform, sequences should be selected that are specific to that isoform. Thus, for example, if one wanted to detect a level of mnk2a, preferably a probe is used that hybridizes to exon 14a, which is absent in mnk2b. Thus the probe may hybridize to a specific sequence in SEQ ID NO: 163. If one wanted to detect a level of mnk2b, preferably a probe is used that hybridizes to the bridging region between exon 13 and exon 14b (e.g. the probe may hybridize to a specific sequence in SEQ ID NO: 164.

If one wanted to detect a level of the long isoform of S6K1, preferably a probe is used that hybridizes to the region which is absent in the shorter isoforms (exons 8, 9, 10, etc.) If one wanted to detect a level of h6A, preferably a probe is used that hybridizes to exon 6A (e.g. the probe may hybridize to a specific sequence in SEQ ID NO: 165). If one wanted to detect a level of h6C, preferably a probe is used that hybridizes to a specific sequence in exon 6C (as set forth in SEQ ID NO: 166).

If one wanted to detect the level of SRSF6, a probe is used that hybridizes to a specific sequence in the SRSF transcript (as set forth in SEQ ID NO: 167). Below is a list of techniques which may be used to detect the splice variants and/or splice factor on the RNA level.

Northern Blot analysis: This method involves the detection of a particular RNA i.e. hnRNP A2/B1 RNA in a mixture of RNAs. An RNA sample is denatured by treatment with an agent (e.g., formaldehyde) that prevents hydrogen bonding between base pairs, ensuring that all the RNA molecules have an unfolded, linear conformation. The individual RNA molecules are then separated according to size by gel electrophoresis and transferred to a nitrocellulose or a nylon-based membrane to which the denatured RNAs adhere. The membrane is then exposed to labeled DNA probes. Probes may be labeled using radio-isotopes or enzyme linked nucleotides. Detection may be using autoradiography, colorimetric reaction or chemiluminescence. This method allows both quantitation of an amount of particular RNA molecules and determination of its identity by a relative position on the membrane which is indicative of a migration distance in the gel during electrophoresis.

RT-PCR analysis: This method uses PCR amplification of relatively rare RNAs molecules. First, RNA molecules are purified from the cells and converted into complementary DNA (cDNA) using a reverse transcriptase enzyme (such as an MMLV-RT) and primers such as, oligo dT, random hexamers or gene specific primers. Then by applying gene specific primers and Taq DNA polymerase, a PCR amplification reaction is carried out in a PCR machine. Those of skills in the art are capable of selecting the length and sequence of the gene specific primers and the PCR conditions (i.e., annealing temperatures, number of cycles and the like) which are suitable for detecting specific RNA molecules. It will be appreciated that a semi-quantitative RT-PCR reaction can be employed by adjusting the number of PCR cycles and comparing the amplification product to known controls.

RNA in situ hybridization stain: In this method DNA or RNA probes are attached to the RNA molecules present in the cells. Generally, the cells are first fixed to microscopic slides to preserve the cellular structure and to prevent the RNA molecules from being degraded and then are subjected to hybridization buffer containing the labeled probe. The hybridization buffer includes reagents such as formamide and salts (e.g., sodium chloride and sodium citrate) which enable specific hybridization of the DNA or RNA probes with their target mRNA molecules in situ while avoiding non-specific binding of probe. Those of skills in the art are capable of adjusting the hybridization conditions (i.e., temperature, concentration of salts and formamide and the like) to specific probes and types of cells. Following hybridization, any unbound probe is washed off and the slide is subjected to either a photographic emulsion which reveals signals generated using radio-labeled probes or to a colorimetric reaction which reveals signals generated using enzyme-linked labeled probes.

In situ RT-PCR stain: This method is described in Nuovo G J, et al. [Intracellular localization of polymerase chain reaction (PCR)-amplified hepatitis C cDNA. Am J Surg Pathol. 1993, 17: 683-90] and Komminoth P, et al. [Evaluation of methods for hepatitis C virus detection in archival liver biopsies. Comparison of histology, immunohistochemistry, in situ hybridization, reverse transcriptase polymerase chain reaction (RT-PCR) and in situ RT-PCR. Pathol Res Pract. 1994, 190: 1017-25]. Briefly, the RT-PCR reaction is performed on fixed cells by incorporating labeled nucleotides to the PCR reaction. The reaction is carried on using a specific in situ RT-PCR apparatus such as the laser-capture microdissection PixCell I LCM system available from Arcturus Engineering (Mountainview, Calif.).

Oligonucleotide microarray—In this method oligonucleotide probes capable of specifically hybridizing with the polynucleotides of the present invention are attached to a solid surface (e.g., a glass wafer). Each oligonucleotide probe is of approximately 20-25 nucleic acids in length. To detect the expression pattern of the polynucleotides of the present invention in a specific cell sample (e.g., blood cells), RNA is extracted from the cell sample using methods known in the art (using e.g., a TRIZOL solution, Gibco BRL, USA). Hybridization can take place using either labeled oligonucleotide probes (e.g., 5'-biotinylated probes) or labeled fragments of complementary DNA (cDNA) or RNA (cRNA). Briefly, double stranded cDNA is prepared from the RNA using reverse transcriptase (RT) (e.g., Superscript II RT), DNA ligase and DNA polymerase I, all according to manufacturer's instructions (Invitrogen Life Technologies, Frederick, MD., USA). To prepare labeled cRNA, the double stranded cDNA is subjected to an in vitro transcription reaction in the presence of biotinylated nucleotides using e.g., the BioArray High Yield RNA Transcript Labeling Kit (Enzo, Diagnostics, Affymetix Santa Clara Calif.). For efficient hybridization the labeled cRNA can be fragmented by incubating the RNA in 40 mM Tris Acetate (pH 8.1), 100 mM potassium acetate and 30 mM magnesium acetate for 35 minutes at 94° C. Following hybridization, the microarray is washed and the hybridization signal is scanned using a confocal laser fluorescence scanner which measures fluorescence intensity emitted by the labeled cRNA bound to the probe arrays.

For example, in the Affymetrix microarray (Affymetrix®, Santa Clara, Calif.) each gene on the array is represented by a series of different oligonucleotide probes, of which, each probe pair consists of a perfect match oligonucleotide and a mismatch oligonucleotide. While the perfect match probe has a sequence exactly complimentary to the particular gene, thus enabling the measurement of the level of expression of the particular gene, the mismatch probe differs from the perfect match probe by a single base substitution at the center base position. The hybridization signal is scanned using the Agilent scanner, and the Microarray Suite software subtracts the non-specific signal resulting from the mismatch probe from the signal resulting from the perfect match probe.

Methods of Detecting the Splice Variants and/or Splice Factor on the Protein Level Determining expression of the splice variants and/or splice factor on the protein level is typically effected using an antibody capable of specifically interacting with same. Methods of detecting the above described proteins include immunoassays which include but are not limited to competitive and non-competitive assay systems using techniques such as Western blots, radioimmunoassays, ELISA (enzyme linked immunosorbent assay), "sandwich" immunoassays, and immunoprecipitation assays and immunohistochemical assays as detailed herein below.

It will be appreciated that in order to avoid detection of more than one isoform of mnk2 or S6K1, it is preferable that the antibody recognizes an epitope of these splice variants which is distinct and not shared by the two isoforms.

Below is a list of techniques which may be used to determine the level of the proteins described herein above on the protein level.

Enzyme linked immunosorbent assay (ELISA): This method involves fixation of a sample (e.g., fixed cells or a proteinaceous solution) containing a protein substrate to a surface such as a well of a microtiter plate. A substrate specific antibody coupled to an enzyme is applied and allowed to bind to the substrate. Presence of the antibody is then detected and quantitated by a colorimetric reaction employing the enzyme coupled to the antibody. Enzymes commonly employed in this method include horseradish peroxidase and alkaline phosphatase. If well calibrated and within the linear range of response, the amount of substrate present in the sample is proportional to the amount of color produced. A substrate standard is generally employed to improve quantitative accuracy.

Western blot: This method involves separation of a substrate from other protein by means of an acrylamide gel followed by transfer of the substrate to a membrane (e.g., nylon or PVDF). Presence of the substrate is then detected by antibodies specific to the substrate, which are in turn detected by antibody binding reagents. Antibody binding reagents may be, for example, protein A, or other antibodies. Antibody binding reagents may be radiolabeled or enzyme linked as described hereinabove. Detection may be by autoradiography, colorimetric reaction or chemiluminescence. This method allows both quantitation of an amount of substrate and determination of its identity by a relative position on the membrane which is indicative of a migration distance in the acrylamide gel during electrophoresis.

Radio-immunoassay (RIA): In one version, this method involves precipitation of the desired protein (i.e., the substrate) with a specific antibody and radiolabeled antibody binding protein (e.g., protein A labeled with $I^{125}$) immobilized on a precipitable carrier such as agarose beads. The number of counts in the precipitated pellet is proportional to the amount of substrate.

In an alternate version of the RIA, a labeled substrate and an unlabelled antibody binding protein are employed. A sample containing an unknown amount of substrate is added in varying amounts. The decrease in precipitated counts from the labeled substrate is proportional to the amount of substrate in the added sample.

Fluorescence activated cell sorting (FACS): This method involves detection of a substrate in situ in cells by substrate specific antibodies. The substrate specific antibodies are linked to fluorophores. Detection is by means of a cell sorting machine which reads the wavelength of light emitted from each cell as it passes through a light beam. This method may employ two or more antibodies simultaneously.

Immunohistochemical analysis: This method involves detection of a substrate in situ in fixed cells by substrate specific antibodies. The substrate specific antibodies may be enzyme linked or linked to fluorophores. Detection is by microscopy and subjective or automatic evaluation. If enzyme linked antibodies are employed, a colorimetric reaction may be required. It will be appreciated that immunohistochemistry is often followed by counterstaining of the cell nuclei using for example Hematoxyline or Giemsa stain.

In situ activity assay: According to this method, a chromogenic substrate is applied on the cells containing an active enzyme and the enzyme catalyzes a reaction in which the substrate is decomposed to produce a chromogenic product visible by a light or a fluorescent microscope.

It will be appreciated that the method of the present invention may also be performed by measuring an activity of the isoforms. For example, the present inventors have shown that mnk2a uniquely phosphorylates p38-MAPK, so analysis of the phosphoyration status of p38-MAPK would allow for the indirect quantification of mnk2a.

For example, the present inventors have shown that the long isoform of S6K1 uniquely phosphorylates Serine 2448 of mTOR, so analysis of the phosphoyration status of Serine 2448 of mTOR would allow for the indirect quantification of the long isoform. The short isoforms of S6K1 (h6A and h6C) indirectly induce the phosphorylation of Threonine 70 of 4E-BP1, so analysis of the phosphoyration status of Threonine 70 of 4E-BP1 would allow for the indirect quantification of the short isoforms.

As mentioned, the diagnosis/staging is carried out by analyzing an amount or activity of the splice variants and/or splice factor in a cell sample of the subject, wherein a difference in an amount or activity thereof beyond a predetermined threshold with respect to a control cell sample is indicative of the disease. It will be appreciated that the amount of change may correspond with a degree or a stage of the disease. Thus, larger differences may indicate a later stage of the disease with a poorer prognosis, whereas lower differences may indicate an early stage of the disease with a better prognosis.

The patient sample typically comprises cells. It may be part of a tissue sample, retrieved during a biopsy. Alternatively, the sample may be a bodily fluid, e.g. blood, urine, saliva, CSF, plasma etc.

For diagnosis of cancer, the cell sample may comprise cells of the primary tumor and/or metastatic effusion thereof.

The predetermined level may be established based on results from control (non-diseased) cells.

The control cell sample typically depends on the patient sample being analyzed. Thus, for example, in the case of colon cancer, the control sample may comprise colon cells of a healthy individual (or at least one not suffering from colon cancer) or from a known stage of colon cancer (e.g. non-metastatic stage). In the case of breast cancer, the control sample may comprise breast cells of a healthy individual (or at least one not suffering from breast cancer) or from a known stage of breast cancer.

The control cells are typically normally differentiated, non-cancerous cells, preferably of the same tissue and specimen as the tested cells suspicious of having the disease. Typically, the amount of change in expression of the splice variants and/or splice factor is statistically significant.

Preferably, the difference is at least 10%, 20%, 30%, 40%, 50%, 80%, 100% (i.e., two-fold), 3 fold, 5 fold or 10 fold different as compared to the control cells.

It will be appreciated that the control data may also be taken from databases and literature.

On obtaining the results of the analysis, the subject is typically informed. Additional diagnostic tests may also be performed so as to corroborate the results of the diagnosing (e.g. gold standard tests, assessing the aggressiveness of the tumor, the patient's health and susceptibility to treatment, etc.).

Imaging studies such as CT and/or MRI may be obtained to further diagnose the disease.

In addition, when the disease is cancer, the diagnosis or choice of therapy may be determined by further assessing the size of the tumor, or the lymph node stage or both, optionally together or in combination with other risk factors.

The present inventors propose that based on the results of the diagnosis, a suitable therapy may be selected—i.e. personalized medicine.

Thus, according to another aspect of the present invention there is provided a method of determining whether a cancer is susceptible to an agent that inhibits the Ras-Raf MAPK pathway comprising determining an amount of Mnk2a and/or Mnk2b in a sample from the subject, wherein an amount of Mnk2b above a predetermined level and/or an amount of Mnk2a below a predetermined level is indicative of a cancer that is susceptible to the agent.

Agents that inhibit the Ras-Raf MAPK pathway include Ras inhibitors, Raf kinase inhibitors and MEK inhibitors.

Raf inhibitors may include, without being limited, sorafenib (Nexavar) or PLX-4032 (vemurafenib) or GSK-2118436 (dabrafenib). In an embodiment, a Raf inhibitor within the meaning of this invention refers to an inhibitor of BRaf (e.g. BRaf V600), particularly to a BRaf V600E inhibitor (such as e.g. PLX-4032 or GSK-2118436).

MEK inhibitors other than the dual compounds according to this invention may include, without being limited to, selumetinib (AZD-6244), or N-[3-[3-cyclopropyl-5-[(2-fluoro-4-iodophenyl)amino]-3,4,6,7-tetrahydr-o-6,8-dimethyl-2,4,7-trioxopyrido[4,3-d]pyrimidin-1(2H)-yl]phenyl]acetamid-e (GSK-1120212).

According to yet another embodiment there is provided a method of determining whether a cancer is susceptible to an agent that inhibits the pTEN pI3K-mTOR pathway comprising determining an amount of a short isoform of S6K1 and/or the long isoform of the S6K1 in a tumor sample from the subject, wherein an amount of the short isoform above a predetermined level is indicative of a cancer that is susceptible to the agent and/or an amount of the long isoform below a predetermined level is indicative of a cancer that is susceptible to the agent.

Agents that inhibit the pTEN pI3K-mTOR pathway include, but are not limited to mTOR inhibitors, PI3K inhibitors and Akt inhibitors.

Non-limiting examples of mTOR inhibitors for use in the methods and compositions described herein include everolimus (e.g. a compound having the structure of Formula III), temsirolimus (e.g. a compound having the structure of Formula II), rapamycin (e.g. a compound having the structure of Formula I), deforolimus, TOP216, OSI-027, TAFA93, nab-rapamycin, tacrolimus, biolimus, CI-779, ABT-578, AP-23675, BEZ-235, QLT-0447, ABI-009, BC-210, salirasib, AP-23841, AP-23573, KU-0059475, 32-deoxorapamycin, 16-pent-2-ynyloxy-32-deoxorapamycin, 16-pent-2-ynyloxy-32 (S or R)-dihydro-rapamycin, 16-pent-2-ynyloxy-32 (S or R)-dihydro-40-O-(2-hydroxyethyl)-rapamycin, 40-O-(2-hydroxyethyl)-rapamycin, 32-deoxorapamycin; 16-pent-2-ynyloxy-32(S)-dihydrorapamycin; socalledrapalogs; AP23464; PI-103, PP242, PP30, Torin1.

PI3K inhibitors may include, without being limited to, BKM-120, XL-147, RG-7321 (GDC-0941), CH-5132799 and BAY-80-6946. In an embodiment, a PI3K inhibitor within the meaning of this invention refers to an inhibitor of PI3K-alpha (such as e.g. BYL-719).

Dual PI3K/mTOR inhibitors may include, without being limited to, BEZ-235, XL-765, PF-4691502, GSK-2126458, RG-7422 (GDC-0980) and PKI-587.

AKT inhibitors may include, without being limited to, MK-2206, or N-{(1S)-2-amino-1-[(3,4-difluorophenyl) methyl]ethyl}-5-chloro-4-(4-chloro-1-methyl-1H-pyrazol-5-yl)-2-furancarboxamide.

The predetermined levels according to these aspects of the present invention may be determined according to control cells as described herein above.

The diagnostic methods described herein above may be manipulated so as to monitor the efficacy of an anti cancer treatment.

Thus, according to another aspect there is provided a method of monitoring an anti cancer treatment in a subject, the method comprising:

(a) administering at least one agent that inhibits the Ras-Raf MAPK pathway to the subject;

(b) detecting a level of Mnk2a and/or Mnk2b in a sample of the subject, wherein an increase in the level of Mnk2a following the administering compared with a level of the Mnk2a prior to the administering and/or a decrease in the level of Mnk2b following the administering compared with a level of the Mnk2b prior to the administering is indicative of a positive response to the anti cancer treatment.

According to still another aspect there is provided a method of monitoring an anti cancer treatment in a subject, the method comprising:

(a) administering at least one agent that inhibits the pTEN pI3K-mTOR pathway to the subject;

(b) detecting a level of a short isoform of S6K1 and/or a long isoform of S6K1 in a sample of the subject, wherein a decrease in the level of the short isoform of S6K1 following the administering compared with a level of the short isoform of S6K1 prior to the administering is indicative of a positive response to the anti cancer treatment and/or an increase in the level of the long isoform of S6K1 following the administering compared with a level of the long isoform of S6K1 prior to the administering is indicative of a positive response to the anti cancer treatment.

The changes in levels prior to and following administration are preferably at least 1.5 fold, 2 fold, 5 fold or more.

It will be appreciated that the tools necessary for diagnosing and monitoring the disease may be provided as a kit, such as an FDA-approved kit, which may contain one or more unit dosage form containing the active agent (e.g. antibody or probe) for detection of at least one marker of the present invention. The kit may be accompanied by instructions for administration. The kit may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration.

Since the level of the specific splice variants and splice factor described herein correlate with disease, the present inventors conceive that assays may be developed to screen for agents which are potentially useful for treating the disease disclosed herein.

Selecting agents useful for treating such diseases may be effected by contacting candidate agents with a population of cells (e.g. cancer cells) and analyzing an expression of a specific splice variant and/or splice factor. Agents which are capable of changing expression of any of these markers in the correct direction, as disclosed herein above are indicative for being useful for treating the above mentioned diseases.

It will be appreciated that the cells used for the screening process may be healthy cells or diseased cells, such as cancer cells.

The cancer cells may be primary cells (e.g. derived from a patient having the cancer) or may be immortalized cells (e.g. cell line). Contacting may be effected in vivo (e.g. in animal models), ex vivo or in vitro.

Once a candidate agent shows that it is capable of regulating expression of any of the above markers, the therapeutic potential thereof may be tested using other known in-vitro tests. The candidate agent's therapeutic potential may also be tested in animal models the related disease.

Once its therapeutic potential has been corroborated, pharmaceutical compositions comprising same may be synthesized, as described herein above.

According to still another aspect there is provided a method of determining a treatment for an inflammatory disorder in a subject, the method comprising determining an amount SRSF6 in a sample from the subject, wherein an amount of the SRSF6 is indicative of the treatment.

Methods of ascertaining an amount of SRSF6 are provided herein above.

Contemplated inflammatory disorders for which a treatment may be determined include all those listed herein above.

Exemplary inflammatory disorders include, but are not limited to cancer (e.g. colon cancer, breast cancer or lung cancer) and inflammatory bowel disorder (IBD).

According to one embodiment, the subject has undergone surgery to remove the cancer (e.g. colon cancer), and the test is performed to ascertain whether the subject requires an additional treatment such as chemotherapy. When the level of SRSF6 in the sample of the subject is above a predetermined level, chemotherapy and/or radiation therapy is indicated. The predetermined level may be determined using a statistically significant number of samples. Control data may be obtained from healthy subjects and/or from subjects who have undergone successful treatment with surgery, who did not require chemotherapy.

Preferably, the predetermined amount is at least 10%, at least 20%, at least 30%, at least 40%, at least 50% higher than the amount in subjects who do not require the chemotherapy (e.g. at least 10%, at least 20%, at least 30%, at least 40%, at least 50% higher than the amount in control subjects).

According to this embodiment, the sample is a tissue sample, i.e. a colon tissue sample which has been removed during surgery (i.e. a biopsy).

According to another embodiment, the subject has been diagnosed with IBD, and the test is performed to ascertain whether the subject requires surgical treatment to remove the colon. When the level of SRSF6 in the sample of the subject is above a predetermined level—this is indicative that the IBD has progressed into dysplasia and surgery is indicated. The predetermined level may be determined using a statistically significant number of samples, as detailed herein above with respect to colon cancer and the need for chemotherapy. Control data may be obtained from healthy subjects and/or from subjects who's IBD has not progressed into dysplasia. According to this embodiment, the sample is a tissue sample, i.e. a colon tissue sample.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

MNK2 Splice Variants and Cancer

Materials and Methods

Plasmids: Mnk2a and Mnk2b cDNAs were amplified by RT-PCR from HeLa RNA extracts using primers coding for an N-terminal T7 tag and subcloned into the EcoRI site of the pCDNA3.1 and pBABE plasmids. Mnk2a-kinase dead (Mnk2aKD), Mnk2aL/S and Mnk2aKKR were generated by site directed mutagenesis. Mnk2aKD: lysine 113 (K113) was replaced by alanine. Mnk2aL/S: leucines 281/285 were replaced by serines. Mnk2aKKR: lysines 60/61 and arginine 62 were replaced by alanines. Mutagenesis primers are described herein below.

```
Mnk2aKD:
L113A Forward:
                                    (SEQ ID NO: 1)
CAGGAGTACGCCGTCGCGATCATTGAGAAGCAG;

L113A Reverse:
                                    (SEQ ID NO: 2)
CTGCTTCTCAATGATCGCGACGGCGTACTCCTG.

Mnk2a L/S:
L/S Forward:
                                    (SEQ ID NO: 3)
TGCGACCTGTGGAGCAGTGGCGTCATCAGTTATATCCTACTCAGCG;

L/S Reverse:
                                    (SEQ ID NO: 4)
CGCTGAGTAGGATATAACTGATGACGCCACTGCTCCACAGGTCGCA.

Mnk2a KKR:
KKR/AAA Forward:
                                    (SEQ ID NO: 5)
GACGCCAAGAAGAGGGGCAAGAAGGCGGCGGCCGGCCGGGCCACCGAC

AGCTTCTC;

KKR/AAA Reverse:
                                    (SEQ ID NO: 6)
GAGAAGCTGTCGGTGGCCCGGCCGGCCGCCGCCTTCTTGCCCCTCTTC

TTGGCGTC
```

pWZL-HA-p38α(D176A+F327S) was generated by subcloning of HA-p38α(D176A+F327S) from pCDNA3.1 (24-26) into the EcoRI site of pWZL-hygro. shMnk2a-1 and shMnk2a-2 were constructed in the MLP vector. shRNA sequences are provided herein below.

```
shMnk2a-1:
                                    (SEQ ID NO: 7)
CAGTGATTCCATGTTTCGTAA;

shMnk2a-2:
                                    (SEQ ID NO: 8)
CAGGTTTGAAGACGTCTACCA
```

Cells: HEK293, MCF-7, MDA-MB-231, Panc-1, WT, $Mnk1^{-/-}$ and $Mnk2^{-/-}$ MEF cells were grown in DMEM supplemented with 10% (v/v) FBS, penicillin and streptomycin. Human breast cells: MCF-10A, were grown in DMEM/F12 supplemented with 5% (v/v) horse serum (HS, Biological Industries, Israel), 20 ng/ml epidermal growth factor (EGF) (Sigma), 10 μg/ml insulin (Biological Industries, Israel), 0.5 μg/ml hydrocortisone (Sigma), 100 ng/ml cholera toxin (Sigma), penicillin and streptomycin. HMLE cells were grown in MEBM/DMEM/F12 supplemented as described above. HMT-3522-S1 cells were grown in DMEM/F12 supplemented with 250 ng/ml insulin, 10 μg/ml transferrin, 5 μg/ml prolactin, 10 ng/ml EGF, $10^{-10}$ M 17β-estradiol, $10^{-8}$ M sodium selenite, 0.5 μg/ml hydrocortisone. HMEC cells were derived from normal breast tissue and were purchased from Cell Lonza and were grown in human mammary epithelial cells serum-free medium (ECACC). MDA-MB-468 cells were grown in Leibovitz-F12 supplemented with 10% (v/v) FBS, penicillin and streptomycin. SUM159 cells were grown in Ham's F12 with 5% calf serum, 5 μg/ml insulin and 1 μg/ml hydrocortisone. All cell lines were grown at 37° C. with 5% carbon dioxide. To generate stable cell pools, NIH 3T3 and MCF-10A cells were infected with pBABE-puro retroviral vector (54) expressing T7-tagged human Mnk2 isoform cDNA. Medium was replaced 24 h after infection, and 24 h later, infected cells were selected for by the addition of puromycin (2 μg/ml) or hygromycin (200 μg/ml) for 72-96 h. In the case of double infection with pWZL-hygro-Ras (54) or pWZL-hygro-p38α, cells were treated with hygromycin for 72 h after selection with puromycin. In the case of infection with MLP-puro-shRNAs vectors, MCF-10A cell transductants were selected for with puromycin (2 μg/ml) for 96 h.

Immunoblotting: Cells were lysed in Laemmli buffer and analyzed for total protein concentration as described previously (17). 30 μg of total protein from each cell lysate was separated by SDS-PAGE and transferred to a nitrocellulose membrane. The membranes were blocked, probed with antibodies and detected using enhanced chemiluminescence. Primary antibodies were anti phospho-eIF4E Ser209 (1:1000), eIF4E (1:1000), phospho-p38 (Thr180/Tyr182) (1:1000), phospho-MNK (T197/T202) (1:1000), phospho-MK2 (1:1,000), MK2 (1:1,000), (Cell Signaling Technology). MNK2 (1:1000, Santa Cruz), β-catenin (1:2,000, Sigma); SRp55 (mAb 8-1-28 culture supernatant); T7 tag (1:5,000, Novagen); p38 (1:1,000, Santa Cruz). Secondary antibodies were HRP-conjugated goat anti-mouse, goat anti-rabbit or donkey anti-goat IgG (H+L) (1:10,000, Jackson Laboratories).

Cytoplasmic/Nuclear Fractionation: Cellular fractionation was performed using the NE-PER (#78833) fractionation kit of Pierce according to the manufacturer's instructions.

Anchorage-independent growth: Colony formation in soft agar was assayed as described previously (17). Plates were incubated at 37° C. and 5% CO2. After 10-18 days, colonies were counted from ten different fields in each of two wells for each transductant pool and the average number of colonies per well was calculated. The colonies were stained and photographed under a light microscope at 100× magnification.

Growth curves: Transductant pools of MCF-10A cells were seeded at 2500 or 5000 cells per well in 96-well plates. Every 24 hours cells were fixed and stained with methylene blue, and the absorbance at 650 nm of the acid-extracted stain was measured on a plate reader (BioRad).

Cell cycle analysis: For cell cycle analysis MCF-10A cells transduced with the indicated viruses were trypsinized, washed twice with PBS and fixed in cold 70% ethanol at −20° C. for 30 min. Cells were then washed once with PBS and incubated for 45 min at room temperature with 250 μg/mL RNAse A and 50 μg/mL propidium iodide. Cell cycle was analyzed with FACScan flow cytometer.

Anoikis experiments: MCF-10A cells were transduced with the indicated retroviruses. Following selection, $1\times10^6$ cells were resuspended in serum-free medium and incubated in 15 ml poly-propylene tubes with 360° rotation, average-speed of 25 rpm in a 37° C. incubator chamber for 48 h. After 48 h, cells were centrifuged at 1000 g for 5 minutes and stained with trypan blue and live and dead cells counted.

Survival and apoptosis assays: MCF-10A or Panc-1 cells were transduced with the indicated retroviruses. Following selection, $1\times10^4$ cells per well were seeded in 96-well plates. 24 h later, the cells were serum starved for another 24 hours. At 24 hours (before treatment) one 96-plate was fixed and served as normalizing control ("Time 0"). After starvation the medium was replaced with starvation medium containing the indicated concentration of anisomycin and the cells were incubated for an additional 24 h. Cells were fixed and stained with methylene blue and the absorbance at 650 nm of the acid-extracted stain was measured on a plate reader (BioRad) and was normalized to cell absorbance at "Time 0". For apoptosis, MCF-10A cells were seeded on 6-well plates ($500\times10^3$ cells/well). 24 hours later cells were incubated with 0.5 or 1 μM anisomycin for 24 or 48 hours. Medium and PBS washes were collected together with cells trypsinized from each well into 15 ml tubes and centrifuged at 1000 g for 5 min Cells were washed with PBS and after another centrifugation were resuspended in 100 μl of PBS. 10 μl of the cell suspension was mixed with 10 μl of 4% trypan blue solution and live/dead cells were counted in Bio-Rad TC-10 Automated Cell Counter. After counting the remaining 90 μl of cell suspension was centrifuged, PBS was discarded and cells were resuspended in 90 μl of Laemmli buffer. Lysates were separated on SDS-PAGE and after Western blotting membranes were probed with antibodies against cleaved caspase 3 (Cell Signaling) to evaluate induction of apoptosis.

RT-PCR: Total RNA was extracted with Tri reagent (Sigma) and 2 μg of total RNA was reverse transcribed using the AffinityScript (Stratagene) reverse transcriptase. PCR was performed on 1/10 (2 μl) of the cDNA, in 50 μl reactions containing 0.2 mM dNTP mix, 10×PCR buffer with 15 mM MgCl2 (ABI), 2.5 units of TaqGold (ABI) and 0.2 mM of each primer; 5% (v/v) DMSO was included in some reactions. PCR conditions were 95° C. for 5 min, then 33 cycles of 94° C. for 30 s, 57° C. for 30 s and 72° C. for 45 s, followed by 10 min at 72° C. PCR products were separated on 1.5% or 2% agarose gels. Primers are listed herein below.

```
Mnk2:
Mnk2a/2b Forward:
                                        (SEQ ID NO: 9)
CCAAGTCCTGCAGCACCCCTG;

Mnk2a Reverse:
                                       (SEQ ID NO: 10)
GATGGGAGGGTCAGGCGTGGTC;

Mnk2b Reverse:
                                       (SEQ ID NO: 11)
GAGGAGGAAGTGACTGTCCCAC;

GAPDH Forward:
                                       (SEQ ID NO: 12)
ATCAAGAAGGTGGTGAAGCAG;

GAPDH Reverse:
                                       (SEQ ID NO: 13)
CTTACTCCTTGGAGGCCATGT.

p38-MAPK target genes (Mouse):
mCOX2 Forward:
                                       (SEQ ID NO: 14)
TACAAGCAGTGGCAAAGGC;

mCOX2 Reverse:
                                       (SEQ ID NO: 15)
CAGTATTGAGGAGAACAGATGGG;

mc-FOS Forward:
                                       (SEQ ID NO: 16)
GGCTTTCCCAAACTTCGACC;

mc-FOS Reverse:
                                       (SEQ ID NO: 17)
GGCGGCTACACAAAGCCAAAC;

mGAPDH Forward:
                                       (SEQ ID NO: 18)
AATCAACGGCACAGTTCAAGGC;

mGAPDH Reverse:
                                       (SEQ ID NO: 19)
GGATGCAGGGATGATGTTCTGG.

p38-MAPK target genes (Human):
COX2 Forward:
                                       (SEQ ID NO: 20)
TCATTCACCAGGCAAATTGC;

COX2 Reverse:
                                       (SEQ ID NO: 21)
TCTTCAAATGATTCATAGGG;

c-FOS Forward:
                                       (SEQ ID NO: 22)
GCTCGCCTGTCAACGCGCAG;

c-FOS Reverse:
                                       (SEQ ID NO: 23)
TGAGGGGCTCTGGTCTGCGA;

SRSF1-NMD:
ASF-A Forward:
                                       (SEQ ID NO: 24)
AGGAGGATTGAGGAGGATCAG;

ASF-B Reverse:
                                       (SEQ ID NO: 25)
CGCTCCATGAATCCTGGTAA.
```

Q-RT-PCR: Total RNA was extracted with Tri reagent (Sigma) and 2 μg of total RNA was reverse transcribed using the AffinityScript (Stratagene) reverse transcriptase. The mRNA levels of FOS, and COX-2 were determined in MCF-10A breast cell lines by performing quantitative PCR with SYBER Green (SYBR® Premix Ex Taq™ # RR041A) using the CFX96 (Bio-Rad) machine. Unknown samples were compared to a standard curve, which is established by serial dilutions of a known concentration of cDNA. The standard that was used is β-Actin. Ct-Threshold cycle from β-Actin and unknown samples were inserted to the standard curve formula and the final value was the ratio between the unknown sample divided by the β-Actin standard gene. Primers are listed herein below. The PCR reaction is composed of the following steps: 1 cycle at 95° C. for 10 seconds; 40 cycles of 95° C. for 5 seconds and 48° C. for 20 seconds.

```
p38-MAPK target genes (Human):
COX2 Forward:
                                       (SEQ ID NO: 26)
CCGAGGTGTATGTATGAGTGT;

COX2 Reverse:
                                       (SEQ ID NO: 27)
CTGTGTTTGGAGTGGGTTTC;

c-FOS Forward:
                                       (SEQ ID NO: 28)
GAACAGTTATCTCCAGAA;

c-FOS Reverse:
                                       (SEQ ID NO: 29)
TTCTCATCTTCTAGTTGG;

SRSF1:
SF2 Forward:
                                       (SEQ ID NO: 30)
GAGTTCGAGGACCCGCGAGACG;

SF2 Reverse:
                                       (SEQ ID NO: 31)
GAGCTCCGCCACCTCCAC;

Mnk2:
Mnk2a/2b Forward:
                                       (SEQ ID NO: 32)
TCCGTGACGCCAAGCAG;

Mnk2a Reverse:
                                       (SEQ ID NO: 33)
GGTCTTTGGCACAGCTG;

Mnk2b Reverse:
                                       (SEQ ID NO: 34)
GAGGAAGTGACTGTCCCAC;

Actin:
Actin Forward:
                                       (SEQ ID NO: 35)
CCCAGCACAATGAAGATCAA;

Actin Reverse:
                                       (SEQ ID NO: 36)
TAGAAGCATTTGCGGTGGAC;

Ndufb9
Ndufb9 For:
                                       (SEQ ID NO: 37)
TATATCTTCCCAGACT;

Ndufb9 Rev:
                                       (SEQ ID NO: 38)
CTCAGAGGGATGCCAGTAATCTA;

HPRT
HPRT For:
                                       (SEQ ID NO: 39)
TGACACTGGCAAAACAATGCA;

HPRT Rev:
                                       (SEQ ID NO: 40)
GGTCCTTTTCACCAGCAAGCT;
```

-continued

```
Krt14
Krt14 For:
                                        (SEQ ID NO: 41)
GACCATTGAGGACCTGAGGA;

Krt14 Rev:
                                        (SEQ ID NO: 42)
CATACTTGGTGCGGAAGTCA;

GAPDH
GAPDH For:
                                        (SEQ ID NO: 43)
TCACCACCATGGAGAAGGC;

GAPDH Rev:
                                        (SEQ ID NO: 44)
GCTAAGCAGTTGGTGGTGCA;
```

Colony survival assay: MCF-10A cell populations transduced with retroviruses encoding for Mnk2 isoforms were transduced with pWZL-hygro-RAS$^{v12}$ Immediately after selection, cells were diluted as indicated with fresh medium and seeded in 6-well plates for 14-20 days. Colonies were fixed and stained with methylene blue, for quantification, the number of colonies in each well was calculated.

Tumor formation in mice: Pools of Ras-MCF-10A cells expressing the indicated Mnk2 isoforms or shRNAs were injected into the rear flanks of NOD-SCID mice (2×10$^6$ cells per site in 100 μl of serum free medium containing 0.25 v/v growth factor stripped matrigel (BD Bioscience) using a 26-gauge needle.

Immunoprecipitation: Cells were lysed with CHAPS buffer, the lysates were cleared by centrifugation at 12,000 g for 15 min, and the supernatant was passed through a 0.45-mm filter. For each cell line, 30 μl of 50% (v/v) protein G-Sepharose beads was incubated with 2 μg of antibody against HA (Santa Cruz) or 2 μg of antibody against T7 (Novagen) for 1.5 h at 4° C. The beads were then incubated while rotating with 0.7 mg of total protein from each lysate for 4 h at 4° C. The beads were washed three times with CHAPS buffer and boiled for 5 min in 50 μl of 2×SDS Laemmli buffer. After SDS-PAGE and transfer the membranes were probed with antibodies against Mnk2 and p38α.

Immunofluorescence: Cells plated on a cover glass were rinsed twice with 1×PBS$^+$ containing $Mg^{++}/Ca^{++}$ and fixed with 4% PFA at room temperature for 30 minutes. Cells were permeabilized with 0.5% NP40 (Fluka) and then washed with 1×PBS$^+$ containing 0.1% Tween 20 (PBS$^+$T). Following permeabilization, cells were blocked with PBS$^+$T containing 20% fetal bovine serum for 45 minutes. Fixed cells were incubated with the following primary antibodies in 1:1000-1:2000 dilutions: Mouse anti T7-tag (Novagen), Rabbit anti p38α (Santa Cruz), Mouse anti HA-tag (Santa Cruz) over night at 4° C. Following incubation, cells were washed once with 1% ammonium chloride and then with PBS$^+$T, and incubated with the following secondary antibodies in 1:1000 dilution; Alexa 594 goat anti Mouse (Invitrogen), Alexa donkey anti rabbit 488 (Jackson) and incubated for 50 minutes at room temperature in the dark. Cover-glasses were washed with 1% ammonium chloride and then with PBS$^+$T. Cover-glasses were placed onto slides with mounting solution (Thermo Scientific Cat# TA-030-FM) containing DAPI (1:1000, Sigma Cat#D9564)). Microscopy was performed on NIKON ECLIPSE Ti/IntenseLight, C-HGFI using the NIS Elements digital system. Quantification of Cytoplasmic and Nuclear cell distribution: Nuclear area was marked by the DAPI stain. The intensity the FITC and Cy3 channels of each cellular fraction was calculate using NIS-Elements/Annotations and Measurements software (Nikon). Dividing the intensity by the area in each cell, we obtain values corresponding to a specific cellular staining in each cell.

Results

Figure 1D:
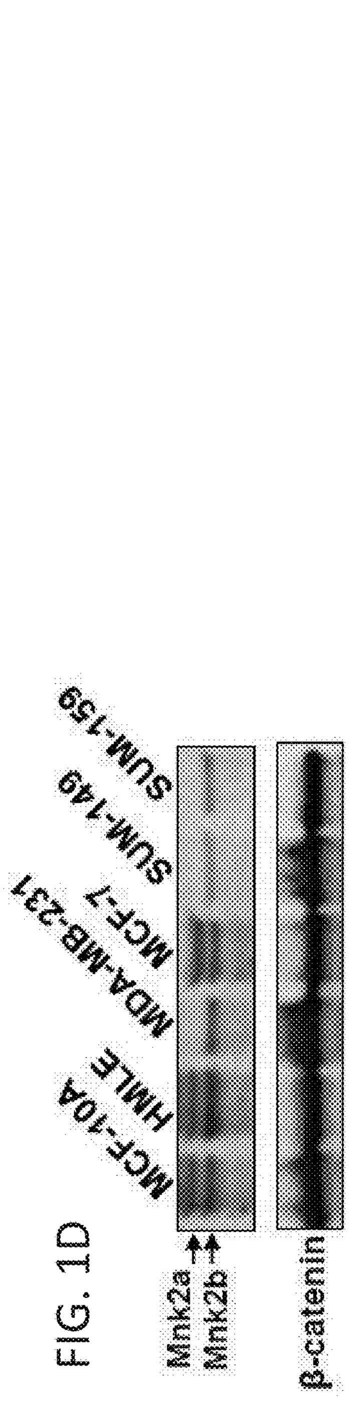
Figure 1E:
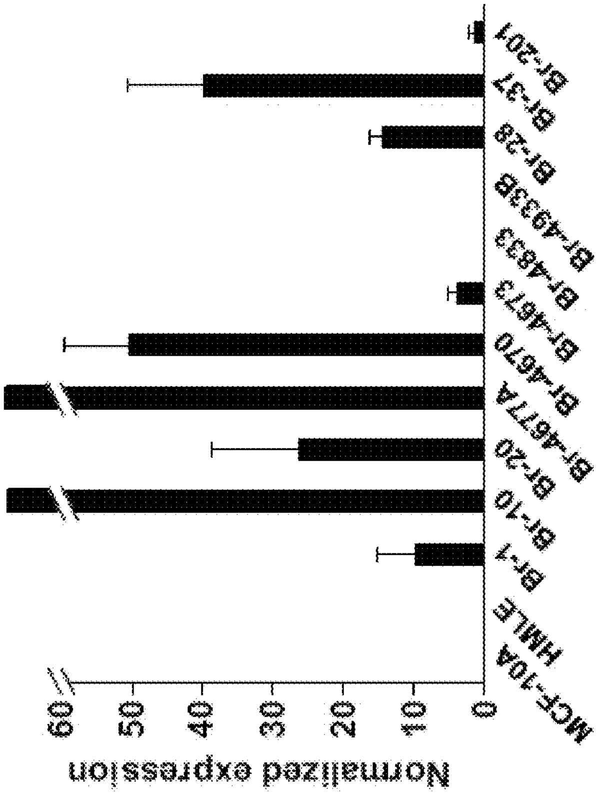
Figure 1F:
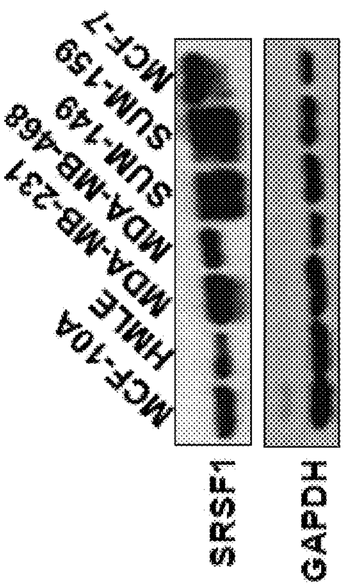
Figures 1G, 1H, 1I:
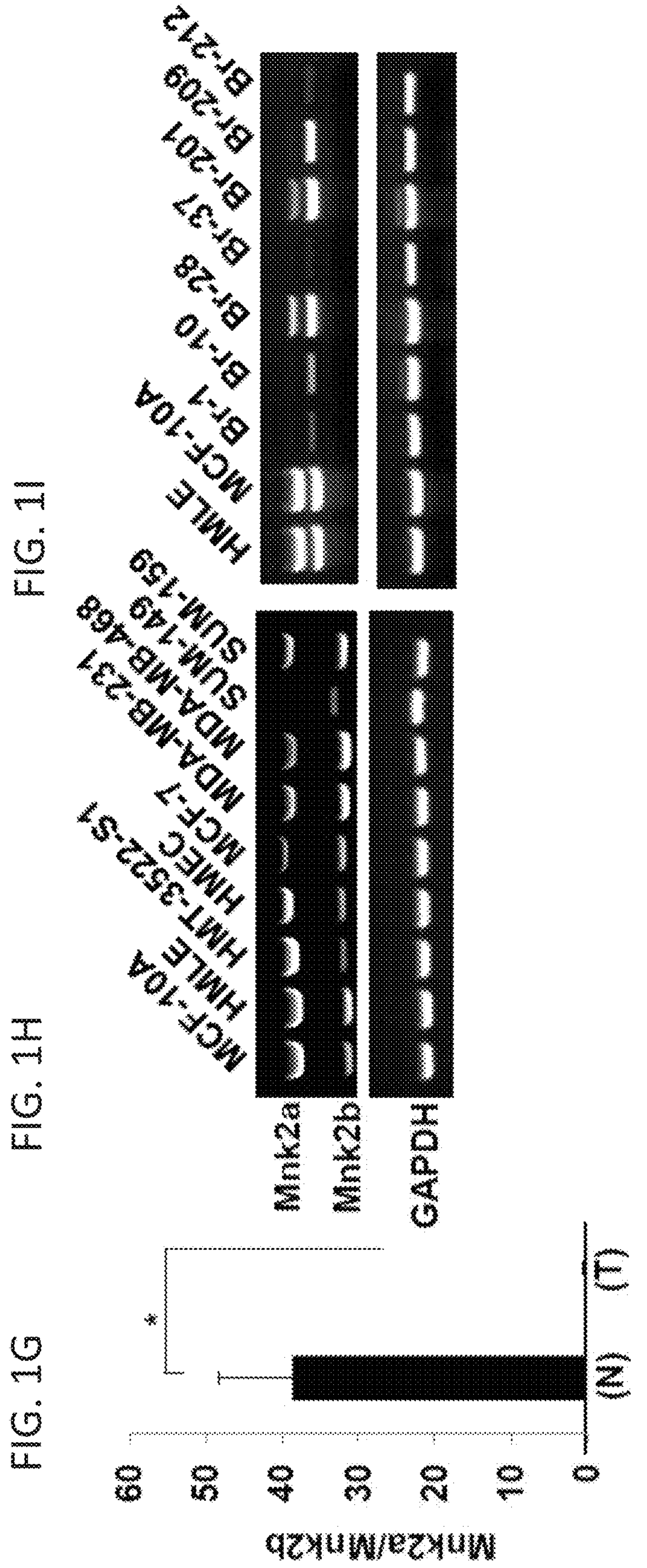
Figure 1J:
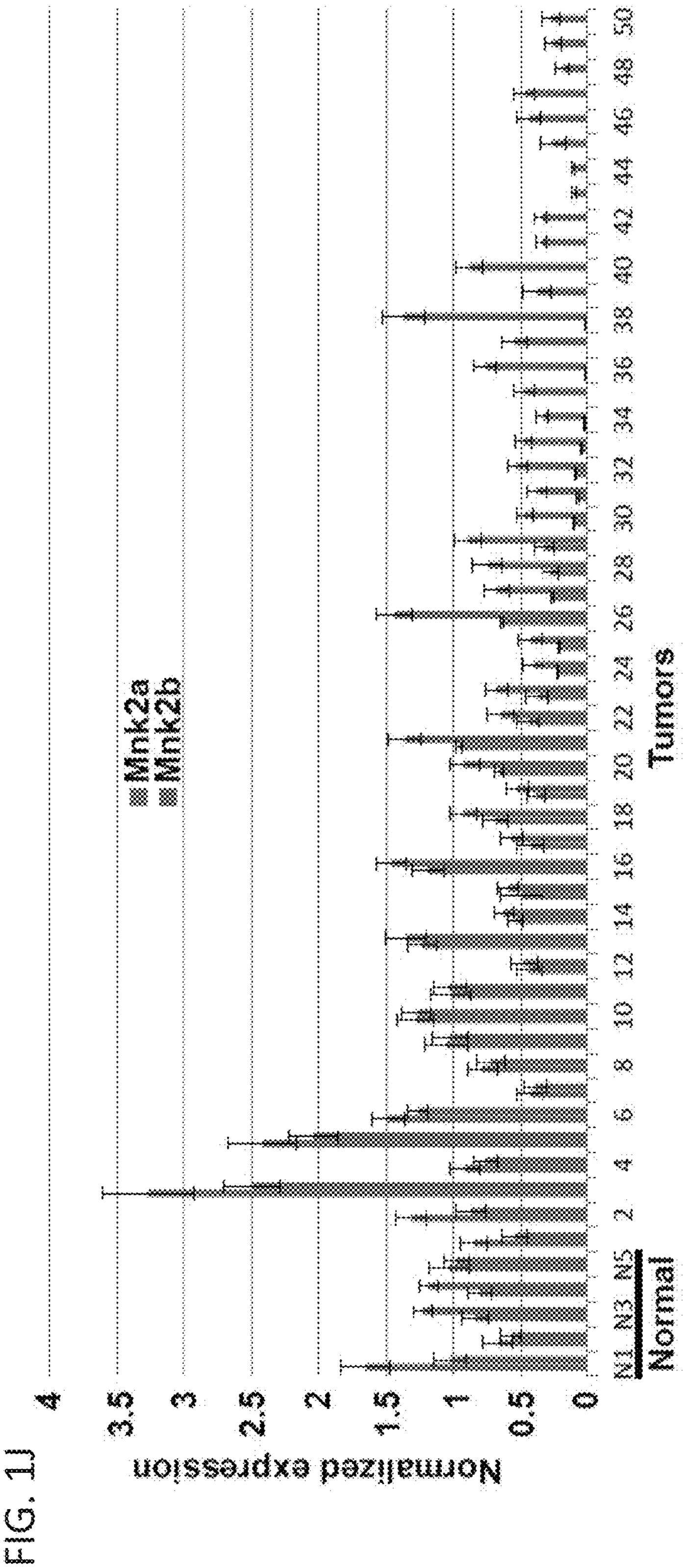
Figure 1K:
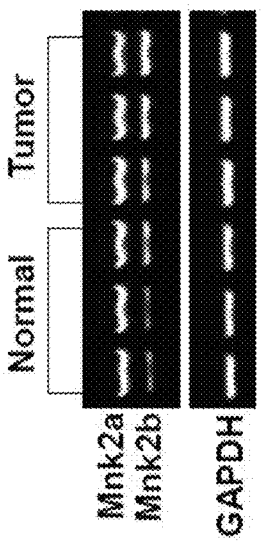

Mnk2a mRNA is Down-regulated by Active Ras in Colon, Breast and Lung Cancers MKNK2, is alternatively spliced to yield two isoforms: Mnk2a and Mnk2b (FIG. 1A). To examine if changes in MKNK2 splicing is a general phenomenon in cancer, the present inventors compared immortal and primary breast cells to breast cancer cell lines, as well as to breast tumor samples. A higher or equal expression of Mnk2a compared to Mnk2b was detected in immortal (MCF-10A, HMLE, HMT-3522-S1) and primary breast cells (HMEC). In contrast, Mnk2a expression was significantly decreased and in some cases Mnk2b increased in tumor cell lines and tumor samples (FIGS. 1B, 1C and 1G-I). Reduced Mnk2a levels compared to Mnk2b could be observed also at the protein level in most breast cancer cell lines, compared to immortal non-transformed cells, except for MCF-7 cells, where Mnk2a protein level remained high, whereas its mRNA was reduced (FIGS. 1B-D). In cancer cell lines, Mnk2a protein levels decreased dramatically, while mRNA levels decreased by approximately 4 fold. This result suggests that Mnk2a protein might be further destabilized in cancer cells. The ratio of Mnk2a to Mnk2b mRNA was also examined in 50 lung tumors and 5 normal lung samples. More than 50% of the tumors showed at least a twofold decrease in Mnk2a levels, while Mnk2b levels remained similar to that of normal lung samples (FIG. 1J). Similarly, a comparison of normal human colon tissue and colon cancer tumor samples showed that on average Mnk2b mRNA was upregulated in colon tumors compared to normal mucosa (FIG. 1K).

Since the splicing factor SRSF1 controls the splicing of Mnk2, the present inventors examined if Mnk2 alternative splicing correlates with SRSF1 expression. It was found that SRSF1 RNA and protein levels were higher in breast tumors than in immortal breast cell lines in correlation with Mnk2 alternative splicing (FIGS. 1E-F). SRSF1 is phosphorylated by SRPK1 and Clk1-4 on its RS domain, which might explain the shift in the corresponding band in some of the breast cancer cell lines (Ngo et al. 2005). Thus, upregulation of SRSF1 levels in cancer cells probably leads to reduced Mnk2a and elevated Mnk2b levels.

Mnk2a has Tumor Suppressive Activity while Mnk2b is Pro-oncogenic In Vitro

Figures 2A, 2B, 2C, 2D, 2E, 2F, 2G:
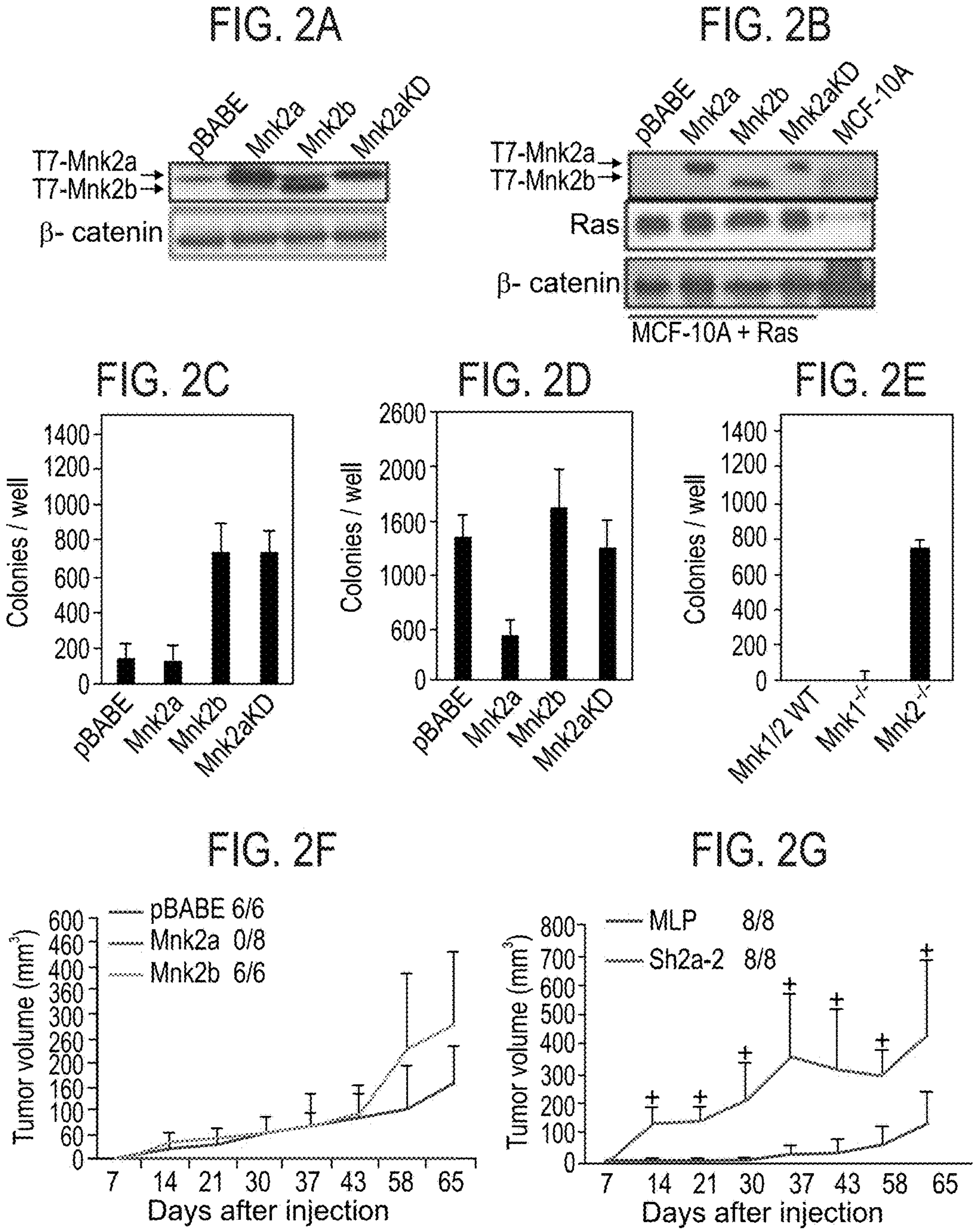
Figures 2H, 2I, 2J, 2K:
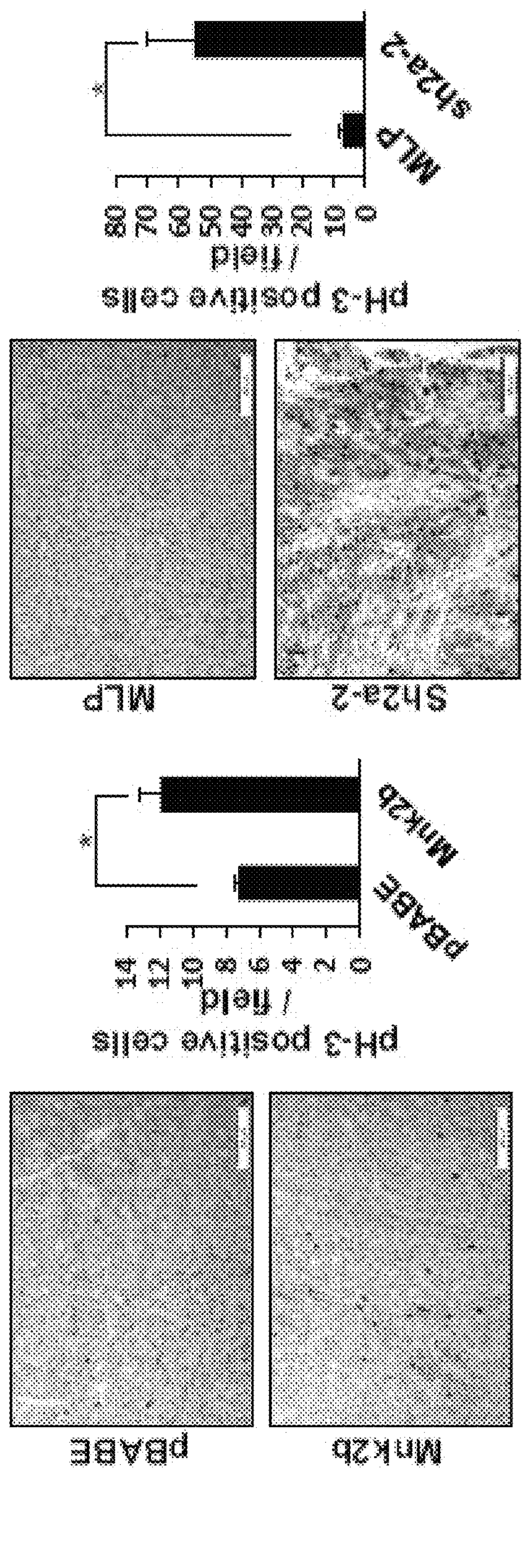
Figure 2L:
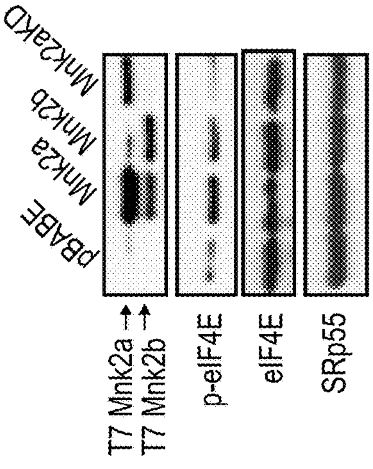
Figure 2M:
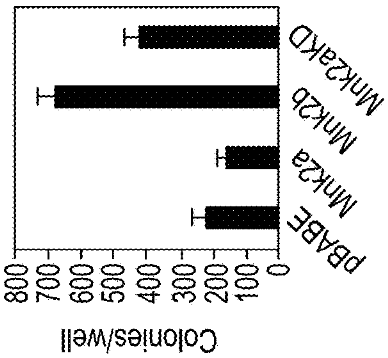
Figure 2N:
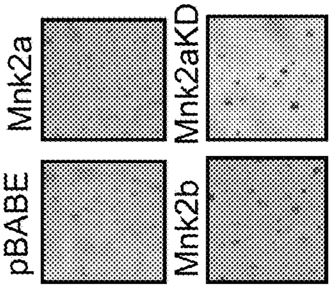
Figure 2O:
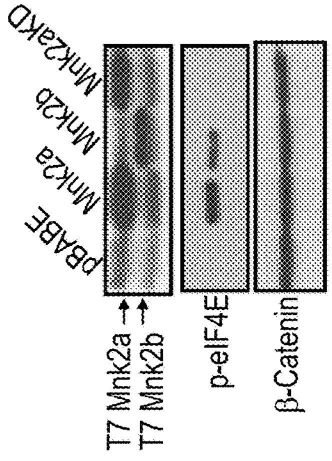
Figure 2P:
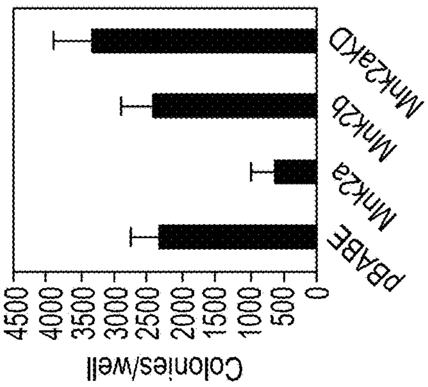
Figure 2Q:
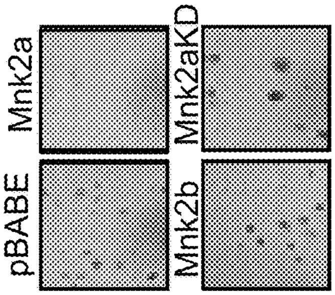
Figures 2R, 2S, 2T, 2U, 2V:
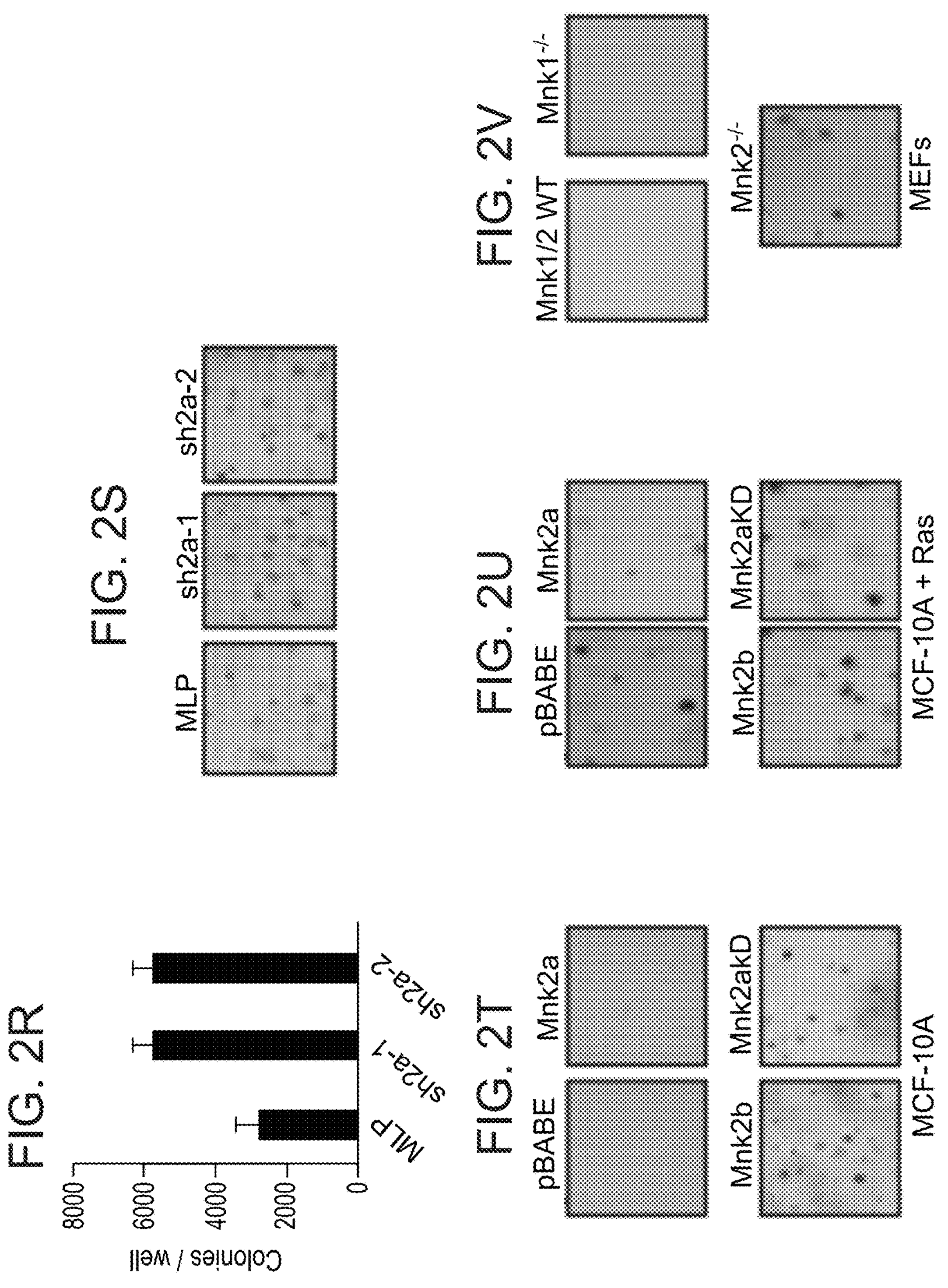
Figure 4D:
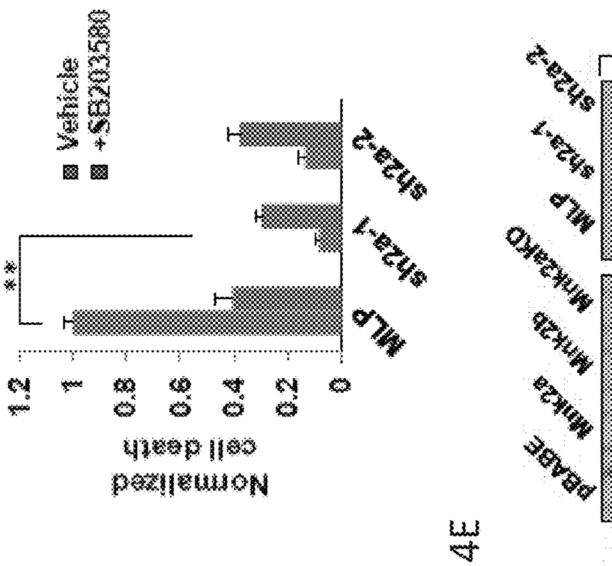
Figure 4E:
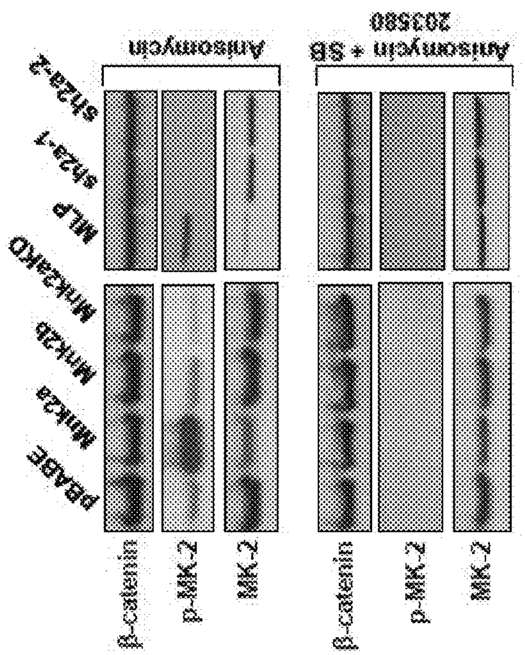
Figure 4A:
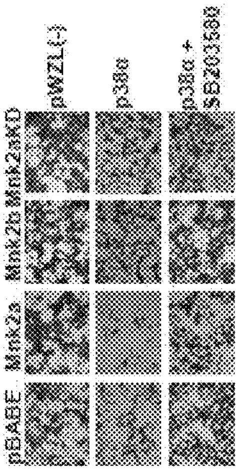
Figure 4B:
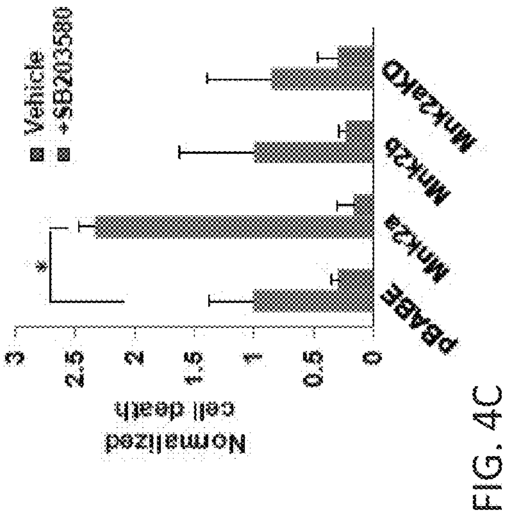
Figure 4C:
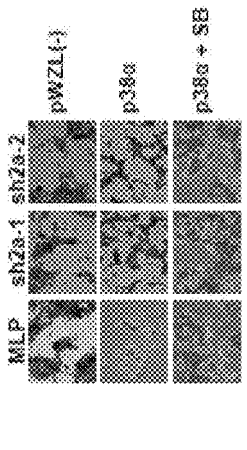
Figure 4I:
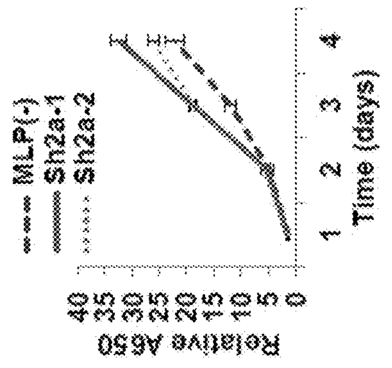
Figure 4H:
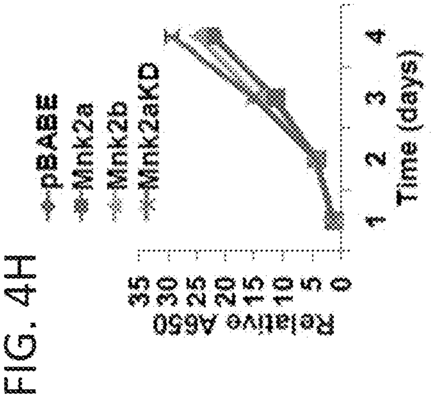

The fact that Mnk2a is downregulated in many cancers led to the hypothesis that Mnk2 alternative splicing might contribute to cancer development and to the oncogenic activity of SRSF1. To examine the role of Mnk2 alternative splicing in cellular transformation non-transformed breast MCF-10A cells transduced with Mnk2 splicing isoforms were seeded into soft agar. Cells expressing Mnk2b or a kinase-dead Mnk2a were transformed and generated colonies in soft agar, while cells expressing Mnk2a did not (FIGS. 2A, C and FIG. 2T). Kinase-dead Mnk2a probably acts in a dominant-negative manner by competing with Mnk2a for substrate binding, while incapable of phosphorylation. Similar results were obtained in another transformation model of NIH 3T3 cells (FIGS. 2L-N). Furthermore, when MCF-10A cells expressing Mnk2 splicing isoforms were transformed by oncogenic Ras, cells co-expressing Mnk2a showed reduced ability to form colonies in soft agar indicating that Mnk2a can block Ras-induced transformation (FIGS. 2B, D and FIG. 2U). Similarly, Mnk2a inhibited colony formation in soft agar of the osteosarcoma cell line U2OS (FIG. S2D-F). Knockdown of Mnk2a enhanced colony formation of MCF-10A and NCI-H460 cells in soft agar, suggesting that Mnk2a is tumor suppressive (FIGS. 3G-J and FIGS. 2R-S). In order to examine the effects of Mnk1 and Mnk2 loss on cellular transformation, immortal MEF cells from WT, Mnk1$^{-/-}$ and Mnk2$^{-/-}$ mice were seeded into soft agar. While WT and Mnk1$^{-/-}$ MEF cells did not form colonies in soft agar, Mnk2$^{-/-}$ MEF cells formed a large number of colonies in soft agar suggesting that these cells are transformed (FIG. 2E, FIG. 2V). To examine the possibility that Mnk2a and 2b exert their effects by changing cell proliferation, the growth rate of cells expressing Mnk2 splicing isoforms was examined. Neither Mnk2a nor 2b expression changed significantly the proliferation rate of the cells or their cell cycle distribution (FIGS. 4H, J-M). However, cells with Mnk2a knockdown had a slightly higher proliferation rate, indicating that Mnk2a reduction may enhance proliferation (FIG. 4I). Taken together, these results suggest that the tumor-suppressive activity of Mnk2a is probably only partly mediated through its effects on cellular proliferation.

Mnk2a has a Tumor Suppressor Activity in Vivo

In order to examine if Mnk2a possesses tumor-suppressor activity in vivo, Ras-transformed MCF-10A cells transduced with Mnk2 splicing isoforms were injected into NOD-SCID mice. It was found that mice injected with Ras-MCF-10A cells expressing either empty vector or Mnk2b formed tumors (6/6), whereas mice injected with Ras-MCF-10A cells expressing Mnk2a did not form any tumors (0/8) (FIG. 2F). Tumors from cells expressing Mnk2b showed an increased mitotic index (FIG. 2H-I) compared with tumors from cells expressing Ras alone but did not show significant enhanced tumor growth (FIG. 2F). Inversely, mice injected with Ras-MCF-10A cells expressing shRNA against Mnk2a showed enhanced tumor growth rate (FIG. 2G) and mitotic index in the tumors (FIGS. 2J-K), indicating that Mnk2a depletion cooperates with and enhances Ras tumorigenicity.

The present inventors also examined the effect of expressing Mnk2a and its kinase-dead form in the pancreatic cancer cell line Panc-1 which possesses mutant Ras as well as low levels of Mnk2a and found that Mnk2a, but not its kinase-dead form inhibited tumor growth in vivo (FIGS. 14A-B).

Collectively, these results suggest that Mnk2a has tumor-suppressor activity and it can antagonize Ras-mediated transformation in vitro and in vivo.

Mnk2a Sensitizes Cells to Stress-Induced Cell Death

Figures 3A, 3B, 3C, 3D, 3E, 3F:
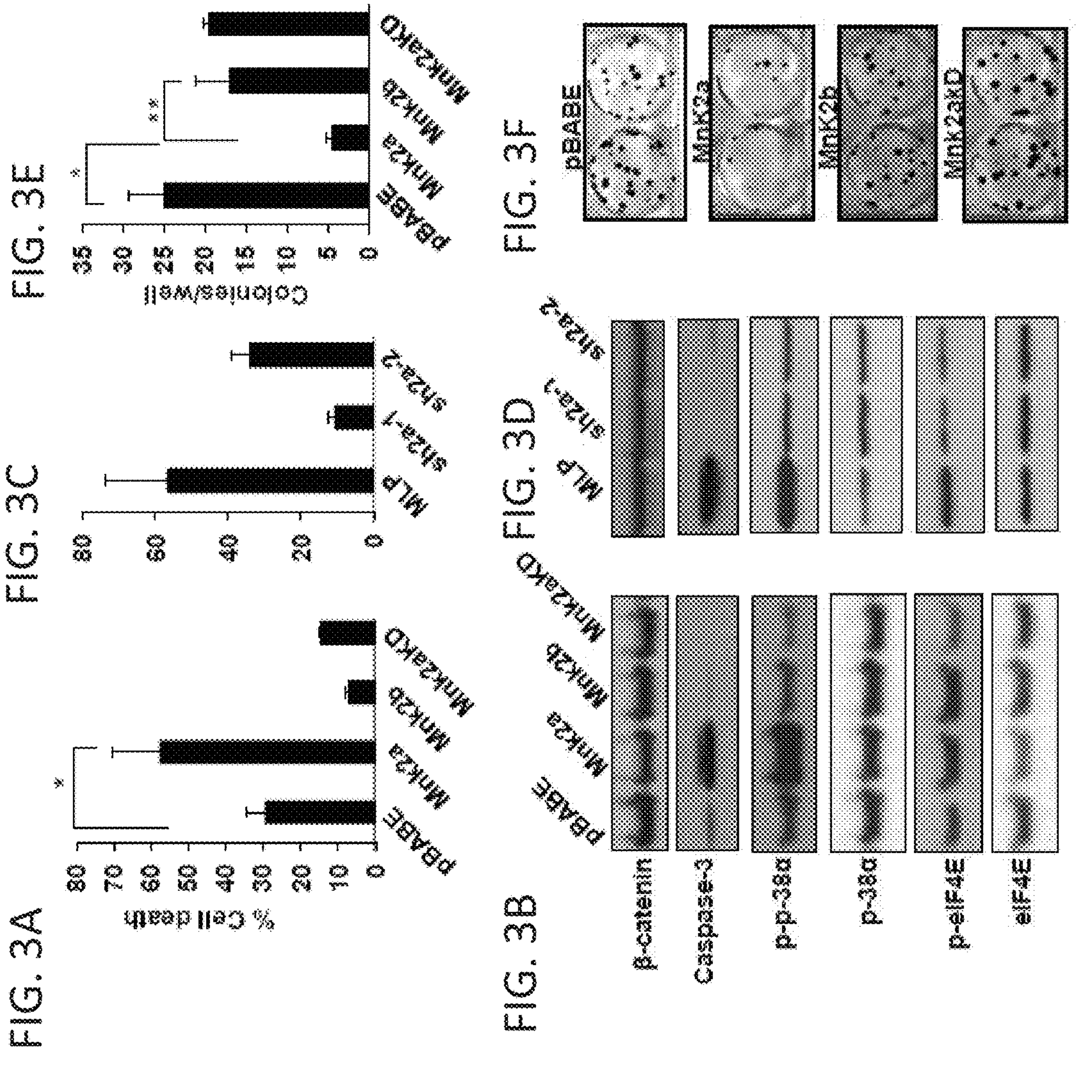
Figure 3G:
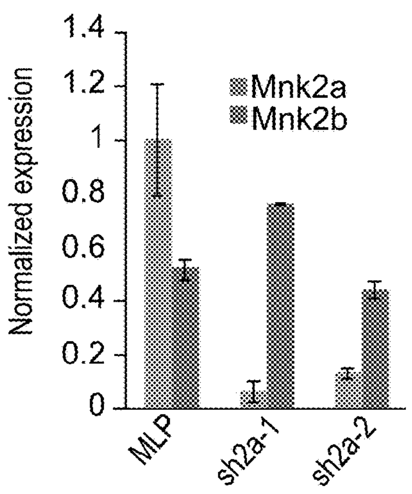
Figure 3H:
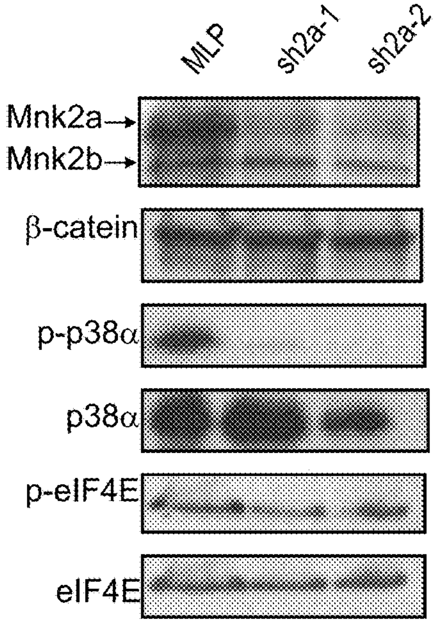
Figure 3I:
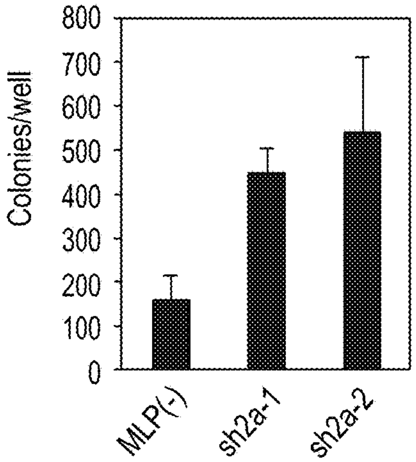
Figure 3J:
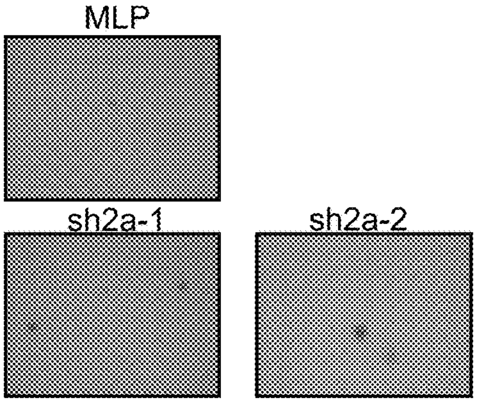
Figure 5C:
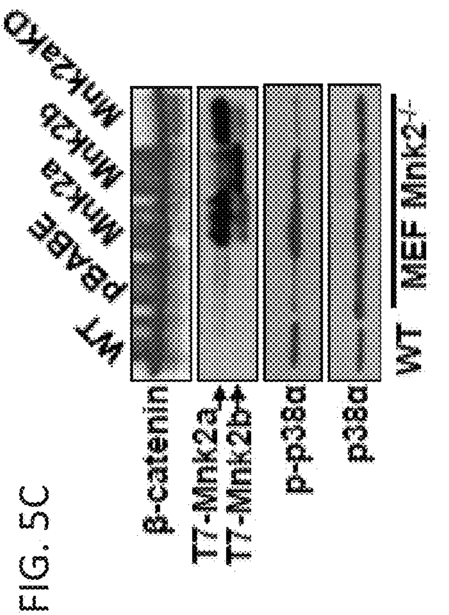
Figure 5D:
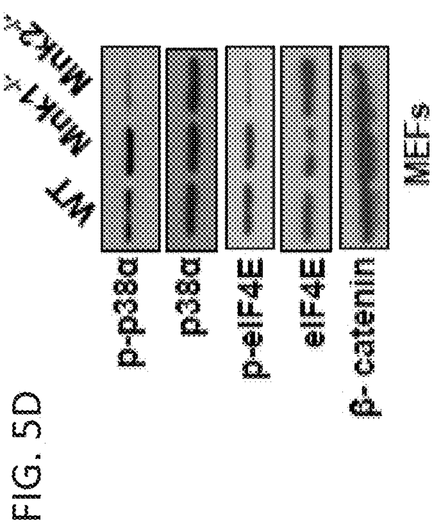
Figure 5A:
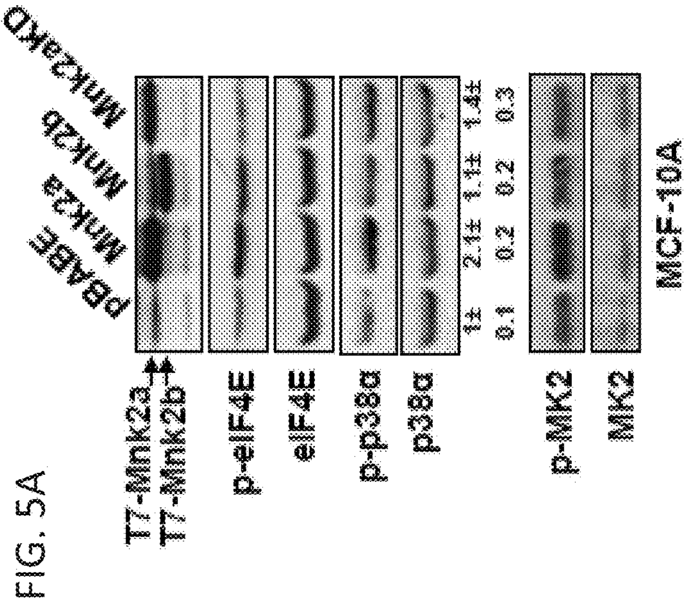
Figure 5B:
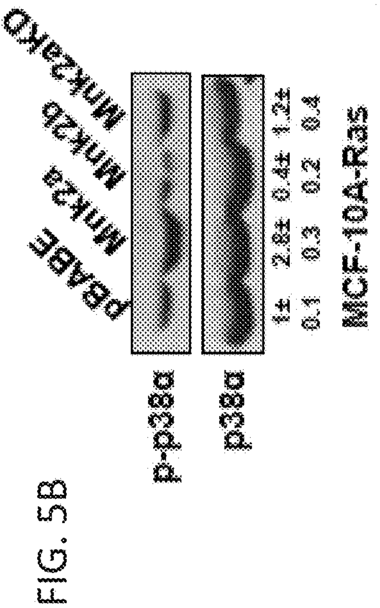
Figures 5E, 5F, 5G, 5H:
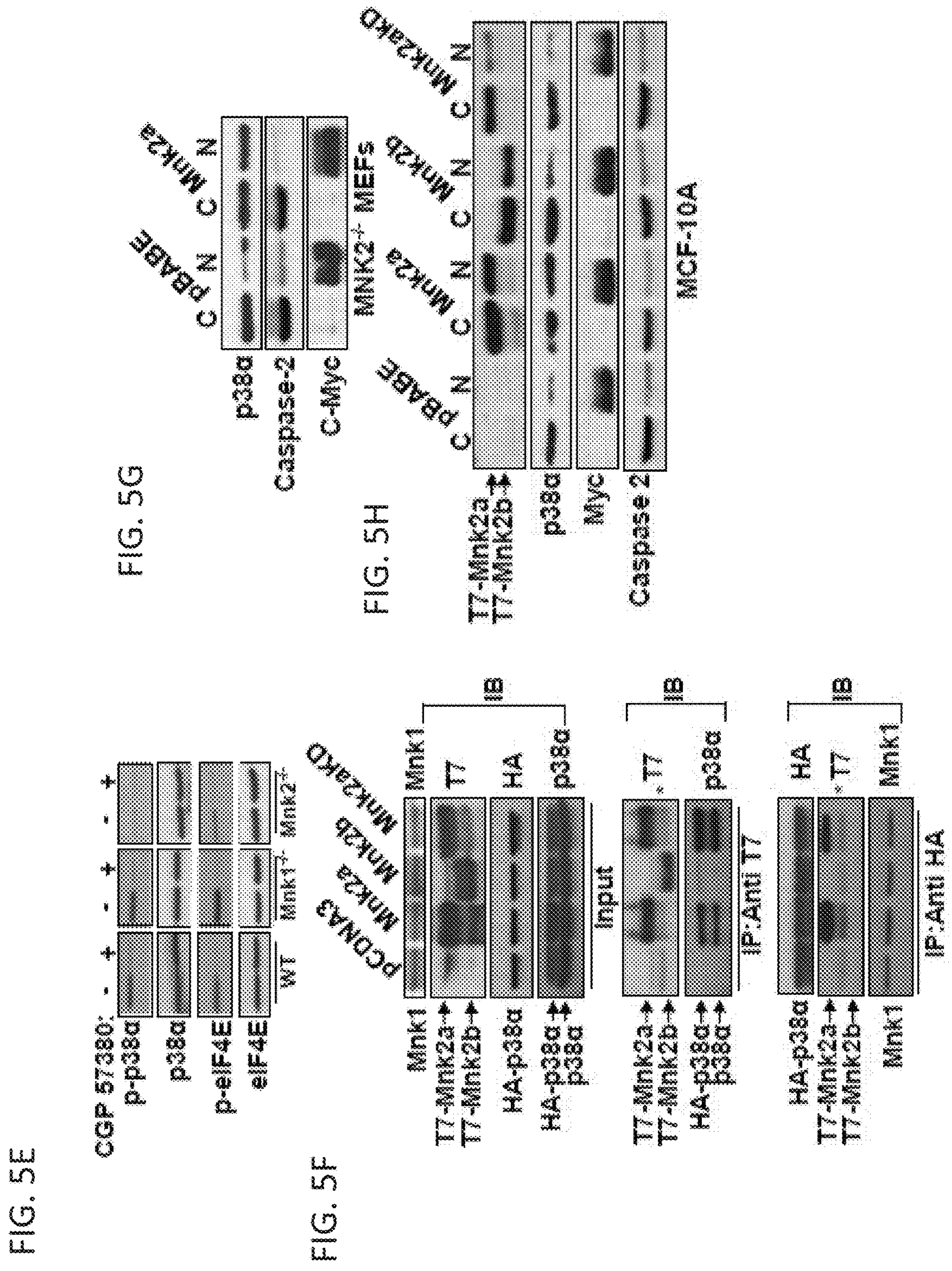
Figures 5I, 5J, 5K, 5L:
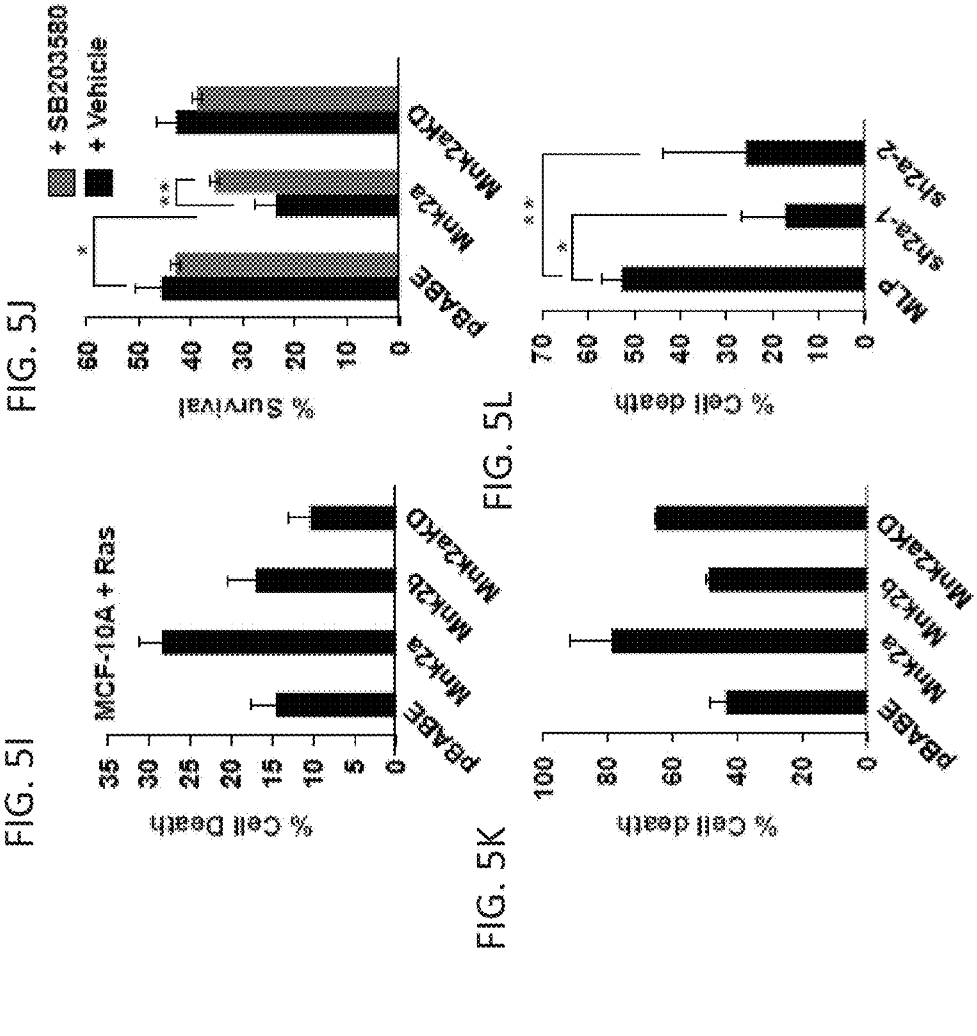

Although Mnk2a showed tumor suppressive activity in vitro and in vivo, its over-expression or down-regulation did not affect cellular proliferation significantly (FIGS. 4H-M). Thus, it was hypothesized that Mnk2a might enhance the sensitivity of cells to apoptosis. Evasion from apoptosis and resistance to stress conditions are important properties of cancer cells. To examine the possible role of Mnk2 splicing isoforms in the response to cellular stress, immortalized breast cells (MCF-10A and Ras-transformed MCF-10A cells) transduced with retroviruses encoding either Mnk2a, 2b or a kinase-dead mutant of Mnk2a were challenged with different stress conditions. While Mnk2a enhanced apoptotic cell death in response to anisomycin treatment, as measured by trypan blue exclusion and caspase 3 cleavage, Mnk2b and the kinase-dead Mnk2a protected against apoptosis (FIGS. 3A-B). Moreover, knockdown of Mnk2a protected MCF-10A cells from anisomycin-induced apoptosis (FIGS. 3C-D). The positive correlation of apoptosis and caspase-3 cleavage with p38-MAPK phosphorylation (FIGS. 3B, D), suggests that Mnk2a pro-apoptotic activity might involve activation of the p38-MAPK pathway. Mnk2a also reduced survival of Ras-transformed MCF-10A cells or MCF-10A cells forced to grow in suspension or stimulated with osmotic shock respectively (FIG. 5I, K). In contrast, knockdown of Mnk2a protected cells from osmotic shock, suggesting that Mnk2a mediated this stress response (FIG. 5L). Mnk2a also inhibited the survival of MCF-10A cells transformed by oncogenic Ras when sparsely seeded for colony survival assay (FIGS. 3E-F), suggesting that Mnk2a sensitizes Ras-transformed cells to low-density stress conditions. One of the stress pathways induced by anisomycin and other cellular insults is the p38-MAPK pathway. In order to examine if p38-MAPK activation is involved in Mnk2a-enhanced cell death, p38-MAPK activity was blocked with the specific inhibitor SB203580. p38-MAPK inhibition partially rescued cells expressing Mnk2a from anisomycin-induced cell death (FIG. 5J).

Figure 4F:
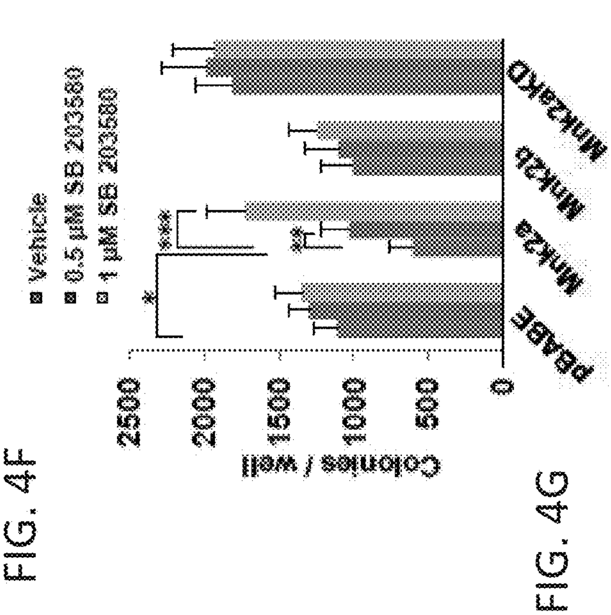
Figure 4G:
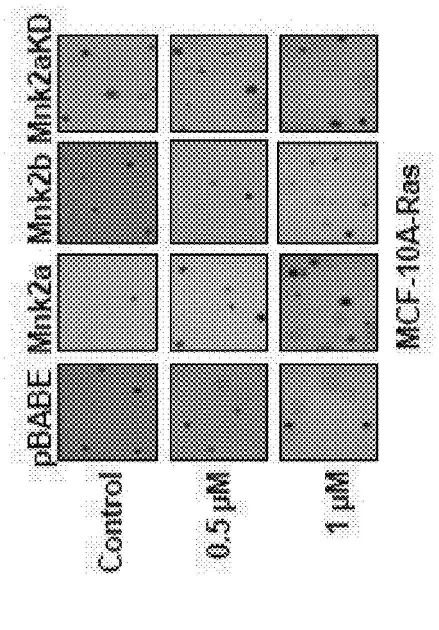
Figure 4J:
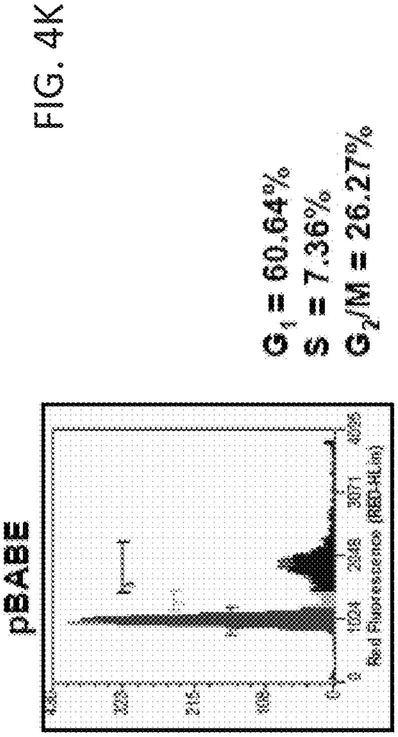
Figure 4K:
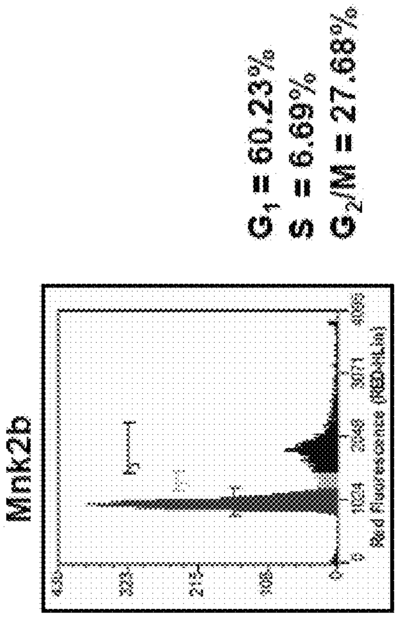
Figure 4L:
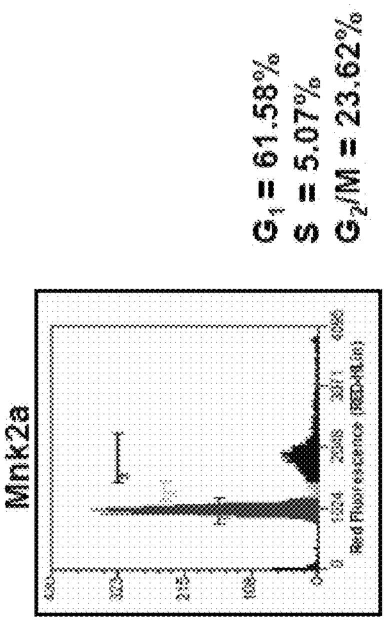
Figure 4M:
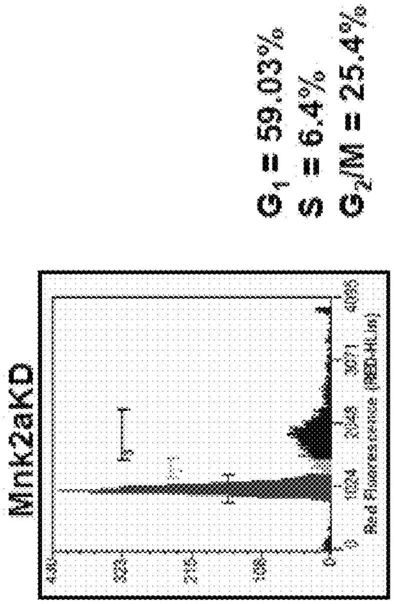

Mnk2a, but not Mnk2b, Enhances p38α-mediated Cell Death and Suppression of Ras-induced Transformation Because Mnk2a, but not Mnk2b, contains a MAPK binding domain (FIG. 1A) and can be activated by ERK and p38-MAPK, the present inventors examined if Mnk2a can mediate stress responses emanating from activated p38-MAPK. MCF-10A cells either expressing Mnk2 isoforms or knocked down for Mnk2a were transduced with a constitutively-active p38α mutant and grown in the absence or presence of the p38 inhibitor SB203580. Cells expressing Mnk2a showed increased cell death upon active p38-MAPK transduction, which was inhibited by SB203580 (FIGS. 4A and 4B). Cells in which Mnk2a was knocked-down showed increased protection from p38-induced cell death (FIGS. 4C-D). SB203580 efficiently inhibited p38 activity, as was measured by phosphorylation of its substrate MK-2 (FIG. 4E). These results suggest that Mnk2a augments p38-MAPK stress activity. To examine if p38-MAPK activation by Mnk2a plays a role in its tumor-suppressive activity, the present inventors measured soft agar colony formation of MCF-10A cells co-transduced with Mnk2a isoforms and oncogenic Ras in the presence or absence of the p38 inhibitor SB203580 Inhibition of p38-MAPK by SB203580 rescued the ability of cells co-transduced with Mnk2a and Ras to form colonies in soft agar, indicating that p38 activation by Mnk2a plays an important role in its ability to suppress Ras-induced transformation (FIGS. 4F-G).

Mnk2a Interacts with, Activates and Induces Nuclear Translocation of p38-MAPK

The fact that Mnk2a might interact with p38-MAPK and enhance p38α-mediated cell death (FIGS. 4A-F), suggests that it might regulate its activity. To determine if Mnk2a activates p38-MAPK, the present inventors examined the phosphorylation status of p38-MAPK in cells expressing Mnk2 splicing isoforms. As expected, phosphorylation of a known substrate of Mnk2, serine 209 of eIF4E, was induced by Mnk2a expression (FIG. 5A and FIGS. 2L-O). Even though previous reports have suggested that Mnk2b has a lower kinase activity than Mnk2a, the present inventors observed that it phosphorylates eIF4E to at least the same extent as does Mnk2a (FIG. 5A and FIGS. 2L-O). The kinase-dead version of Mnk2a did not enhance eIF4E phosphorylation (FIG. 5A and FIGS. 2L-O). In contrast, only cells expressing Mnk2a showed increased p38-MAPK phosphorylation, indicating that p38-MAPK is activated (FIGS. 5A-C). Moreover, knockdown of Mnk2a in MCF-10A cells or MEF cells from Mnk2$^{-/-}$, but not from Mnk1$^{-/-}$ mice, showed reduced p38-MAPK basal phosphorylation level, which was restored upon introduction of ectopic human Mnk2a (FIGS. 5C-D; FIG. 3D; and FIG. 3H). Introduction of human Mnk2b into Mnk2$^{-/-}$ MEF cells also elevated p38 phosphorylation, but to a lesser extent (FIG. 5C). In addition, it was determined that the phosphorylation state of the p38-MAPK substrate MK2, was enhanced in cells expressing Mnk2a, but not Mnk2b or kinase-dead Mnk2a (FIG. 5A). To further examine if the kinase activity of Mnk2a is important for p38 phosphorylation, the present inventors treated WT, Mnk1$^{-/-}$ and Mnk2$^{-/-}$ MEFs with the Mnk1/2 kinase inhibitor CGP. Mnk2$^{-/-}$ MEFs showed reduced p38 phosphorylation compared to WT or Mnk1$^{-/-}$ MEFs and this basal phosphorylation could not be further reduced by CGP 57380 (FIG. 5E, FIG. 8D-F). It was noted that in WT and Mnk1$^{-/-}$ MEFs and in MCF-10A cells, Mnk1/2 inhibition reduced p38-MAPK phosphorylation on the known MEK3/6 phosphorylation sites T180, Y182, similar to its effect on eIF4E S209 phosphorylation (FIG. 5E). Finally, p38 phosphorylation was examined in immortal breast cells and in breast cancer cells and it was observed that in the latter (which tend to express low Mnk2a levels) (FIGS. 1B and 1D), p38 phosphorylation is lower than in the non-transformed cells (FIG. 8A, B). These results suggest that Mnk2a is an upstream activator of p38-MAPK in normal and cancer cells. Collectively, these results suggest that the pro-apoptotic effect of Mnk2a or protective effects of its knockdown do not correlate with its effects on eIF4E phosphorylation, which has been assumed to promote survival or transformation, but is rather mediated by p38.

The present inventors next examined whether Mnk2 isoforms can differentially interact with p38α MAPK in cells. Co-immunoprecipitation of transfected or endogenous p38α from HEK293 cells, demonstrated that Mnk2a and Mnk2aKD, unlike Mnk2b, efficiently bound p38α (FIG. 5F) Importantly, even though Mnk2aKD was bound to p38α (FIG. 5F), it did not cause activation of p38, as measured by p38 or MK2 phosphorylation (FIG. 3B; FIG. 4E; and FIGS. 5A-C). Finally, to rule out the possibility that Mnk2 isoforms compete with Mnk1 for p38α binding, Mnk1 binding to p38α was examined with respect to Mnk2 isoforms. It was found that Mnk1 was bound to HA-p38α. However, its binding was not affected by any of the Mnk2 isoforms, suggesting that either they do not bind to the same residues in p38α or do not compete for its binding (FIG. 5F). Taken together, these results suggest that Mnk2a interacts with p38α and leads to its activation.

Figure 8G:
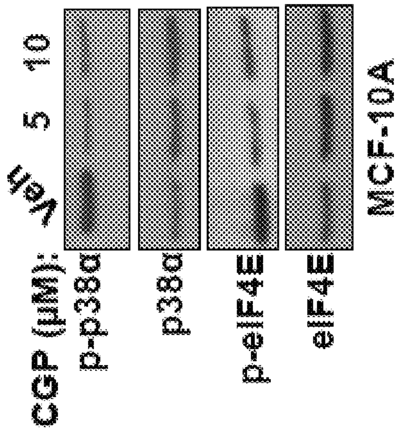
Figure 8H:
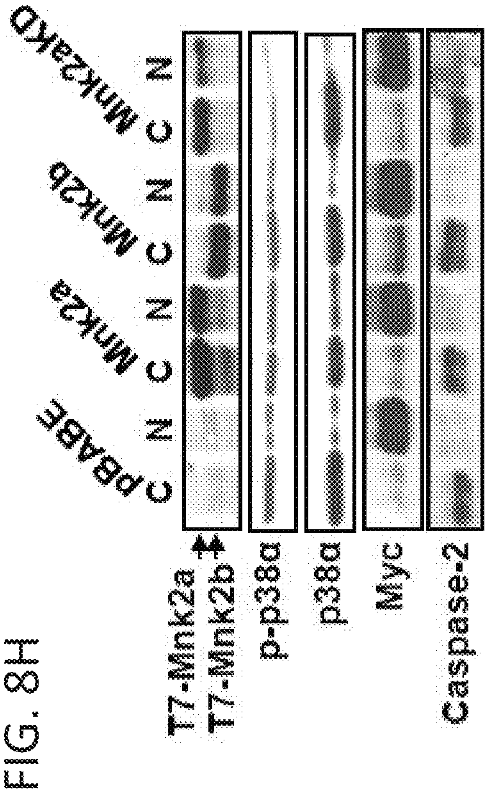

Upon activation, p38-MAPK is translocated to the nucleus and phosphorylates transcription factors that mediate some of its stress response. Both Mnk2 isoforms contain a putative NLS domain which might result in their nuclear localization (FIG. 1A). Previous reports suggested that there is a nuclear fraction of Mnk2b while Mnk2a is mostly cytoplasmic. Using cytoplasmic and nuclear fractionation, as well as immunofluorescent staining (FIG. 5G-H; FIG. 6; FIG. 8H; FIG. 9; FIGS. 10A-D and FIGS. 12A-B), it was observed that both Mnk2a and Mnk2b can be detected in the nucleus (FIG. 5H; FIGS. 10A-D; FIG. 8H and FIG. 9). However, cells that express Mnk2a showed an increased nuclear fraction of total and phosphorylated p38-MAPK (FIGS. 5G-H; FIG. 6; FIGS. 10A-D and FIG. 8H), indicating that Mnk2a leads to both p38-MAPK activation and its translocation into the nucleus. Importantly, Mnk2$^{-/-}$ MEFs had low p38-MAPK phosphorylation levels (FIG. 5D) and low levels of nuclear p38-MAPK which were elevated by introduction of exogenous Mnk2a (FIG. 5G and FIGS. 12A-B), whereas transduction with Mnk2a induced translocation of p38-MAPK into the nucleus (FIG. 5G and FIGS. 12A-B). Taken together, these results suggest that Mnk2a affects the activation and cellular distribution of p38α-MAPK.

Mnk2a Co-localizes with p38-MAPK and Affects its Cellular Localization

Figure 10B:
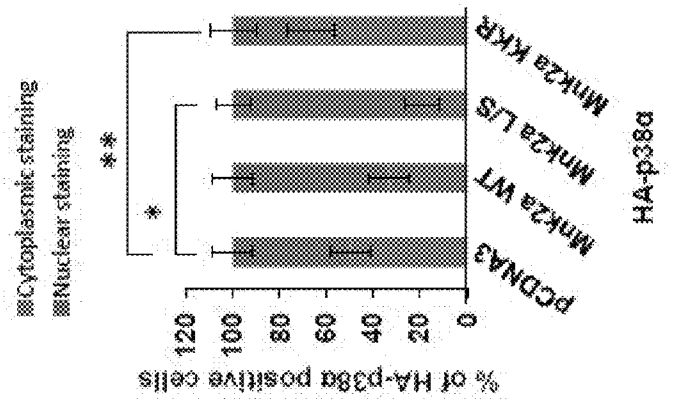
Figure 10A:
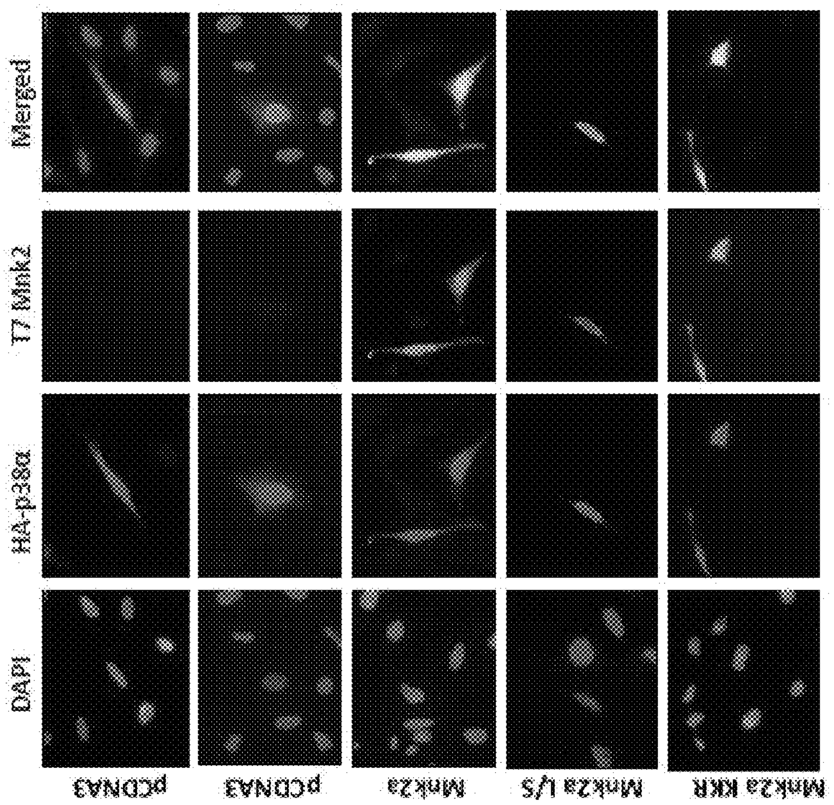
Figure 10D:
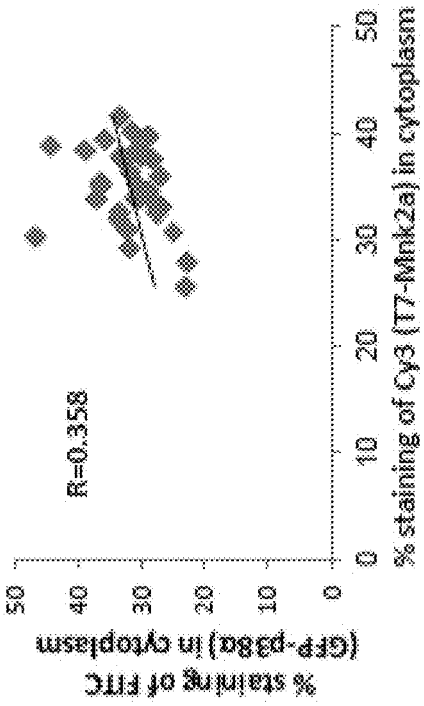
Figure 10C:
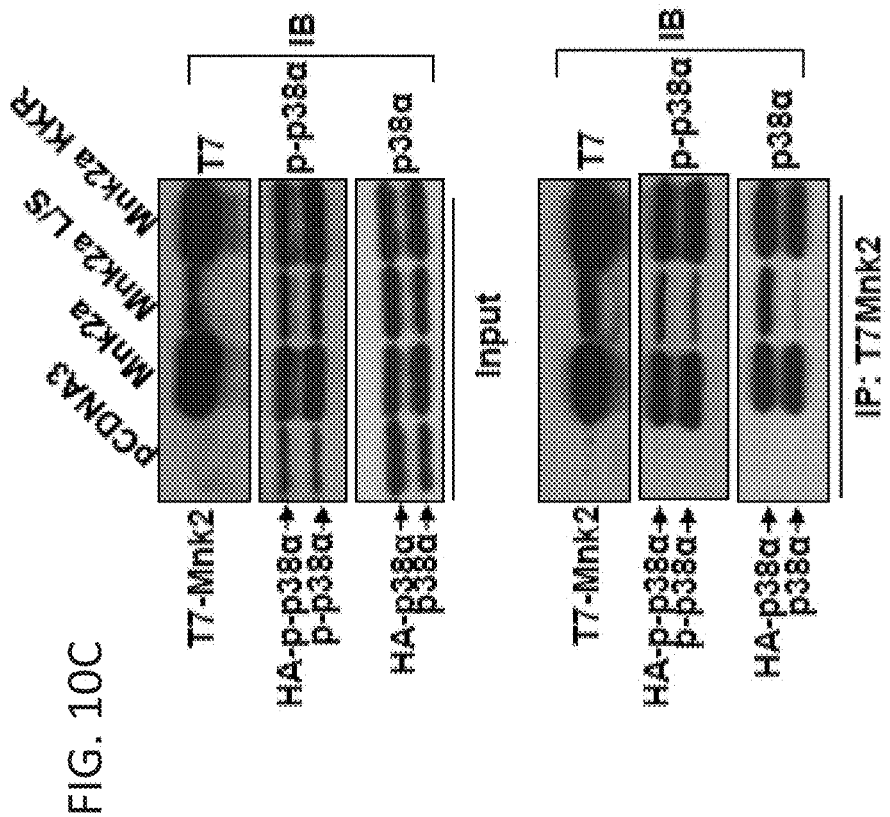
Figures 11A, 11B, 11C, 11D:
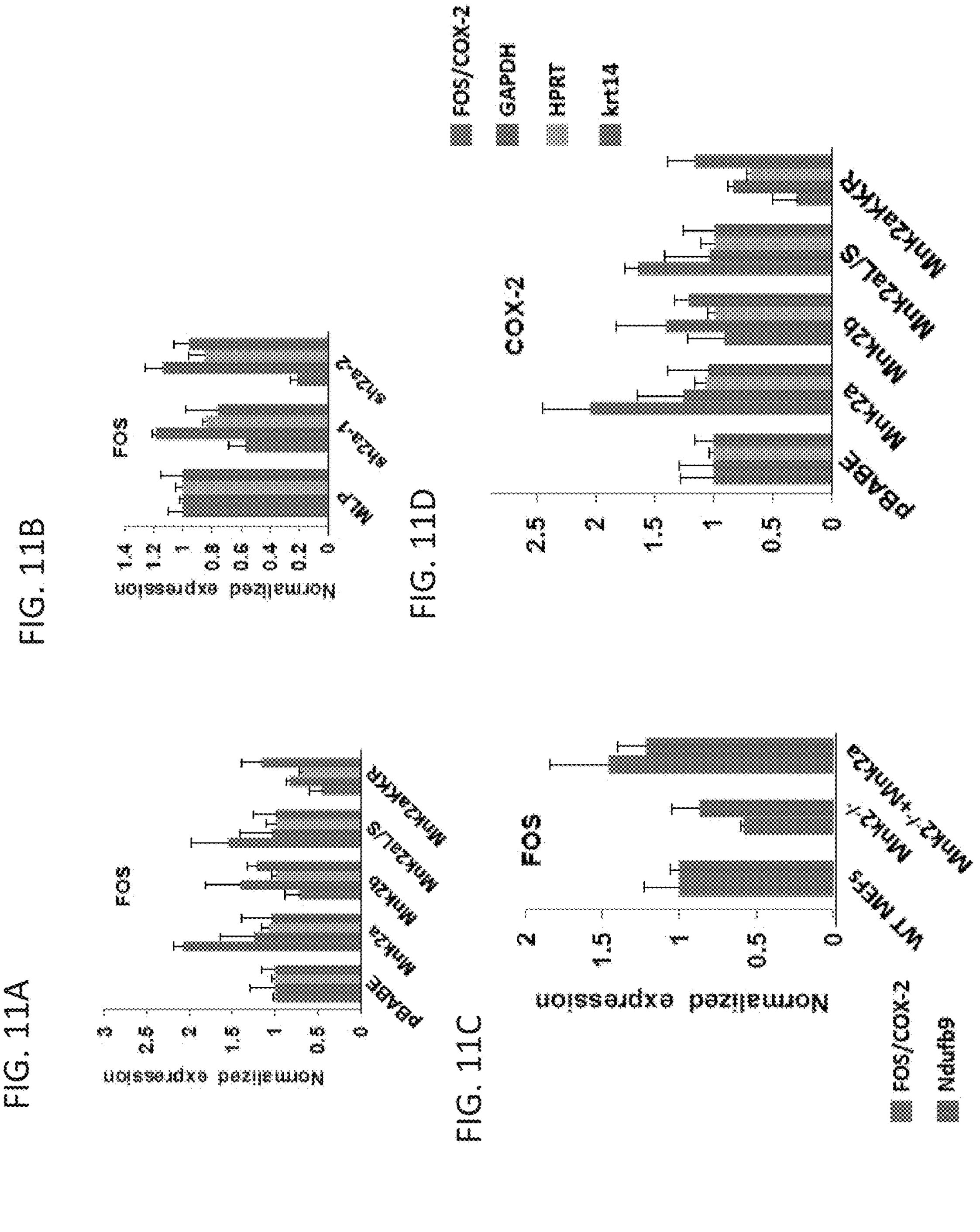
Figure 11F:
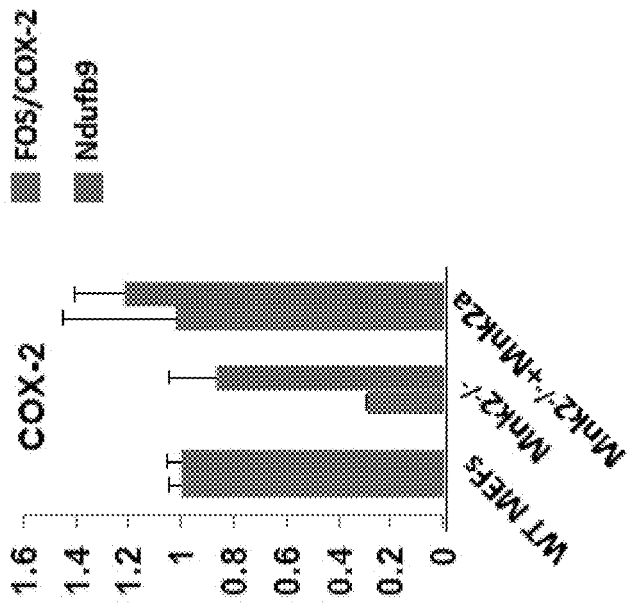
Figure 11E:
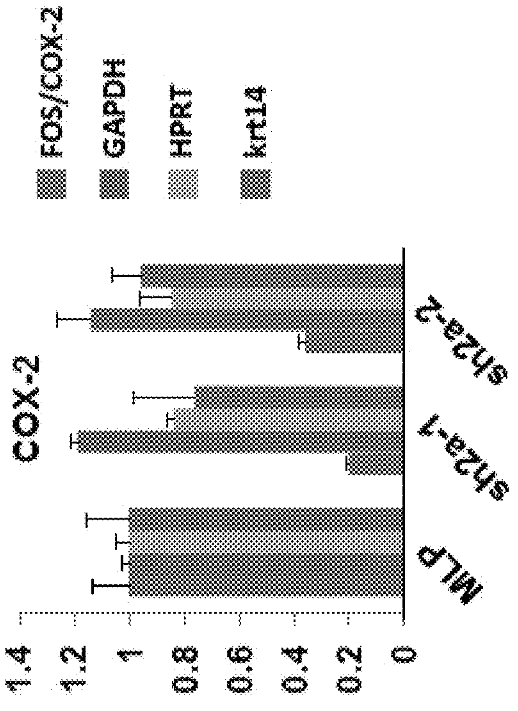

In order to examine if Mnk2a affects p38-MAPK cellular localization, two Mnk2a mutants were generated. In the first mutant (KKR) the putative nuclear localization signal of Mnk2a (69-KKRGKKKKR-77-SEQ ID NO: 45) was mutated to (KKRGKKAAA-SEQ ID NO: 46), in which the last KKR was replaced with three alanines (AAA). This mutant is expected to be mostly cytoplasmic, as was shown for the homologous mutation in Mnk1 (Parra-Palau et al. 2003). In the second mutant (L/S) the putative nuclear export signal (NES) of Mnk2 was mutated. Although in Mnk1 the NES motif is localized to a different region (Parra-Palau et al. 2003), the present inventors identified a similar motif (LxxxLxxL) in Mnk2 in the C-terminal region (starting at amino acid 281 of Mnk2a) and mutated the last two lysines to serines. Mutating the nuclear export signal is expected to render this Mnk2a mutant mostly nuclear. Indeed, when transfected into HeLa cells or transduced into MCF-10A cells these Mnk2a mutants showed the expected localization: the nuclear localization of Mnk2 L/S was enhanced, while that of Mnk2 KKR was decreased, when compared to that of Mnk2a (FIG. 6; FIG. 9 and FIGS. 10A-D). When co-transfected with HA-tagged or GFP-tagged p38-MAPK, Mnk2a colocalized with p38-MAPK. Mnk2a L/S rendered p38-MAPK mostly nuclear and colocalized with it in the nucleus. Mnk2a KKR colocalized with p38-MAPK in both the cytoplasm and nucleus, but was less nuclear than Mnk2a (FIG. 6A; FIGS. 10A-B). Both Mnk2a, KKR and the L/S mutants can interact with HA-tagged and endogenous p38α as was demonstrated by co-immunoprecipitation (FIG. 10C) and can pull-down ransfer-p38α (FIG. 10C). In addition, the L/S and KKR mutants had similar effects on the localization of endogenous p38α in MCF-10A cells transduced with retroviruses expressing these mutants (FIG. 6B). Finally, in Mnk2$^{-/-}$ MEFs p38α is mostly cytoplasmic, and expression of Mnk2a in these cells increased the nuclear fraction of p38α, as measured by both fractionation (FIG. 5G) and immunofluorescent staining of endogenous p38α(FIGS. 12A-B). Overall, these results suggest that Mnk2a and p38-MAPK are colocalized in both the cytoplasm and nucleus, and that Mnk2a can affect the cellular localization of p38α-MAPK.

Mnk2a Localization Affects Induction of p38-MAPK Target Genes and Apoptosis

Figures 7A, 7B, 7C, 7D:
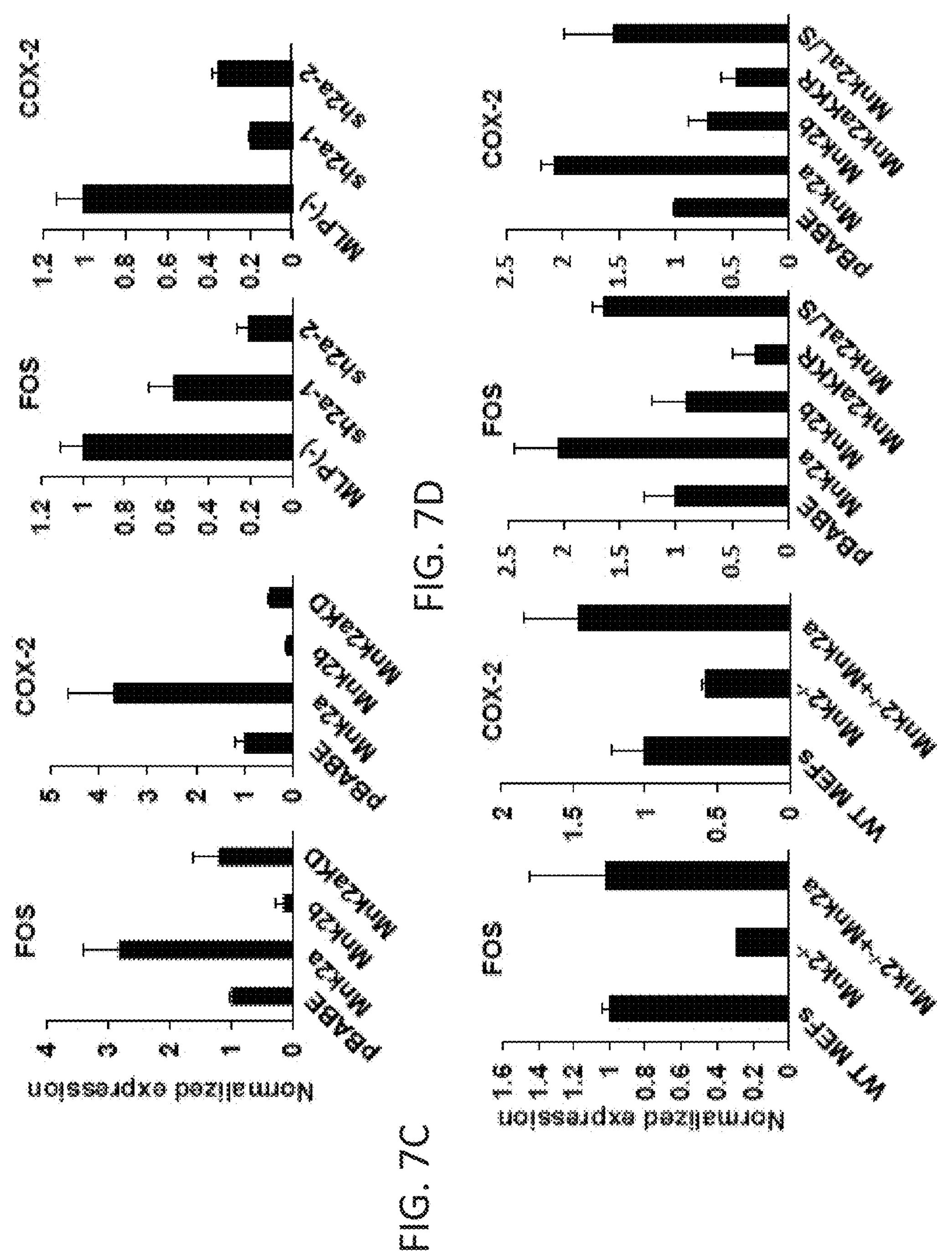

To examine if p38-MAPK activation and nuclear translocation induced by Mnk2a leads to induction of p38-MAPK target genes, expression of FOS and COX-2 was examined, both targets of p38-MAPK stress response (Ferreiro et al. 2010). Expression of both genes was induced in MCF-10A cells expressing Mnk2a and reduced in cells expressing Mnk2b or kinase-dead Mnk2a (FIG. 7A). Moreover, knockdown of Mnk2a inhibited FOS and COX-2 expression (FIG.

Figure 5M:
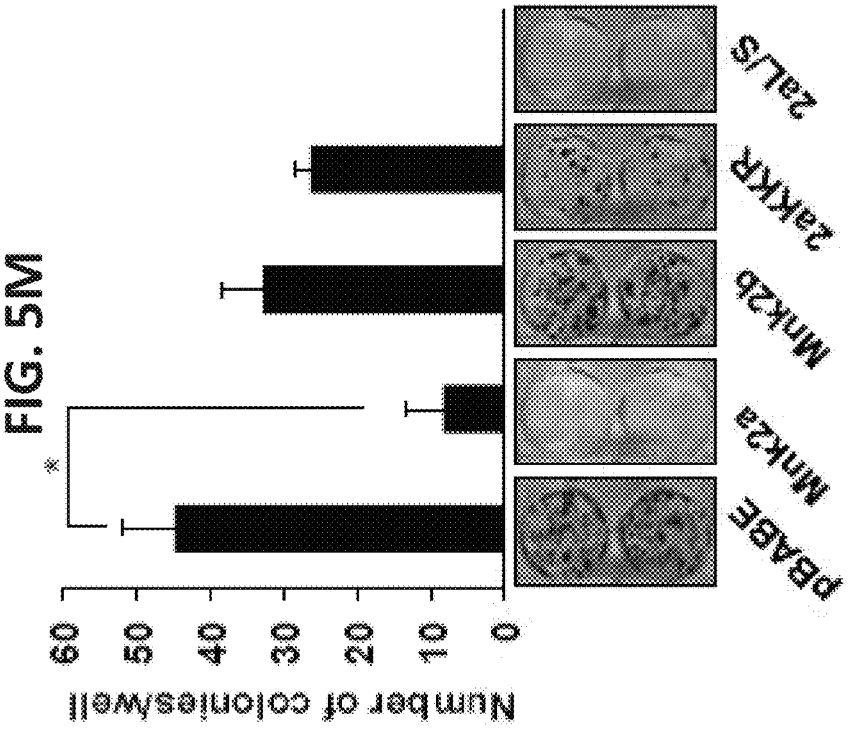
Figure 7F:
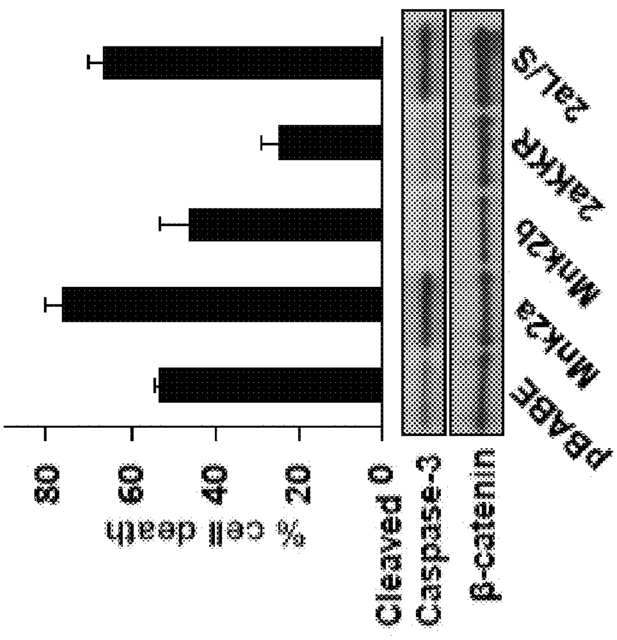
Figure 7E:
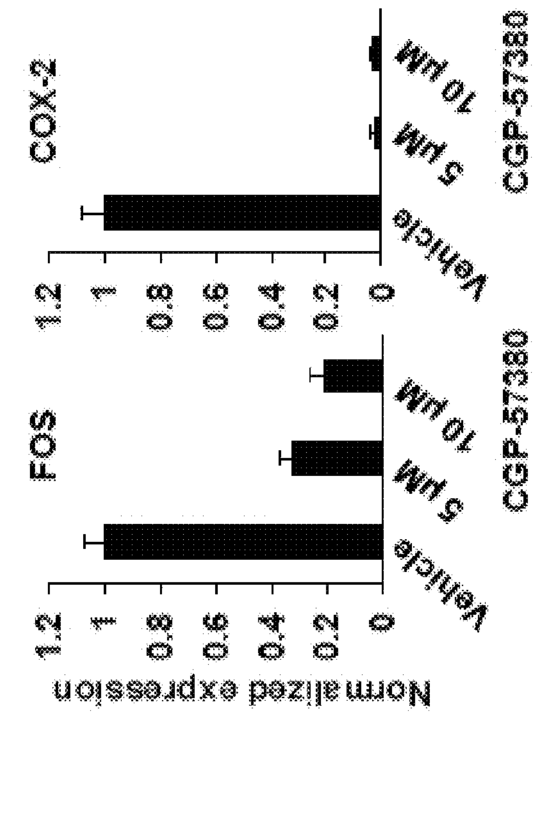

7B). $Mnk2^{-/-}$ MEF cells showed reduced expression of the target genes and upon transduction with Mnk2a the expression of these genes was elevated back to normal levels or above (FIG. 7C). Interestingly, while Mnk2a L/S could activate p38-MAPK target genes similarly to Mnk2a, the KKR mutant did not activate the expression of FOS and COX2 (FIG. 7D). To examine if Mnk1/2 kinase activity modulates the expression of p38α target genes, we treated MCF-10A cells with the Mnk1/2 kinase inhibitor CGP 57380 Inhibition of Mnk1/2 kinase activity, which reduced p38-MAPK phosphorylation (FIG. 8G), also reduced the expression p38-MAPK target genes (FIG. 7E). These results suggest that p38-MAPK phosphorylation by Mnk2a may play a critical role in the induction of p38α targets genes. Mnk2b inhibited the expression of FOS and COX-2 below the basal level (FIG. 7A). To rule out general effects of Mnk2a and Mnk2b on transcription, we measured expression of several housekeeping genes. We found no effects of Mnk2a overexpression, knockdown or knockout on the expression of these genes (FIGS. 11A-F). To examine if Mnk2a localization can affect its pro-apoptotic activity, cells expressing Mnk2a isoforms and the KKR and L/S mutants were treated with anisomycin and cell death was measured. These cells were seeded sparsely for colony survival assay. It was found that while Mnk2a and the L/S mutant sensitized cells to apoptosis, the KKR mutant did not induce apoptosis or decrease colony survival, in correlation with its inability to induce p38α target genes (FIG. 7F and FIG. 5M). Taken together, these results indicate that Mnk2a, not only activates p38-MAPK, but it also regulates the expression of p38-MAPK target genes, altering the transcriptional program of the cells and leading to induction of apoptosis.

MKNK2 is Under-expressed in Colon, Melanoma, Esophagus and Head and Neck Tumors Another support for the notion that Mnk2a is downregulated in human cancer and play a negative role in cancer development comes from expression arrays that measure Mnk2 levels in normal and cancer cells. In the Oncomine database, several measurements show significant reduction of Mnk2 levels (probes in the Affymatrix expression array measure the Mnk2a transcript) in several cancers including colon cancer, esophagus cancer, Head-Neck, Melanoma and Sarcoma. In breast cancer, both Mnk1 and Mnk2 expression (measuring Mnk2a in the affymetrix expression array) positively correlates with patient survival suggesting that Mnk1 and Mnk2 are markers for good prognosis of breast cancer patients (FIGS. 13A-B).

Summary of Example 1

The process of alternative splicing is widely misregulated in cancer and many tumors express new splicing isoforms, which are absent in the corresponding normal tissue (Aplin et al. 2002; Xi et al. 2008; Venables et al. 2009). Many oncogenes and tumor suppressors are differentially spliced in cancer cells and it has been shown that many of these cancer-specific isoforms contribute to the transformed phenotype of cancer cells (Venables 2004; Roy et al. 2005; Srebrow and Kornblihtt 2006). The present inventors have now shown that MKNK2 alternative splicing is modulated in cancer cells to down-regulate the expression of the tumor suppressive isoform Mnk2a and enhance the expression of the pro-oncogenic isoform Mnk2b. Both splicing isoforms phosphorylate the translation initiation factor eIF4E. However, only Mnk2a binds to and activates p38-MAPK leading to enhanced activation of the p38 stress pathway, induction of its target genes and enhanced cell death.

The present inventors sought to examine the role of Mnk2 alternative splicing in cancer and the biological and biochemical properties of Mnk2a and Mnk2b splicing isoforms. It was found that Mnk2a is down-regulated, while in some cases Mnk2b is up-regulated, in several cancers such as colon, breast and lung cancers (FIGS. 1A-K). Mnk2 alternative splicing switch correlated with SRSF1 levels in both cancer cell lines and tumors (FIGS. 1A-F).

To elucidate the role of Mnk2 splicing isoforms in cancer development, the present inventors examined the oncogenic activity of Mnk2 splicing isoforms in vitro and in vivo. It was found that Mnk2b, the kinase-dead form of Mnk2a as well as Mnk2a knockdown could transform MCF-10A cells. In addition, MEF cells from $Mnk2^{-/-}$ but not $Mnk1^{-/-}$ mice were transformed (FIG. 2E and FIG. 2V). Furthermore, Mnk2a could antagonize Ras-mediated transformation both in vitro and in vivo (FIGS. 2A-K). These results suggest that Mnk2a possesses a tumor-suppressive activity in vitro and in vivo.

In light of the finding that Mnk2 isoforms did not significantly affect cellular proliferation (FIGS. 4H-M), it was hypothesized that Mnk2a anti- and Mnk2b pro-oncogenic activity is mediated by their effects on cell death and stress-resistance or sensitivity. The present inventors thus examined the response of cells, with either up-regulation or knock down of Mnk2 isoforms, to cellular stress and transformation assays. It was found that Mnk2a, but not Mnk2b or a Mnk2a kinase-dead version, enhanced cellular response to stress and augmented the apoptotic activity of an active mutant form of p38α (FIGS. 4A-G). Moreover, knockdown of Mnk2a, enhanced the survival of cells transduced with the active mutant form of p38α (FIGS. 4A-G) (Diskin et al. 2004; Askari et al. 2007; Avitzour et al. 2007). These results indicate that Mnk2 alternative splicing can modulate the p38-MAPK stress response. Furthermore, inhibition of p38-MAPK by the pharmacological inhibitor SB203580 rescued Panc-1 cells from Mnk2a-induced sensitivity to anisomycin treatment (FIG. 5J) and MCF-10A cells from inhibition of Ras-induced transformation in vitro (FIGS. 4F-G). These results suggest that the tumor suppressive activity of Mnk2a is mediated by activation of the p38-MAPK pathway.

Next, the present inventors examined if Mnk2 isoforms can activate the p38-MAPK pathway and found that only Mnk2a could enhance p38-MAPK phosphorylation, translocation into the nucleus and phosphorylation of its substrate MK2 (FIGS. 5A-H). Moreover, cells with Mnk2a knockdown or MEF cells from MKNK2 knockout mice showed reduced p38-MAPK phosphorylation and translocation into the nucleus, which could be restored by introduction of exogenous Mnk2a (FIG. 5G). Interestingly, both Mnk2a and Mnk2b, but not the kinase-dead mutant of Mnk2a phosphorylated eIF4E to a similar extent suggesting that eIF4E phosphorylation cannot account for their different biological activity. The present results suggest that Mnk2b uncouples eIF4E phosphorylation from activation of the p38-MAPK stress pathway and thus sustains only the pro-oncogenic arm of the pathway. Moreover, the kinase-dead Mnk2a mutant probably acts in a dominant-negative manner by competing with Mnk2a for p38-MAPK binding while being unable to phosphorylate it and thus preventing its activation. It was further found that Mnk2 isoforms can differentially interact with p38α-MAPK in cells. In co-immunoprecipitation assays Mnk2a binds p38α while Mnk2b does not bind p38α efficiently suggesting that this interaction might be important for p38α activation by Mnk2a (FIG. 5F) Importantly, even though Mnk2aKD was bound to p38α it did not cause activation or translocation of p38 as measured by p38 or MK2 phosphorylation and by cellular fractionation (FIG. 5A-H). It was also found that the kinase activity of Mnk2a is required for activation of p38α and its target genes as both the kinase-dead form of Mnk2a or application of the Mnk1/2 kinase inhibitor CGP 57380 inhibited these activities (FIGS. 5E; FIGS. 8D-F, G and FIG. 7E). Taken together these results indicate that Mnk2 kinase activity is required to enable activation of p38-MAPK and its downstream targets.

In all of the experimental systems the present inventors demonstrate that while both p38 and eIF4E phosphorylation is enhanced by Mnk2a overexpression and reduced by its knockdown, only p38 phosphorylation correlates with the degree of apoptosis (FIGS. 3A-F). This is also demonstrated in the comparison of WT and $Mnk1^{-/-}$ MEFs to $Mnk2^{-/-}$ MEFS. $Mnk2^{-/-}$ cells show lower phosphorylation levels of both p38 and eIF4E (FIG. 5D) and behave as transformed cells as they form colonies in soft agar while the others do not (FIG. 2E). In this latter case, lower levels of eIF4E phosphorylation did not inhibit transformation and moreover, these cells were transformed probably because they lost the activation of the tumor suppressive arm of p38. Results from these gain and loss of function experimental systems suggest that p38, but not eIF4E, phosphorylation/activation determines the fate of these cells.

The present inventors have identified a new mechanism, in which Mnk2a interacts with and induces translocation of p38-MAPK into the nucleus, and thus inducing transcription of its target genes which results in increased apoptosis. Both Mnk2a and Mnk2b phosphorylate eIF4E on serine 209, which contributes to cellular transformation, but Mnk2b, which cannot bind p38-MAPK, uncouples this phosphorylation from induction of the p38-MAPK stress response.

In conclusion, the present results identify Mnk2 alternative splicing as a mechanism for elimination a tumor suppressor (Mnk2a), which is a modulator of the p38-MAPK stress pathway and for generating the pro-oncogenic isoform (Mnk2b).

Example 2

Splicing of S6K1

Materials and Methods

Cells: NIH 3T3 cells were grown in DMEM supplemented with 10% (v/v) calf serum (BS), penicillin and streptomycin. Human breast cells: MCF-10A, were grown in DMEM/F12 supplemented with 5% (v/v) horse serum, 50 ng/ml epidermal growth factor (EGF), 10 μg/ml insulin, 0.5 μg/ml hydrocortisone, 100 ng/ml cholera toxin, penicillin and streptomycin. MCF-7, MDA-MB-231 and HEK293 cells were grown in DMEM, HMLE cells were grown in MEBM/DMEM/F12 and MDA-MB-468 cells were grown in Leibovitz-F12, supplemented with 10% (v/v) FBS, penicillin and streptomycin. SUM159 cells were grown in Ham's F12 with 5% (v/v) calf serum, 5 μg/ml insulin and 1 μg/ml hydrocortisone. S6K1/2 double knockout Mouse Embryonic Fibroblasts (MEFs) were immortalized by the 3T3 protocol.

Stable cell lines: NIH 3T3 and MCF-10A cells were infected with pBABE-puro retroviral vectors encoding T7-tagged S6K1 isoforms human and mouse cDNAs as described (McCurrach and Lowe, 2001). Infected cells were selected with puromycin (2 μg/ml) or hygromycin (200 μg/ml) for 72-96 h. In the case of double infection with pWZL-hygro-Ras (McCurrach and Lowe, 2001), cells were treated with hygromycin for 72 h after selection with puromycin. In the case of infection with MLP-puro-shRNAs vectors, MCF-10A cell transductants were selected with puromycin (2 μg/ml) for 96 h.

Immunoblotting: Cells were lysed in Laemmli buffer and analyzed for total protein concentration as described (Golan-Gerstl et al., 2011). Primary antibodies. Sigma; β-catenin (1:2,000) transfer-ERK (1:10000 T202/Y204), Santa Cruz; β-actin (1:200), Total Akt (1:200 sc1619), GAPDH (1:1000 sc25778), Myc (1:1000 sc40). Novagen; T7 tag (1:5,000); BD Transduction Laboratories; Total S6K1-anti-p70. Cell Signaling Technologies; Total ERK1/2 (1:1,000); transfer-4E-BP1 Thr70 (1:1000 #2855), 4E-BP1 (1:1000 #9452), transfer-S6K1 Thr389 (1:1000 #9205), p-S6 ser240/244 (1:1000 #2215), Total S6 (1:1000 #2217), transfer-Akt ser473 (1:1000 #9271), RAS (1:1000 #3339), p-S2448-mTOR (1:1000 #2972), Secondary antibodies: HRP-conjugated goat anti-mouse, anti-rabbit or anti-goat IgG (H+L) (1:10,000 Jackson Laboratories).

Immunoprecipitation: HEK293 cells were transfected with myc-mTOR and pCDNA3-T7-Iso-2/h6A/h6C/pCDNA3 or pCDNA-T7-Iso-1 S6K1 with empty pCDNA. 48 hours after transfection cells were lysed in CHAPS buffer as described (Sarbassov et al., 2004). After protein quantitation, 1 μg of anti-T7 antibody bound to 40 μl of 50% protein G-sepharose was incubated with 800 μg of total protein lysate over night. After washing 4 times with CHAPS buffer, beads were incubated with 50 μl of 2× Laemmli buffer and separated by SDS-PAGE.

Colony survival assay: S6K1/2 DKO MEF cell populations were transduced with retroviruses encoding for empty pB(−) vector or T7-Iso-1 S6K1. After selection, cells were seeded sparsely (200 cells/well of 6-well plates) and were grown for 14 days. Colonies were fixed and stained with methylene blue.

Dual luciferase reporter assay: MCF-10A cells were co-transfected using Fugene 6 (Roche) with the dual reporter vector pLPL (Cap-Renilla-IRES-Luciferase) (Gerlitz et al., 2002) and the indicated S6K1 isoforms. Cap-dependent translation (Renilla luciferase activity) and IRES-mediated translation (Firefly luciferase activity) were measured with the Promega Stop and Glow assay kit according to the manufacturer's instructions.

EGF and IGF-1 activation: $3\times10^5$ MCF-10A cells were seeded in 6 well plates. 24 h later, cells where washed with PBS and medium was replaced to a serum and growth factor free media for 24 hours. Cells were stimulated with 50 ng/ml IGF-1 or 50 ng/ml EGF for 4 hours. After 4 hours cells were lysed in Laemmli buffer for Western Blot analysis.

Anchorage-independent growth: Colony formation in soft agar was assayed as described (Karni et al., 2007; McCurrach and Lowe, 2001). After 14-21 days, colonies from ten different fields in each of two wells were counted for each transductant pool, and the average number of colonies per well was calculated.

Growth curves: MCF-10A cells were infected with the indicated retroviruses. Following selection, 2000 or 3500 cells per well were seeded in 96-well plates and grown in DMEM/F12 media with 5% or 0.2% Horse Serum. Cells were fixed and stained with methylene blue, and the absorbance at λ=650 nm of the acid-extracted stain was measured on a plate reader (BioRad).

Three dimensional morphogenesis of mammary epithelial cells assay: MCF-10A cells were infected with the indicated retroviruses. Following selection, 1500 cells per well were seeded in 96-well in Growth factor-reduced Matrigel (BD Bioscience, Cat#25300. In some cases 2.5 or 5 ng/ml of EGF or 10 μg/ml of insulin were added to assay medium of seeded cells.

Wound healing assay: MCF-10A cells were seeded in a 6 well plate until formation of a confluent monolayer, and a "wound" was created by scratching the monolayer with a p200 pipette tip as described in (Liang et al., 2007). Cells were washed with PBS and growth medium was replaced to DMEM/F12 media with 5% horse serum without EGF and insulin. The wound was photographed (×100 magnification) after matching the reference point in a phase contrast microscope and wound area was measured using Photoshop record measurement analysis tools.

Xenograft tumor formation in mice: Pools of Ras-MCF-10A cells expressing the indicated S6K1 isoforms were injected sub-cutaneously into the rear flanks of NOD-SCID mice ($2\times10^6$ cells per site in 100 μl of serum free media containing 0.25 v/v matrigel (BD Bioscience) using a 26-gauge needle.

In Vitro Kinase Assay: HEK293 were seeded on 10 cm plates (3×106) and 24 hours later were transfected with 20 mg of empty pcDNA3, 20 mg pcDNA3-T7-Iso-2, 3 mg pcDNA-T7-Iso-1 (and 17 mg of empty pcDNA3) or 4 mg pcDNA-T7-Iso-1 K123A S6K1 (and 16 mg of empty pcDNA3) (different isoform amounts were transfected due to different expression levels). Forty-eight hours after transfection, cells were lysed in CHAPS buffer. After protein quantitation, 1 mg of anti-T7 antibody bound to 40 ml of 50% protein G-sepharose was incubated with 800 mg of total protein lysate over night. Beads were then washed 3 times with CHAPS buffer and once with DB buffer (12.5 mMHEPES pH 7.5, 100 mMKCL, 0.5 mMDTT, 6.25% Glycerol). The supernatant was removed and beads were resuspended with reaction mix containing recombinant 200 ng GST-S6 (AbnovaCat. no. H00006194-P01) in 50 ml reaction buffer containing: (20 mM ATP, 30 mM MgCl, 10 mM HEPES pH 7.5, 50 mM EGTA, 10 mM b-glycerophosphate, 5 mM NaVO4, 50 mM b-mercaptoethanol and 0.5 mM DTT). Reactions were shaken for 1 hour at 300 C. Reactions were stopped by the addition of 50 ml of cold DB (12.5 mM HEPES pH 7.5, 100 mM KCL, 0.5 mM DTT, 6.25% Glycerol) followed by the addition of 30 ml 4× Laemmli buffer. 50 ml of the final volume was separated by SDS-PAGE, transferred to nitrocellulose by Western blotting and the membrane was probed with the indicated antibodies to view the phosphorylation levels and total levels of the recombinant protein GST-S6 as well as the levels of S6K1 isoforms in the reaction.

RT-PCR: Total RNA was extracted from cells at 80% confluency with Trizol reagent (Sigma) and 2 mg of total RNA was reverse transcribed using the AffinityScriptII (Stratagene). RT-PCR was performed on 1/10(2 ml) of the cDNA, in 50-ml reactions containing 0.2 mM dNTP mix, 103 PCR buffer with 15 mM MgCl2 (ABI), 2.5 units of TaqGold (ABI) and 0.2 mM of each primer; 5% (v/v) DMSO was included in some reactions. PCR conditions were 95° C. for 5 min, then 33 cycles of 94° C. for 30 s, 60° C. for 30 s and 72° C. for 45 sec, followed by 10 min at 72° C. PCR products were separated on 1.5% agarose gel.

TABLE I

| | | |
|---|---|---|
| Cloning primers | hS6K1-T7-BH1 For | GGGGAAGGATCCATGGCATCGATGACAGGTGGCCAACAGATGGGTATGAGGCGACGAAGGAGGCGGG-SEQ ID NO: 47 |
| | hS6K1-ER1 6a Rev | GGGGAACTTAAGCAATTCAAGGAAAGAAAGCCGC-SEQ ID NO: 48 |
| | hS6K1-ER1 6c Rev | GGGGAACTTAAGCTCAAAAGAATAAAGGGCTGAATC-SEQ ID NO: 49 |
| | hS6K1-ER1 e15 rev | GGGGAACTTAAGTCATAGATTCATACGCAGGTGC-SEQ ID NO: 50 |
| Detection primers RT-PCR | hS6K1 e5 For | CTCTACCTCATCCTTGAGTATCTCAGTG-SEQ ID NO: 51 |
| | hS6K1 e6C rev | CTCAAAAGAATAAAGGGCTGAATC-SEQ ID NO: 52 |
| | hS6K1 Iso1 rev | Catagattcatacgcaggtgc-SEQ ID NO: 53 |
| | GAPDH For | ATCAAGAAGGTGGTGAAGCAG-SEQ ID NO: 54 |
| | GAPDH Rev | CTTACTCCTTGGAGGCCATGT-SEQ ID NO: 55 |
| | β-actin for | CGTGGACATCCGCAAAG-SEQ ID NO: 56 |
| | β-actin Rev | GGAAGGTGGACAGCGAG-SEQ ID NO: 57 |
| Point mutation primers | hS6K1 K123A For | ATATTTGCCATGGCGGTGCTTAAAAAGGCA-SEQ ID NO: 58 |
| | hS6K1 K123A Rev | TGCCTTTTTAAGCACCGCCATGGCAAATAT-SEQ ID NO: 59 |
| Knock-down shRNA sequences | S6K1 Iso-1 sh1 For | TGCTGTTGACAGTGAGCGCGGCATGGAACATTGTGAGAAATAGTGAAGCCACAGATGTATTTCTCACAATGTTCCATGCCATGCCTACTGCCTCGGA-SEQ ID NO: 60 |
| | S6K1 Iso-1 sh2 For | TGCTGTTGACAGTGAGCGCTGGAACATTGTGAGAAATTTGTAGTGAAGCCACAGATGTACAAATTTCTCACAATGTTCCATTGCCTACTGCCTCGGA-SEQ ID NO: 61 |
| Real time primers-Q-PCR | Detection of Iso-1 | S6K1 e7 For: GGGCATTTACATCAAAAGGG-SEQ ID NO: 62 S6K1 e8 Rev: CCAAAGTCTGTTAGTTTCACATGAC-SEQ ID NO: 63 |
| | Detection of 6C | S6K1 e5 For: CCTTTCAGACTGGTGGAAAACTCTACC-SEQ ID NO: 64 |

TABLE I-continued

| | |
|---|---|
| | S6K1 e6+6c Rev (exon junction): GCTTCTTTGTTAGAAAAGGCCAGGCAG-SEQ ID NO: 65 |
| Detection of 6A | S6K1 e6 For: GAATATTTATGGAAGACACTGCCTG-SEQ ID NO: 66 |
| | S6K1 e6C+6a Rev (exon junction): GTTAGAAAAGGCCAATTCAAGGAAAG-SEQ ID NO: 67 |
| β-actin For | GGCACCCAGCACAATGAAGA-SEQ ID NO: 68 |
| β-actin Rev | AGGATGGAGCCGCCGATC-SEQ ID NO: 69 |

Statistical Analysis: All data presented as histograms refer to a mean value±SEM of the total number of independent experiments. An unpaired, two-tailed t test was used to determine p values for FIGS. 19C and 25B.

Results

S6K1 Short Isoforms are Up-regulated in Breast Cancer Cell Lines and Tumors

Figure 17A:
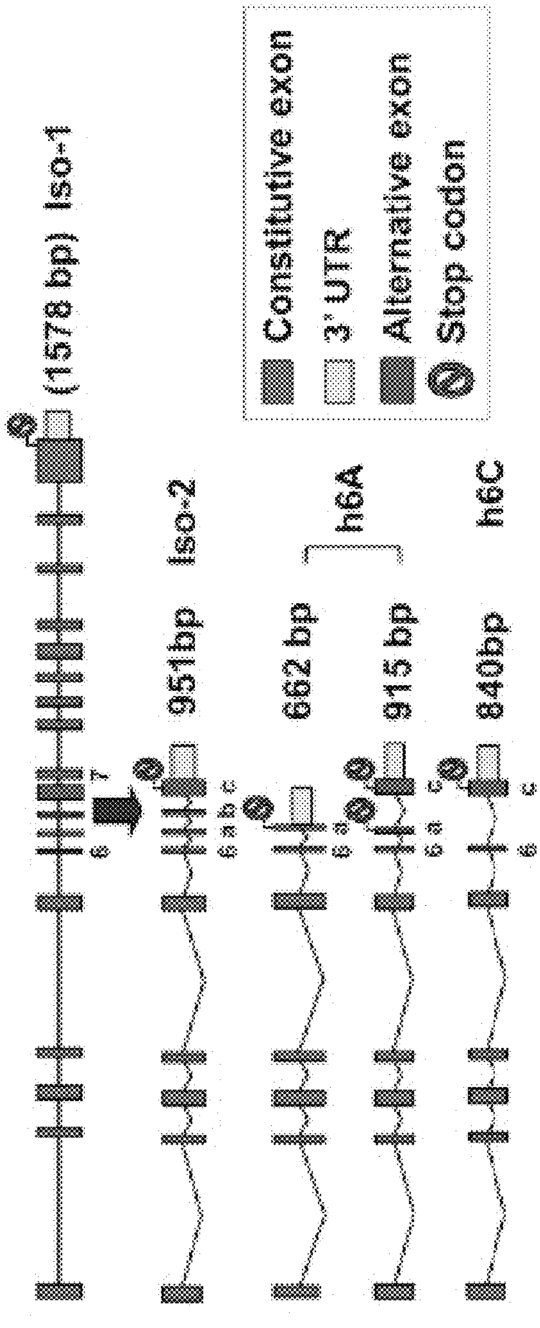

The gene RPS6KB1 encoding for p85/p70 S6K1 can be alternatively spliced to form a number of truncated isoforms. In mouse cells the splicing factor SRSF1 induces the inclusion of three additional exons (a-b-c) located between exon 6 and 7 (FIG. 17A). By PCR, cloning and sequencing, the present inventors have discovered that in human there are two alternative exons in this region: a and c, which can be included together or individually generating two protein isoforms which are referred to herein as h6A and h6C (FIGS. 17A, 18D-E and Table 2, herein below). All of these isoforms in mouse or human which include combinations of exons 6 (a-c), are termed S6K1 short isoforms. Inclusion of the alternative exons mentioned above results in exposure of alternative poly adenylation sites and alterations in the reading frame that in turn generate a stop codon in exon 6c in mouse and exons 6a or 6c in humans. The presence of these stop codons creates transcripts containing approximately half of the original S6K1 coding sequence (Iso-1), and lacking more than half of the conserved kinase domain (FIG. 19A).

TABLE 2

| Gene name | Exon forward<br>Exon reverse | Description<br>Over-expression (BEAS-2B) | Knockdown (H460) | Knockdown (RKO) |
|---|---|---|---|---|
| BIN1 | E11 For<br>E14 Rev | No change | No change | No change |
| INSR | E 10 For<br>hE12 Rev | Skipping | Inclusion | Inclusion |
| MKNK2 | E11 For<br>E13a Rev<br>E13b Rev | Skipping | Inclusion (13a) | No change |
| SRSF6 | E2 For<br>E3b Rev<br>E4 Rev | Inclusion | No change | Lower expression<br>No splicing change |
| BRCA1 | E8 For<br>E11 Rev | No change | Higher expression | No change |
| TEAD1 | E2-E5 | NE | Inclusion | Lower expression<br>No splicing change |
| TP73 | E2 For<br>E2 Rev | No change | Higher expression | No change |
| TP73 | E1 For<br>E3 For<br>E4 Rev | Lower expression | Higher expression | Lower expression |
| CHEK2 | E1 For<br>E3 Rev | NE | No change | No change |
| CHEK2 | E5 For<br>E7 Rev<br>E8 Rev | No change | Higher expression | Lower expression |
| TSC1 | E14 for<br>E17 Rev | NE | Higher expression | Lower expression |
| TSC2 | E2 For<br>E4 Rev | NE | Higher expression | Lower expression |
| TSC2 | E12 For<br>E16 Rev | NE | No change | Lower expression |
| c-Myb | E8 For<br>E10 Rev | No change | Higher expression | Lower expression |
| B-Myb | E7 For<br>E9 Rev | No change | No change | No change |
| DLG1 | E1 For<br>E5 Rev | Skipping | Inclusion | No change |
| DAPK1 | E17 For<br>E21 Rev | NE | Poor product | Lower expression |

TABLE 2-continued

| | | Description | | |
|---|---|---|---|---|
| Gene name | Exon forward Exon reverse | Over-expression (BEAS-2B) | Knockdown (H460) | Knockdown (RKO) |
| DAPK1 | E13 For E15 Rev | NE | Poor product | Lower expression |
| DAPK1 | E15 For E16 Rev | NE | Poor product | No change |
| VHL | E1 For E3 Rev | NE | No change | NE |
| DVL2 | E4 For E6 Rev | NE | No change | No change |
| DVL2 | E11 For E13 Rev | NE | No change | No change |
| PML | E6 For E9 Rev | NE | No change | NE |
| CASP9 | E2 For E7 Rev | No change | No change | NE |

NE, not examined.

Figure 17B:
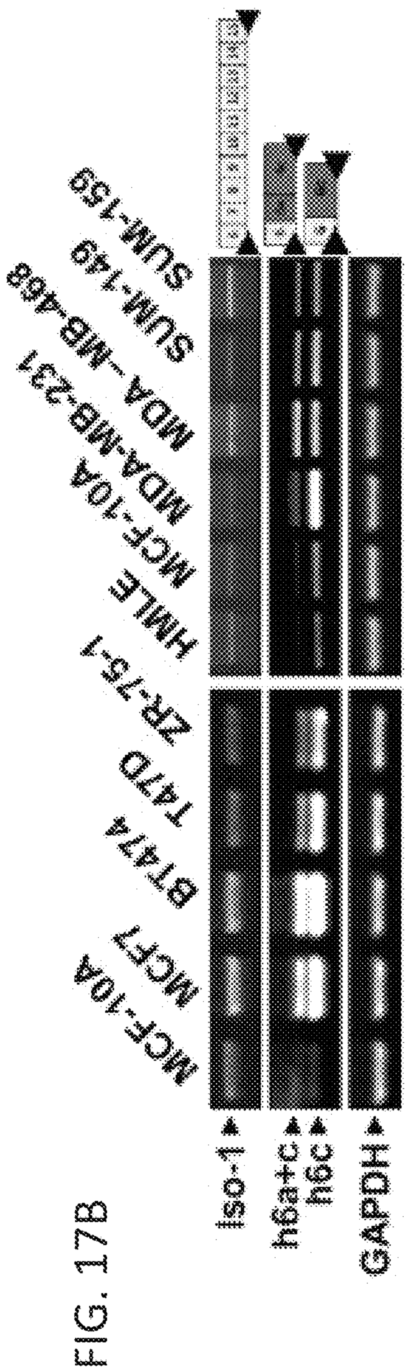
Figure 17D:
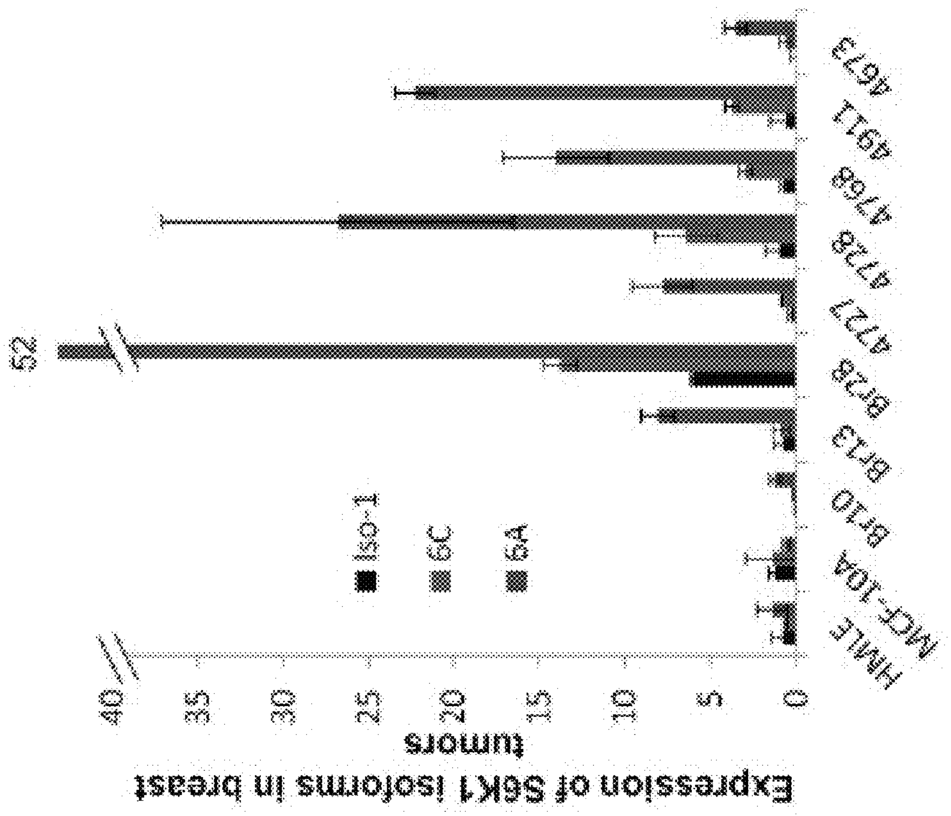
Figure 17C:
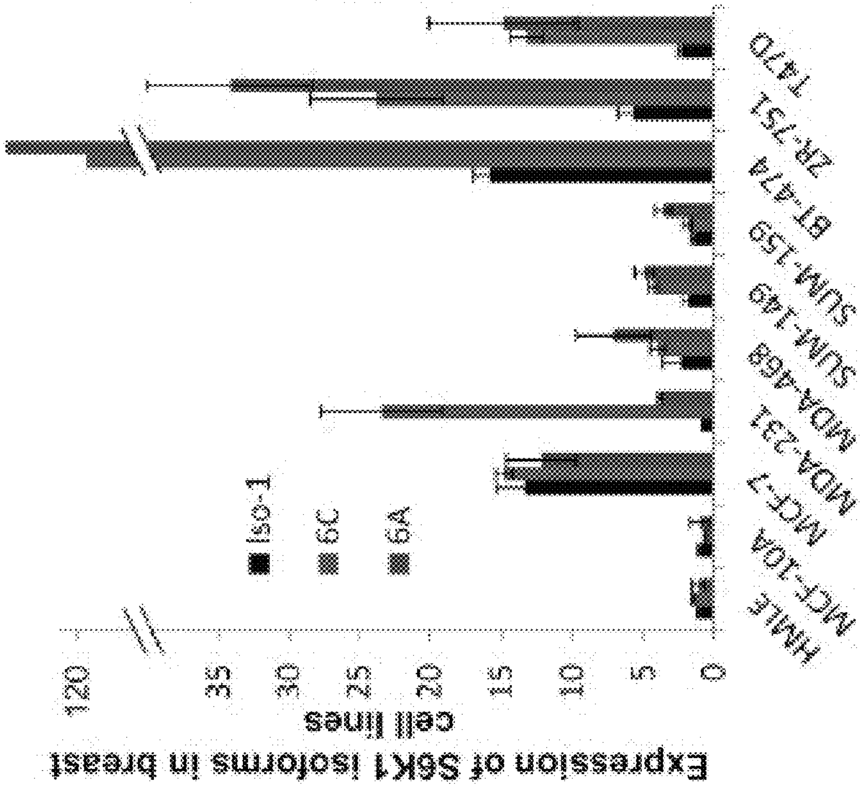
Figure 18G:
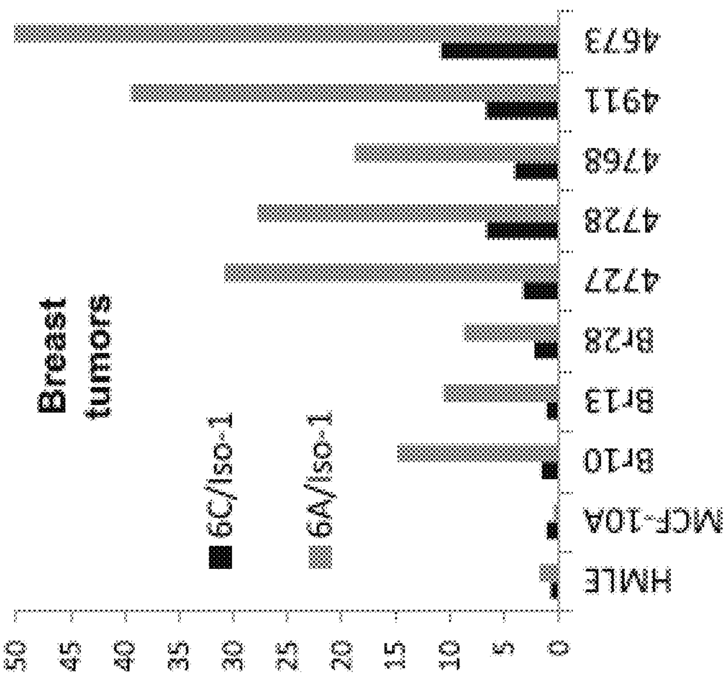
Figure 18F:
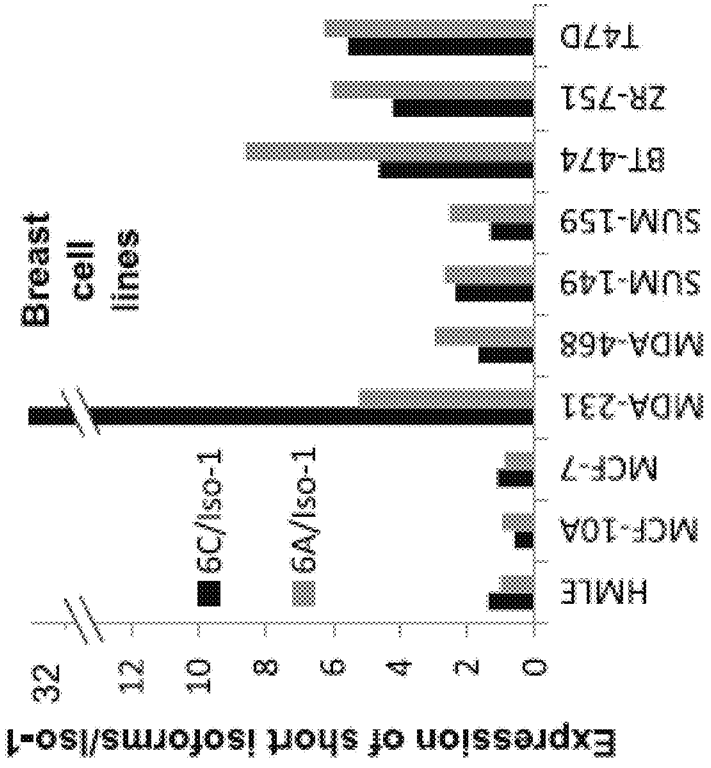
Figure 19A:
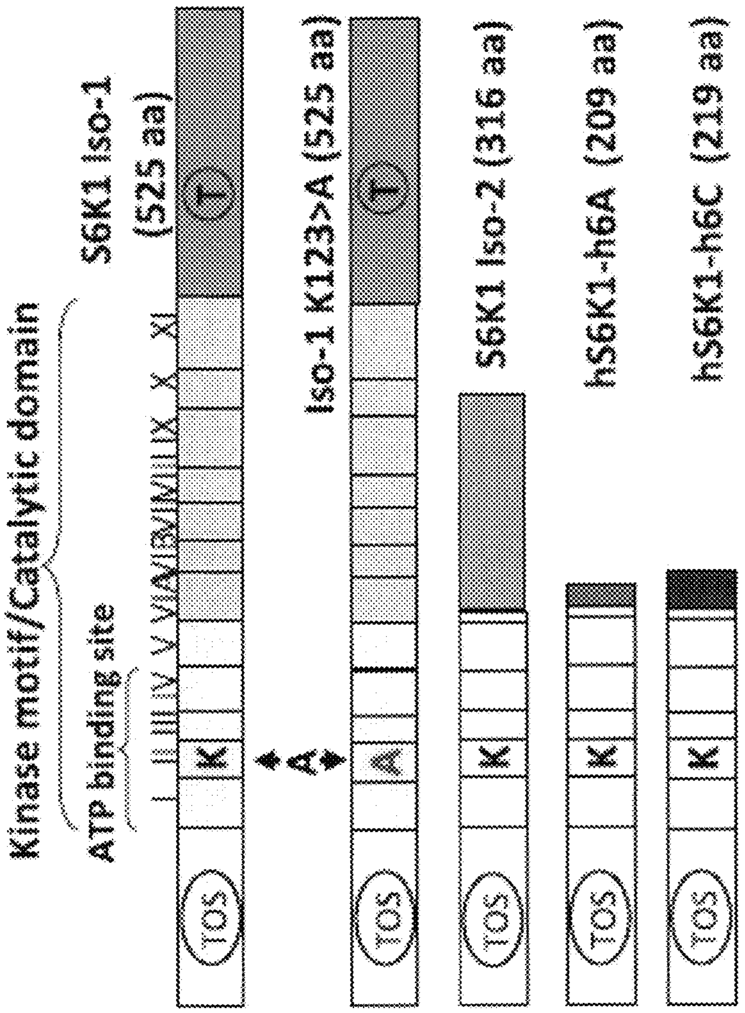

In all of these alternative splicing events, the presence of a poly adenylation sequence, and in the case of h6A also a premature stop codon (PTC) located less then 55 bp from the next exon junction complex, prevents degradation of the generated transcripts by the Nonsense Mediated Decay (NMD) mechanism (FIGS. 17A, 18E). It was found that while in immortal breast cells (MCF-10A, HMLE) the expression of S6K1 short isoforms is relatively low, in breast cancer cell lines inclusion of exons 6a and 6c is significantly increased, especially in metastatic breast carcinoma cell lines (FIGS. 17B, 18A). Indeed, while in both primary and immortal breast cells S6K1 short protein isoforms were hardly detected at the protein level, in breast cancer cell lines elevated protein levels of S6K1 short isoforms were detected (FIG. 18C). In human breast tumor samples, elevated expression of S6K1 h6A and h6C isoforms compared to the immortal breast cell lines were found (FIGS. 17D, 18F-G). Interestingly, whereas most analyzed breast cancer cell lines and tumor samples presented high expression of S6K1 short isoforms, elevated expression of the full length isoform, Iso-1 was not detected in most tumors (FIGS. 17B-D). Two of the cell lines that showed elevated Iso-1 expression (MCF-7, BT474) possess amplification of the RPS6KB1 gene and except for MCF-7, all tumors and cell lines showed an increase in short isoforms/Iso-1 ratio (FIGS. 18F-G) indicating that an alternative splicing switch in S6K1 occurs in breast cancer.

All S6K1 protein isoforms are identical in their N-terminus but share only partial homology in their kinase domain and differ from each other in their C-terminus. Iso-1, Iso-2, h6A and h6C contain distinct sequences in their C-terminus consisting of 330,121, 12 or 24 amino acids respectively (FIG. 19A).

S6K1 Short Isoforms Enhance Motility and Anchorage Independent Growth

Figures 19B, 19C, 19D:
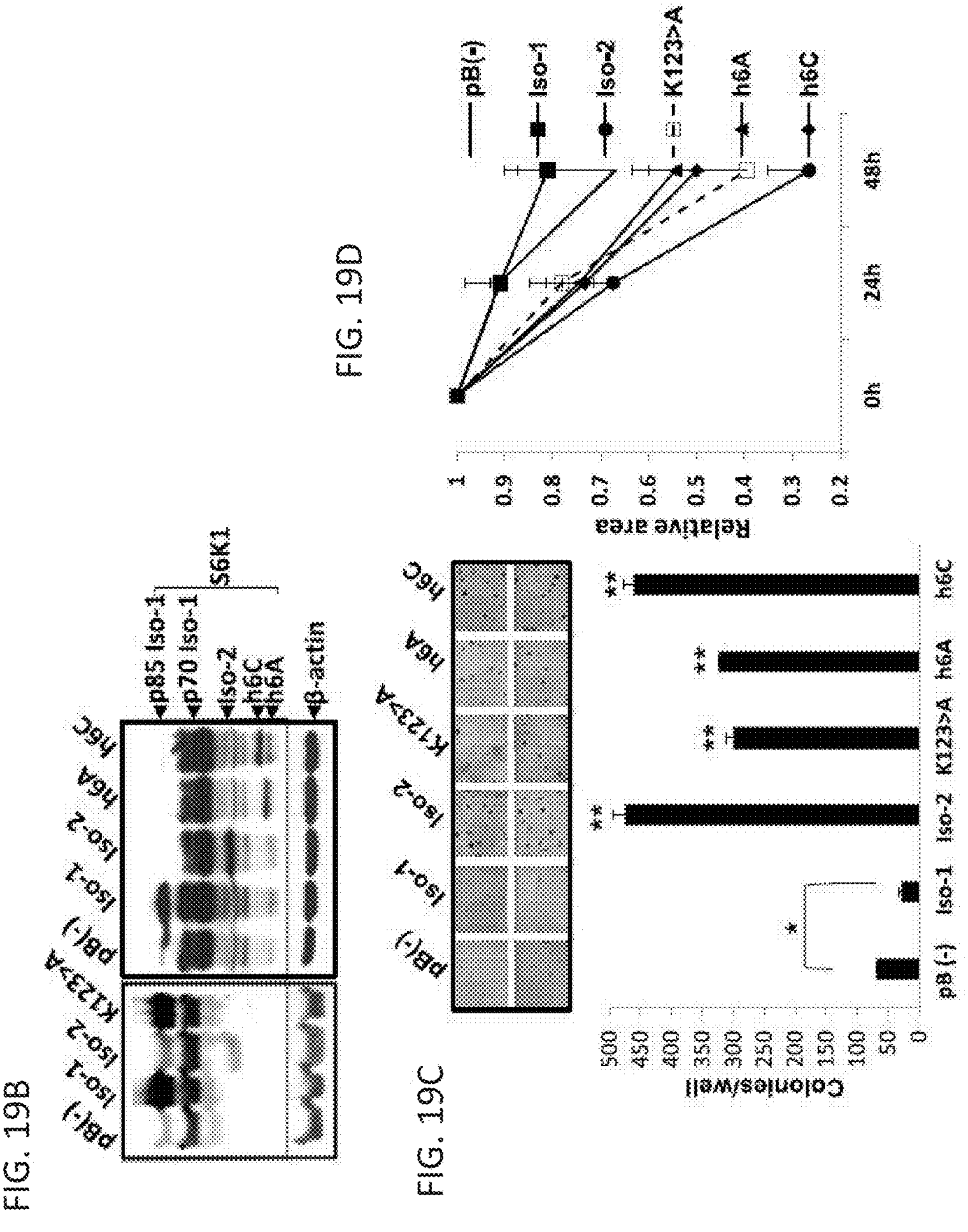
Figure 19E:
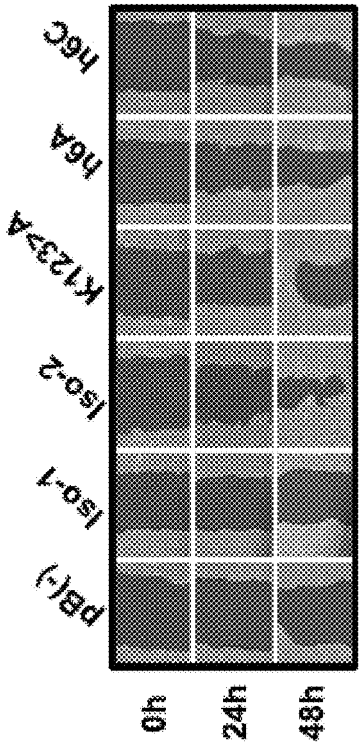
Figure 20C:
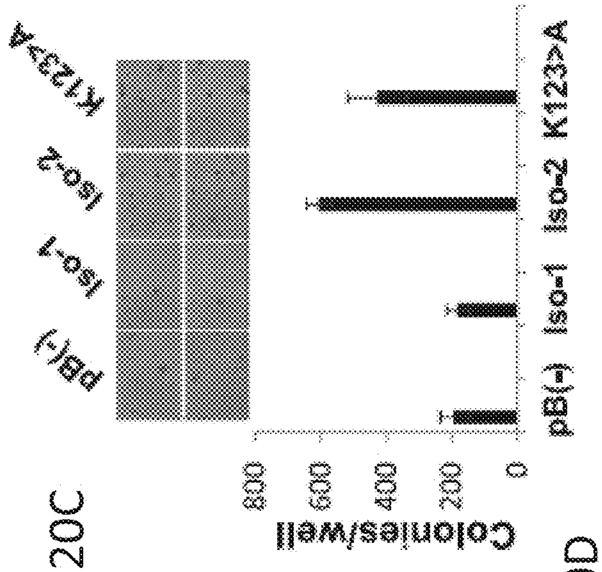
Figure 20D:
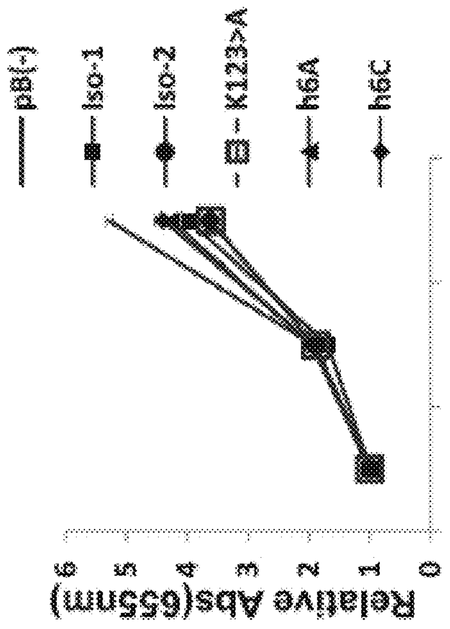
Figure 20A:
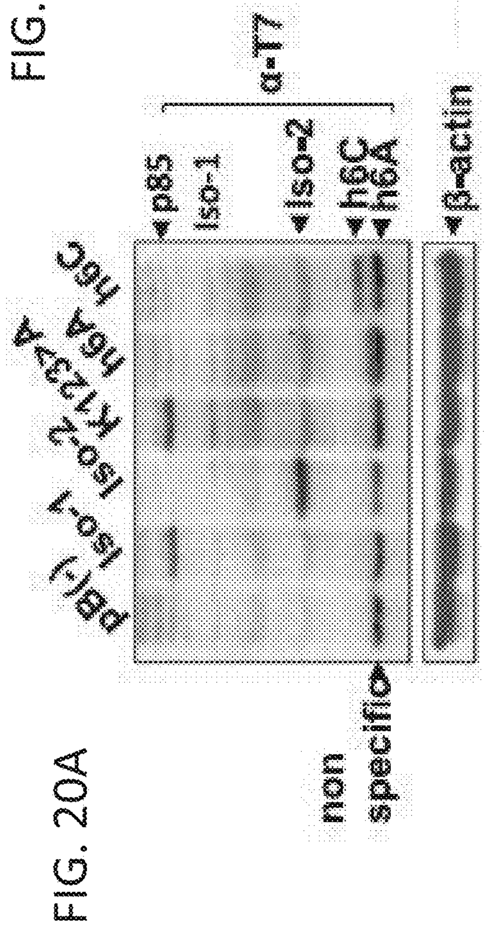
Figure 20B:
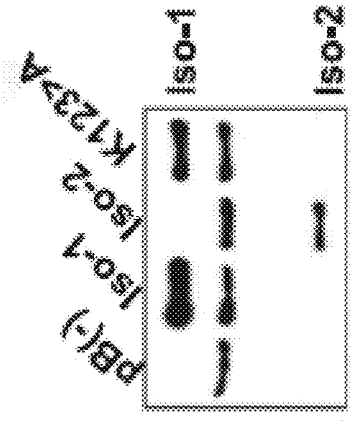
Figure 20G:
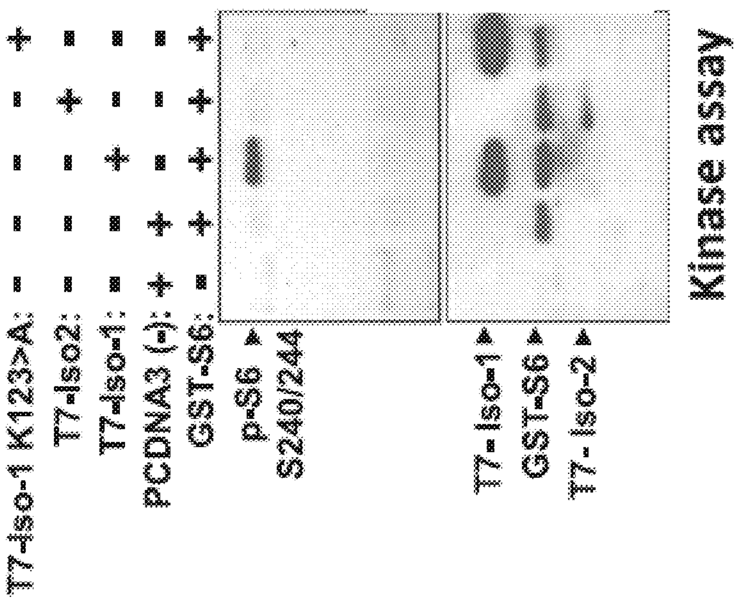

The present inventors sought to examine the oncogenic activity of S6K1 isoforms in human breast epithelial cells. It was found that Iso-2, h6A and h6C were able to transform human immortal breast MCF-10A cells and mouse NIH3T3 cells enabling them to form colonies in soft agar despite the relatively low expression of the short isoforms in comparison to Iso-1 (FIGS. 19B-C and 20A-C). The kinase dead version of Iso-1 (Iso-1 K123>A), enhanced transformation and increased the ability of MCF-10A and NIH 3T3 cells to form colonies in soft agar as well (FIGS. 19C and 20C). An in vitro kinase assay using S6 as a substrate shows that the short isoform Iso-2 and the kinase dead K123>A version of Iso-1 have no kinase activity (FIG. 20G). The oncogenic effects of S6K1 short isoforms did not require a functional kinase activity since all short S6K1 isoforms share truncated kinase domains and cannot phosphorylate ribosomal protein S6, or mTOR, both known S6K1 substrates (FIGS. 20E-G and 25A). In contrast to the expression of S6K1 short isoforms, overexpression of Iso-1, the long active kinase, did not enhance colony formation in soft agar and even reduced the basal level of colony formation (FIG. 19C).

Figure 20E:
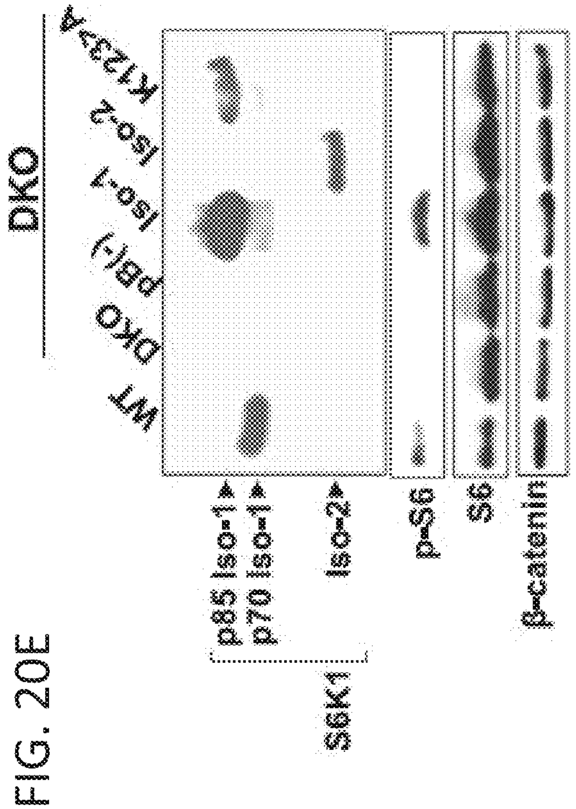
Figure 20F:
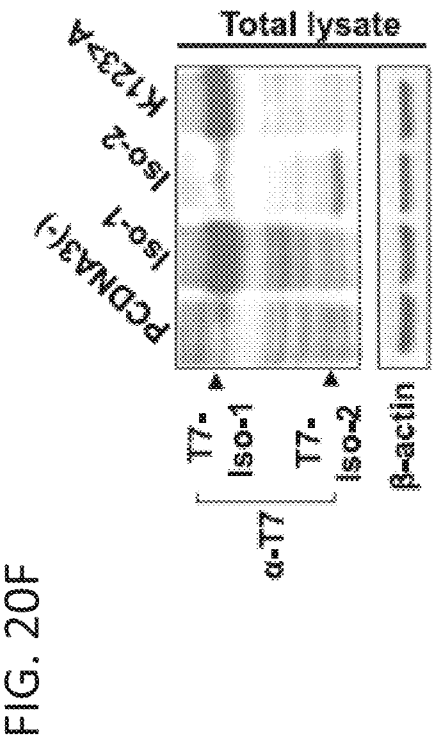

One characteristic of cellular transformation is enhancement of cell motility. MCF-10A cells expressing the shorter isoforms or the kinase dead version of Iso-1 (Iso-1 K123>A) showed accelerated migration rate compared to cells transduced with S6K1 Iso-1 or the empty vector in a tissue culture wound healing assay (FIGS. 20D-E). In order to exclude the possibility that these effects are the result of changes in proliferation, the proliferation rate of the cells was measured. Cells overexpressing the shorter variants, empty vector or Iso-1 K123>A did not show enhanced proliferation rate in comparison to Iso-1 (FIG. 20D). Altogether, these results suggest that S6K1 short kinase inactive isoforms promote transformation of MCF-10A cells.

Expression of S6K1 Short Isoforms Enables Growth Factor-independent Three Dimensional Acini Formation and Elevates 4E-BP1 Phosphorylation The immortal breast epithelial cells MCF-10A possess the ability to grow into spheroid structures (acini) when grown on matrigel. To study the effects of S6K1 isoforms on growth of three dimensional (3D) reconstituted basement membrane cultures, MCF-10A cells transduced with S6K1 isoforms were seeded in the presence or absence of growth factors necessary for acini formation in MCF-10A cells. Cells overexpressing S6K1 truncated isoforms, as well as the kinase-dead version of Iso-1, formed large, hyper proliferative three-dimensional structures (FIGS. 21A-C) with slight morphological disruption (FIG. 22A), even when grown in the presence of only one of the growth factors. This suggests that S6K1 isoforms can replace the strong proliferative signal provided by either EGF or Insulin/IGF1. This observation is further underscored by the fact that the kinase active isoform of S6K1 (Iso-1) failed to support growth factor independent acinus formation and may even inhibit basal proliferation in matrigel (FIGS. 21A-B and 22A).

Insulin/IGF-1 and EGF activate their corresponding receptors leading to activation of several mitogenic signaling cascades, among them the Ras-Raf-MAPK-ERK and the PI3K-Akt-mTOR pathways. It was hypothesized that S6K1 short isoforms affect acinus proliferation by activating the Insulin/IGF-1 and EGF signaling downstream of the receptors, bypassing the need for growth factor activation (FIGS. 21A-B). Thus, the present inventors sought to investigate the activities of these signaling pathways. The phosphorylation state of known downstream effectors of these pathways; Akt, ERK and 4E-BP1, was measured in MCF-10A cells overexpressing S6K1 isoforms with and without growth factor activation. It was found that overexpression of S6K1 kinase inactive isoforms stimulated the phosphorylation of 4E-BP1, even under serum starvation conditions (FIGS. 21D-E, 22D). Under these conditions, we observed only a slight and inconsistent activation of Akt or ERK (FIGS. 22B-D). Notably, while overexpression of S6K1 Iso-1 failed to increase 4E-BP1 phosphorylation under serum starvation conditions compared to cells transduced with empty vector (FIGS. 21D-E and 21D), knockdown of this isoform in MCF-10A cells increased 4E-BP1 phosphorylation (FIGS. 21F-G), supporting the notion that Iso-1 plays an opposite role than S6K1 kinase inactive isoforms. Thus, the increased level of 4E-BP1 phosphorylation that was observed, even in serum- and growth factor-deprived cells, may contribute to the transforming phenotype of cells harboring S6K1 short isoforms (FIGS. 19C-E, 21A-B and 20C). Moreover, 4E-BP1 phosphorylation is higher in most breast cancer cells compared to immortal non transformed cells in correlation with elevated levels of S6K1 short isoforms (FIGS. 17B-C, 18A and 22E).

S6K1 Iso-1 Inhibits Ras-induced Transformation in Vitro and in Vivo

Figures 21A, 21B, 21C:
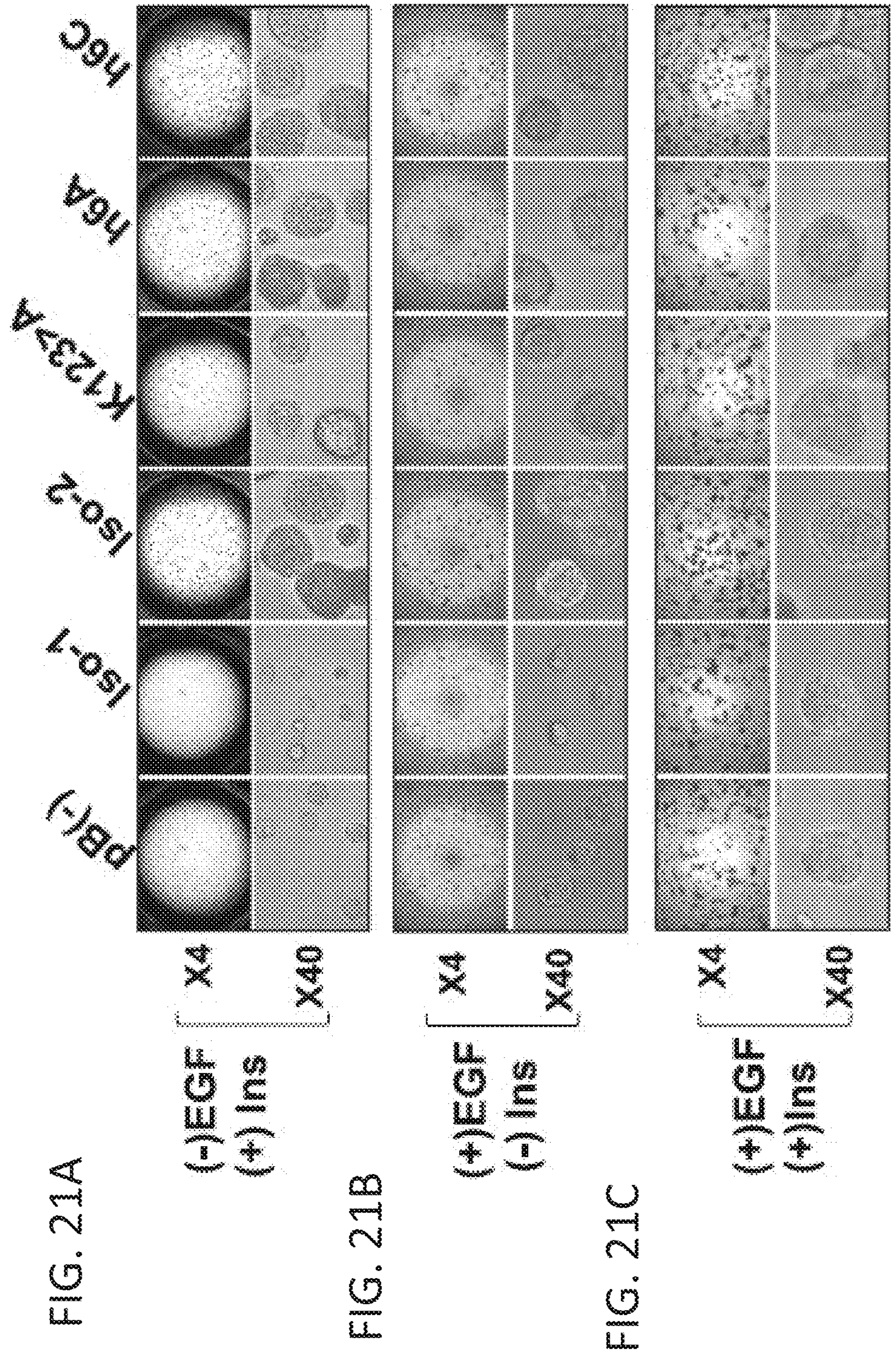
Figure 21D:
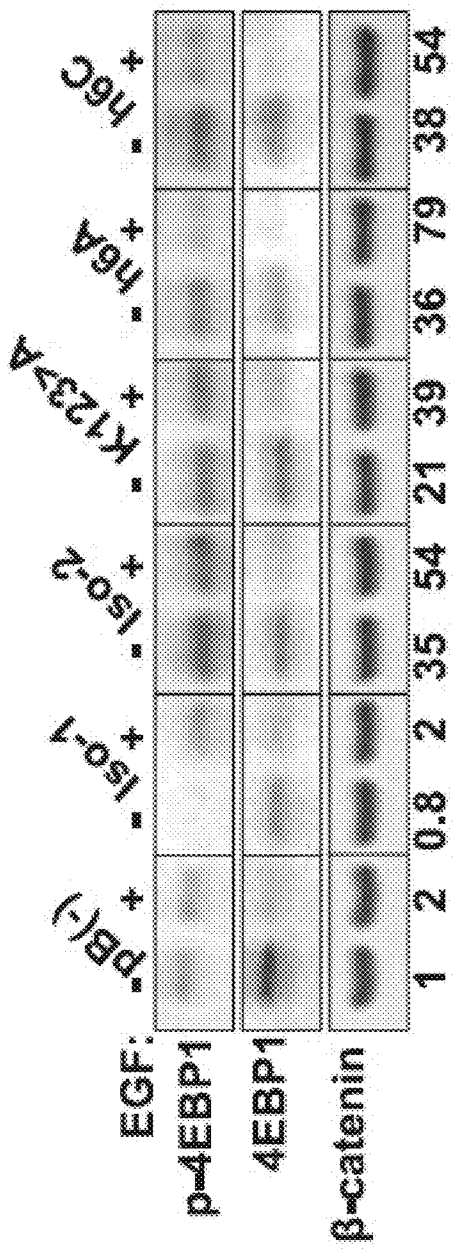
Figure 21E:
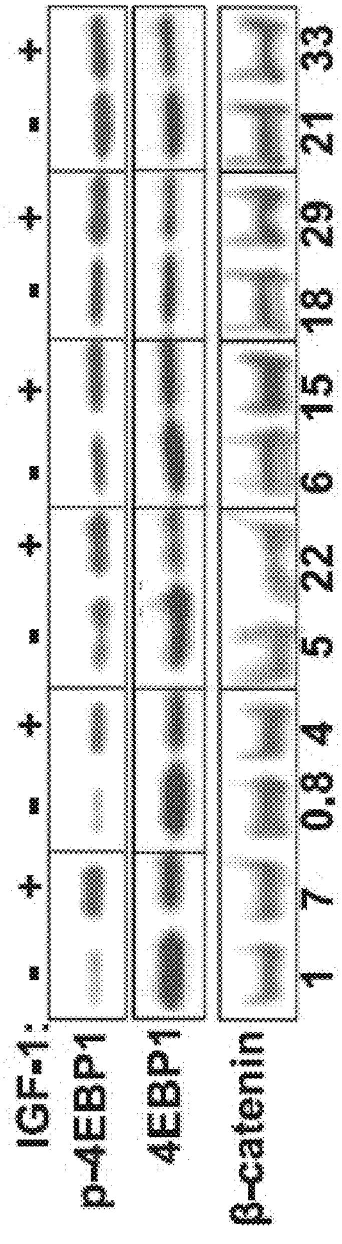
Figure 21G:
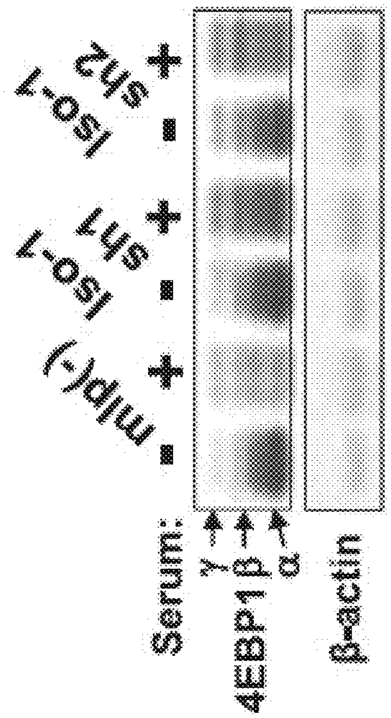
Figure 21F:
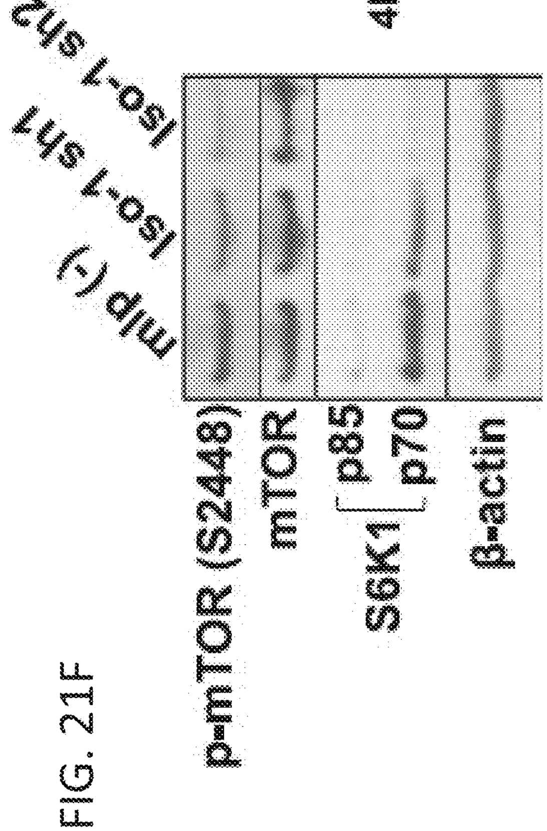
Figure 22A:
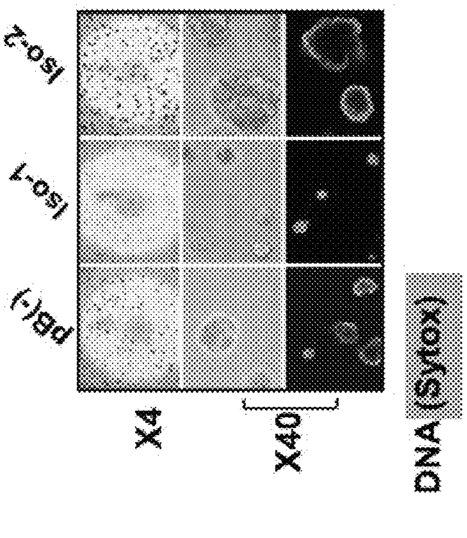
Figure 22B:
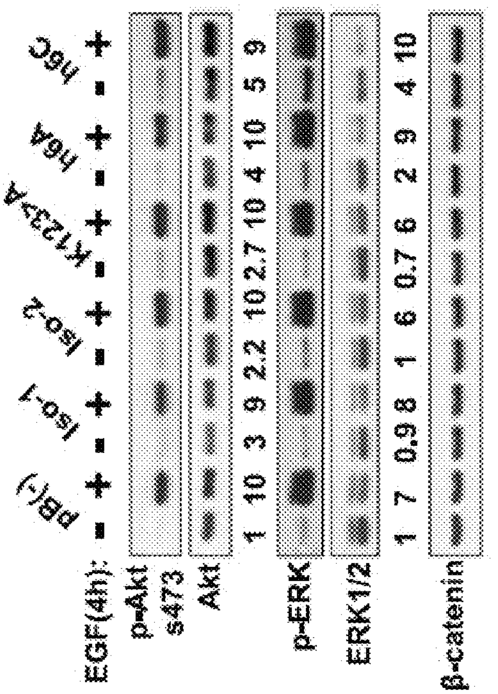
Figure 22C:
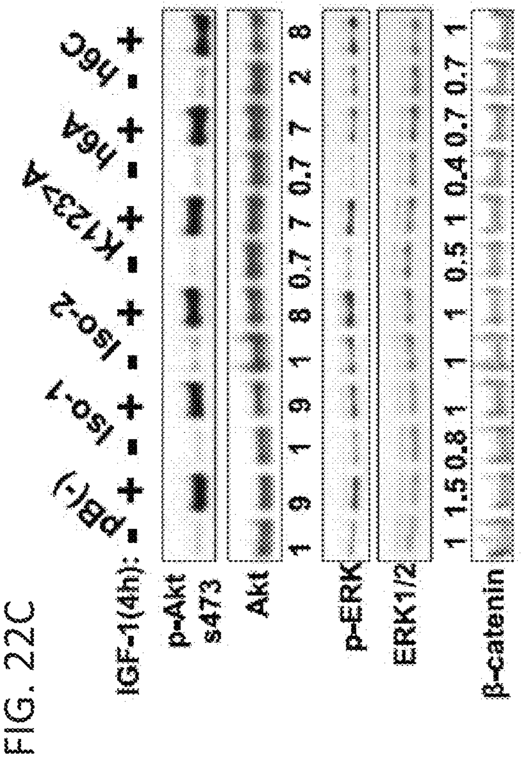
Figure 22E:
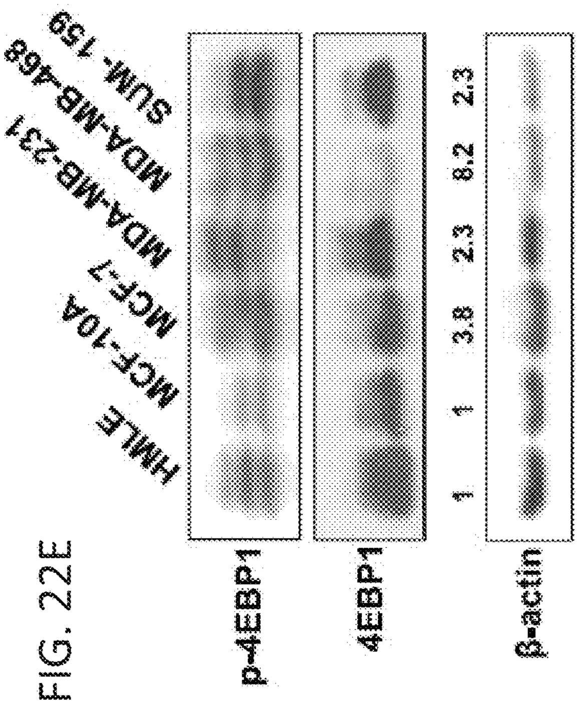
Figure 22D:
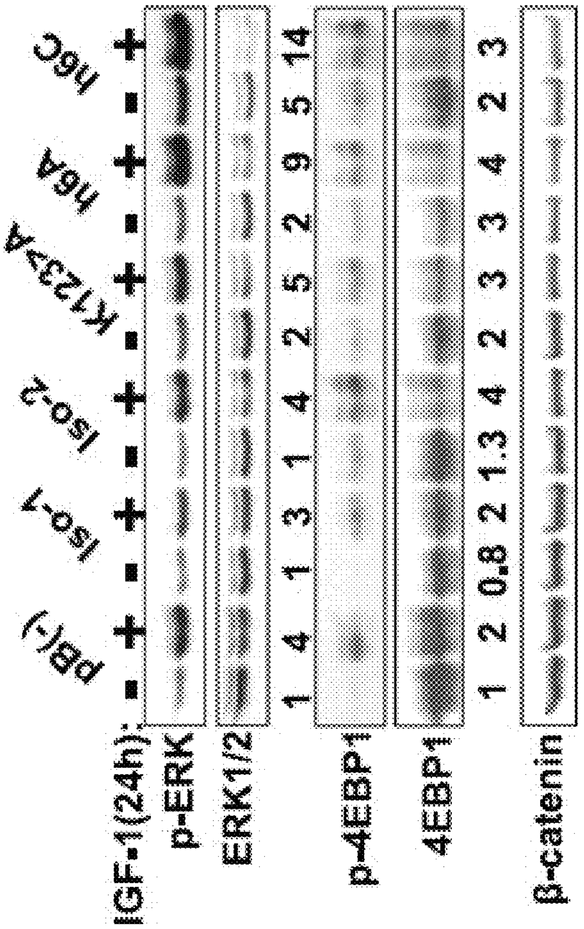
Figure 23B:
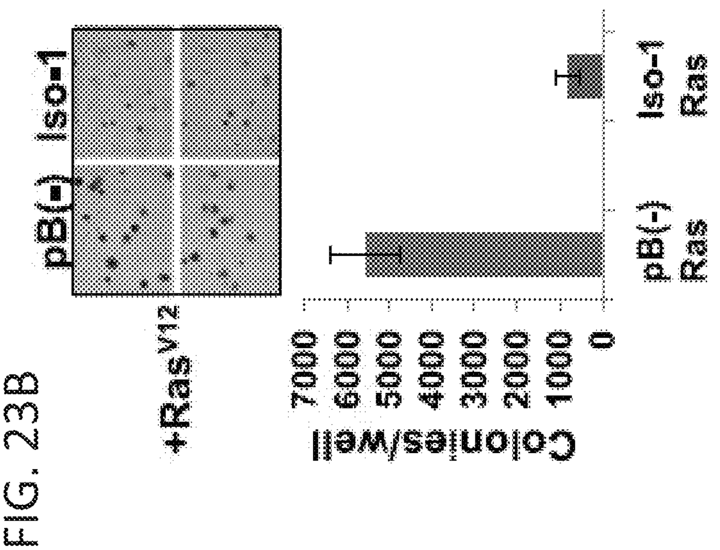
Figure 23A:
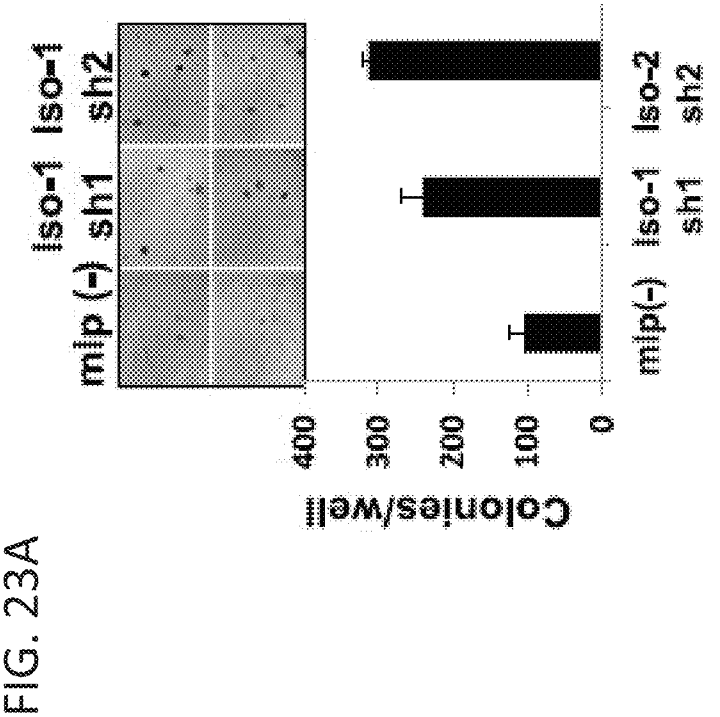
Figure 23E:
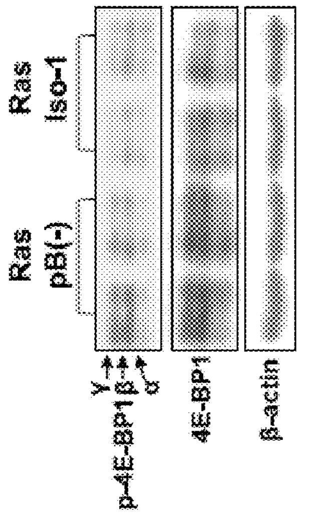
Figure 23D:
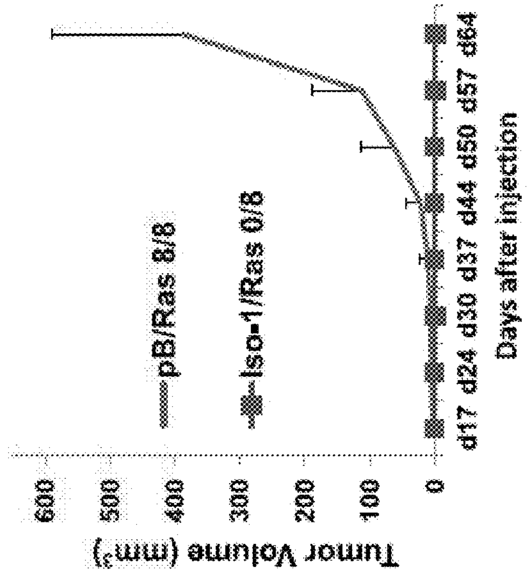
Figure 24C:
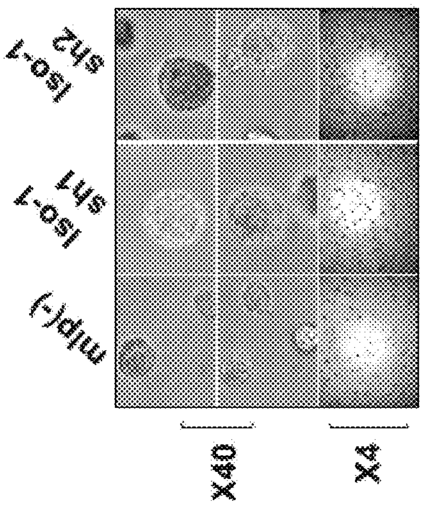
Figure 24D:
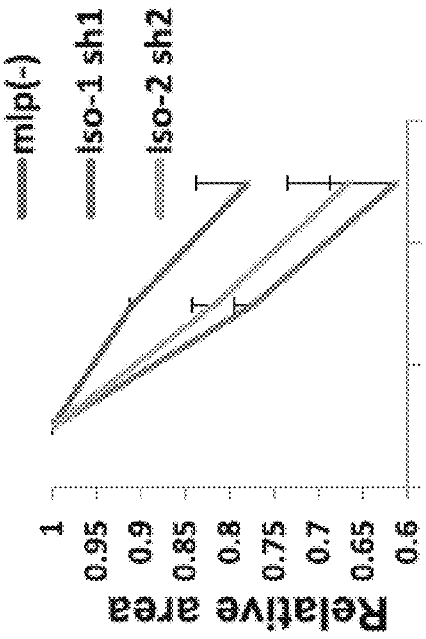
Figure 24A:
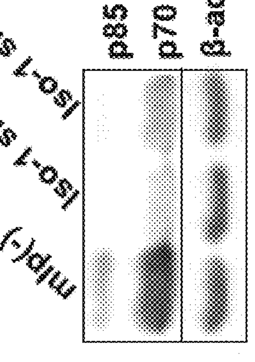
Figure 24B:
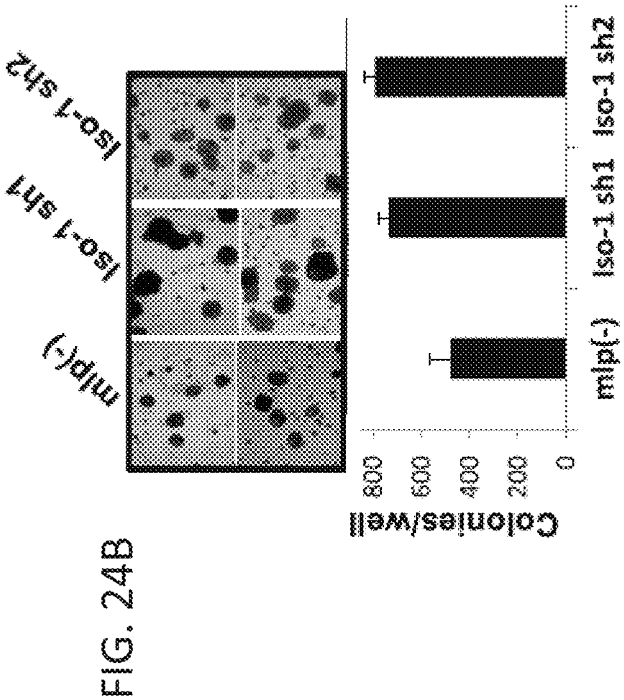

The present results, unexpectedly, indicated that the full length S6K1 Iso-1 did not support growth factor-independent acinus formation, as opposed to the short isoforms (FIGS. 21A-C). To further study the possibility that S6K1 Iso-1 acts as a tumor suppressor, its expression was silenced in the immortal MCF-10A cell line using Iso-1 specific shRNAs (FIG. 21F). Reduced phosphorylation of mTOR S2448, a known substrate of p70 S6K1 was measured in these cells (FIG. 21F). Knockdown of S6K1 Iso-1 in MCF-10A cells increased both colony formation in soft agar and acinus number and size in matrigel (FIGS. 23A, 24C). Similar results were obtained using NCI-H460 lung carcinoma cells (FIG. 24A-B). Even though overexpression of Iso-1 did not significantly decrease cell motility (FIGS. 23D-E) its knockdown in MCF-10A cells was sufficient to increase motility (FIG. 24D).

Figure 23C:
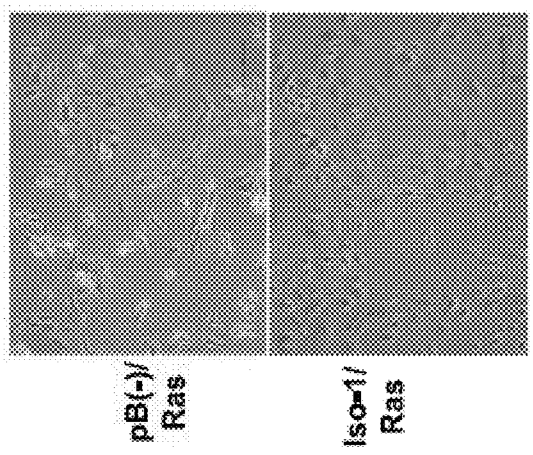
Figure 24E:
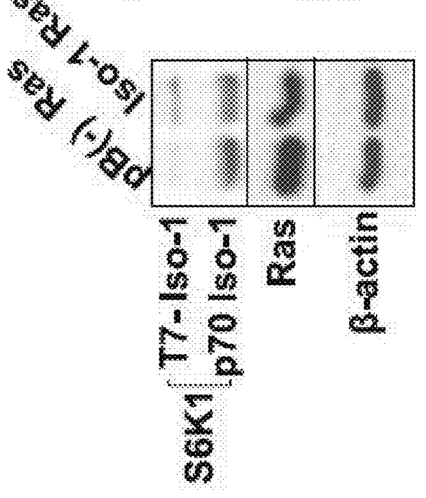
Figure 24F:
Figure 24G:
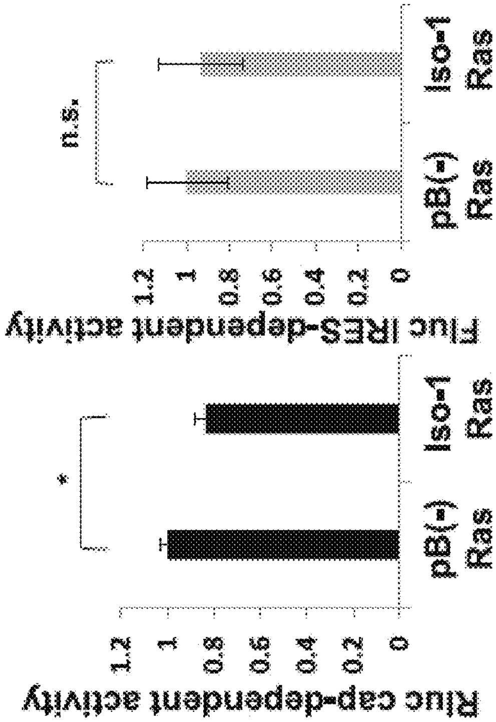

To examine if Iso-1 can suppress the oncogenic potential of transformed cells, the present inventors co-expressed S6K1 Iso-1 with an active RAS mutant (H-Ras$^{V12}$) in MCF-10A cells (FIG. 24E). Cells co-expressing the kinase active S6K1 isoform (Iso-1) and oncogenic RAS formed fewer and smaller colonies in soft agar compared to cells co-expressing Ras and empty vector, suggesting that S6K Iso-1 possesses tumor suppressive activity (FIG. 23B). Moreover, cells co-expressing Iso-1/Ras did not gain the spindle/fibroblastic shape that is characteristic of cells transformed with an oncogene such as Ras (FIG. 23C). The same cell pools were injected subcutaneously into NOD-SCID mice. Supporting the results in vitro, it was found that RAS-transformed cells co-expressing Iso-1 did not form tumors in vivo, (0 tumor formed of 8 injections) as opposed to the empty vector (8/8 tumors formed) (FIGS. 23D and 244F). 4E-BP1 phosphorylation levels were lower in cells co-expressing Iso-1 and H-Ras$^{V12}$ than in cells expressing H-Ras$^{V12}$ alone (compare the γbands in FIG. 23E). Moreover, cells co-expressing Iso-1 and Ras$^{V12}$ showed about 20% decrease in Cap-dependent translation in correlation with the decreased phosphorylation of 4E-BP1 (FIG. 24G). Taken together, this data suggests that S6K1 Iso-1 is a putative tumor suppressor.

S6K1 Short Isoforms Bind mTORC1 and Enhance Cap-dependent Translation and Mcl-1 Expression It was hypothesized that S6K1 short isoforms might directly bind and activate mTORC1. To test this possibility the present inventors co-transfected myc-tagged mTOR and T7 tagged Iso-1 or Iso-2 (as a representative of the short isoforms). Immunoprecipitation of transfected S6K1 with anti-T7 antibody revealed that only S6K1 Iso-2 interacts with mTOR (FIGS. 25A-B). The fact that an interaction between S6K1 Iso-1 and mTOR was not observed might be explained by T389 phosphorylation of S6K1 (FIG. 25B). This phosphorylation activates S6K1 Iso-1 leading to its release from mTORC1.

Cells overexpressing S6K1 short inactive isoforms showed elevated levels of cap-dependent translation under serum starvation conditions as measured by a reporter gene measuring Cap-versus IRES-mediated translation from the same transcript (FIGS. 25C-D). Indeed, Iso-1 overexpressing MCF-10A cells exhibited only a slight decrease in 4E-BP1 phosphorylation that was consistent with a slight decrease of cap-dependent translation, compared to cells expressing empty vector (FIGS. 21D-E and 25D). Moreover, on the background of H-Ras$^{V12}$ transformation, Iso-1 decreased both 4E-BP1 phosphorylation and cap-dependent translation (FIGS. 23E and 24G), suggesting that Iso-1 tumor suppressive effect can be clearly detected on the background of a strong oncogene such as mutant Ras but not in a non-transformed cell system such as MCF-10A cells.

The present inventors next examined if S6K1 short isoforms alter the expression of proteins known to be controlled by mTORC1-4E-BP1 translational regulation and can contribute to cell transformation. One such protein is Mcl-1, a key antiapoptotic protein that was shown to be translationally controlled by mTORC1. It was found that Mcl-1 protein levels are elevated in MCF-10A cells overexpressing S6K1 kinase inactive isoforms, but not Iso-1 or empty vector (FIG. 25E). Interestingly, Mcl-1 was also elevated by Iso-1 knockdown (FIG. 25F). S6K family consists of two kinases, S6K1 and S6K2 (RPS6KB1 and RPS6KB2 respectively), that are known to have redundant activities. No changes in S6K2 protein levels in either Iso-1 knockdown or S6K1 kinase inactive isoforms overexpression were detected (FIGS. 26A-B), indicating that the biological effects that were observed are due to up or downregulation of S6K1 Iso-1 or the short S6K1 isoforms.

Figures 27A, 27B, 27C, 27D, 27E, 27F:
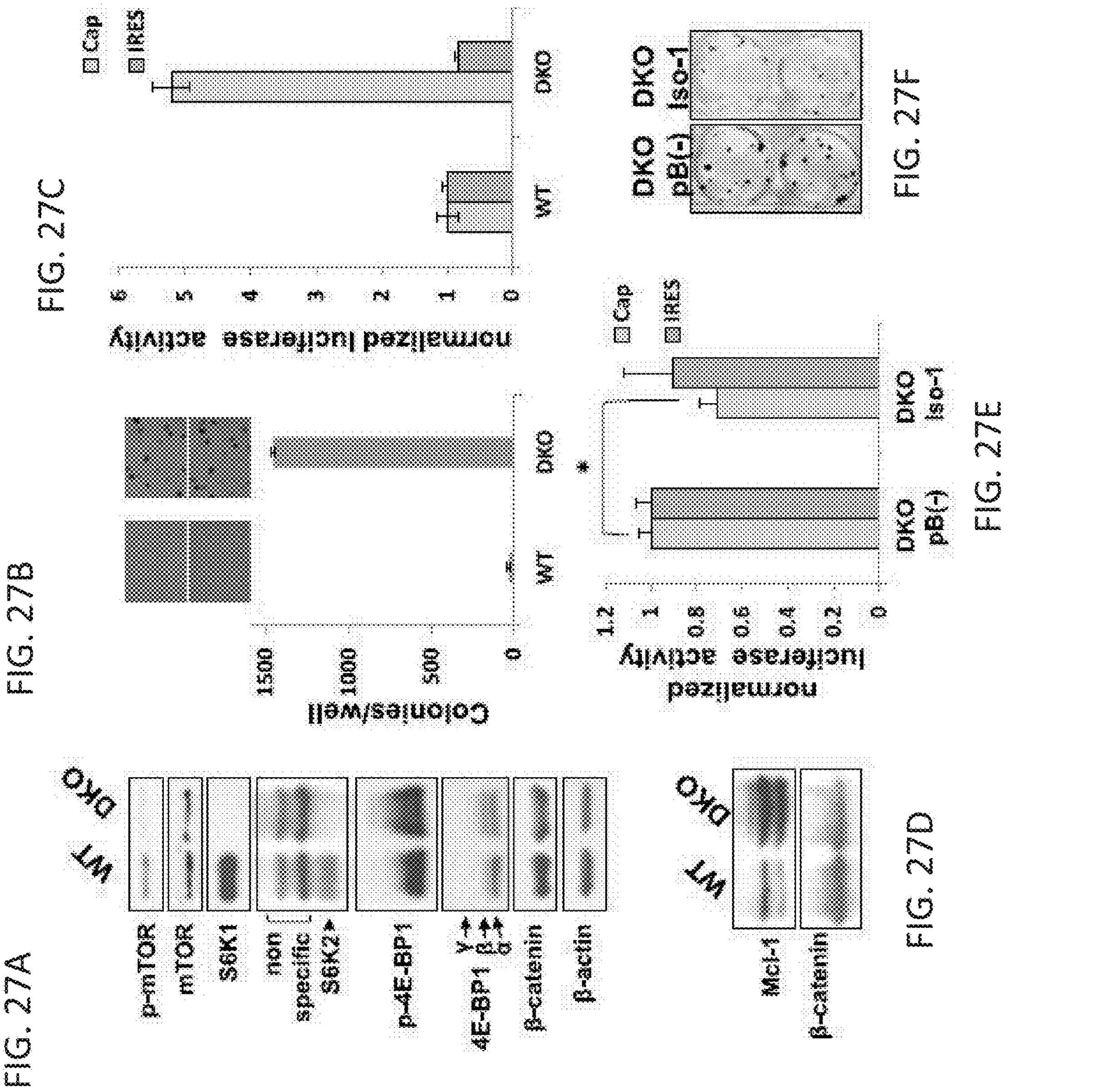

Loss of S6K1/2 Enhances Cap-dependent Translation, Mcl-1 Expression and Transformation In order to establish definitive proof that S6K1 Iso-1 is a tumor suppressor and to rule out any possible compensation or interference by S6K2, the present inventors analysed S6K1 and S6K2 double-knockout (DKO) mouse embryonic fibroblasts (MEFs) (FIG. 27A). Serum starved S6K DKO MEFs showed elevated phosphorylation levels of 4E-BP1 (FIG. 27A). In addition, S6K DKO MEFs formed significantly higher number of colonies in soft agar and also presented 5-fold increase in cap-dependent translation, indicating that these cells are transformed (FIG. 27B-C). Furthermore, Western blot analysis of S6K DKO MEFs revealed high levels of expression of Mcl-1 (FIG. 27D) in agreement with what was observed in Iso-1 knockdown in MCF-10A cells (FIG. 25F). The fact that the DKO cells show minor/negligible mTOR phosphorylation (FIG. 27A) and no S6 phosphorylation (FIG. 20F), but were transformed, supports the notion that mTOR S2448 phosphorylation is not essential for its ability to phosphorylate 4E-BP1.

Figure 27G:
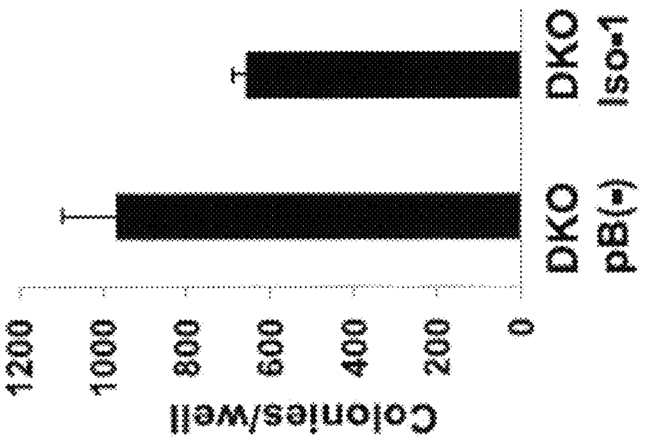

Expression of Iso-1 in S6K DKO MEFs (FIG. 20E) partially reduced cap-dependent translation, colony survival and growth of colonies in soft agar showing that Iso-1 harbors tumor suppressive ability (FIGS. 27E-G). The transformed phenotype of S6K DKO MEFs was not completely reversed by the ectopic expression of S6K1 Iso-1, probably due to the absence of S6K2 in this cell system that might contribute to the tumor suppressive phenotype of S6K1.

The Oncogenic Activities of S6K1 Short Isoforms are Mediated by mTORC1 Inactivation of 4E-BP1

S6K1 short isoforms activated mTORC1 as measured by 4E-BP1 phosphorylation (FIGS. 21D-E, 22D). The present inventors next examined, using two complementary strategies, if this activation is required for their oncogenic activities: 1) Inhibition of mTORC1 by the pharmacological inhibitor rapamycin and 2) expression of a phosphorylation-defective 4E-BP1 which is mutated in its phosphorylation sites and cannot dissociate from eIF4E upon mTORC1 activation. They transduced MCF-10A cells expressing the mouse S6K1 short isoform (Iso-2) with phosphorylation-defective 4E-BP1 (4E-BP1$^{5A}$ or 4E-BP1$^{4A}$), where each of the five (or four) insulin and rapamycin-responsive 4E-BP1 phosphorylation sites have been mutated to alanine.

Figure 29A:
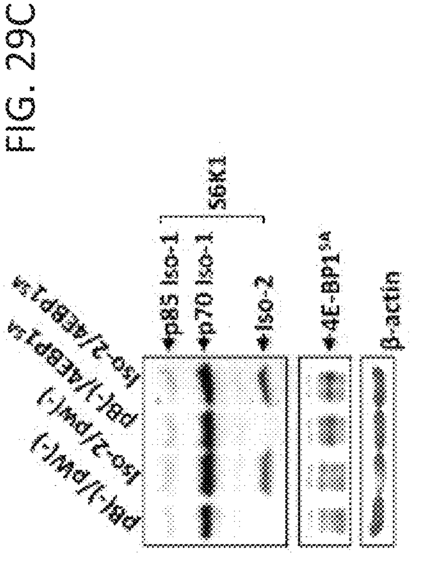
Figure 29B:
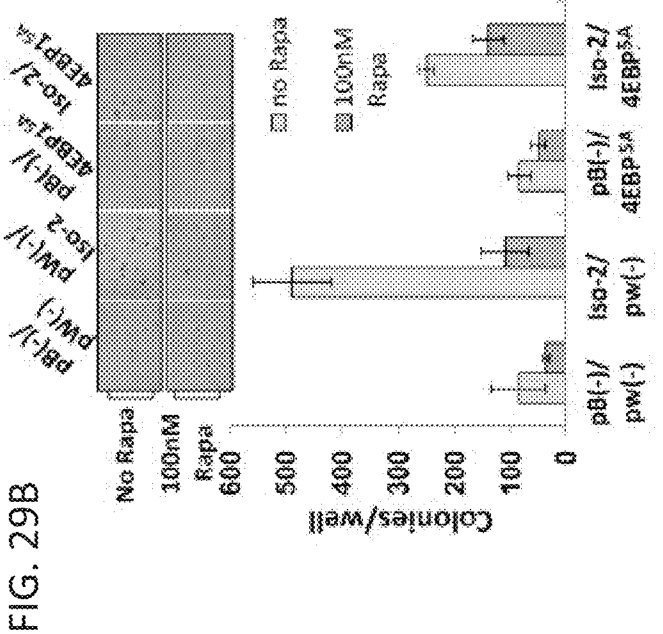
Figure 29C:
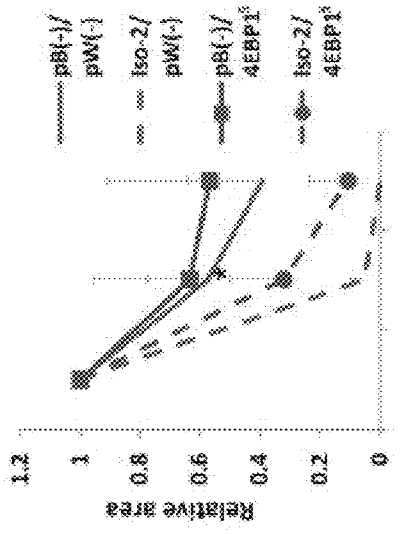
Figure 29D:
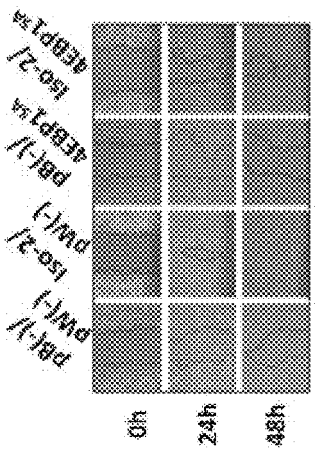

Co-expression of both Iso-2 and mutant 4E-BP1 decreased colony formation in soft agar two fold relative to cells expressing Iso-2 alone (FIGS. 29A-B and 29A-B). Similarly, rapamycin reduced the number of colonies formed in soft agar in cells overexpressing Iso-2 to the background level of cell expressing empty vector (FIG. 29B). These results suggest that mTORC1 activation and 4E-BP1 phosphorylation plays a major role in the oncogenic capabilities of S6K1 short isoforms. Expression of mutant 4E-BP1 together with Iso-2 also partially decreased cell motility compared to cells expressing Iso-2 alone (FIG. 29C-D).

Figure 29E:
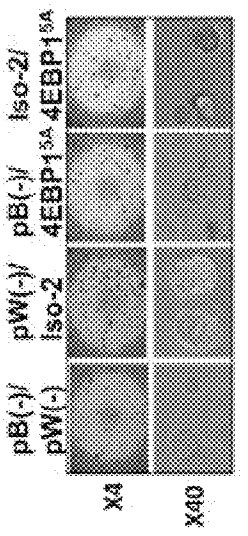

Next, the present inventors investigated whether 4E-BP1 phosphorylation is important for Iso-2 mediated growth factor independent 3D proliferation in matrigel. Expression of 4E-BP1$^{5A}$ strongly inhibited Iso-2 ability to induce growth factor independent acinus formation in matrigel (FIG. 29E). Taken together, these results suggest that the mechanism of action of S6K1 short isoforms is mediated mostly by 4E-BP1 phosphorylation through mTORC1 activation.

Summary of Example 2

The present example shows that in human cells S6K1 has two alternatively spliced short isoforms that are over-produced in breast cancer cell lines and tumors. Furthermore, all of S6K1 short splicing variants lack an autoinhibitory C-terminus domain, half of the kinase domain and do not exhibit kinase activity, at least on the known S6K1 substrate, rpS6 (FIGS. 19A, 20E-G). Overexpression of mouse or human S6K1 short isoforms enhanced transformation, anchorage-independent growth, cell motility and growth factor-independent three-dimensional acinus formation of human breast epithelial cells (FIGS. 19A-E, 21A-C, 20C and 22A). Surprisingly, the long, kinase active S6K1 isoform (Iso-1), inhibited 3D acinus formation, reduced 4E-BP1 phosphorylation, cap-dependent translation and transformation in vitro and in vivo, demonstrating many properties that characterize a tumor suppressor. The present results suggest that only S6K1 short isoforms, but not Iso-1, interact with and activate mTORC1 leading to elevated 4E-BP1 phosphorylation, enhanced cap-dependent translation and upregulation of the anti-apoptotic protein Mcl-1. Inhibition of mTORC1 or 4E-BP1 phosphorylation can partially reverse the oncogenic activity of S6K1 short isoforms suggesting that their oncogenic properties are at least in part mediated by this pathway.

A Switch in RPS6KB1 Alternative Splicing Up Regulates Oncogenic Isoforms in Breast Cancer.

It was found that many breast cancer cell lines and tumors switch the splicing of RPS6KB1 to elevate the human short isoforms of S6K1 h6A and h6C (FIGS. 17B-D, 18F-G). It was found that while all the short S6K1 isoforms, as well as the kinase-dead form of Iso-1, induced anchorage independent growth, enhanced motility and growth factor-independent three dimensional acinus formation in matrigel, the active S6K1 isoform (Iso-1) did not (FIGS. 19A-C, 20C and 21A-G). Moreover, in most of these assays Iso-1 showed an opposite effect, indicating that these splicing isoforms possess antagonistic activities. Several lines of evidence suggest that Iso-1 acts as a functional tumor suppressor: a) when co-expressed with an active Ras$^{V12}$ mutant, Iso-1 inhibited Ras-induced transformation in vitro and in vivo (FIG. 23A-E) suggesting it possesses an anti tumorigenic activity. b) Iso-1 knockdown in MCF-10A cells induced transformation, colony formation in soft agar, acinus formation, increased motility and elevated Mcl-1 levels (FIGS. 23A, 25F and 24C-D). c) Loss of S6K1 and S6K2 had dramatic effect on cellular transformation, as immortalized MEFs from S6K1/2 DKO mice were transformed, formed large numbers of colonies in soft agar and showed increased levels of the anti-apoptotic protein Mcl-1 (FIGS. 27A-G), which is translationally regulated by mTORC1. d) Re-introduction of S6K1 Iso-1 partially inhibited the transformed phenotypes of S6K1/2 DKO cells indicating that Iso-1 possesses tumor suppressive activities, but might require also the presence of S6K2 in these cells to restore its full capability as an anti tumorigenic protein (FIGS. 27A-G).

The present report provides the first direct evidence for the pro- and anti-tumorigenic effects of stable knockdown or overexpression of S6K1 long isoform (Iso-1) respectively. It should be noted that the pro-oncogenic effect of Iso-1 knockdown does not involve S6K2, as the latter remained unchanged (FIGS. 26A-B). Notably, the catalytic activity of S6K1 is essential for its tumor suppressive activity, as the kinase-dead point mutant completely abrogated this activity. In addition, the fact that Iso-1 inhibited Ras transformation, but only partially inhibited cap-dependent translation raises the possibility that Iso-1 phosphorylates additional substrates other than those in the mTOR pathway, that contribute to its tumor suppressor activity independently of cap-dependent translation. Importantly, S6K1 short isoforms are catalytically inactive and did not induce phosphorylation of the known S6K1 substrates, the ribosomal protein S6 or mTOR itself in an in vitro kinase assay and upon transfection into cells (FIGS. 20E-G, 25E, 25A and 22C). Altogether, these results suggest that Isoform-1 of S6K1 has tumor suppressive properties, while the short isoforms are pro-oncogenic. The results suggest that the gain of h6A and h6C observed in breast cancer cells and tumors is a mechanism to switch-off a tumor suppressive isoform and to turn-on an oncogenic one.

RPS6KB1 Splicing Isoforms Modulate the Activity of mTORC1

Surprisingly, it was found that most S6K1 short isoforms activated mainly 4E-BP1 phosphorylation without a significant activation of Akt or ERK and in a growth factor-independent manner (FIGS. 21A-G and 22A-E). In accordance with increased 4E-BP1 phosphorylation, cells expressing S6K1 short isoforms showed elevated cap-dependent translation and upregulation of Mcl-1, while Iso-1 expressing cells showed low or basal cap-dependent translation, similar to the control cells expressing empty vector or reduced cap-dependent translation in Ras-transformed cells (FIGS. 24G, 25A-F). Moreover, loss of S6K1 and S6K2 enhanced cap-dependent translation in MEF cells which was partially inhibited by S6K1 Iso-1 re-introduction (FIGS. 27A-G) indicating that S6K1 and S6K2 activities suppress cap-dependent translation and transformation (FIGS. 27A-G). Although surprising, previous studies support this result: Cells from a knockin mouse of a mutant S6 gene (rpS6$^{P-/-}$) where all five phosphorylation sites were replaced to alanines, showed a two fold increase in global translation as measured by methionine incorporation and a two fold increase in proliferation rate as compared to MEFs from WT littermates. Combining these two findings, both inactivation of the "kinase" (S6K1/2 DKO) or inhibition of phosphorylation of the substrate (rpS6$^{P-/-}$), gave similar results of increased translation. This suggests that S6 phosphorylation might inhibit rather than increase translation. Other studies did not find reduced translation upon S6K1/2 loss even though they did not observe increased translation. These results suggest that the growth factor independent growth observed in matrigel (FIG. 21A-G) could be explained by the ability of S6K1 short isoforms to activate mTORC1 that in turn inactivates 4E-BP1 even under low nutrient conditions. Enhanced cap-dependent translation contributes to cancer development by elevating the translation of several oncogenes and anti-apoptotic genes such as Mcl-1, Bcl-X, MDM2, HIF-1α, β-catenin, c-myc, cyclin D1 and others, which are translationally regulated by cap-dependent translation and the mTORC1 pathway. It was found that, at least in the case of the anti-apoptotic protein Mcl-1, overexpression of S6K1 short isoforms, Iso-1 knockdown or S6K1/2 knockout enhanced its expression (FIGS. 25E-F, 27D). To examine if S6K1 short isoforms can interact with mTOR the present inventors co-expressed mTOR with S6K1 Iso-1 or Iso-2 and found that only the short isoform could pull down mTOR, whereas Iso-1 did not, even though its expression was much higher (FIGS. 25A-B).

The oncogenic activities of S6K1 short isoforms are partly mediated through 4E-BP1 and mTORC1 activation.

Figure 29F:
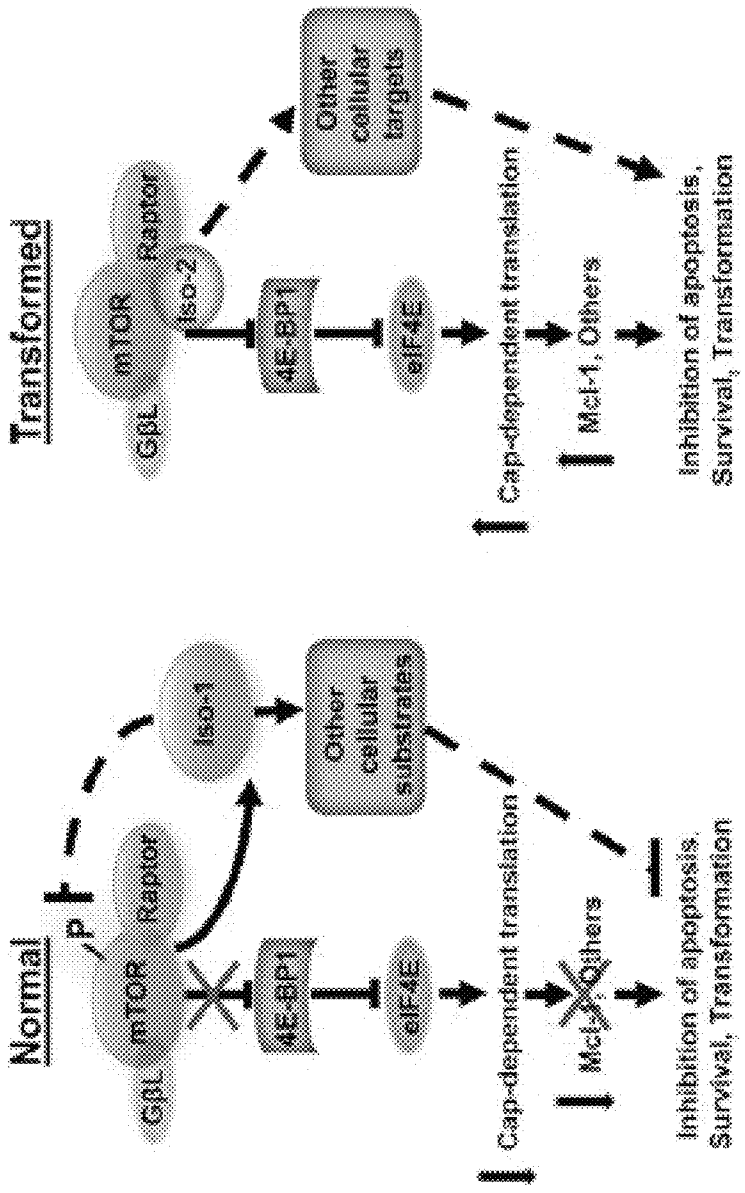

The present inventors examined the contribution of mTORC1-4E-BP1 axis to S6K1 short isoform mediated oncogenesis and found that inhibition of eIF4E/4E-BP1 dissociation greatly inhibited motility, anchorage-independent growth and growth factor-independent acinus formation in matrigel (FIGS. 29A-F and 28A-B). These results suggest that most of the oncogenic effects of S6K1 short isoforms are mediated by mTORC1 activation. However, the possibility cannot be ruled out that S6K1 short isoforms affect other oncogenic signaling pathways as suggested by the fact that expression of a dominant-negative 4E-BP1 did not fully suppress colony formation in soft agar and motility induced by S6K1 short isoforms. These results also suggest that S6K1 is not only a substrate of mTOR, but that it may also modulate the activity of mTOR increasing 4E-BP1 phosphorylation when S6K1 short isoforms are elevated (FIGS. 21A-G and 22D). In addition, S6K1 Iso-1 can phosphorylate mTOR at Serine 2448, (FIGS. 21F, 25A and 27A), although the consequences of this phosphorylation on mTOR activity are not fully understood. S6K1 short isoforms cannot be phosphorylated by mTOR at Threonine 389 and by phosphoinositide-dependent kinase 1 (PDK1) at Threonine 229, as they lack both phosphorylation sites. However, both Iso-1 and the short isoforms should be able to bind mTORC1, since all of them contain the Raptor binding motif mTOR-signaling (TOS) motif. Thus, while Iso-1 activity responds to mitogenic and nutritional stimuli, as well as energy status, the short isoforms are refractory to any of these signals, yet they can still affect mTORC1. Indeed, the present data suggests that these short isoforms transmit through mTORC1 activation, a constitutive mitogenic/metabolic signal, even in the absence of growth factors (FIGS. 21A-G, 22A-E). In addition, S6K1 short isoforms cannot induce mTOR S2448 phosphorylation, as they lack a functional kinase domain and are catalytically inactive (FIGS. 20E-G, and 25A). Thus, it is conceived that Iso-1 phosphorylates mTOR and inhibits cap-dependent translation and transformation. Iso-1 also phosphorylates other cellular substrates that might lead to suppression of transformation. In contrast, the short isoforms bind to the same or other cellular targets and thereby induce opposite effects. S6K1 short isoforms can bind directly to mTORC1 and enhance its activity possibly by competing with Iso-1 for mTOR binding (FIG. 29F). Nevertheless, the mechanism by which S6K1 short isoforms activate mTOR is yet to be determined.

The present inventors have discovered new alternatively spliced variants of the gene encoding S6K1. These findings provide additional insight into the oncogenic switch that can be caused by alternative splicing. Furthermore, a new mode of mTORC1 activation has been identified, which may open a new direction in manipulating mTORC1 activity for cancer therapy. In addition, the present inventors show that, the balance between S6K1 short isoforms and Iso-1 is tipped towards those short isoforms in most tumors examined, suggesting that this splicing event can be a useful marker for breast cancer development. Moreover, since S6K1 short isoforms activate mTORC1 and this activation is important for tumorigenesis, it can be expected that the newly approved active site mTOR inhibitors will act more efficiently on tumors where the S6K1 alternative splicing switch has occurred.

Example 3

The Splicing Factor SRSF6 is Amplified and is an Oncoprotein in Lung and Colon Cancers Materials and Methods Cells and viral transductions: MLE cells were grown in HITES medium, BEAS-2B cells-were grown in BEB medium (Lonza), NCI-H460 and LcLc-103H cells in RPMI and RKO cells in DMEM. All the media were supplemented with 10% FCS, 2 mM L-Glutamine, 0.1 mg/ml penicillin, 0.1 mg/ml streptomycin. For overexpression cells were infected with pBABE-puro retroviral vector expressing T7-tagged human SRSF6 cDNA. Medium was replaced 24 h after infection, and 24 h later, infected cells were selected for by the addition of puromycin (2 μg/ml) for 72-96 h. For knockdown experiments cells were infected with MLP-puro-shRNAs vectors, cell transductants were selected for with puromycin (2 μg/ml) for 96 h. shRNA sequences appear herein below.

Tumor Samples: Tumor samples were obtained from CHTN (Cooperative Human Tissue Network, Philadelphia, Pa., USA). The lung tumors were stage III adenocarcinomas. The breast tumors were invasive ductal carcinomas. The normal tissues were the histologically normal tissues adjacent to cancerous tissues. DNA copy numbers and expression of SRSF6 were determined by Q-PCR or Q-RT-PCR as described below.

Gene copy number measurements: Blood and colorectal tumor samples were collected at the Department of Surgery, Aarhus University Hospital, Aarhus, Denmark. All tissue samples were collected immediately after surgery and snap frozen in liquid nitrogen. Tumor and matched germline DNA (extracted from blood and/or adjacent normal mucosa) from 37 adenomas and 28 carcinomas were labeled and hybridized to the SNP6.0 array according to the manufacturers instructions (Affymetrix, Santa Clara, Calif.). Data preprocessing, normalization, probe summarization and calculation of raw total copy-number estimates were done using the CRMAv2 method implemented in the aroma.affymetrix R package. Segmentation of the .cn files produced by aroma. affymetrix were done using the Rseg package. This package allows sample-specific thresholds for calling gains and losses to be defined and corrects for artifacts induced by the normalization in case of unbalanced abnormalities. Gain or loss at the specified gene loci were called when the log ratio copy number between tumor and germline was ≥0.17 or ≤−0.17, respectively.

Immunoblotting: Cells were lysed in Laemmli buffer and analyzed for total protein concentration. 30 μg of total protein from each cell lysate was separated by SDS-PAGE and transferred to a nitrocellulose membrane. The membranes were blocked, probed with antibodies and detected using enhanced chemiluminescence. Primary antibodies were against β-catenin (1:2,000, Sigma); SRp55 (SRSF6) (mAb 8-1-28 culture supernatant); T7 tag (1:5,000, Novagen); GAPDH (1:2000, Santa Cruz). Secondary antibodies were HRP-conjugated goat anti-mouse, goat anti-rabbit or donkey anti-goat IgG (H+L) (1:10,000, Jackson Laboratories).

Anchorage-independent growth: Colony formation in soft agar was assayed as described previously. Plates were incubated at 37° C. and 5% $CO_2$. After 10-18 days, colonies were counted from ten different fields in each of two wells for each transductant pool and the average number of colonies per well was calculated. The colonies were stained and photographed under a light microscope at 100× magnification.

Growth curves: Transductant pools of MLE or BEAS-2B cells were seeded at 2500 or 5000 cells per well in 96-well plates. Every 24 hours cells were fixed and stained with methylene blue, and the absorbance at 650 nm of the acid-extracted stain was measured on a plate reader (BioRad).

Survival assays: MLE cells were transduced with the indicated retroviruses. Following selection, $1\times10^4$ cells per well were seeded in 96-well plates. 24 h later, the cells were serum starved for another 24 hours. At 24 hours (before treatment) one 96-plate was fixed and served as normalizing control ("Time 0"). After starvation the medium was replaced with starvation medium containing the indicated concentrations of CDDP (Sigma) and the cells were incubated for an additional 24 h. Cells were fixed and stained with methylene blue as described previously [1] and the absorbance at 650 nm of the acid-extracted stain was measured on a plate reader (BioRad) and was normalized to cell absorbance at "Time 0".

RT-PCR: Total RNA was extracted with Tri reagent (Sigma) and 2 μg of total RNA was reverse transcribed using the AffinityScript (Stratagene) reverse transcriptase. PCR was performed on 1/10(2 μl) of the cDNA, in 50 μl reactions containing 0.2 mM dNTP mix, 10×PCR buffer with 15 mM $MgCl_2$ (ABI), 2.5 units of TaqGold (ABI) and 0.2 mM of each primer; 5% (v/v) DMSO was included in some reactions. PCR conditions were 95° C. for 5 min, then 33 cycles of 94° C. for 30 s, 57° C. for 30 s and 72° C. for 45 s, followed by 10 min at 72° C. PCR products were separated on 1.5% or 2% agarose gels. Primers are listed herein below.

TABLE 3

| Gene name | Exon forward Exon reverse | Sequence (5'-3') |
|---|---|---|
| BIN1 | E11 For | CCTCCAGATGGCT CCCCTGC-SEQ ID NO: 70 |
| | E14 Rev | CCCGGGGGCAGGT CCAAGCG-SEQ ID NO: 71 |
| mBIN1 | For | AAGCCCAGAAGG TGTTCGAG-SEQ ID NO: 72 |
| | Rev | TGGCTGAGATGG GGACTT-SEQ ID NO: 73 |
| INSR | E 10 For | AGATCCTGAAGGA GCTGGAGGAG-SEQ ID NO: 74 |
| | hE12 Rev | GGTCGAGGAAGTG TTGGGGAA-SEQ ID NO: 75 |
| | mE12 Rev | GAGGAGACGTTGG GGAAATCTG-SEQ ID NO: 76 |
| MKNK2 | E11 For | CCAAGTCCTGCAGC ACCCCTG-SEQ ID NO: 77 |
| | E13a Rev | GATGGGAGGGTCAG GCGTGGTC-SEQ ID NO: 78 |
| | E13b Rev | GAGGAGGAAGTG ACTGTCCCAC-SEQ ID NO: 79 |
| SRSF6 | E2 For | GTACGGCTTCGTG GAGTTCGAGG-SEQ ID NO: 80 |
| | E3b Rev | GGCAAAAGGCTGC TGTCGTCATGG-SEQ ID NO: 81 |
| | E4 Rev | CTGGATCTGCTTCCA GAGTAAGAT-SEQ ID NO: 82 |
| qPCR: SRSF6 | RA3 QF: | CGATCCCCTAAAG AAAATGGAA-SEQ ID NO: 83 |
| | RA3 QR: | GGCCTTTGAGGG TGGAACA-SEQ ID NO: 84 |
| | RA3 QP (6-FAM): | ATCAAGGAGCCAGT CCCGTTCCAATT-(TAMRA)-SEQ ID NO: 85 |
| | RA4 QF: | ATGAACATGCCGT AGTGCCTTT-SEQ ID NO: 86 |
| | RA4 QR: | GGTGAACAA TCGGGAGGAA-SEQ ID NO: 87 |
| | RA4 QP: (6-FAM): | TGGCCAGTTTGAGT CCTGCCTACTTTGA-(TAMRA)-SEQ ID NO: 88 |

TABLE 3 -continued

| Gene name | Exon forward Exon reverse | Sequence (5'-3') |
|---|---|---|
| qPCR: β-actin | β-actin forward primer: | GCAAAGACCTGTAC GCCAACA-SEQ ID NO: 89 |
| | β-actin reverse primer: | TGCATCCTGTCG GCAATG-SEQ ID NO: 90 |
| | β-actin probe (6-FAM): | TGGCGGCACCACC ATGTACC-(TAMRA)-SEQ ID NO: 91 |
| BRCA1 | E8 For | CCAACTCTCTAACC TTGGAACTGTG-SEQ ID NO: 92 |
| | E11 Rev | CTTCCAGCCCATC TGTTATGTTG-SEQ ID NO: 93 |
| mBRCA1 | E7 For | GAAATCTGTCTAC ATTGAACTAG-SEQ ID NO: 94 |
| | E10 Rev | CCTTTCAGTTGCA TGATTCTC-SEQ ID NO: 95 |
| P73 | E2 For | GGACGGACGCCG ATGCC-SEQ ID NO: 96 |
| | E2 Rev | GGTCCATGGTGCTG CTCAGC-SEQ ID NO: 97 |
| P73 | E1 For | AGGGGACGCAGCG AAACCGGG-SEQ ID NO: 98 |
| | E3 For | GGAACCAGACA GCACCTACTTC-SEQ ID NO: 99 |
| | E4 Rev | CGTCCAGGTGGC TGACTTGGC-SEQ ID NO: 100 |
| mP73 | E1 For | GCATCCAGGCGAG GAGGCAACG-SEQ ID NO: 101 |
| | E4 Rev | GCACTGCTGAGCAAA TTGAACTGGG-SEQ ID NO: 102 |
| CHEK2 | E1 For | AGGTACAGTCCTCT GCTCAGG-SEQ ID NO: 103 |
| | E3 Rev | GACTACTTCAGCCT TATGGACTG-SEQ ID NO: 104 |
| CHEK2 | E5 For | ATGTGTGAATGACA ACTACTGG-SEQ ID NO: 105 |
| | E7 Rev | TGATGTATTCATCT CTTAATGCC-SEQ ID NO: 106 |
| | E8 Rev | CTTTACCTCTCCAC AGGCACC-SEQ ID NO: 107 |
| TSC1 | E14 for | AAGAGCCACCTGG CAGCAAAGG-SEQ ID NO: 108 |
| | E17 Rev | CATGGCAGCATTAT GTTCCTCC-SEQ ID NO: 109 |
| TSC2 | E2 For | GGCCTCAACAATC GCATCCG-SEQ ID NO: 110 |
| | E4 Rev | CCAACATCCATCC ACTGCAGG-SEQ ID NO: 111 |
| TSC2 | E12 For | GAGTCCTCCCTCCT GAACCTG-SEQ ID NO: 112 |
| | E16 Rev | GCAGGCAGGGTGTA CAGCTTGG-SEQ ID NO: 113 |
| c-Myb | E8 For | CCACACATGCAGC TACCCCG-SEQ ID NO: 114 |
| | E10 Rev | CACAGTCTGGTCTCT ATGAAATGG-SEQ ID NO: 115 |
| B-Myb | E7 For | GGAAGTCTTCTGACC AACTGGC-SEQ ID NO: 116 |
| | E9 Rev | GCAGCATGTTTCTGG TGCAGGGG-SEQ ID NO: 117 |
| DLG1 | E1 For | CGCCAGGAGCCGGAC CCGCGC-SEQ ID NO: 118 |
| | E5 Rev | GCCAGGGGGGCACAG GCAG-SEQ ID NO: 119 |
| DAPK1 | E17 For | CAATTTGGACATCTC CAACAAG-SEQ ID NO: 120 |
| | E21 Rev | CTGGATGTCGATGGC CTTGGTG-SEQ ID NO: 121 |
| DAPK1 | E13 For | CACGGGACACCTCCA TTACTC-SEQ ID NO: 122 |
| | E15 Rev | CTTGTCCTGGATATTG GGATTTG-SEQ ID NO: 123 |
| DAPK1 | E15 For | TCTGGAGAGATGGCC CTCCACG-SEQ ID NO: 124 |
| | E16 Rev | GGCAGAGGCTGTCAG GAGGGG-SEQ ID NO: 125 |
| VHL | E1 For | AACTTCGACGGCGAG CCGCAG-SEQ ID NO: 126 |
| | E3 Rev | CTGTGTCAGCCGCTC CAGGTC-SEQ ID NO: 127 |
| DVL2 | E4 For | CCCTAATGTGTCCAG CAGCCA-SEQ ID NO: 128 |
| | E6 Rev | CCTCTCCAGGCGGGG TGGCCTC-SEQ ID NO: 129 |
| DVL2 | E11 For | ATGAGCCCATCCAGCC AATTG-SEQ ID NO: 130 |
| | E13 Rev | AGCTCTCACAGCCACC ACTGAG-SEQ ID NO: 131 |
| PML | E6 For | CCAGTGGCGCCGGGGA GGCAG-SEQ ID NO: 132 |
| | E9 Rev | GAAGAAGTTTGGGAGG CCAGGCC-SEQ ID NO: 133 |
| Caspase 8 | E4 For | TCTGTGCCCAAATCAA CAAG-SEQ ID NO: 134 |
| | E9 Rev | GCCACCAGCTAAAAA CATTCC-SEQ ID NO: 135 |
| Caspase 9 | E2 For | AGACCAGTGGACATT GGTTC-SEQ ID NO: 136 |
| | E7 Rev | GGTCCCTCCAGGAAA CAAA-SEQ ID NO: 137 |
| GAPDH | For | ATCAAGAAGGTGGTG AAGCAG-SEQ ID NO: 138 |
| | Rev | CTTACTCCTTGGAGGC CATGT-SEQ ID NO: 139 |
| β-Actin | For | CGTGGACATCCGCAAAG-SEQ ID NO: 140 |
| | Rev | GGAAGGTGGACAGCGAG-SEQ ID NO: 141 |
| SRSF6 shRNA-1 | | TTATAAAGCTTGAGTTAT GTAAGATTTAA-SEQ ID NO: 142 >NM_026499 Start position: 1625 GAATTCAAAAATTAAATC TTACATAACTCAAGCTTTAT AACCAATTATAAAGCTTGAG TTATGTAAGATTTAAGTCGAC GGTGTTTCGTCCTTTCCACAA-SEQ ID NO: 143 |
| SRSF6 shRNA-2 | | TGTTAATAGGACATCATAT GGTAATAGAC-SEQ ID NO: 144 >NM_006275.4 Start position: 3216 GAATTCAAAAAGTCTATT |

TABLE 3 -continued

| Gene name | Exon forward Exon reverse | Sequence (5'-3') |
| --- | --- | --- |
| | | ACCATATGATGTCCTATTA ACACCAATGTTAATAGGAC ATCATATGGTAATAGACGTC GACGGTGTTTCGTCCTTT CCACAA-SEQ ID NO: 145 |

Tumor formation in mice: Pools of MLE or BEAS-2B cells expressing SRSF6 or the empty vector or NCI-H460 and RKO cells expressing SRSF6 shRNAs as indicated were injected into the rear flanks of NOD-SCID mice ($2\times10^6$ cells per site in 100 ml of serum free medium containing 0.25 v/v growth factor stripped matrigel (BD Bioscience) using a 26-gauge needle.

Statistical analysis: For growth curve comparisons between two cell lines, we used a within and between ANOVA with 3 time points as the within predictor and 2 types of cell lines as the between predictor. The interaction term between time points and cell line test whether the growth rates differ. For all other statistical comparisons, we used student's t-test (two-tailed) for independent samples where equal variances are assumed. P values associated with these tests are indicated in the figure legends.

Results

SRSF6 is Amplified and Overexpressed in Lung and Colon Cancers

The DNA copy number and expression levels of several splicing factors from the SR and hnRNP A/B protein families was analyzed in colon and lung normal and tumor samples. It was found that SRSF6 (SRp55) was amplified in 12% of lung and breast as well as in 37% of colon tumor samples examined. Notably, in colon tumors only hnRNP A2/B1 was amplified to a similar extent and no other SR or hnRNP A/B protein had similar elevated gene copy numbers (FIG. 30A). SRSF6 was also overexpressed as measured by its mRNA levels in ~50% of lung and colon tumors examined (FIG. 30A). Moreover, analyses of public databases show elevated gene copy numbers and significant overexpression of SRSF6 in colon tumors compared to normal colon or rectum samples and in gastric and bladder tumors. These results suggest that SRSF6 is a marker for colon and lung cancer development and may play a role in the development of these cancers.

Figures 31A, 31B, 31C, 31D, 31E, 31F:
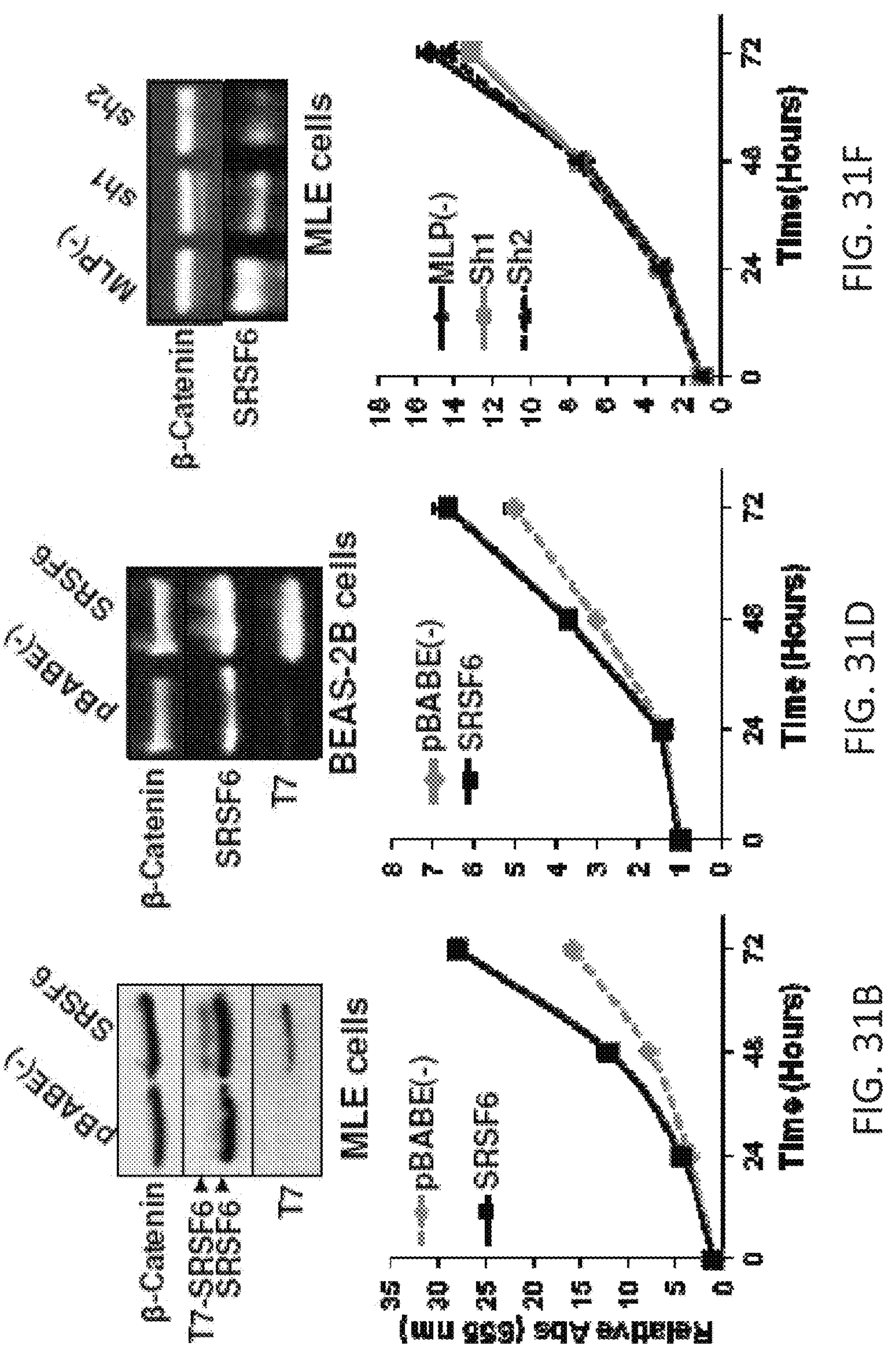
Figure 31G:
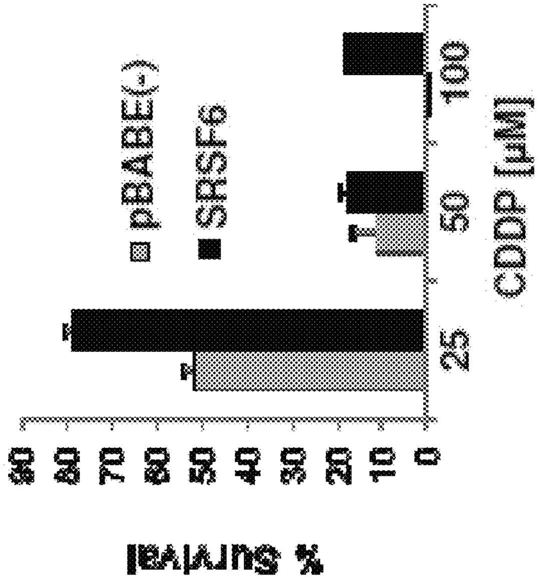

SRSF6 Enhances Proliferation and Inhibits Cell Death of Mouse Lung Epithelial Cells To investigate if SRSF6 promotes cellular transformation the present inventors examined if its overexpression can enhance proliferation or reduce cell death of normal lung cells and the reverse, if knockdown of SRSF6 can inhibit proliferation or enhance cell death of lung and colon cancer cells. Overexpression of SRSF6 in immortal mouse lung epithelial cells (MLE) or immortal human lung epithelial cells (BEAS-2B), enhanced their proliferation compared to cells expressing empty vector (FIGS. 31A-D). Knockdown of SRSF6 in MLE cells did not inhibit their proliferation, suggesting that SRSF6 is not required for proliferation of these cells but its overexpression might trigger abnormal proliferation (FIGS. 31E-F). In addition, SRSF6 overexpression in MLE cells rendered them more resistant to chemotherapy-induced cell death as measured by their survival after treatment with cis-platinum (FIG. 31G). These results suggest that SRSF6 is both an anti-apoptotic agent and can also enhance proliferation.

Figures 32A, 32B, 32C, 32D, 32E, 32F:
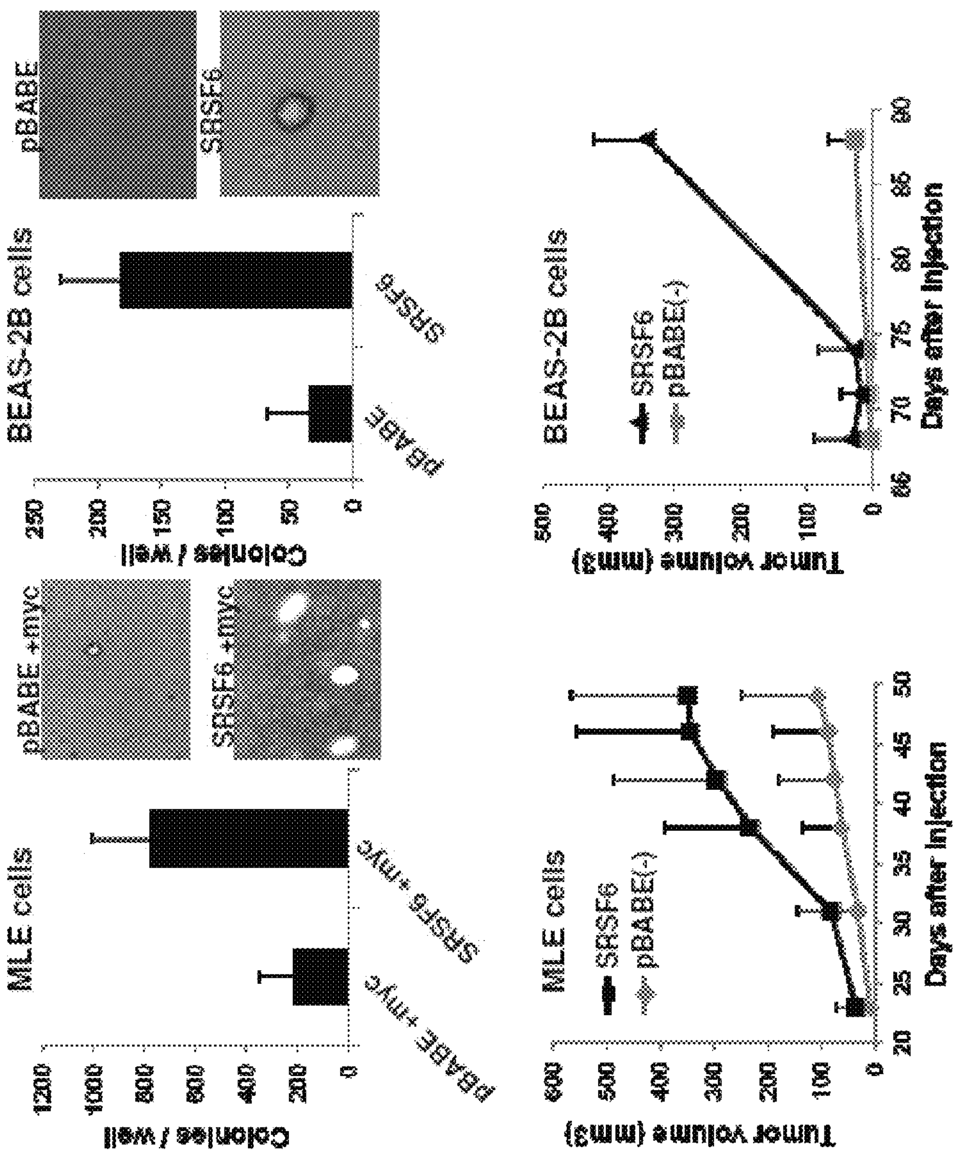

SRSF6 Cooperates with Myc and Its Up-regulation Transforms Mouse and Human Lung Epithelial Cells in Vitro and in Vivo The present inventors next examined if SRSF6 can enhance anchorage-independent growth of MLE and BEAS-2B cells. Because MLE cells failed to form colonies in soft agar in the absence or presence of SRSF6 alone they co-expressed the proto-oncogene c-myc together with SRSF6 in MLE cells. c-myc expression alone was not sufficient to induce colony formation in soft agar of MLE cells (FIGS. 32A-B). However, co-expression of SRSF6 and c-myc induced colony formation in soft agar (FIGS. 32A-B). They next examined if SRSF6 can transform immortal human bronchial epithelial cells (BEAS-2B). It was found that expression of SRSF6 alone was sufficient to transform BEAS-2B cells which formed colonies in soft agar (FIGS. 32C-D) To further investigate if SRSF6 can render cells tumorigenic in vivo, MLE and BEAS-2B cells expressing SRSF6 or the empty vector were injected subcutaneously into NOD-SCID mice. It was found that SRSF6 overexpression converted MLE and BEAS-2B cells into tumorigenic cells that formed tumors in mice (FIGS. 32E-F). These results indicate that SRSF6 is a cellular proto-oncogene in lung cancer which is not only up-regulated in lung and colon cancers but may be a causative factor in lung tumor development.

Figures 33A, 33B, 33C, 33D:
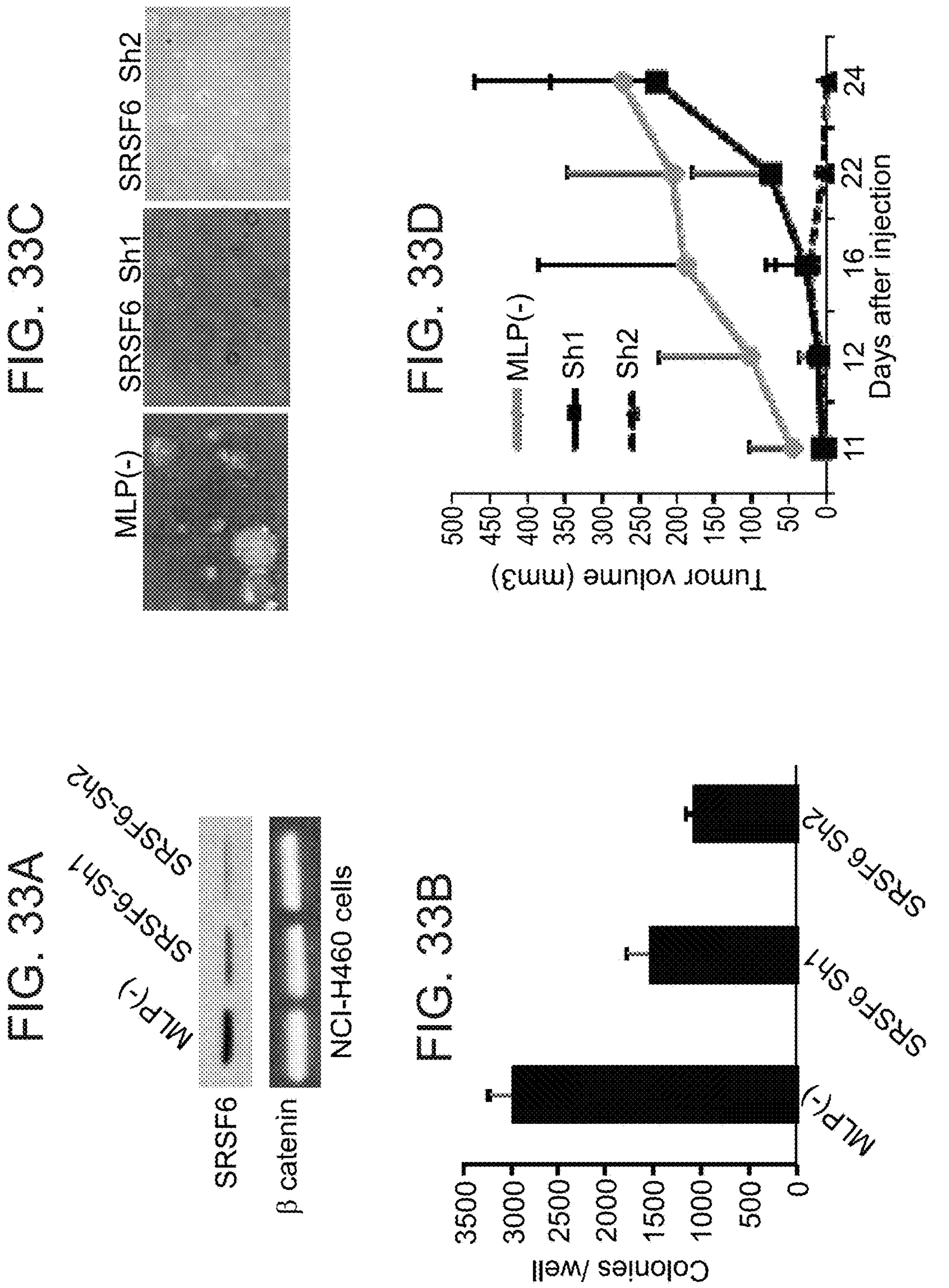
Figure 33E:
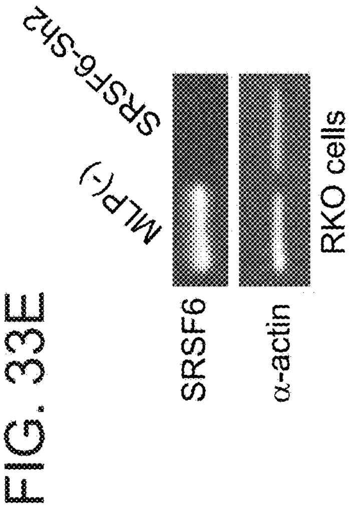
Figure 33F:
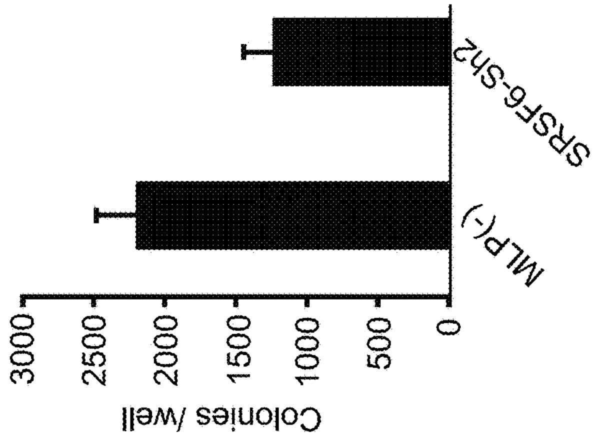
Figure 33G:
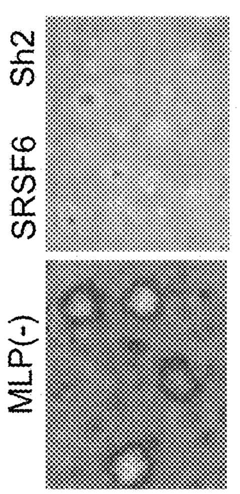
Figure 33H:
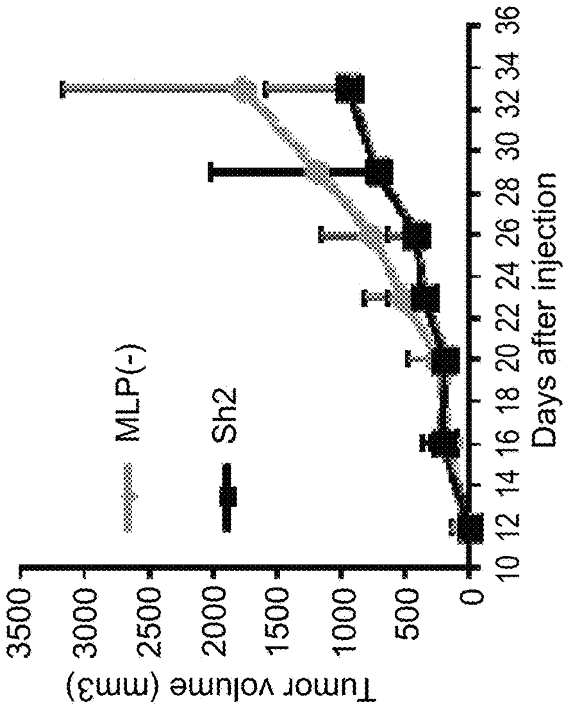

Knockdown of SRSF6 Inhibits Transformation and Tumorigenesis of Lung and Colon Cancer Cells To examine if SRSF6 is required for tumor maintenance the effects of knockdown of SRSF6 on transformation of colon and lung tumor cell lines were examined. It was found that stable SRSF6 knockdown (FIGS. 33A, E) inhibited colony formation in soft agar of NCI-H460 lung cancer cells as well as of RKO colon cancer cells (FIGS. 33B-C, F-G). Furthermore, when injected into NOD-SCID mice the ability of these cells to form tumors in vivo was strongly inhibited, indicating that SRSF6 is required for both tumor initiation and maintenance (FIGS. 33D, H).

SRSF6 Regulates the Splicing of Tumor Suppressors and Oncogenes

In order to identify alternative splicing events which are regulated by SRSF6 and might contribute to its oncogenic activity, the present inventors examined the effects of SRSF6 up- or down-regulation on splicing events reported to be altered in cancer and that contribute to the transformed phenotype (FIG. 34A-B). It was found that splicing of the insulin receptor (INSR) was changed upon up- or down-regulation of SRSF6. INSR exon 11 alternative splicing was shown to be regulated by some SR proteins and hnRNP A/B proteins, and modulates the affinity of the insulin receptor to its ligand —insulin or IGF-II. A switch in INSR splicing in cancer which leads to elevated skipping of exon 11 has been reported in several cancers. It was found that SRSF6 upregulation increases the skipping of INSR exon 11 while its knockdown elevated exon 11 inclusion (FIGS. 34A-B). These results suggest that SRSF6 regulates INSR alternative splicing and leads to the production of the more mitogenic isoform of the insulin receptor. Another splicing target of SRSF6 identified was the kinase Mnk2 (MKNK2). It was found that while SRSF6 upregulation did not change MKNK2 splicing in BEAS-2B cells, its knockdown in NCI-H460 cells reduced the formation of the pro-oncogenic Mnk2b isoform, and increased levels of the tumors suppressive Mnk2a isoform (FIGS. 34A-B). DLG-1 is a putative tumor suppressor which has been implicated in cell polarity and tissue organization and its expression is downregulated in cancer and contributes to enhanced invasion. It was found that while SRSF6 overexpression did not affect DLG-1 splicing in BEAS-2B cells, its knockdown induced inclusion of exons 3-4, and the production of the full-length tumor suppressor DLG-1 (FIGS. 34A-B).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating a cancer associated with a decrease in expression of MAP Kinase Interacting Serine/Threonine Kinase 2a (Mnk2a) in a subject in need thereof, the method comprising administering to the subject a therapeutically effective amount of a polynucleotide agent that hybridizes to to a MAP Kinase Interacting Serine/Threonine Kinase (Mnk2 gene) transciption product such that the ratio of the splice variant MAP Kinase Interacting Serine/Threonine Kinase 2a (Mnk2a): MAP Kinase Interacting Serine/Threonine Kinase 2b (Mnk2b) is increased, thereby treating the cancer associated with a decrease in expression of Mnk2a.

2. The method of claim 1, wherein said polynucleotide agent hybridizes to the pre-mRNA transcribed from the Mnk2 gene.

3. The method of claim 1, wherein said polynucleotide agent hybridizes to a Mnk2b specific splice site.

4. The method of claim 1, wherein said polynucleotide agent comprises peptide nucleic acids or locked nucleic acids.

5. The method of claim 1, wherein said polynucleotide agent comprises a modification selected from the group consisting of phosphorothioation, 2-o-methyl protection, 2'-O-methoxyethyl sugar modification and LNA modification.

6. The method of claim 1, wherein said polynucleotide agent comprises an RNA silencing agent to Mnk2b.

7. The method of claim 1, wherein said cancer associated with with a decrease in expression of MAP Kinase Interacting Serine/Threonine Kinase 2a (Mnk2a) is selected from the group consisting of breast cancer, colon cancer, lung cancer and glioblastoma.

* * * * *